United States Patent
Wang et al.

(10) Patent No.: US 10,654,918 B2
(45) Date of Patent: May 19, 2020

(54) INFLAMMATORY DISEASE DIAGNOSIS AND METHODS OF TREATMENT USING DOWN-REGULATORS OF LIPOPOLYSACCHARIDE-RESPONSIVE BEIGE-LIKE ANCHOR

(71) Applicants: Jia-Wang Wang, Tampa, FL (US); Richard F. Lockey, Tampa, FL (US)

(72) Inventors: Jia-Wang Wang, Tampa, FL (US); Richard F. Lockey, Tampa, FL (US)

(73) Assignee: University of South Florida, Tampa, FL (US)

( * ) Notice: Subject to any disclaimer, the term of this patent is extended or adjusted under 35 U.S.C. 154(b) by 110 days.

(21) Appl. No.: 15/661,784

(22) Filed: Jul. 27, 2017

(65) Prior Publication Data
US 2018/0002413 A1  Jan. 4, 2018

Related U.S. Application Data

(62) Division of application No. 14/223,490, filed on Mar. 24, 2014, now Pat. No. 9,738,706.

(60) Provisional application No. 61/804,451, filed on Mar. 22, 2013.

(51) Int. Cl.

| | |
|---|---|
| *A61P 11/06* | (2006.01) |
| *A61K 38/17* | (2006.01) |
| *A61K 31/7105* | (2006.01) |
| *C12N 15/113* | (2010.01) |
| *C07K 16/18* | (2006.01) |
| *A61K 35/16* | (2015.01) |
| *A61K 31/69* | (2006.01) |
| *A61K 45/06* | (2006.01) |
| *A61K 31/713* | (2006.01) |
| *C07K 14/47* | (2006.01) |
| *A61K 39/00* | (2006.01) |

(52) U.S. Cl.
CPC .............. *C07K 16/18* (2013.01); *A61K 31/69* (2013.01); *A61K 31/713* (2013.01); *A61K 35/16* (2013.01); *A61K 38/1709* (2013.01); *A61K 45/06* (2013.01); *C12N 15/113* (2013.01); *A61K 2039/505* (2013.01); *C07K 14/4702* (2013.01); *C07K 14/4713* (2013.01); *C07K 2317/76* (2013.01); *C12N 2310/14* (2013.01); *C12N 2310/141* (2013.01); *C12N 2310/531* (2013.01); *C12N 2330/10* (2013.01); *C12N 2330/50* (2013.01)

(58) Field of Classification Search
None
See application file for complete search history.

(56) References Cited

U.S. PATENT DOCUMENTS 7,704,963 B2 * 4/2010 Kerr ...................... C07K 14/47
435/455

OTHER PUBLICATIONS

Lam et al, 2015. Am J Neurodegener Dis. 4(2): 28-39.*
Webb, 2014. Biochemical Pharmacology. 87: 121-130.*

* cited by examiner

*Primary Examiner* — Zachary C Howard
(74) *Attorney, Agent, or Firm* — Michele L. Lawson; Smith & Hopen, P.A.

(57) ABSTRACT

Anti-cytokine therapy has revolutionized immunological disease treatment, but is not always effective and subject to treatment resistance as the cytokine cascade is highly redundant and multiple cytokines are involved in inflammation. Targeting a critical common regulator of inflammatory effectors is desirable. Lipopolysaccharide (LPS)-responsive beige-like anchor (LRBA) is a master regulator of multiple genes important for inflammation. Subcellular localization shows that LRBA translocated to the nucleus upon LPS stimulation and colocalized with multiple proteins associated with the endosome membrane system, indicating a critical role in membrane/vesicle trafficking essential for deposition, secretion and signal transduction of immune effectors. Deregulation, deficiency, down-regulation and overexpression of LRBA causes defective trafficking and signaling of immune effector molecules, resulting in immunodeficiency and autoimmunity diseases associated with a broader spectrum of severe symptoms when compared to other CVID genes. Modulating LRBA through antibodies, dominant negative mutants, or small interference RNA can be used to treat inflammatory diseases.

7 Claims, 82 Drawing Sheets
Specification includes a Sequence Listing.

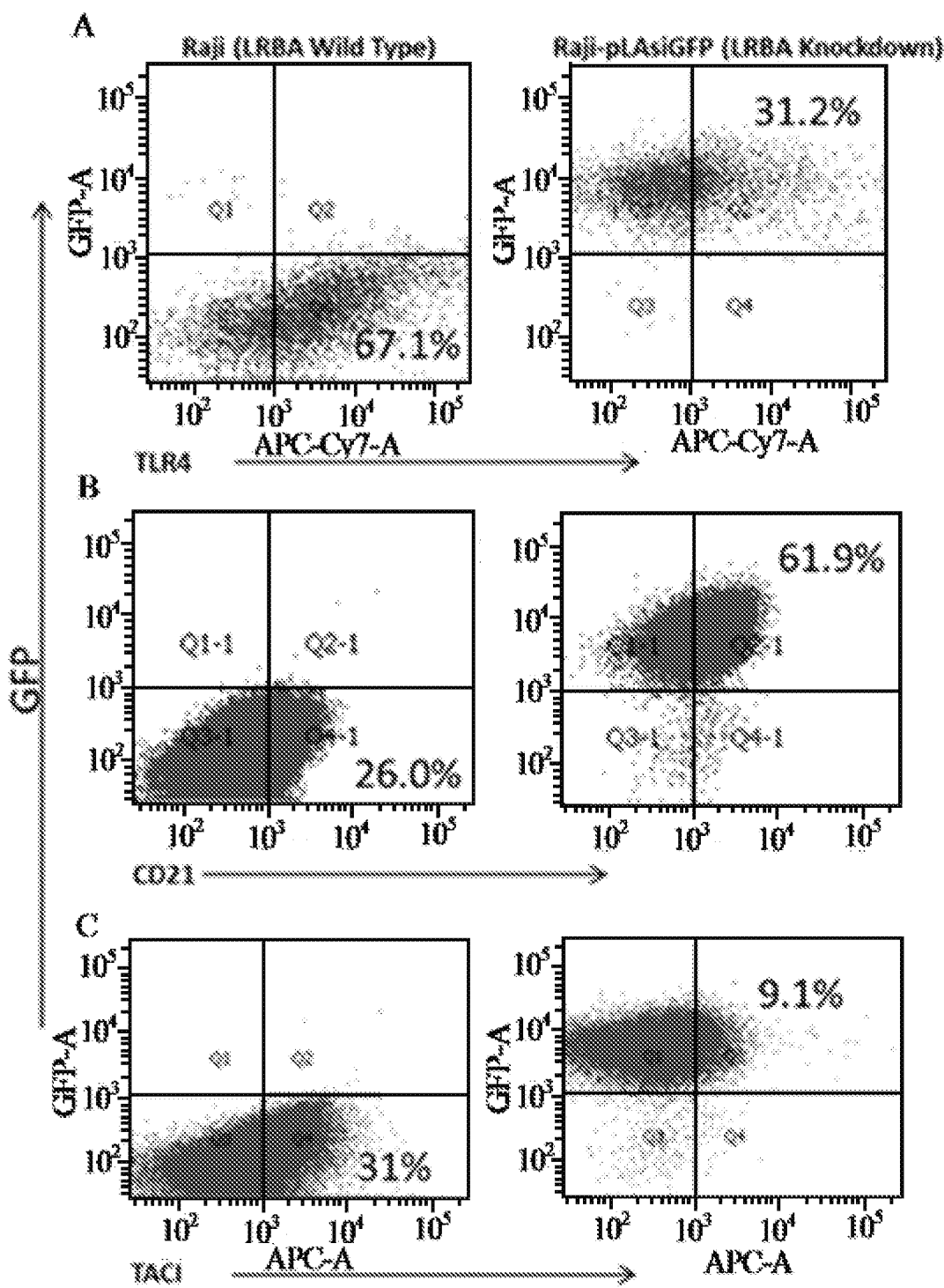
FIG 16A-C

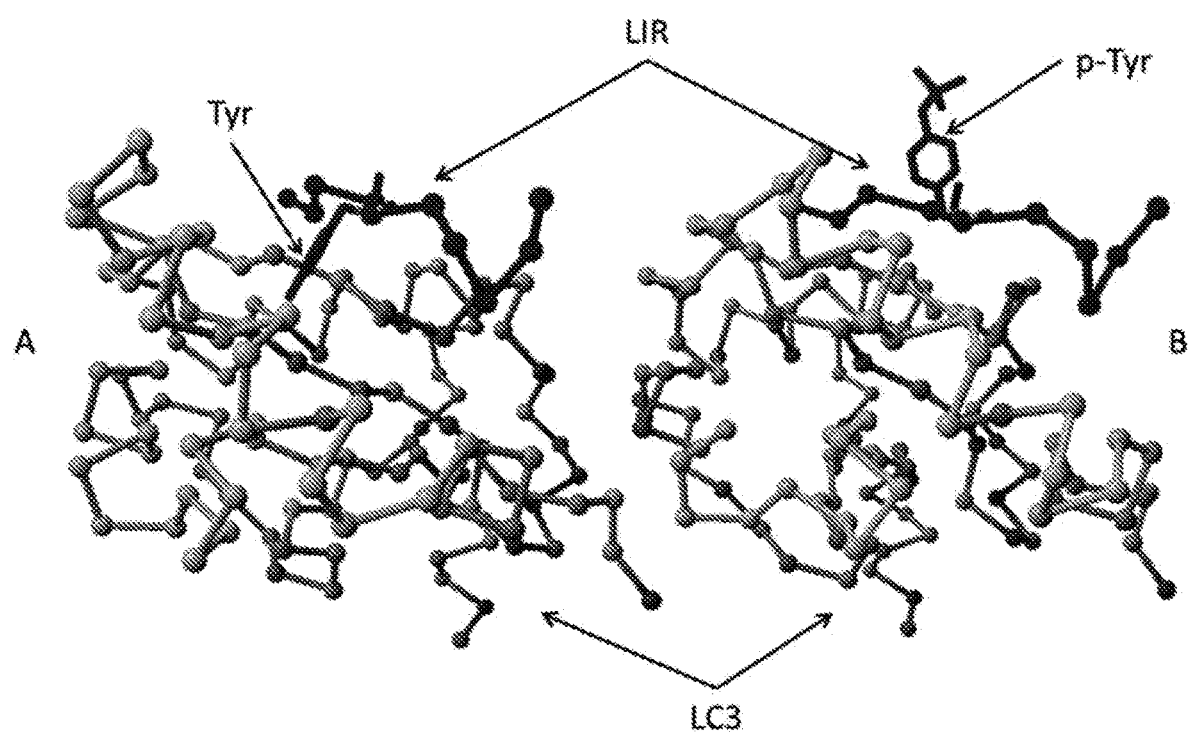
FIG. 24 A-B

Seq ID No. 19

P53 P53
TAGAACCTGCACGAGAGTGGGGGAGGAGT<u>GAGCCTGTTC</u>GGGGGCCTCTT<u>GGACCTGCCT</u>TC

P53
ACCCA<u>GAACCCAGCTTT</u>TTGAGCCCGGGAGAAGCGGGTGGCTAGTAGTGGGGTGCCTTTAGT
AACTTACTTGACCGACAATAACTATTTCCCTCTTGTCCCCTCAAAACCCTAAAACAAAACCT
AGCCTATTTAACATATATTTAATCTTCCAATAGGGTTTGGCGTTGTTGTCAGCCTCGGGGAG

NFκB
AGAGATTGGACAAATATCTCCAAGAGGAGGAGGGCGACGCCA|AGGACTTTCC|CATCAACTG
                                     ↓  ↓
                                     T  A

Transcription start
CTTTGGGGTATCTCCACAAGTTGAAGAGGGACCCTTTCGTTTGCATTGCGTGTGTTGTGC
TCATTACCAGTGCAGCGACTGCCGTCCCAGGGTGACTCTGAGTTGTCCTTTATCGTGAGCTA
GCA|ATG| GCT AGC GAA GAC AAT CGT GTC CCT TCC CCG CCA CCA ACA GGT
GAT GAC GGG GGA GGT GGA GGG AGA GAA GAA ACC CCT ACT GAA GGG NFκB
GGT GCA TTG TCT CTG AAA CC|A GGG CTC CCC| ATC AGG GGC ATC ::luciferase
                   ↓     ↓
                   T     A

FIG. 27

| Seq ID No. | | | | | | | | | | | | | | | | |
|---|---|---|---|---|---|---|---|---|---|---|---|---|---|---|---|---|
| 23. | T | T | T | G | G | T | G | A | C | A | T | G | T | T | G | G | G | A | G | T | Human LRBA |
| 24. | | | | | | | | | | | | | | | | | | | | | |
| | | | | | | | | C | A | T | G | T | T | C | C | C | A | A | C | C | C | T | miR-150 |
| 25. | A | T | C | T | C | G | T | T | G | A | C | A | T | G | T | T | G | G | G | A | G | T | Mouse LRBA |

FIG. 30A

| Seq ID No. | | | | | | | | | | | | | | | miRNA-181 ↓ | | | | | | | | | | | |
|---|---|---|---|---|---|---|---|---|---|---|---|---|---|---|---|---|---|---|---|---|---|---|---|---|---|---|
| | | | | | | 70 | | | | | | | | | 80 | | | | | | | | | | 90 | |
| 23. | Hsa | Z | - | - | - | C | A | C | A | U | C | U | G | A | A | U | G | U | A | A | C | U | U | A | A | A | U | U |
| 24. | Ptr | Z | - | - | - | C | A | C | A | U | C | U | G | A | A | U | G | U | A | A | C | U | U | A | A | A | U | U |
| 25. | Mml | Z | - | - | - | C | A | C | A | U | C | U | G | A | A | U | G | U | A | A | C | U | U | A | A | A | U | U |
| --. | Oga | - | - | - | - | - | - | - | - | - | - | - | - | - | - | - | - | - | - | - | - | - | - | - | - | - | - | - |
| --. | Tbe | - | - | - | - | - | - | - | - | - | - | - | - | - | - | - | - | - | - | - | - | - | - | - | - | - | - | - |
| 26. | Mmu | J | - | - | - | C | A | C | A | U | C | U | G | A | A | U | G | U | A | A | C | U | U | A | A | A | U | U |
| 27. | Rno | J | - | - | - | C | A | C | A | U | C | U | G | A | A | U | G | U | A | A | C | U | U | A | A | A | U | U |
| --. | Cpo | - | - | - | - | - | - | - | - | - | - | - | - | - | - | - | - | - | - | - | - | - | - | - | - | - | - | - |
| 28. | Ocu | J | - | - | - | C | A | C | A | U | C | U | G | A | A | U | G | U | A | A | C | U | G | A | A | A | U | U |
| 29. | Sar | J | - | - | - | C | C | C | A | U | C | U | G | A | A | U | G | U | A | A | C | U | U | A | A | A | G | U |
| 30. | Eeu | J | - | - | - | C | C | C | A | U | C | U | G | A | A | U | G | U | A | A | C | U | U | A | A | A | U | G |
| 31. | Cfa | J | - | - | - | C | A | C | A | U | C | U | G | A | A | U | G | U | A | A | C | U | U | A | A | A | U | U |
| 32. | Fca | J | - | - | - | C | A | C | A | U | C | U | G | A | A | U | G | U | A | A | C | U | U | A | A | A | U | U |
| 33. | Eca | J | - | - | - | C | A | C | A | U | C | U | G | A | A | U | G | U | A | A | C | U | U | A | A | A | U | U |
| 34. | Bta | J | - | - | - | C | A | C | A | U | C | C | G | A | A | U | G | U | A | A | C | U | U | A | A | A | U | U |
| 35. | Dno | J | - | - | - | U | A | C | A | U | C | U | G | A | A | U | G | U | A | A | C | U | U | A | G | A | U | U |
| 36. | Laf | J | - | - | - | U | A | C | A | U | C | U | G | A | A | U | G | U | A | A | C | U | U | C | A | A | U | U |
| 37. | Ete | J | - | - | - | U | A | C | A | U | C | U | G | A | A | U | G | U | A | A | C | U | U | A | A | A | U | U |
| 38. | Mdo | J | - | - | - | U | A | C | A | C | C | U | G | A | A | U | G | U | A | A | C | U | U | A | A | A | U | U |
| 39. | Oan | J | A | A | U | U | A | C | A | U | C | U | G | A | A | U | G | U | A | A | C | U | U | A | A | A | U | U |
| 40. | Aca | J | - | - | - | A | A | C | A | U | C | U | G | A | A | U | G | U | A | A | C | U | U | A | A | A | C | U |
| 41. | Gca | J | - | - | - | C | C | U | A | U | C | U | G | A | A | U | G | U | A | A | C | U | U | A | A | A | U | U |
| 42. | Xtr | J | - | - | - | U | A | C | A | U | C | U | G | A | A | U | G | U | A | A | U | U | U | A | A | A | U | G |

FIG. 30B

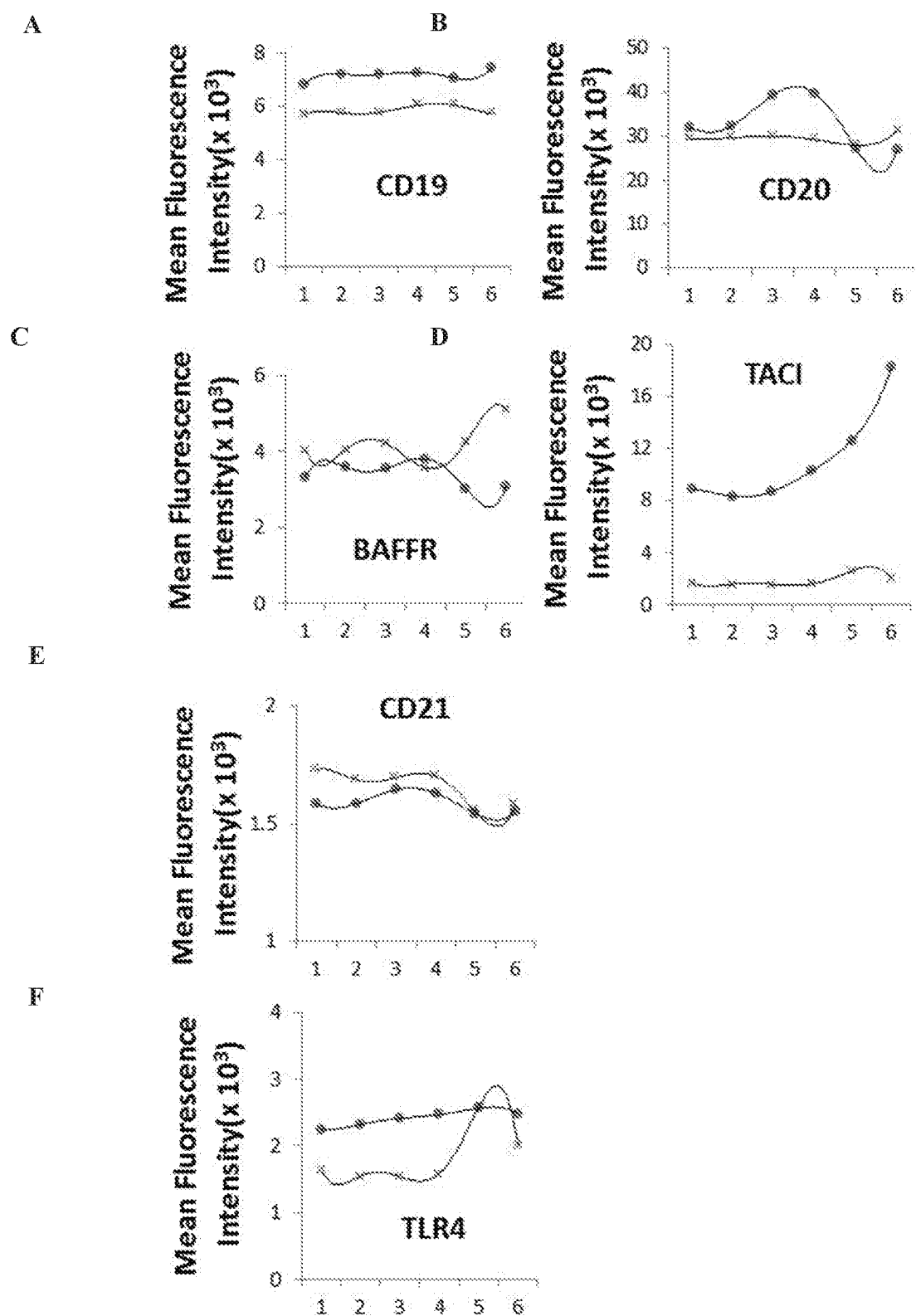
FIG. 38A-F

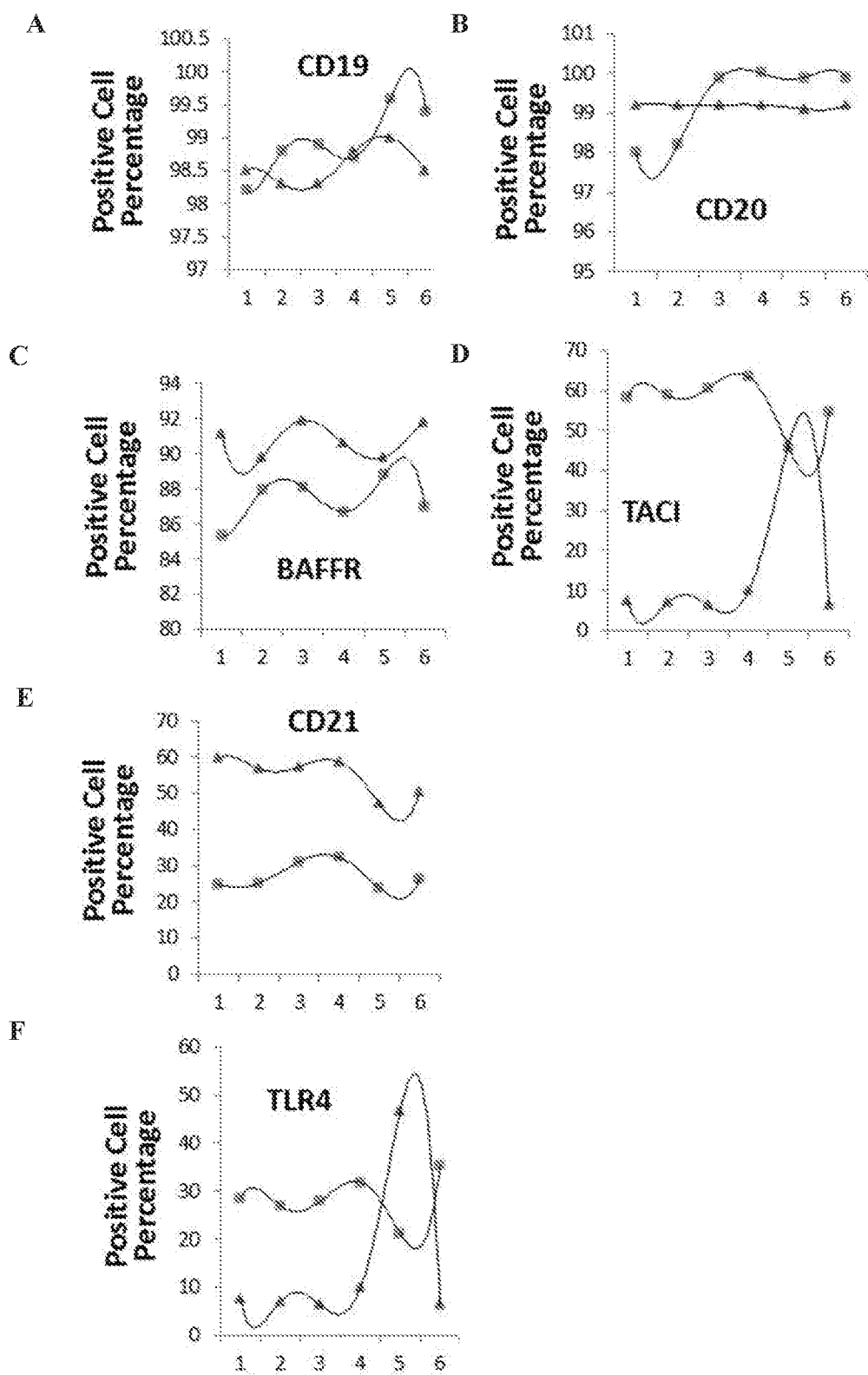
FIG. 39A-F

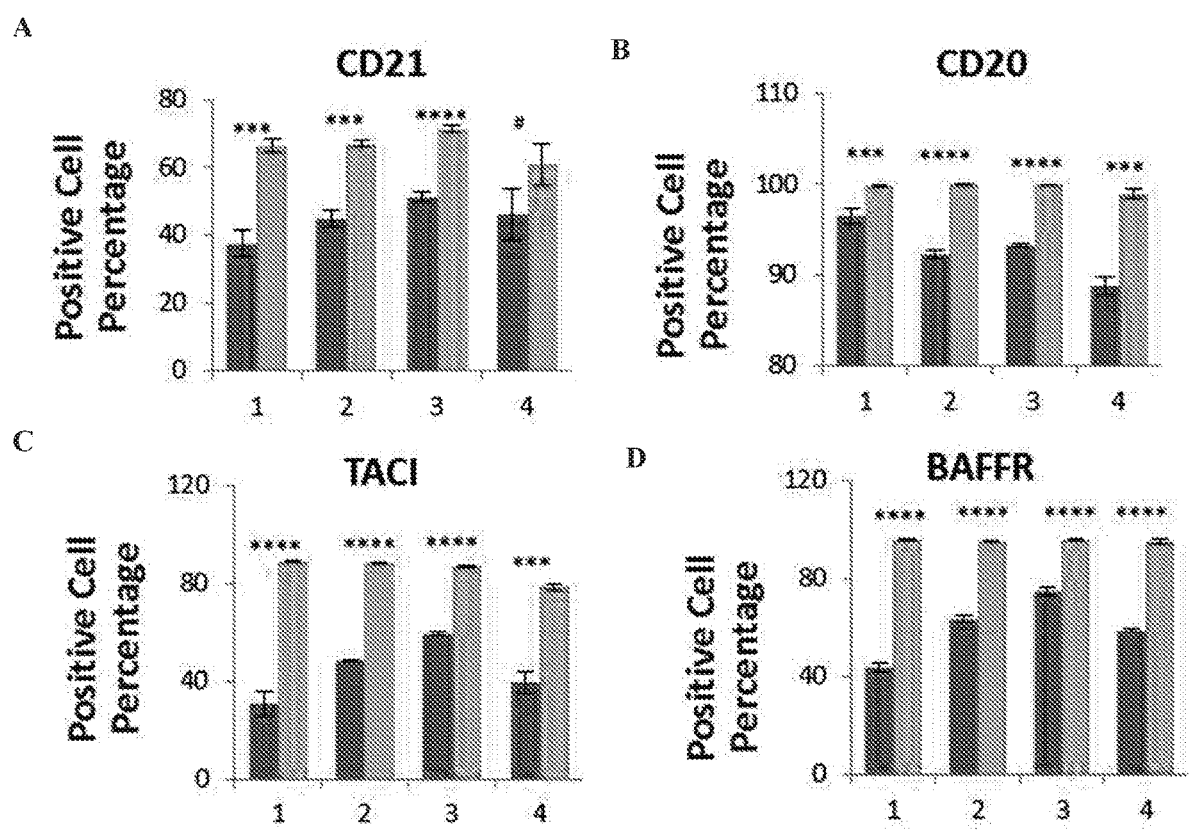
FIG. 40A-D

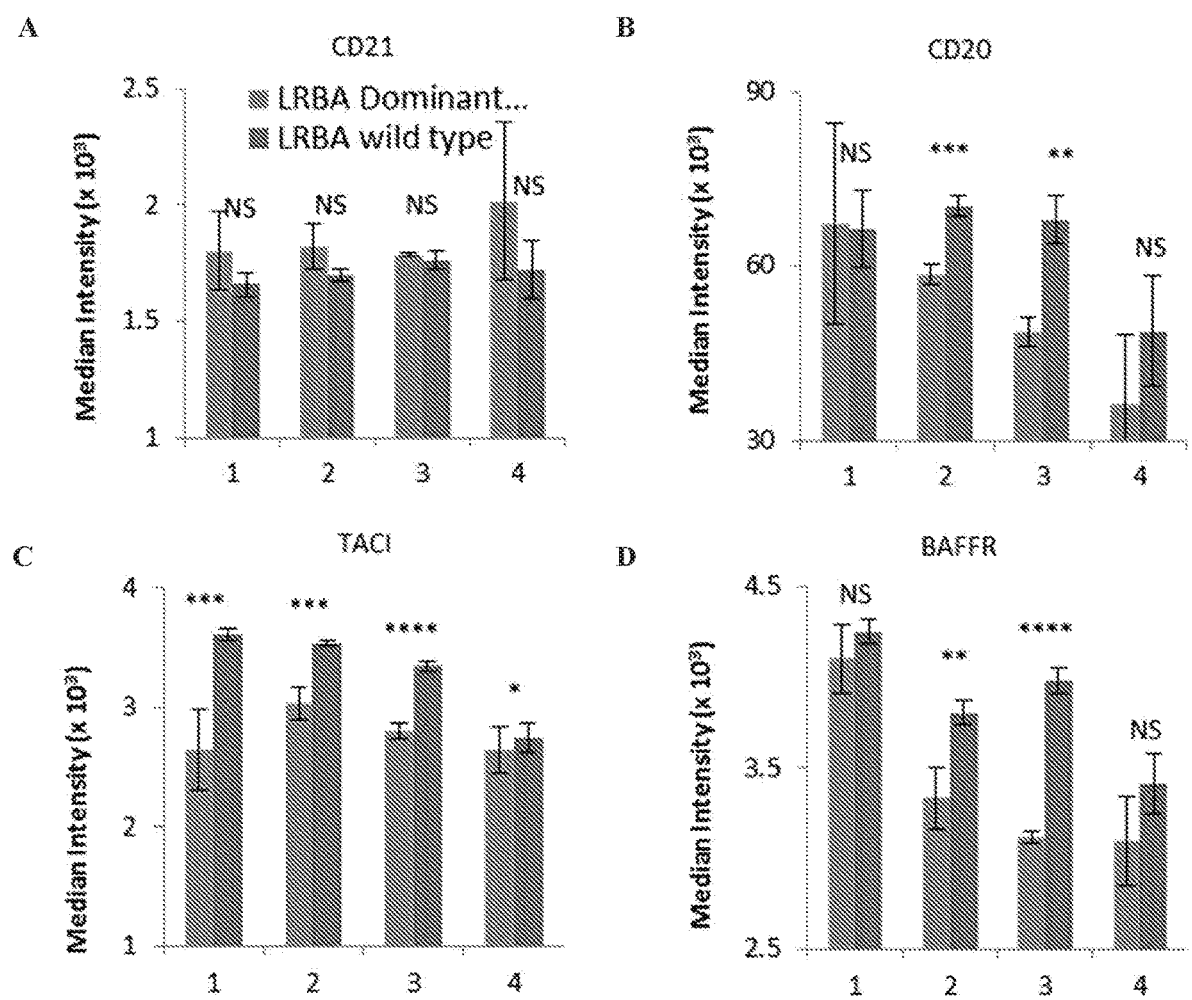
FIG. 41A-D

```
TTTTGGTTGACATGTTGGGAGT  Human LRBA
    ||||  |   ||||||||
GTGACCATGTTCCCAACCCTCT  miR-150
    || ||  |   ||||||||
ATCTCGTTGACATGTTGGGAGT  Mouse Lrba
```

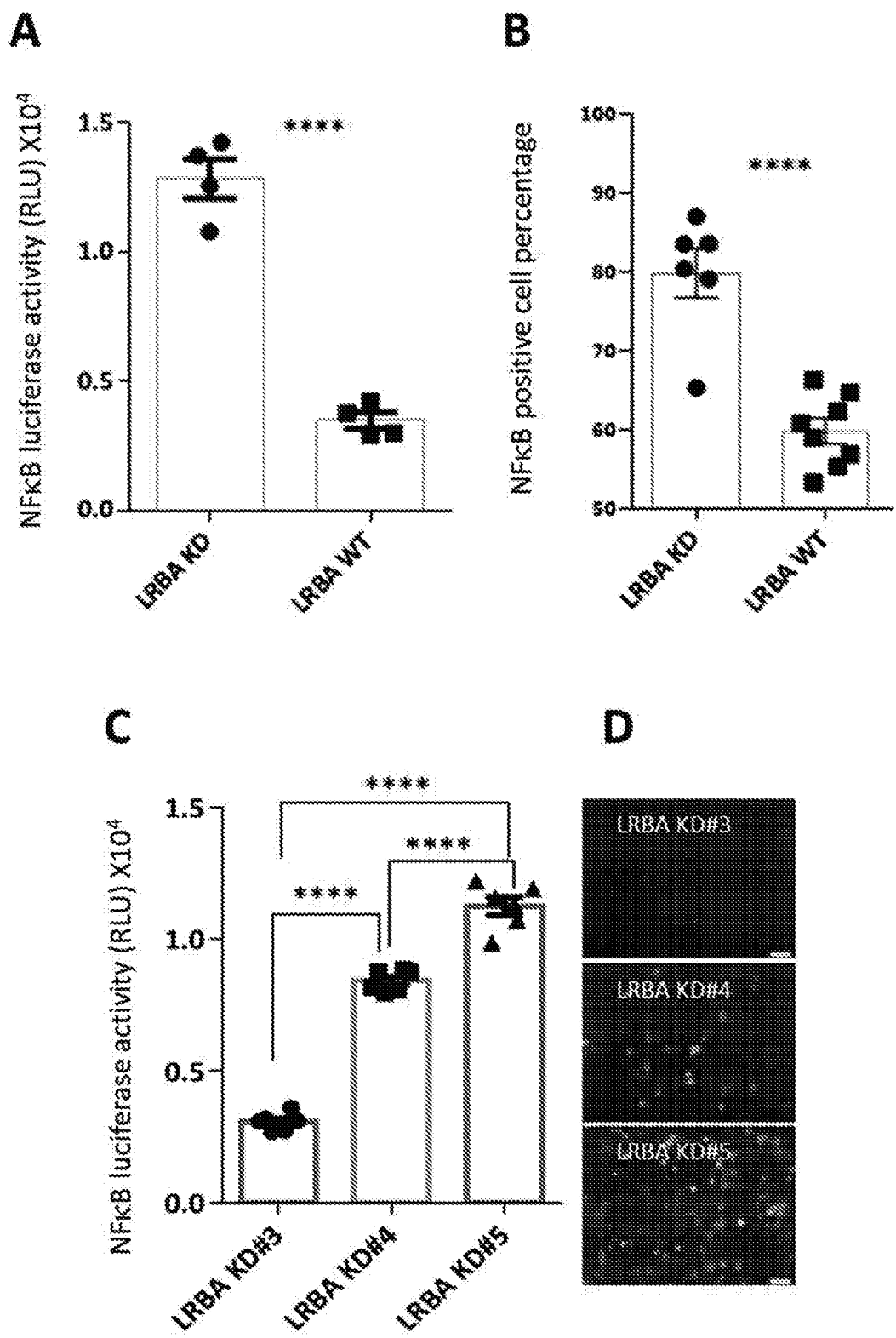
FIG. 45A-D

A
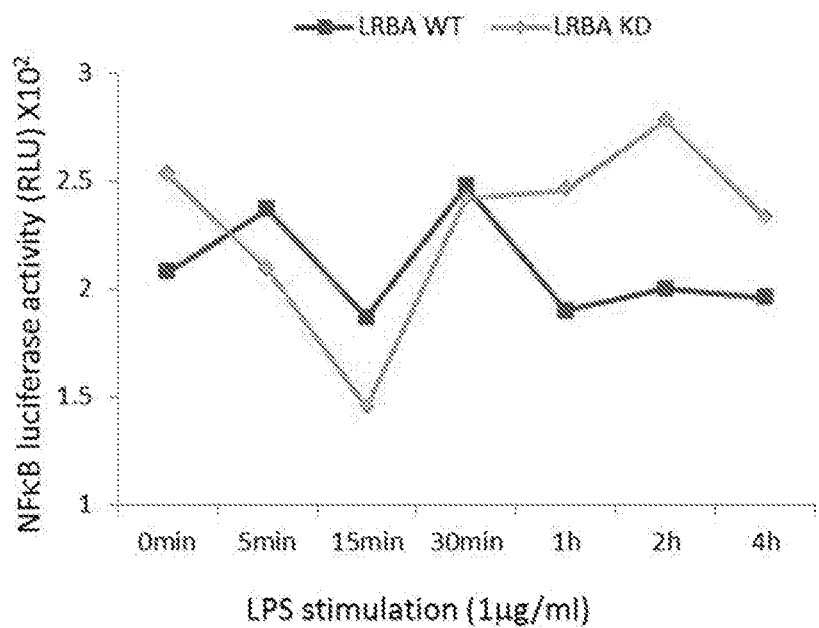
B
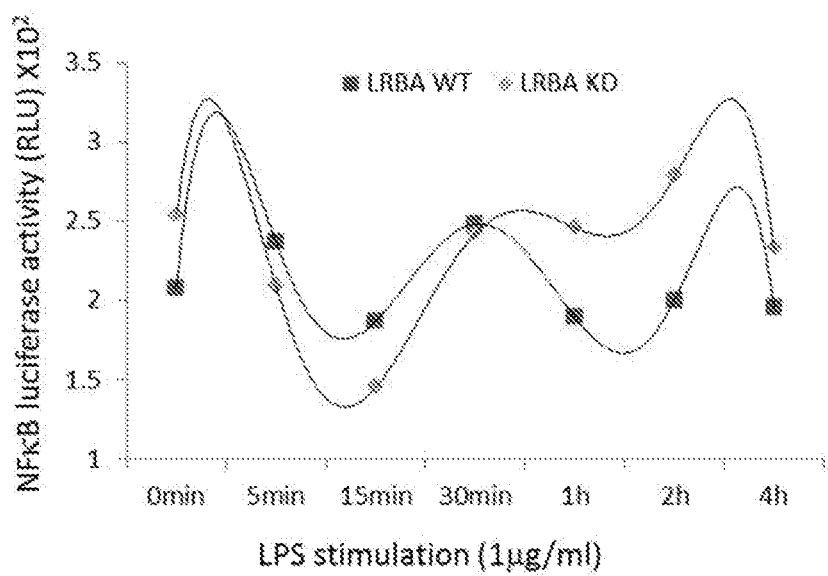
FIG. 46A-B

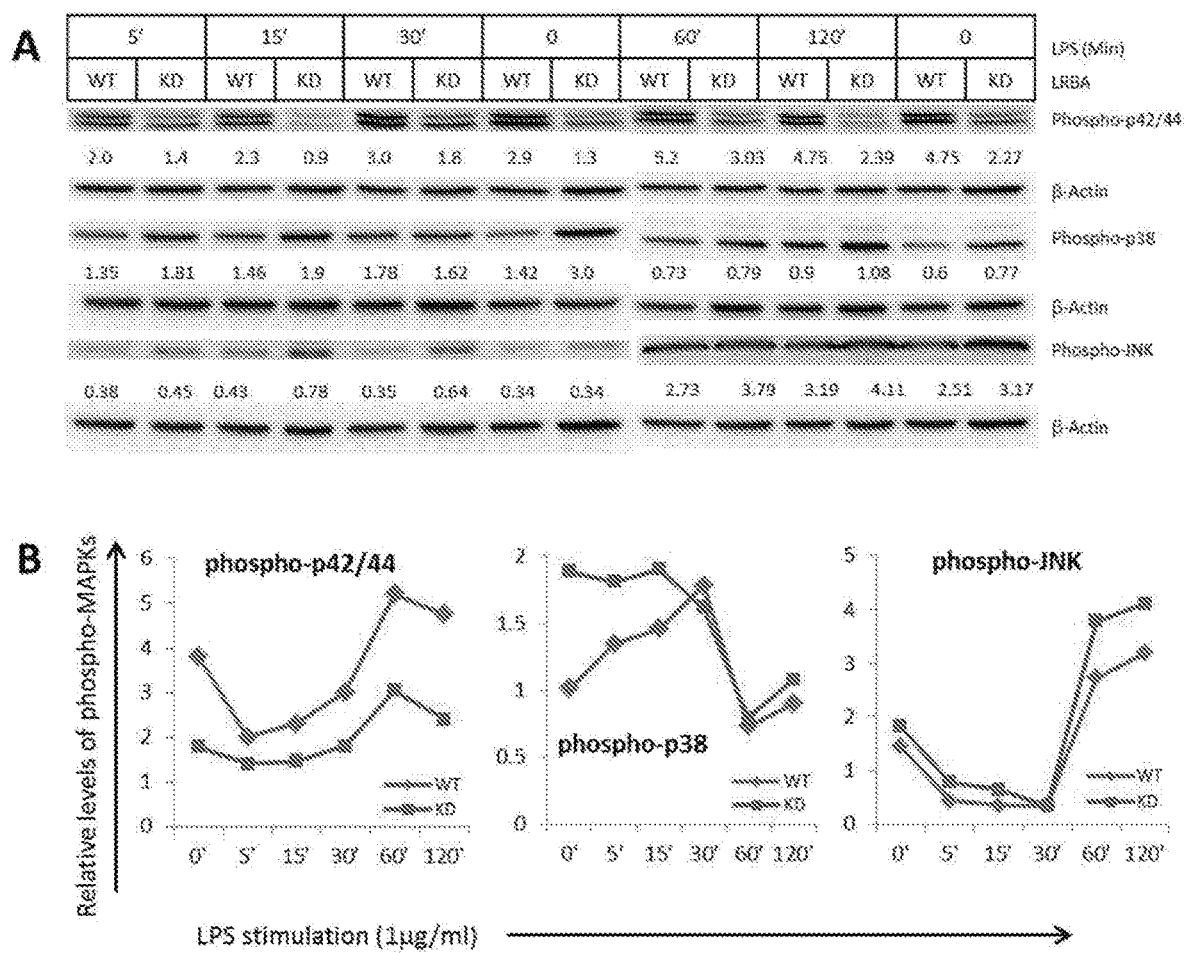
FIG. 47A-B

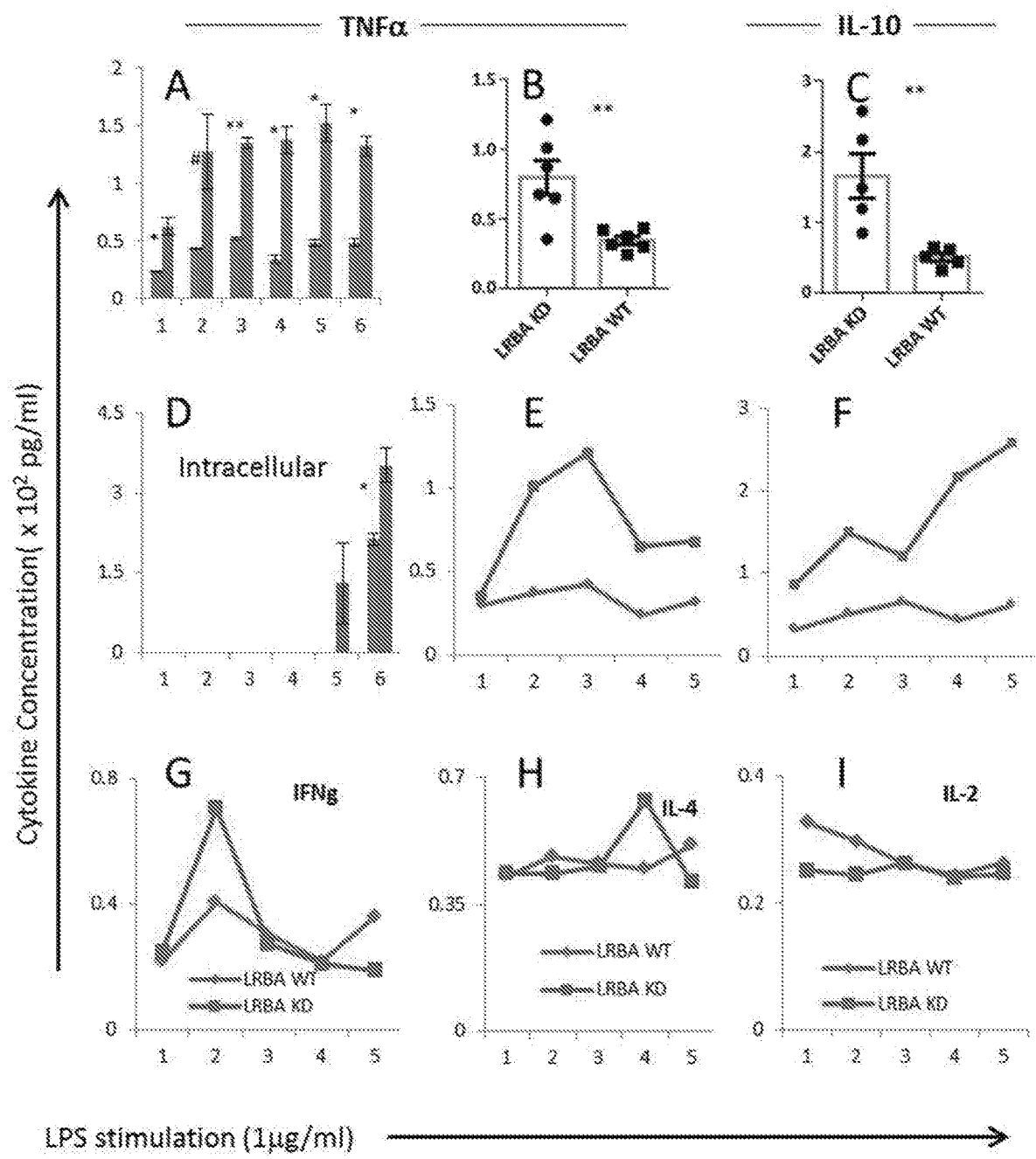
FIG. 48A-I

SEQUENCE LISTING

```
<160> NUMBER OF SEQ ID NOS: 44

<210> SEQ ID NO 1
<211> LENGTH: 2863
<212> TYPE: PRT
<213> ORGANISM: Homo sapiens

<400> SEQUENCE: 1

Met Ala Ser Glu Asp Asn Arg Val Pro Ser Pro Pro Thr Gly Asp
1               5                   10                  15

Asp Gly Gly Gly Gly Arg Glu Glu Thr Pro Thr Glu Gly Gly Ala
                20                  25                  30

Leu Ser Leu Lys Pro Gly Leu Pro Ile Arg Gly Ile Arg Met Lys Phe
        35                  40                  45

Ala Val Leu Thr Gly Leu Val Glu Val Gly Glu Val Ser Asn Arg Asp
    50                  55                  60

Ile Val Glu Thr Val Phe Asn Leu Leu Val Gly Gly Gln Phe Asp Leu
65                  70                  75                  80

Glu Met Asn Phe Ile Ile Gln Glu Gly Glu Ser Ile Asn Cys Met Val
                85                  90                  95

Asp Leu Leu Glu Lys Cys Asp Ile Thr Cys Gln Ala Glu Val Trp Ser
            100                 105                 110

Met Phe Thr Ala Ile Leu Lys Lys Ser Ile Arg Asn Leu Gln Val Cys
        115                 120                 125

Thr Glu Val Gly Leu Val Glu Lys Val Leu Gly Lys Ile Glu Lys Val
    130                 135                 140
```

```
Asp Asn Met Ile Ala Asp Leu Leu Val Asp Met Leu Gly Val Leu Ala
145                 150                 155                 160

Ser Tyr Asn Leu Thr Val Arg Glu Leu Lys Leu Phe Phe Ser Lys Leu
                165                 170                 175

Gln Gly Asp Lys Gly Arg Trp Pro Pro His Ala Gly Lys Leu Leu Ser
            180                 185                 190

Val Leu Lys His Met Pro Gln Lys Tyr Gly Pro Asp Ala Phe Phe Asn
        195                 200                 205

Phe Pro Gly Lys Ser Ala Ala Ile Ala Leu Pro Pro Ile Ala Lys
210                 215                 220

Trp Pro Tyr Gln Asn Gly Phe Thr Phe His Thr Trp Leu Arg Met Asp
225                 230                 235                 240

Pro Val Asn Asn Ile Asn Val Asp Lys Asp Lys Pro Tyr Leu Tyr Cys
                245                 250                 255

Phe Arg Thr Ser Lys Gly Leu Gly Tyr Ser Ala His Phe Val Gly Gly
            260                 265                 270

Cys Leu Ile Val Thr Ser Ile Lys Ser Lys Gly Lys Gly Phe Gln His
        275                 280                 285

Cys Val Lys Phe Asp Phe Lys Pro Gln Lys Trp Tyr Met Val Thr Ile
290                 295                 300

Val His Ile Tyr Asn Arg Trp Lys Asn Ser Glu Leu Arg Cys Tyr Val
305                 310                 315                 320

Asn Gly Glu Leu Ala Ser Tyr Gly Glu Ile Thr Trp Phe Val Asn Thr
                325                 330                 335

Ser Asp Thr Phe Asp Lys Cys Phe Leu Gly Ser Ser Glu Thr Ala Asp
            340                 345                 350

Ala Asn Arg Val Phe Cys Gly Gln Met Thr Ala Val Tyr Leu Phe Ser
        355                 360                 365

Glu Ala Leu Asn Ala Ala Gln Ile Phe Ala Ile Tyr Gln Leu Gly Leu
370                 375                 380

Gly Tyr Lys Gly Thr Phe Lys Phe Lys Ala Glu Ser Asp Leu Phe Leu
385                 390                 395                 400

Ala Glu His His Lys Leu Leu Leu Tyr Asp Gly Lys Leu Ser Ser Ala
                405                 410                 415

Ile Ala Phe Thr Tyr Asn Pro Arg Ala Thr Asp Ala Gln Leu Cys Leu
            420                 425                 430

Glu Ser Ser Pro Lys Asp Asn Pro Ser Ile Phe Val His Ser Pro His
        435                 440                 445

Ala Leu Met Leu Gln Asp Val Lys Ala Val Leu Thr His Ser Ile Gln
450                 455                 460

Ser Ala Met His Ser Ile Gly Gly Val Gln Val Leu Phe Pro Leu Phe
465                 470                 475                 480

Ala Gln Leu Asp Tyr Arg Gln Tyr Leu Ser Asp Glu Ile Asp Leu Thr
                485                 490                 495

Ile Cys Ser Thr Leu Leu Ala Phe Ile Met Glu Leu Leu Lys Asn Ser
            500                 505                 510

Ile Ala Met Gln Glu Gln Met Leu Ala Cys Lys Gly Phe Leu Val Ile
        515                 520                 525

Gly Tyr Ser Leu Glu Lys Ser Ser Lys Ser His Val Ser Arg Ala Val
530                 535                 540

Leu Glu Leu Cys Leu Ala Phe Ser Lys Tyr Leu Ser Asn Leu Gln Asn
545                 550                 555                 560
```

-continued

Gly Met Pro Leu Leu Lys Gln Leu Cys Asp His Val Leu Leu Asn Pro
                565                 570                 575
Ala Ile Trp Ile His Thr Pro Ala Lys Val Gln Leu Met Leu Tyr Thr
            580                 585                 590
Tyr Leu Ser Thr Glu Phe Ile Gly Thr Val Asn Ile Tyr Asn Thr Ile
        595                 600                 605
Arg Arg Val Gly Thr Val Leu Leu Ile Met His Thr Leu Lys Tyr Tyr
610                 615                 620
Tyr Trp Ala Val Asn Pro Gln Asp Arg Ser Gly Ile Thr Pro Lys Gly
625                 630                 635                 640
Leu Asp Gly Pro Arg Pro Asn Gln Lys Glu Met Leu Ser Leu Arg Ala
                645                 650                 655
Phe Leu Leu Met Phe Ile Lys Gln Leu Val Met Lys Asp Ser Gly Val
            660                 665                 670
Lys Glu Asp Glu Leu Gln Ala Ile Leu Asn Tyr Leu Leu Thr Met His
        675                 680                 685
Glu Asp Asp Asn Leu Met Asp Val Leu Gln Leu Leu Val Ala Leu Met
690                 695                 700
Ser Glu His Pro Asn Ser Met Ile Pro Ala Phe Asp Gln Arg Asn Gly
705                 710                 715                 720
Leu Arg Val Ile Tyr Lys Leu Leu Ala Ser Lys Ser Glu Gly Ile Arg
                725                 730                 735
Val Gln Ala Leu Lys Ala Met Gly Tyr Phe Leu Lys His Leu Ala Pro
            740                 745                 750
Lys Arg Lys Ala Glu Val Met Leu Gly His Gly Leu Phe Ser Leu Leu
        755                 760                 765
Ala Glu Arg Leu Met Leu Gln Thr Asn Leu Ile Thr Met Thr Thr Tyr
770                 775                 780
Asn Val Leu Phe Glu Ile Leu Ile Glu Gln Ile Gly Thr Gln Val Ile
785                 790                 795                 800
His Lys Gln His Pro Asp Pro Asp Ser Ser Val Lys Ile Gln Asn Pro
                805                 810                 815
Gln Ile Leu Lys Val Ile Ala Thr Leu Leu Arg Asn Ser Pro Gln Cys
            820                 825                 830
Pro Glu Ser Met Glu Val Arg Arg Ala Phe Leu Ser Asp Met Ile Lys
        835                 840                 845
Leu Phe Asn Asn Ser Arg Glu Asn Arg Arg Ser Leu Leu Gln Cys Ser
850                 855                 860
Val Trp Gln Glu Trp Met Leu Ser Leu Cys Tyr Phe Asn Pro Lys Asn
865                 870                 875                 880
Ser Asp Glu Gln Lys Ile Thr Glu Met Val Tyr Ala Ile Phe Arg Ile
                885                 890                 895
Leu Leu Tyr His Ala Val Lys Tyr Glu Trp Gly Gly Trp Arg Val Trp
            900                 905                 910
Val Asp Thr Leu Ser Ile Thr His Ser Lys Val Thr Phe Glu Ile His
        915                 920                 925
Lys Glu Asn Leu Ala Asn Ile Phe Arg Glu Gln Gln Gly Lys Val Asp
930                 935                 940
Glu Glu Ile Gly Leu Cys Ser Ser Thr Ser Val Gln Ala Ala Ser Gly
945                 950                 955                 960
Ile Arg Arg Asp Ile Asn Val Ser Val Gly Ser Gln Gln Pro Asp Thr
                965                 970                 975
Lys Asp Ser Pro Val Cys Pro His Phe Thr Thr Asn Gly Asn Glu Asn

```
                980             985             990
     Ser Ser Ile Glu Lys Thr Ser Ser Leu Glu Ser Ala Ser Asn Ile Glu
              995             1000            1005
     Leu Gln Thr Thr Asn Thr Ser Tyr Glu Glu Met Lys Ala Glu Gln
         1010            1015            1020
     Glu Asn Gln Glu Leu Pro Asp Glu Gly Thr Leu Glu Glu Thr Leu
         1025            1030            1035
     Thr Asn Glu Thr Arg Asn Ala Asp Asp Leu Glu Val Ser Ser Asp
         1040            1045            1050
     Ile Ile Glu Ala Val Ala Ile Ser Ser Asn Ser Phe Ile Thr Thr
         1055            1060            1065
     Gly Lys Asp Ser Met Thr Val Ser Glu Val Thr Ala Ser Ile Ser
         1070            1075            1080
     Ser Pro Ser Glu Glu Asp Ala Ser Glu Met Pro Glu Phe Leu Asp
         1085            1090            1095
     Lys Ser Ile Val Glu Glu Glu Asp Asp Tyr Val Glu Leu
         1100            1105            1110
     Lys Val Glu Gly Ser Pro Thr Glu Glu Ala Asn Leu Pro Thr Glu
         1115            1120            1125
     Leu Gln Asp Asn Ser Leu Ser Pro Ala Ala Ser Glu Ala Gly Glu
         1130            1135            1140
     Lys Leu Asp Met Phe Gly Asn Asp Asp Lys Leu Ile Phe Gln Glu
         1145            1150            1155
     Gly Lys Pro Val Thr Glu Lys Gln Thr Asp Thr Glu Thr Gln Asp
         1160            1165            1170
     Ser Lys Asp Ser Gly Ile Gln Thr Met Thr Ala Ser Gly Ser Ser
         1175            1180            1185
     Ala Met Ser Pro Glu Thr Thr Val Ser Gln Ile Ala Val Glu Ser
         1190            1195            1200
     Asp Leu Gly Gln Met Leu Glu Glu Gly Lys Lys Ala Thr Asn Leu
         1205            1210            1215
     Thr Arg Glu Thr Lys Leu Ile Asn Asp Cys His Gly Ser Val Ser
         1220            1225            1230
     Glu Ala Ser Ser Glu Gln Lys Ile Ala Lys Leu Asp Val Ser Asn
         1235            1240            1245
     Val Ala Thr Asp Thr Glu Arg Leu Glu Leu Lys Ala Ser Pro Asn
         1250            1255            1260
     Val Glu Ala Pro Gln Pro His Arg His Val Leu Glu Ile Ser Arg
         1265            1270            1275
     Gln His Glu Gln Pro Gly Gln Gly Ile Ala Pro Asp Ala Val Asn
         1280            1285            1290
     Gly Gln Arg Arg Asp Ser Arg Ser Thr Val Phe Arg Ile Pro Glu
         1295            1300            1305
     Phe Asn Trp Ser Gln Met His Gln Arg Leu Leu Thr Asp Leu Leu
         1310            1315            1320
     Phe Ser Ile Glu Thr Asp Ile Gln Met Trp Arg Ser His Ser Thr
         1325            1330            1335
     Lys Thr Val Met Asp Phe Val Asn Ser Ser Asp Asn Val Ile Phe
         1340            1345            1350
     Val His Asn Thr Ile His Leu Ile Ser Gln Val Met Asp Asn Met
         1355            1360            1365
     Val Met Ala Cys Gly Gly Ile Leu Pro Leu Leu Ser Ala Ala Thr
         1370            1375            1380
```

-continued

```
Ser Ala Thr His Glu Leu Glu Asn Ile Glu Pro Thr Gln Gly Leu
1385                1390                1395

Ser Ile Glu Ala Ser Val Thr Phe Leu Gln Arg Leu Ile Ser Leu
1400                1405                1410

Val Asp Val Leu Ile Phe Ala Ser Ser Leu Gly Phe Thr Glu Ile
1415                1420                1425

Glu Ala Glu Lys Ser Met Ser Ser Gly Gly Ile Leu Arg Gln Cys
1430                1435                1440

Leu Arg Leu Val Cys Ala Val Ala Val Arg Asn Cys Leu Glu Cys
1445                1450                1455

Gln Gln His Ser Gln Leu Lys Thr Arg Gly Asp Lys Ala Leu Lys
1460                1465                1470

Pro Met His Ser Leu Ile Pro Leu Gly Lys Ser Ala Ala Lys Ser
1475                1480                1485

Pro Val Asp Ile Val Thr Gly Gly Ile Ser Pro Val Arg Asp Leu
1490                1495                1500

Asp Arg Leu Leu Gln Asp Met Asp Ile Asn Arg Leu Arg Ala Val
1505                1510                1515

Val Phe Arg Asp Ile Glu Asp Ser Lys Gln Ala Gln Phe Leu Ala
1520                1525                1530

Leu Ala Val Val Tyr Phe Ile Ser Val Leu Met Val Ser Lys Tyr
1535                1540                1545

Arg Asp Ile Leu Glu Pro Gln Asn Glu Arg His Ser Gln Ser Cys
1550                1555                1560

Thr Glu Thr Gly Ser Glu Asn Glu Asn Val Ser Leu Ser Glu Ile
1565                1570                1575

Thr Pro Ala Ala Phe Ser Thr Leu Thr Thr Ala Ser Val Glu Glu
1580                1585                1590

Ser Glu Ser Thr Ser Ser Ala Arg Arg Arg Asp Ser Gly Ile Gly
1595                1600                1605

Glu Glu Thr Ala Thr Gly Leu Gly Ser His Val Glu Val Thr Pro
1610                1615                1620

His Thr Ala Pro Pro Gly Val Ser Ala Gly Pro Asp Ala Ile Ser
1625                1630                1635

Glu Val Leu Ser Thr Leu Ser Leu Glu Val Asn Lys Ser Pro Glu
1640                1645                1650

Thr Lys Asn Asp Arg Gly Asn Asp Leu Asp Thr Lys Ala Thr Pro
1655                1660                1665

Ser Val Ser Val Ser Lys Asn Val Asn Val Lys Asp Ile Leu Arg
1670                1675                1680

Ser Leu Val Asn Ile Pro Ala Asp Gly Val Thr Val Asp Pro Ala
1685                1690                1695

Leu Leu Pro Pro Ala Cys Leu Gly Ala Leu Gly Asp Leu Ser Val
1700                1705                1710

Glu Gln Pro Val Gln Phe Arg Ser Phe Asp Arg Ser Val Ile Val
1715                1720                1725

Ala Ala Lys Lys Ser Ala Val Ser Pro Ser Thr Phe Asn Thr Ser
1730                1735                1740

Ile Pro Thr Asn Ala Val Ser Val Val Ser Ser Val Asp Ser Ala
1745                1750                1755

Gln Ala Ser Asp Met Gly Gly Glu Ser Pro Gly Ser Arg Ser Ser
1760                1765                1770
```

```
Asn Ala Lys Leu Pro Ser Val Pro Thr Val Asp Ser Val Ser Gln
1775                1780                1785

Asp Pro Val Ser Asn Met Ser Ile Thr Glu Arg Leu Glu His Ala
1790                1795                1800

Leu Glu Lys Ala Ala Pro Leu Leu Arg Glu Ile Phe Val Asp Phe
1805                1810                1815

Ala Pro Phe Leu Ser Arg Thr Leu Leu Gly Ser His Gly Gln Glu
1820                1825                1830

Leu Leu Ile Glu Gly Thr Ser Leu Val Cys Met Lys Ser Ser Ser
1835                1840                1845

Ser Val Val Glu Leu Val Met Leu Leu Cys Ser Gln Glu Trp Gln
1850                1855                1860

Asn Ser Ile Gln Lys Asn Ala Gly Leu Ala Phe Ile Glu Leu Val
1865                1870                1875

Asn Glu Gly Arg Leu Leu Ser Gln Thr Met Lys Asp His Leu Val
1880                1885                1890

Arg Val Ala Asn Glu Ala Glu Phe Ile Leu Ser Arg Gln Arg Ala
1895                1900                1905

Glu Asp Ile His Arg His Ala Glu Phe Glu Ser Leu Cys Ala Gln
1910                1915                1920

Tyr Ser Ala Asp Lys Arg Glu Asp Glu Lys Met Cys Asp His Leu
1925                1930                1935

Ile Arg Ala Ala Lys Tyr Arg Asp His Val Thr Ala Thr Gln Leu
1940                1945                1950

Ile Gln Lys Ile Ile Asn Ile Leu Thr Asp Lys His Gly Ala Trp
1955                1960                1965

Gly Asn Ser Ala Val Ser Arg Pro Leu Glu Phe Trp Arg Leu Asp
1970                1975                1980

Tyr Trp Glu Asp Asp Leu Arg Arg Arg Arg Phe Val Arg Asn
1985                1990                1995

Pro Leu Gly Ser Thr His Pro Glu Ala Thr Leu Lys Thr Ala Val
2000                2005                2010

Glu His Val Cys Ile Phe Lys Leu Arg Glu Asn Ser Lys Ala Thr
2015                2020                2025

Asp Glu Asp Ile Leu Ala Lys Gly Lys Gln Ser Ile Arg Ser Gln
2030                2035                2040

Ala Leu Gly Asn Gln Asn Ser Glu Asn Glu Ile Leu Leu Glu Gly
2045                2050                2055

Asp Asp Asp Thr Leu Ser Ser Val Asp Glu Lys Asp Leu Glu Asn
2060                2065                2070

Leu Ala Gly Pro Val Ser Leu Ser Thr Pro Ala Gln Leu Val Ala
2075                2080                2085

Pro Ser Val Val Val Lys Gly Thr Leu Ser Val Thr Ser Ser Glu
2090                2095                2100

Leu Tyr Phe Glu Val Asp Glu Asp Pro Asn Phe Lys Lys Ile
2105                2110                2115

Asp Pro Lys Ile Leu Ala Tyr Thr Glu Gly Leu His Gly Lys Trp
2120                2125                2130

Leu Phe Thr Glu Ile Arg Ser Ile Phe Ser Arg Arg Tyr Leu Leu
2135                2140                2145

Gln Asn Thr Ala Leu Glu Ile Phe Met Ala Asn Arg Val Ala Val
2150                2155                2160

Met Phe Asn Phe Pro Asp Pro Ala Thr Val Lys Lys Val Val Asn
```

```
              2165                2170                2175

Tyr Leu Pro Arg Val Gly Val Gly Thr Ser Phe Gly Leu Pro Gln
    2180                2185                2190

Thr Arg Arg Ile Ser Leu Ala Ser Pro Arg Gln Leu Phe Lys Ala
    2195                2200                2205

Ser Asn Met Thr Gln Arg Trp Gln His Arg Glu Ile Ser Asn Phe
    2210                2215                2220

Glu Tyr Leu Met Phe Leu Asn Thr Ile Ala Gly Arg Ser Tyr Asn
    2225                2230                2235

Asp Leu Asn Gln Tyr Pro Val Phe Pro Trp Val Ile Thr Asn Tyr
    2240                2245                2250

Glu Ser Glu Glu Leu Asp Leu Thr Leu Pro Thr Asn Phe Arg Asp
    2255                2260                2265

Leu Ser Lys Pro Ile Gly Ala Leu Asn Pro Lys Arg Ala Ala Phe
    2270                2275                2280

Phe Ala Glu Arg Tyr Glu Ser Trp Glu Asp Asp Gln Val Pro Lys
    2285                2290                2295

Phe His Tyr Gly Thr His Tyr Ser Thr Ala Ser Phe Val Leu Ala
    2300                2305                2310

Trp Leu Leu Arg Ile Glu Pro Phe Thr Thr Tyr Phe Leu Asn Leu
    2315                2320                2325

Gln Gly Gly Lys Phe Asp His Ala Asp Arg Thr Phe Ser Ser Ile
    2330                2335                2340

Ser Arg Ala Trp Arg Asn Ser Gln Arg Asp Thr Ser Asp Ile Lys
    2345                2350                2355

Glu Leu Ile Pro Glu Phe Tyr Tyr Leu Pro Glu Met Phe Val Asn
    2360                2365                2370

Phe Asn Asn Tyr Asn Leu Gly Val Met Asp Asp Gly Thr Val Val
    2375                2380                2385

Ser Asp Val Glu Leu Pro Pro Trp Ala Lys Thr Ser Glu Glu Phe
    2390                2395                2400

Val His Ile Asn Arg Leu Ala Leu Glu Ser Glu Phe Val Ser Cys
    2405                2410                2415

Gln Leu His Gln Trp Ile Asp Leu Ile Phe Gly Tyr Lys Gln Gln
    2420                2425                2430

Gly Pro Glu Ala Val Arg Ala Leu Asn Val Phe Tyr Tyr Leu Thr
    2435                2440                2445

Tyr Glu Gly Ala Val Asn Leu Asn Ser Ile Thr Asp Pro Val Leu
    2450                2455                2460

Arg Glu Ala Val Glu Ala Gln Ile Arg Ser Phe Gly Gln Thr Pro
    2465                2470                2475

Ser Gln Leu Leu Ile Glu Pro His Pro Pro Arg Gly Ser Ala Met
    2480                2485                2490

Gln Val Ser Pro Leu Met Phe Thr Asp Lys Ala Gln Gln Asp Val
    2495                2500                2505

Ile Met Val Leu Lys Phe Pro Ser Asn Ser Pro Val Thr His Val
    2510                2515                2520

Ala Ala Asn Thr Gln Pro Gly Leu Ala Thr Pro Ala Val Ile Thr
    2525                2530                2535

Val Thr Ala Asn Arg Leu Phe Ala Val Asn Lys Trp His Asn Leu
    2540                2545                2550

Pro Ala His Gln Gly Ala Val Gln Asp Gln Pro Tyr Gln Leu Pro
    2555                2560                2565
```

```
Val Glu Ile Asp Pro Leu Ile Ala Ser Asn Thr Gly Met His Arg
    2570            2575                2580

Arg Gln Ile Thr Asp Leu Leu Asp Gln Ser Ile Gln Val His Ser
    2585            2590                2595

Gln Cys Phe Val Ile Thr Ser Asp Asn Arg Tyr Ile Leu Val Cys
    2600            2605                2610

Gly Phe Trp Asp Lys Ser Phe Arg Val Tyr Ser Thr Asp Thr Gly
    2615            2620                2625

Arg Leu Ile Gln Val Val Phe Gly His Trp Asp Val Val Thr Cys
    2630            2635                2640

Leu Ala Arg Ser Glu Ser Tyr Ile Gly Gly Asn Cys Tyr Ile Leu
    2645            2650                2655

Ser Gly Ser Arg Asp Ala Thr Leu Leu Leu Trp Tyr Trp Asn Gly
    2660            2665                2670

Lys Cys Ser Gly Ile Gly Asp Asn Pro Gly Ser Glu Thr Ala Ala
    2675            2680                2685

Pro Arg Ala Ile Leu Thr Gly His Asp Tyr Glu Val Thr Cys Ala
    2690            2695                2700

Ala Val Cys Ala Glu Leu Gly Leu Val Leu Ser Gly Ser Gln Glu
    2705            2710                2715

Gly Pro Cys Leu Ile His Ser Met Asn Gly Asp Leu Leu Arg Thr
    2720            2725                2730

Leu Glu Gly Pro Glu Asn Cys Leu Lys Pro Lys Leu Ile Gln Ala
    2735            2740                2745

Ser Arg Glu Gly His Cys Val Ile Phe Tyr Glu Asn Gly Leu Phe
    2750            2755                2760

Cys Thr Phe Ser Val Asn Gly Lys Leu Gln Ala Thr Met Glu Thr
    2765            2770                2775

Asp Asp Asn Ile Arg Ala Ile Gln Leu Ser Arg Asp Gly Gln Tyr
    2780            2785                2790

Leu Leu Thr Gly Gly Asp Arg Gly Val Val Val Arg Gln Val
    2795            2800                2805

Ser Asp Leu Lys Gln Leu Phe Ala Tyr Pro Gly Cys Asp Ala Gly
    2810            2815                2820

Ile Arg Ala Met Ala Leu Ser Tyr Asp Gln Arg Cys Ile Ile Ser
    2825            2830                2835

Gly Met Ala Ser Gly Ser Ile Val Leu Phe Tyr Asn Asp Phe Asn
    2840            2845                2850

Arg Trp His His Glu Tyr Gln Thr Arg Tyr
    2855            2860

<210> SEQ ID NO 2
<211> LENGTH: 13
<212> TYPE: PRT
<213> ORGANISM: Homo sapiens

<400> SEQUENCE: 2

Glu Glu Glu Asp Asp Asp Tyr Val Glu Leu Lys Val Glu
1               5                   10

<210> SEQ ID NO 3
<211> LENGTH: 7
<212> TYPE: PRT
<213> ORGANISM: Homo sapiens

<400> SEQUENCE: 3
```

Asp Asp Asp Tyr Val Glu Leu
1               5

<210> SEQ ID NO 4
<211> LENGTH: 13
<212> TYPE: PRT
<213> ORGANISM: Homo sapiens

<400> SEQUENCE: 4

Glu Lys Glu Asp Asp Glu Trp Ile Leu Val Asp Phe Ile
1               5                   10

<210> SEQ ID NO 5
<211> LENGTH: 13
<212> TYPE: PRT
<213> ORGANISM: Homo sapiens

<400> SEQUENCE: 5

Glu Asp Glu Val Gly Asp Trp Leu Ile Ile Asp Leu Pro
1               5                   10

<210> SEQ ID NO 6
<211> LENGTH: 10
<212> TYPE: PRT
<213> ORGANISM: Homo sapiens

<400> SEQUENCE: 6

Gly Gly Gly Arg Asn Asn Tyr Tyr Cys Cys
1               5                   10

<210> SEQ ID NO 7
<211> LENGTH: 10
<212> TYPE: PRT
<213> ORGANISM: artificial
<220> FEATURE:
<223> OTHER INFORMATION: Mutated NFkB binding sequence from H sapiens

<400> SEQUENCE: 7

Gly Gly Thr Arg Asn Asn Tyr Tyr Ala Cys
1               5                   10

<210> SEQ ID NO 8
<211> LENGTH: 387
<212> TYPE: DNA
<213> ORGANISM: artificial
<220> FEATURE:
<223> OTHER INFORMATION: Dominant negative DNA construct against LRBA

<400> SEQUENCE: 8
aggctcatgc ttcagacaaa tttaatcaca atgaccacat ataatgtgct gtttgagatt      60
cttatagaac agattggtac tcaggtgata cataaacagc atccagatcc tgattcttca     120
gtgaagatac aaaaccctca gatactaaaa gtaattgcga ccctacttcg aaattctccc     180
cagtgcccag agagcatgga ggttcgcaga gcctttcttt ctgacatgat taaacttttt     240
aataacagta gagaaaacag gaggagcttg ctacaatgct ctgtgtggca agaatggatg     300
ctttctctct gctattttaa tcctaagaat tcagatgagc aaaagataac agaaatggta     360
tacgccatat tcagaatcct gctttac                                         387

<210> SEQ ID NO 9
<211> LENGTH: 44
<212> TYPE: DNA
<213> ORGANISM: artificial

```
<220> FEATURE:
<223> OTHER INFORMATION: Primer for cloning LRBA-GFP construct

<400> SEQUENCE: 9
tgtacaagta ctcagatcgg ctcatgcttc agacaaattt aatc                        44

<210> SEQ ID NO 10
<211> LENGTH: 40
<212> TYPE: DNA
<213> ORGANISM: artificial
<220> FEATURE:
<223> OTHER INFORMATION: Primer sequence 2 for LRBA-GFP construct

<400> SEQUENCE: 10
agttatctag atccggtggt aaagcaggat tctgaatatg                              40

<210> SEQ ID NO 11
<211> LENGTH: 123
<212> TYPE: PRT
<213> ORGANISM: Homo sapiens

<400> SEQUENCE: 11
```

Gln Thr Asn Leu Ile Thr Met Thr Thr Tyr Asn Val Leu Phe Glu Ile
1               5                   10                  15

Leu Ile Glu Gln Ile Gly Thr Gln Val Ile His Lys Gln His Pro Asp
            20                  25                  30

Pro Asp Ser Ser Val Lys Ile Gln Asn Pro Gln Ile Leu Lys Val Ile
        35                  40                  45

Ala Thr Leu Leu Arg Asn Ser Pro Gln Cys Pro Glu Ser Met Glu Val
    50                  55                  60

Arg Arg Ala Phe Leu Ser Asp Met Ile Lys Leu Phe Asn Asn Ser Arg
65                  70                  75                  80

Glu Asn Arg Arg Ser Leu Leu Gln Cys Ser Val Trp Gln Glu Trp Met
                85                  90                  95

Leu Ser Leu Cys Tyr Phe Asn Pro Lys Asn Ser Asp Glu Gln Lys Ile
            100                 105                 110

Thr Glu Met Val Tyr Ala Ile Phe Arg Ile Leu
        115                 120

```
<210> SEQ ID NO 12
<211> LENGTH: 123
<212> TYPE: PRT
<213> ORGANISM: Homo sapiens

<400> SEQUENCE: 12
```

Gln Thr Asn Leu Ile Thr Met Thr Thr Tyr Asn Val Leu Phe Glu Ile
1               5                   10                  15

Leu Ile Glu Gln Ile Gly Thr Gln Val Ile His Lys Gln His Pro Asp
            20                  25                  30

Pro Asp Ser Ser Val Lys Ile Gln Asn Pro Gln Ile Leu Lys Val Ile
        35                  40                  45

Ala Thr Leu Leu Arg Asn Ser Pro Gln Cys Pro Glu Ser Met Glu Val
    50                  55                  60

Arg Arg Ala Phe Leu Ser Asp Met Ile Lys Leu Phe Asn Asn Ser Arg
65                  70                  75                  80

Glu Asn Arg Arg Ser Leu Leu Gln Cys Ser Val Trp Gln Glu Trp Met
                85                  90                  95

Leu Ser Leu Cys Tyr Phe Asn Pro Lys Asn Ser Asp Glu Gln Lys Ile
            100                 105                 110

-continued

```
Thr Glu Met Val Tyr Ala Ile Phe Arg Ile Leu
        115                 120

<210> SEQ ID NO 13
<211> LENGTH: 221
<212> TYPE: PRT
<213> ORGANISM: Homo sapiens

<400> SEQUENCE: 13

Gly Trp Arg Val Trp Val Asp Thr Leu Ser Ile Thr His Ser Lys Val
1               5                   10                  15

Thr Phe Glu Ile His Lys Glu Asn Leu Ala Asn Ile Phe Arg Glu Gln
            20                  25                  30

Gln Gly Lys Val Asp Glu Glu Ile Gly Leu Cys Ser Ser Thr Ser Val
        35                  40                  45

Gln Ala Ala Ser Gly Ile Arg Arg Asp Ile Asn Val Ser Val Gly Ser
    50                  55                  60

Gln Gln Pro Asp Thr Lys Asp Ser Pro Val Cys Pro His Phe Thr Thr
65                  70                  75                  80

Asn Gly Asn Glu Asn Ser Ser Ile Glu Lys Thr Ser Ser Leu Glu Ser
                85                  90                  95

Ala Ser Asn Ile Glu Leu Gln Thr Thr Asn Thr Ser Tyr Glu Glu Met
            100                 105                 110

Lys Ala Glu Gln Glu Asn Gln Glu Leu Pro Asp Glu Gly Thr Leu Glu
        115                 120                 125

Glu Thr Leu Thr Asn Glu Thr Arg Asn Ala Asp Leu Glu Val Ser
    130                 135                 140

Ser Asp Ile Ile Glu Ala Val Ala Ile Ser Ser Asn Ser Phe Ile Thr
145                 150                 155                 160

Thr Gly Lys Asp Ser Met Thr Val Ser Glu Val Thr Ala Ser Ile Ser
                165                 170                 175

Ser Pro Ser Glu Glu Asp Ala Ser Glu Met Pro Glu Phe Leu Asp Lys
            180                 185                 190

Ser Ile Val Glu Glu Glu Glu Asp Asp Asp Tyr Val Glu Leu Lys Val
        195                 200                 205

Glu Gly Ser Pro Thr Glu Glu Ala Asn Leu His Arg Ile
    210                 215                 220

<210> SEQ ID NO 14
<211> LENGTH: 539
<212> TYPE: PRT
<213> ORGANISM: Homo sapiens

<400> SEQUENCE: 14

Arg Leu Met Leu Gln Thr Asn Leu Ile Thr Met Thr Thr Tyr Asn Val
1               5                   10                  15

Leu Phe Glu Ile Leu Ile Glu Gln Ile Gly Thr Gln Val Ile His Lys
            20                  25                  30

Gln His Pro Asp Pro Asp Ser Ser Val Lys Ile Gln Asn Pro Gln Ile
        35                  40                  45

Leu Lys Val Ile Ala Thr Leu Leu Arg Asn Ser Pro Gln Cys Pro Glu
    50                  55                  60

Ser Met Glu Val Arg Arg Ala Phe Leu Ser Asp Met Ile Lys Leu Phe
65                  70                  75                  80

Asn Asn Ser Arg Glu Asn Arg Arg Ser Leu Leu Gln Cys Ser Val Trp
                85                  90                  95
```

```
Gln Glu Trp Met Leu Ser Leu Cys Tyr Phe Asn Pro Lys Asn Ser Asp
            100                 105                 110

Glu Gln Lys Ile Thr Glu Met Val Tyr Ala Ile Phe Arg Ile Leu Leu
            115                 120                 125

Tyr His Ala Val Lys Tyr Glu Trp Gly Gly Trp Arg Val Trp Val Asp
            130                 135                 140

Thr Leu Ser Ile Thr His Ser Lys Val Thr Phe Glu Ile His Lys Glu
145                 150                 155                 160

Asn Leu Ala Asn Ile Phe Arg Glu Gln Gln Gly Lys Val Asp Glu Glu
                165                 170                 175

Ile Gly Leu Cys Ser Ser Thr Ser Val Gln Ala Ala Ser Gly Ile Arg
            180                 185                 190

Arg Asp Ile Asn Val Ser Val Gly Ser Gln Gln Pro Asp Thr Lys Asp
                195                 200                 205

Ser Pro Val Cys Pro His Phe Thr Thr Asn Gly Asn Glu Asn Ser Ser
            210                 215                 220

Ile Glu Lys Thr Ser Ser Leu Glu Ser Ala Ser Asn Ile Glu Leu Gln
225                 230                 235                 240

Thr Thr Asn Thr Ser Tyr Glu Glu Met Lys Ala Glu Gln Glu Asn Gln
                245                 250                 255

Glu Leu Pro Asp Glu Gly Thr Leu Glu Glu Thr Leu Thr Asn Glu Thr
            260                 265                 270

Arg Asn Ala Asp Asp Leu Glu Val Ser Ser Asp Ile Ile Glu Ala Val
            275                 280                 285

Ala Ile Ser Ser Asn Ser Phe Ile Thr Thr Gly Lys Asp Ser Met Thr
            290                 295                 300

Val Ser Glu Val Thr Ala Ser Ile Ser Ser Pro Ser Glu Glu Asp Ala
305                 310                 315                 320

Ser Glu Met Pro Glu Phe Leu Asp Lys Ser Ile Val Glu Glu Glu Glu
            325                 330                 335

Asp Asp Asp Tyr Val Glu Leu Lys Val Glu Gly Ser Pro Thr Glu Glu
            340                 345                 350

Ala Asn Leu Pro Thr Glu Leu Gln Asp Asn Ser Leu Ser Pro Ala Ala
            355                 360                 365

Ser Glu Ala Gly Glu Lys Leu Asp Met Phe Gly Asn Asp Asp Lys Leu
            370                 375                 380

Ile Phe Gln Glu Gly Lys Pro Val Thr Glu Lys Gln Thr Asp Thr Glu
385                 390                 395                 400

Thr Gln Asp Ser Lys Asp Ser Gly Ile Gln Thr Met Thr Ala Ser Gly
                405                 410                 415

Ser Ser Ala Met Ser Pro Glu Thr Thr Val Ser Gln Ile Ala Val Glu
            420                 425                 430

Ser Asp Leu Gly Gln Met Leu Glu Glu Gly Lys Lys Ala Thr Asn Leu
            435                 440                 445

Thr Arg Glu Thr Lys Leu Ile Asn Asp Cys His Gly Ser Val Ser Glu
            450                 455                 460

Ala Ser Ser Glu Gln Lys Ile Ala Lys Leu Asp Val Ser Asn Val Ala
465                 470                 475                 480

Thr Asp Thr Glu Arg Leu Glu Leu Lys Ala Ser Pro Asn Val Glu Ala
                485                 490                 495

Pro Gln Pro His Arg His Val Leu Glu Ile Ser Arg Gln His Glu Gln
            500                 505                 510
```

```
Pro Gly Gln Gly Ile Ala Pro Asp Ala Val Asn Gly Gln Arg Arg Asp
    515                 520                 525

Ser Arg Ser Thr Val Phe Arg Ile Pro Glu Phe
    530                 535

<210> SEQ ID NO 15
<211> LENGTH: 23
<212> TYPE: PRT
<213> ORGANISM: Homo sapiens

<400> SEQUENCE: 15

Gly Gly Gly Ala Thr Ala Thr Thr Gly Thr Ala Gly Ala Ala Ala Cys
1               5                   10                  15

Thr Gly Thr Cys Thr Thr Thr
            20

<210> SEQ ID NO 16
<211> LENGTH: 41
<212> TYPE: DNA
<213> ORGANISM: artificial
<220> FEATURE:
<223> OTHER INFORMATION: Primer for GFP-LRBA dominant negative construct

<400> SEQUENCE: 16
agttatctag atccggtgga actcaggaat acgaaacaca g                            41

<210> SEQ ID NO 17
<211> LENGTH: 39
<212> TYPE: DNA
<213> ORGANISM: artificial
<220> FEATURE:
<223> OTHER INFORMATION: Primer for GFPLIRF dominant negative LRBA
      construct

<400> SEQUENCE: 17
tgtacaagta ctcagatcgt ggctggcgtg tatgggtag                              39

<210> SEQ ID NO 18
<211> LENGTH: 38
<212> TYPE: DNA
<213> ORGANISM: artificial
<220> FEATURE:
<223> OTHER INFORMATION: Primer GFPLIRR for LRBA dominant negative
      construct

<400> SEQUENCE: 18
agttatctag atccggtgta gattagcttc ctcagtag                               38

<210> SEQ ID NO 19
<211> LENGTH: 554
<212> TYPE: DNA
<213> ORGANISM: Homo sapiens

<400> SEQUENCE: 19
agttatctag atccggtgta gattagcttc ctcagtaggg acctgccttc acccagaacc        60 cagcttttg agcccgggag aagcgggtgg ctagtggggt gcctttagta acttacttga       120
ccgacaataa ctatttccct cttgtcccct caaaaccta aaacaaaacc tagcctattt       180
aacatatatt taatcttcca atagggtttg gcgttgttgt cagcctcggg gagagagatt      240
ggacaaatat ctccaagagg aggagggcga cgccaaggac tttccacatc aactgctttg      300
gggtatctcc acaagttgga agagggaccc tttcgttttg cattgcgtgt gttgtgctca      360
ttaccagtgc agcgactgcc gtcccagggt gactctgagt tgtcctttat cgtgagctag      420
```

```
caatggctag cgaagacatt cgtgtccctt ccccgccacc aacaggtgat gacgggggag    480
gtggagggag agaagaaacc cctactgaag ggggtgcatt gtctctgaaa ccagggctcc    540
ccatcagggg catc                                                      554
```

```
<210> SEQ ID NO 20
<211> LENGTH: 22
<212> TYPE: DNA
<213> ORGANISM: Homo sapiens

<400> SEQUENCE: 20
ttttggttga catgttggga gt                                              22

<210> SEQ ID NO 21
<211> LENGTH: 22
<212> TYPE: DNA
<213> ORGANISM: Homo sapiens

<400> SEQUENCE: 21
gtgaccatgt tcccaaccct ct                                              22

<210> SEQ ID NO 22
<211> LENGTH: 22
<212> TYPE: DNA
<213> ORGANISM: Mus musculus

<400> SEQUENCE: 22
atctcgttga catgttggga gt                                              22

<210> SEQ ID NO 23
<211> LENGTH: 23
<212> TYPE: RNA
<213> ORGANISM: Homo sapiens

<400> SEQUENCE: 23
cacaucugaa uguaacuuaa auu                                             23

<210> SEQ ID NO 24
<211> LENGTH: 23
<212> TYPE: RNA
<213> ORGANISM: Pan troglodytes

<400> SEQUENCE: 24
cacaucugaa uguaacuuaa auu                                             23

<210> SEQ ID NO 25
<211> LENGTH: 23
<212> TYPE: RNA
<213> ORGANISM: Macaca mulatta

<400> SEQUENCE: 25
cacaucugaa uguaacuuaa auu                                             23

<210> SEQ ID NO 26
<211> LENGTH: 23
<212> TYPE: RNA
<213> ORGANISM: Mus musculus

<400> SEQUENCE: 26
cacaucugaa uguaacuuaa auu                                             23

<210> SEQ ID NO 27
```

-continued

<210> SEQ ID NO 27
<211> LENGTH: 23
<212> TYPE: RNA
<213> ORGANISM: Rattus norvegicus

<400> SEQUENCE: 27
cacaucugaa uguaacuuaa auu                                        23

<210> SEQ ID NO 28
<211> LENGTH: 23
<212> TYPE: RNA
<213> ORGANISM: Oryctolagus cuniculus

<400> SEQUENCE: 28
cacaucugaa uguaacugaa auu                                        23

<210> SEQ ID NO 29
<211> LENGTH: 23
<212> TYPE: RNA
<213> ORGANISM: Sorex araneus

<400> SEQUENCE: 29
cccaucugaa uguaacuuaa agu                                        23

<210> SEQ ID NO 30
<211> LENGTH: 23
<212> TYPE: RNA
<213> ORGANISM: Erinaceus europaeus

<400> SEQUENCE: 30
cccaucugaa uguaacuuaa aug                                        23

<210> SEQ ID NO 31
<211> LENGTH: 23
<212> TYPE: RNA
<213> ORGANISM: Canis familiaris

<400> SEQUENCE: 31
cacaucugaa uguaacuuaa auu                                        23

<210> SEQ ID NO 32
<211> LENGTH: 23
<212> TYPE: RNA
<213> ORGANISM: Felis catus

<400> SEQUENCE: 32
cacaucugaa uguaacuuaa auu                                        23

<210> SEQ ID NO 33
<211> LENGTH: 23
<212> TYPE: RNA
<213> ORGANISM: Equus caballus

<400> SEQUENCE: 33
cacaucugaa uguaacuuaa auu                                        23

<210> SEQ ID NO 34
<211> LENGTH: 23
<212> TYPE: RNA
<213> ORGANISM: Bos taurus

<400> SEQUENCE: 34
cacauccgaa uguaacuuaa auu                                        23

```
<210> SEQ ID NO 35
<211> LENGTH: 23
<212> TYPE: RNA
<213> ORGANISM: Dasypus novemcinctus

<400> SEQUENCE: 35
uacaucugaa uguaacuuag auu                                              23

<210> SEQ ID NO 36
<211> LENGTH: 23
<212> TYPE: RNA
<213> ORGANISM: Loxodonta africana

<400> SEQUENCE: 36
uacaucugaa uguaacuuca auu                                              23

<210> SEQ ID NO 37
<211> LENGTH: 23
<212> TYPE: RNA
<213> ORGANISM: Echinops telfairi

<400> SEQUENCE: 37
uacaucugaa uguaacuuaa auu                                              23

<210> SEQ ID NO 38
<211> LENGTH: 23
<212> TYPE: RNA
<213> ORGANISM: Monodelphis domestica

<400> SEQUENCE: 38
uacaccugaa uguaacuuaa auu                                              23

<210> SEQ ID NO 39
<211> LENGTH: 26
<212> TYPE: RNA
<213> ORGANISM: Ornithorhynchus anatinus

<400> SEQUENCE: 39
aauuacaucu gaauguaacu uaaauu                                           26

<210> SEQ ID NO 40
<211> LENGTH: 23
<212> TYPE: RNA
<213> ORGANISM: Anolis carolinensis

<400> SEQUENCE: 40
aacaucugaa uguaacuuaa acu                                              23

<210> SEQ ID NO 41
<211> LENGTH: 23
<212> TYPE: RNA
<213> ORGANISM: Gallus gallus

<400> SEQUENCE: 41
ccuaucugaa uguaacuuaa auu                                              23

<210> SEQ ID NO 42
<211> LENGTH: 23
<212> TYPE: RNA
<213> ORGANISM: Xenopus tropicalis

<400> SEQUENCE: 42
uacaucugaa uguaauuuaa aug                                              23
```

```
<210> SEQ ID NO 43
<211> LENGTH: 61
<212> TYPE: DNA
<213> ORGANISM: artificial
<220> FEATURE:
<223> OTHER INFORMATION: top strand of shRNA based on human LRBA
      sequence

<400> SEQUENCE: 43
gggatattgt agaaactgtc tttttcaaga gaaaagacag tttctacaat atcccttttt    60
t                                                                   61

<210> SEQ ID NO 44
<211> LENGTH: 61
<212> TYPE: DNA
<213> ORGANISM: artificial
<220> FEATURE:
<223> OTHER INFORMATION: bottom strand of shRNA based on human LRBA

<400> SEQUENCE: 44
ccctataaca tctttgacag aaaaagttct cttttctgtc aaagatgtta tagggaaaaa    60
a                                                                   61
```

INFLAMMATORY DISEASE DIAGNOSIS AND METHODS OF TREATMENT USING DOWN-REGULATORS OF LIPOPOLYSACCHARIDE-RESPONSIVE BEIGE-LIKE ANCHOR

CROSS REFERENCE TO RELATED APPLICATIONS

This application is a divisional, and claims priority to, U.S. Nonprovisional patent application Ser. No. 14/223,490, entitled, "Inflammatory Disease Diagnosis and Methods of Treatment using Lipopolysaccharide-Responsive Beige-Like Anchor", filed Mar. 24, 2014, which claims priority to U.S. Provisional Patent Application 61/804,451, entitled, "Inflammatory Disease Diagnosis and Methods of Treatment using Lipopolysaccharide-Responsive Beige-Like Anchor", filed Mar. 22, 2013, the contents of which are herein incorporated by reference.

FIELD OF INVENTION

This invention relates to inflammation as part of chronic diseases. Specifically, the invention addresses treating inflammatory diseases through modulation of lipopolysaccharide-responsive beige-like anchor (LRBA).

BACKGROUND OF THE INVENTION

Lipopolysaccharide (LPS)-responsive beige-like anchor (LRBA) was initially identified as an LPS-upregulated gene, encoding a 2863-amino acid, multiple-protein, as seen in FIG. 1 (Kerr, W. G., Heller, M. & Herzenberg, L. A. Analysis of lipopolysaccharide-response genes in B-lineage cells demonstrates that they can have differentiation stage-restricted expression and contain SH2 domains. *Proc Natl Acad Sci USA* 93, 3947-52 (1996); Wang, J. W., Howson, J., Haller, E. & Kerr, W. G. Identification of a novel lipopolysaccharide-inducible gene with key features of both A kinase anchor proteins and chs1/beige proteins. *J Immunol* 166, 4586-95 (2001)). Human LRBA and murine Lrba proteins are 90% identical (2587/2859) with 94% positive (2690/2859) amino acid homology. Three murine Lrba isoforms with differences at the C-terminal were identified (Wang, et al. Identification of a novel lipopolysaccharide-inducible gene with key features of both A kinase anchor proteins and chs1/beige proteins. 2001. *J Immunol* 166, 4586-95), while the human LRBA has two major isoforms (Wang, et al., Identification of a novel lipopolysaccharide-inducible gene with key features of both A kinase anchor proteins and chs1/beige proteins. 2001. J Immunol 166, 4586-95; Lopez-Herrera, et al., Deleterious Mutations in LRBA Are Associated with a Syndrome of Immune Deficiency and Autoimmunity. 2012. *Am J Hum Genet* 90, 986-1001).

LRBA is mainly localized to Golgi complex (GC), but also found in cell membrane, endosomes and vesicles. This is similar to neurobeachin (Nbea) (Wang, J. W. et al. Deregulated expression of LRBA facilitates cancer cell growth. *Oncogene* 23, 4089-97 (2004); Wang, X. et al. Neurobeachin: A protein kinase A-anchoring, beige/Chediak-higashi protein homolog implicated in neuronal membrane traffic. 2000. *J Neurosci* 20, 8551-65), an autism candidate gene and isoform of LRBA, has very similar localizations to that of LRBA and is implicated in post-Golgi membrane traffic and regulatory secretion pathway of large dense-core vesicles containing growth factors and hormones (Volders, et al., Drosophila rugose is a functional homolog of mammalian Neurobeachin and affects synaptic architecture, brain morphology, and associative learning. 2012. *J Neurosci* 32, 15193-204; Castermans, et al., SCAMPS, NBEA and AMISYN: three candidate genes for autism involved in secretion of large dense-core vesicles. 2010. *Hum Mol Genet* 19, 1368-78), isoform, Neurobeachin (Wang, et al., Deregulated expression of LRBA facilitates cancer cell growth. 2004. *Oncogene* 23, 4089-97; Wang, et al., Neurobeachin: A protein kinase A-anchoring, beige/Chediak-higashi protein homolog implicated in neuronal membrane traffic. 2000. *J Neurosci* 20, 8551-65).

The exact function of LRBA is unknown. LRBA has structural similarity to lysosomal trafficking regulator (LYST) and potentially is an A-kinase anchoring protein (AKAP)(1). It belongs to the WDL-BEACH-WD40 (WBW) gene family containing the WBW super domain. The WBW proteins appear to function as scaffolding proteins in vesicle trafficking (Wang, et al., Identification of a novel lipopolysaccharide-inducible gene with key features of both A kinase anchor proteins and chs1/beige proteins. 2001. *J Immunol* 166, 4586-95; Lopez-Herrera, et al., Deleterious Mutations in LRBA Are Associated with a Syndrome of Immune Deficiency and Autoimmunity 2012. *Am J Hum Genet* 90, 986-1001; Wang, et al., Deregulated expression of LRBA facilitates cancer cell growth. 2004. *Oncogene* 23, 4089-97) and are important in human diseases (Cullinane, A. R., Schaffer, A. A. & Huizing, M. The BEACH Is Hot: A LYST of Emerging Roles for BEACH-Domain Containing Proteins in Human Disease. 2013. *Traffic* 14(7):749-66). There are nine WBW human family members, which all appear to function as scaffolding proteins in vesicle trafficking regulation, involved in lysosome size regulation; LRBA, lysosomal trafficking regulator (LYST), neutral sphingomyelinase activation associated factor (NSMAF), WD and FYVE zinc finger domain containing protein 3 (WDFY3), WDFY4, neurobeachin-like 1 (NBEAL1), neurobeachin-like 2 (NBEAL2), neurobeachin (NBEA), WD repeat domain 81 (WDR81). They appear to be involved in vesicle trafficking as scaffolding proteins and regulating lysosome size (LYST and NSMAF), apoptosis (NSMAF, LRBA), autophagy (LYST, WD and WDFY3, LRBA), granule size (LYST, NBEAL2, and NBEA), or synapse formation (NBEA).

These family members are important in human diseases. For example, mutations of four WBW genes (LYST, LRBA, NBEAL2 and WDFY4) cause recessive Mendelian diseases and NBEA is a current candidate for autism (Cullinane, A. R., Schaffer, A. A. & Huizing, M. The BEACH Is Hot: A LYST of Emerging Roles for BEACH-Domain Containing Proteins in Human Disease. 2013. *Traffic;* 14(7):749-66)). The WD and FYVE zinc finger domain containing protein 4 (WDFY4) is strongly associated with SLE in Asian populations. NSMAF is a TNF adaptor protein which is required for the TNF-induced expression of cytokines, such as IL-6 and CXCL-2 (Adam-Klages, et al., FAN, a novel WD-repeat protein, couples the p55 TNF-receptor to neutral sphingomyelinase. 1996. *Cell* 86, 937-47; Montfort, et al., FAN stimulates TNF(alpha)-induced gene expression, leukocyte recruitment, and humoral response. 2009. *J Immunol* 183, 5369-78).

Accordingly, LRBA is extensively associated with the endomembrane system and vesicle trafficking. Vesicle trafficking is essential for deposition and signal transduction of membrane proteins and protein secretions, which also controls proper functioning of the immune system.

NBEA, which has 75% of protein homology with LRBA, is an isoform of LRBA linked to autism, platelet development, obesity, and multiple myeloma in humans (O'Neal, et al., Neurobeachin (NBEA) is a target of recurrent interstitial deletions at 13q13 in patients with MGUS and multiple myeloma. 2009. *Exp Hematol* 37, 234-44) and body length, synaptic spine patterns of neurons, and obesity in mice (Cullinane, et al., The BEACH Is Hot: A LYST of Emerging Roles for BEACH-Domain Containing Proteins in Human Disease. 2013. *Traffic;* 14(7):749-66). It has very similar subcellular localizations to that of LRBA and is implicated in post-Golgi membrane traffic and the regulatory secretion pathway of large dense-core vesicles containing growth factors and hormones (Wang, J. W. et al. Deregulated expression of LRBA facilitates cancer cell growth. 2004. *Oncogene* 23, 4089-97; Volders, et al., Drosophila rugose is a functional homolog of mammalian Neurobeachin and affects synaptic architecture, brain morphology, and associative learning. 2012. *J Neurosci* 32, 15193-204; Castermans, et al., SCAMPS, NBEA and AMISYN: three candidate genes for autism involved in secretion of large dense-core vesicles. 2010. *Hum Mol Genet* 19, 1368-78; Wang, et al., Neurobeachin: A protein kinase A-anchoring, beige/ Chediak-higashi protein homolog implicated in neuronal membrane traffic. 2000. *J Neurosci* 20, 8551-65). NBEA binds to an important signaling complex, protein kinase A, and acts as a negative regulator of vesicle secretion, as does LRBA ortholog Beige Protein Homolog 1 (Bph1) in yeast. NBEA homozygous knockout mice died perinatally due to the lack of synaptic transmissions (Su, et al., Neurobeachin is essential for neuromuscular synaptic transmission. 2004. *J Neurosci* 24, 3627-36; Medrihan, et al., Neurobeachin, a protein implicated in membrane protein traffic and autism, is required for the formation and functioning of central synapses. 2009. *Journal of Physiology-London* 587, 5095-5106), suggesting the protein is important in trafficking cargo proteins to pre- and post-synaptic compartments (Niesmann, K. et al. Dendritic spine formation and synaptic function require neurobeachin. 2011. *Nat Commun* 2:557).

LRBA orthologues Bph1 and rugose (rg) (*Drosophila*) are not essential and is both cytosolic and membrane peripherally bound. Deletion of Bph1 increases secretion of carboxypeptidase Y in *Saccharomyces cerevisiae* and missorting of alkaline phosphatase. The vacuole morphology is not affected by disruption or overexpression of Bph1. The growth of the delta Bph1 strain is impaired by low pH, potassium acetate or calcofluor white, a fluorescent stain that binds strongly to the cell wall which contains cellulose and chitin, probably due to a defect on trafficking from the GC. Genetically, Bph1 interacts with VPS9, FLO1, FLO9, BTS1, OKP1, VPS9, BTS1 and OKP1. These data suggest that Bph1 is involved in protein sorting and cell wall formation (Shiflett, et al., Bph1p, the *Saccharomyces cerevisiae* homologue of CHS1/Beige, functions in cell wall formation and protein sorting. 2004. *Traffic* 5, 700-710). Mutations of rg in *Drosophila* are embryonic semi-lethal, exhibiting a reduced lifespan of the organism and severe rough eye phenotype, caused by cell type-specific apoptosis with increased Jun N-terminal kinase activity and decreased EGFR signaling activity (Wech & Nagel, Mutations in rugose promote cell type-specific apoptosis in the Drosophila eye. 2005. *Cell Death Differ* 12, 145-52). Genetically, rg interacts with 14 genes, including multiple components of EGFR, Notch, RAS and MAPK pathways (Schreiber, et al., Genetic screen for modifiers of the rough eye phenotype resulting from overexpression of the Notch antagonist hairless in *Drosophila*. 2002. *Genesis* 33, 141-52; Shamloula, et al., rugose (rg), a *Drosophila* A kinase Anchor Protein, Is Required for Retinal Pattern Formation and Interacts Genetically With Multiple Signaling Pathways. 2002. *Genetics* 161, 693-710).

Similarly, LRBA appears to interact with multiple important signal transduction pathways, including EGFR, Notch, PKA, Ras, E2F1, p53, MAPK, NF-κB, cytokines, immunoglobulins (IgG, IgA, IgE and IgM etc.), CVID receptors and TLRs (Wang, et al., Deregulated expression of LRBA facilitates cancer cell growth. 2004. *Oncogene* 23, 4089-97; de Souza, et al., SEL-2, the *C. elegans* neurobeachin/LRBA homolog, is a negative regulator of lin-12/Notch activity and affects endosomal traffic in polarized epithelial cells. 2007. *Development* 134, 691-702; Schreiber, et al., Genetic screen for modifiers of the rough eye phenotype resulting from overexpression of the Notch antagonist hairless in *Drosophila*. 2002. *Genesis* 33, 141-52; Shamloula, et al., rugose (rg), a *Drosophila* A kinase Anchor Protein, Is Required for Retinal Pattern Formation and Interacts Genetically With Multiple Signaling Pathways. 2002. *Genetics* 161, 693-710).

LRBA orthologue in *Dictyostelium* is essential for cytokinesis (Kwak, et al., LvsA, a protein related to the mouse beige protein, is required for cytokinesis in Dictyostelium. 1999. *Mol Biol Cell* 10, 4429-39). LRBA orthologue, sel-2, also called F10F2.1, in *Caenorhabditis elegans*, is a negative regulator of lin-12/Notch activity in the vulval precursor cells, which are polarized epithelial cells maintained through regulated activity of the basolateral LET-23/EGF receptor and apical LIN-12/Notch. Loss of sel-2 activity causes basolateral mislocalization and increased accumulation of LIN-12/Notch and basolateral LET-23/EGF, indicating that SEL-2 is involved in endosomal traffic and may be involved in the efficient delivery of cell surface proteins to the lysosome (de Souza, et al., SEL-2, the *C. elegans* neurobeachin/LRBA homolog, is a negative regulator of lin-12/ Notch activity and affects endosomal traffic in polarized epithelial cells. 2007. Development 134, 691-702). Two RII binding motifs were predicted for sel-2, both human and murine LRBA, by aligning with the known B1 and B2 PKA RII tethering sites in rg2.

Mutations of LRBA cause common variable immunodeficiency and autoimmunity, resulting in LRBA's synonym name, common variable immune deficiency-8 (CVID8). Six germ lines of LRBA mutations reported to date cause common variable immunodeficiency (CVID) with autoimmunity, manifested as hypogammaglobulinemia, antibody deficiency, defective B-cell differentiation, recurrent bacterial infections, particularly respiratory infections, and variable autoimmune disorders including idiopathic thrombocytopenic purpura, autoimmune hemolytic anemia, and inflammatory bowel disease (Spickett, et al., Common variable immunodeficiency: how many diseases? 1997. *Immunol Today* 18, 325-8). Other CVID gene mutations include members of the B cell coreceptor complex (CD1919, CD2120 and CD8121), CD2022, transmembrane activator and calcium modulator and cyclophilin ligand interactor (TACI; Salzer, et al. Mutations in TNFRSF13B encoding TACI are associated with common variable immunodeficiency in humans. 2005. *Nat Genet* 37, 820-8) and B cell-activating factor receptor (BAFFR; Warnatz, K. et al. B-cell activating factor receptor deficiency is associated with an adult-onset antibody deficiency syndrome in humans 2009. *Proc Natl Acad Sci USA* 106, 13945-50), and inducible costimulator (ICOS; Grimbacher, et al. Homozygous loss of ICOS is associated with adult-onset common variable immunodeficiency. 2003. *Nat Immunol* 4, 261-8). The discoveries of CVID-causing mutations of these genes show that a monogenic defect may produce the whole spectrum of CVID, and that it is possible to unravel the genetic causes underlying most human diseases thought to be polygenic (Yong, et al., The role of costimulation in antibody deficiencies: ICOS and common variable immunodeficiency. 2009. *Immunol Rev* 229, 101-13). It is caused by defective B cell differentiation and impaired secretion of immunoglobulins (Saiki, et al., Three distinct stages of B-cell defects in common varied immunodeficiency. 1982. *Proc Natl Acad Sci USA* 79, 6008-12; Bryant, et al., Classification of patients with common variable immunodeficiency by B cell secretion of IgM and IgG in response to anti-IgM and interleukin-2. 1990. *Clin Immunol Immunopathol* 56, 239-48). CVID is a diagnosis of exclusion and is highly heterogeneous, genetically, immunologically and clinically (Gathmann, et al., The European internet-based patient and research database for primary immunodeficiencies: update 2011. 2012. *Clin Exp Immunol* 167, 479-91; Eibel, et al., Common variable immunodeficiency at the end of a prospering decade: towards novel gene defects and beyond. 2010. *Curr Opin Allergy Clin Immunol* 10, 526-33; Park, et al., Common variable immunodeficiency: a new look at an old disease. 2008. *Lancet* 372, 489-502). About two-third of CVID subjects have an autoimmune problem17, most commonly autoimmune hemolytic anemia (AHA), autoimmune thrombocytopenia, rheumatoid arthritis, and pernicious anemia (Cunningham-Rundles& Bodian, Common variable immunodeficiency: clinical and immunological features of 248 patients. 1999. *Clin Immunol* 92, 34-48). The etiology of about 80% of CVID remains unknown18, although over the past ten years, significant progress has been made in elucidating genetic mechanisms that result in a CVID phenotype.

Unlike the other seven CVID proteins, which are usually small (~27 kD) and localized on the cell membrane, LRBA is a 319 kD multiple-domain protein (Kerr, et al., Analysis of lipopolysaccharide-response genes in B-lineage cells demonstrates that they can have differentiation stage-restricted expression and contain SH2 domains. 1996. *Proc Natl Acad Sci USA* 93, 3947-52; Wang, et al., Identification of a novel lipopolysaccharide-inducible gene with key features of both A kinase anchor proteins and chs1/beige proteins. 2001. *J Immunol* 166, 4586-95) and A kinase anchor protein (AKAP), which could serve as a scaffold to interact with multiple proteins. Additionally, most CVID genes are B cell membrane receptors, except for ICOS which is on T cells, while LRBA is ubiquitously expressed as a vesicle trafficking regulator, required for homeostasis and activation of plasma membrane receptors (Wang, et al., Identification of a novel lipopolysaccharide-inducible gene with key features of both A kinase anchor proteins and chs1/beige proteins. 2001. *J Immunol* 166, 4586-95; Cullinane, et al., The BEACH Is Hot: A LYST of Emerging Roles for BEACH-Domain Containing Proteins in Human Disease. 2013. *Traffic;* 14(7):749-66). Thus, LRBA may regulate other CVID genes, for example, CD19, CD20 and BAFFR, because their levels are low when LRBA is absent (Lopez-Herrera, et al., Deleterious Mutations in LRBA Are Associated with a Syndrome of Immune Deficiency and Autoimmunity. 2012. *Am J Hum Genet* 90, 986-1001). Further, LRBA deficiency causes both immunodeficiency and autoimmunity (Lopez-Herrera, et al., Deleterious Mutations in LRBA Are Associated with a Syndrome of Immune Deficiency and Autoimmunity 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Parvaneh, et al., Primary immunodeficiencies: a rapidly evolving story. 2013. *J Allergy Clin Immunol* 131, 314-23). All 11 LRBA deficient CVID subjects identified thus far have autoimmune diseases, as seen in Table 1. TACI mutations also are associated with autoimmunity but to a lesser degree (36% vs. 23% of patients with wild-type TACI) (Salzer, et al., Relevance of biallelic versus monoallelic TNFRSF13B mutations in distinguishing disease-causing from risk-increasing TNFRSF13B variants in antibody deficiency syndromes. 2009. *Blood* 113, 1967-76). LRBA is the only CVID protein that is a protein kinase A anchor and thus can function as protein kinase A (PKA) to regulate protein activity by phosphorylation. In addition to these above unique features, LRBA also is unique in regulating autophagy, apoptosis, membrane dynamics and receptor signaling, all of which are important for inflammation (Kerr, et al., Analysis of lipopolysaccharide-response genes in B-lineage cells demonstrates that they can have differentiation stage-restricted expression and contain SH2 domains. 1996. *Proc Natl Acad Sci USA* 93, 3947-52; Wang, et al., Identification of a novel lipopolysaccharide-inducible gene with key features of both A kinase anchor proteins and chs1/beige proteins. 2001. *J Immunol* 166, 4586-95). The average age of symptom onset is three years, earlier than the mean age of 26.3 years for most CVID. In addition to immunological disorders, LRBA-deficient patients have an array of other medical problems which include: retarded growth, failure to thrive, growth hormone deficiency, asthma, monoarthritis, seizure disorders, granulomatous infiltration, finger clubbing, hepatosplenomegaly, allergic dermatitis, and nephrotic syndrome (Lopez-Herrera, et al., Deleterious Mutations in LRBA Are Associated with a Syndrome of Immune Deficiency and Autoimmunity 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2; Cunningham-Rundles & Bodian, Common variable immunodeficiency: clinical and immunological features of 248 patients. 1999. *Clin Immunol* 92, 34-48).

TABLE 1

Clinical features of LRBA-deficient patients

| Clinical conditions | Manifestations |
|---|---|
| Patient 1-5 from the study[1] | |
| Patient 1 | |
| Autoimmune | Idiopathic thrombocytopenic purpura (ITP). |
| Treatment | Intravenous immunoglobulin (IVIG) replacement |
| Immunologic investigations | low immunoglobulin levels |

TABLE 1-continued

Clinical features of LRBA-deficient patients

| Clinical conditions | Manifestations |
|---|---|
| Non-immunological disorders | Severely retarded growth, significant clubbing, strabismus as a result of abducens nerve palsy along with hemiplegia, cerebral mass. |
| Recurrent infections | Lymphoid interstitial pneumonia (LIP). Pleuropneumonia, chronic lung disease, bilateral bronchiectasis. |

Patient 2

| | |
|---|---|
| Autoimmune | Self-limiting ITP; Asthma satisfactorily treated with inhaled steroids. Reactive monoarthritis responded well to local steroid injections. |
| Immunologic investigations | Low immunoglobulin levels. |
| Non-immunological disorders | Growth retarded (both weight and height were below the fifth percentile since the age of 2). |
| Recurrent infections | Serous otitis media, massive pneumonia along with loculated empyema, chronic lung disease with bilateral bronchiectasis. |

Patient 3

| | |
|---|---|
| Chronic diarrhea | Severe diarrhea with no detectable bacterial or parasitic infection. |
| Autoimmune | ITP, lymphadenopathy, autoimmune haemolytic anemia (AIHA), atrophic gastritis with autoantibodies against intrinsic factor, and a submaxillar abscess, granulomatous infiltration with T cells, plasma cells, and macrophages but showed low B cell numbers. |
| Immunologic investigations | A moderate IgG hypogammaglobulinemia and complete IgA deficiency but a normal neutrophil count; intermittently elevated IgM; swelling of hilar and mediastinal lymph nodes with a mixed lymphoid follicular hyperplasia with the absence of the follicular mantle zone. |
| Recurrent infections | Perineal molluscum contagiosum, recurrent warts, recurrent mild respiratory infections, severe recurrent pneumonias, including several interstitial pneumonias, a lymphoid interstitial pneumonia and bronchiectasis. |
| Treatment | The interstitial lung disease was treated with methylprednisolone. Attempts to taper steroids were frequently associated with relapses, and long-term treatment with infliximab was initiated and allowed the discontinuation of methylprednisolone. Infliximab had little improvement of the chronic diarrhea. IVIG replacement. |

Patient 4

| | |
|---|---|
| Chronic diarrhea and autoimmune | ITP, AIHA and autoimmune enteropathy (which can be classified as Crohn disease) |
| Non-immunological disorders | Failure to thrive. |
| Immunologic investigations | Low immunoglobulin levels. |
| Treatment | IVIG replacement and antibiotic prophylaxis |
| Recurrent infections | Recurrent upper-respiratory-tract infections, several episodes of pneumonia recurrent respiratory and gastrointestinal infections, severe lower respiratory-tract infections along with finger clubbing, hepatosplenomegaly an obstruction of the small airways and bronchiectasis, recurrent conjunctivitis and urticaria and a corpulmonale with consecutive right-heart failure. |
| Treatment | Antibacterials, antifungals, and IVIG. |

Patient 5

| | |
|---|---|
| Chronic diarrhea and autoimmune | Recurrent chronic diarrhea, autoimmune phenomena, hypothyroidism, and or AIHA allergic dermatitis, intestinal inflammation and subtotal villous atrophy, autoimmune phenomena, hypothyroidism, and myasthenia gravis. no signs of ITP or AIHA, bronchiectasis; Died at the age of 19 after respiratory failure |
| Non-immunological disorders | Retarded growth |
| Immunologic investigations | Selective IgA and IgG2 deficiency, IgG and IgM levels declined gradually. |
| Recurrent infections | Recurrent upper-respiratory-tract infections, including sinusitis and otitis media, pneumonia. |

Patient 6-10 from the study[2]

Patient 6

| | |
|---|---|
| Immunologic investigations | Normal serum IgG, IgA, IgM, and IgE levels and normal numbers of CD3+ T lymphocytes, CD4+ and CD8+ T-cell subsets, B cells, and natural killer (NK) cells. Normal T-cell proliferation to the mitogens PHA and ConA and a normal increase in antibody titers |

TABLE 1-continued

Clinical features of LRBA-deficient patients

| Clinical conditions | Manifestations |
| --- | --- |
| | after vaccination with tetanus toxoid, diphtheria, toxoid and *Haemophilus influenzae* capsular antigens. |
| Recurrent infections | no history of recurrent infections |
| Treatment | Responded to intravenous immunoglobulin (IVIG) replacement therapy and a short course of prednisone. |

Patient 7

| | |
| --- | --- |
| Chronic diarrhea and autoimmune | Nephrotic syndrome; mucous non-bloody stools; lymphocytic infiltration of the lamina propria; villous atrophy and marked inflammation. |
| Treatment | Prednisone and azathioprine with poor compliance; monthly intramuscular vitamin B12 injections; human growth hormone replacement. |
| Immunologic investigations | Normal serum IgG, IgA, IgM, and IgE levels and normal numbers of $CD3^+$ T lymphocytes, $CD4^+$ and $CD8^+$ T-cell subsets, B lymphocytes, and NK cells, normal T-cell proliferation to the mitogens PHA and ConA and a normal increase in antibody titers after vaccination with pneumococcal vaccine. |
| Non-immunological disorders | Clubbing; growth hormone deficiency. |
| Recurrent infections | No history of recurrent infections. |
| Anemia | Megaloblastic anemia. |

Patient 8

| | |
| --- | --- |
| Chronic diarrhea and autoimmune | Non-mucous and non-bloody chronic diarrhea; mucosal inflammation with lymphocytic infiltration but no granulomas or ulcerations; recurrent arthritis in the large joints, mainly the knees with inflammation. |
| Treatment | Chronic diarrhea improved on oral prednisone. |
| Immunologic investigations | Low serum IgG and IgA levels and decreased B-cell numbers but normal numbers of T cells, T-cell subsets, and NK cells; markedly reduced T-cell proliferation in response to PHA and anti-CD3 mAb. |
| Recurrent infections | Recurrent otitis media and pneumonia; bilateral bronchiectasis and finger clubbing. |

Patient 9

| | |
| --- | --- |
| Chronic diarrhea and autoimmune | Chronic non-bloody and non-mucous diarrhea; duodenal villous atrophy; autoimmune thrombocytopenia and autoimmune hemolytic anemia both of which responded to treatment with steroids and rituximab. |
| Immunologic investigations | Low serum IgG and IgA levels and decreased B-cell numbers but normal numbers of T cells, T-cell subsets, and NK cells; markedly reduced T-cell proliferation in response to PHA and anti-CD3 mAb. |
| Recurrent infections | no history of recurrent infections |

Patient 10

| | |
| --- | --- |
| Chronic diarrhea | Chronic diarrhea with no blood or mucus. |
| Immunologic investigations | Low serum IgG and IgA levels and normal numbers of T cells, T-cell subsets, B cells, and NK cells; markedly reduced T-cell proliferation in response to PHA and anti-CD3 mAb. |
| Recurrent infections | no history of recurrent infections or autoimmune hematologic manifestations. |

Patient 11 the study 8

| | |
| --- | --- |
| Chronic diarrhea and autoimmune | Chronic diarrhea associated with an autoimmune enteropathy, duodenal villous atrophy and large bowel lymphocytic infiltration; erythema nodosum, transient arthritis of both feet, and recurrent hemolytic anemia; extensive lung infiltration of a mixture of $CD3^+$ T and $CD20^+$ B cells. |
| Immunologic investigations | Raised IgG levels, raised inflammatory markers, and a low number of natural killer cells; normal lymphocyte subsets, double-negative T cells, T-cell proliferation assays, IgA, IgM, tetanus vaccine responses, and a nitroblue tetrazolium test; lymphadenopathy, splenomegaly, neutropenia, and thrombocytopenia, antineutrophil antibodies; normal $CD 19^+$ B cells and IgG level, a new-onset antibody deficiency with absent vaccine responses. |
| Treatment | Several courses of steroids, rituximab (with prophylactic immunoglobulin replacement), and mycophenolate mofetil. |
| Non-immunological disorders | Growth failure. |
| Recurrent infections | No significant history of infections except for a psoas abscess associated with chronic neutropenia; five years after initial |

TABLE 1-continued

Clinical features of LRBA-deficient patients

| Clinical conditions | Manifestations |
|---|---|
| | presentation, after multiple courses of rituximab, developed recurrent infections, after withdrawal of immunoglobulin therapy. |

[1]Lopez-Herrera, et al., Deleterious Mutations in LRBA Are Associated with a Syndrome of Immune Deficiency and Autoimmunity. 2012. *Am J Hum Genet* 90, 986-1001.
[2]Alangari, et al., LPS-responsive beige-like anchor (LRBA) gene mutation in a family with inflammatory bowel disease and combined immunodeficiency. 2012. *J Allergy Clin Immunol* 130, 481-8 e2.

As LRBA is structurally conserved throughout the eukaryotic kingdom, it may be involved in pathways similar to its orthologues and paralogues. Mutations in lysosomal trafficking regulator (LYST), which is a paralogue gene of LRBA, causes Chediak-Higashi syndrome (CHS), and A-kinase anchoring proteins (Kerr, et al., Analysis of lipopolysaccharide-response genes in B-lineage cells demonstrates that they can have differentiation stage-restricted expression and contain SH2 domains. 1996. *Proc Natl Acad Sci USA* 93, 3947-52; Wang, et al., Identification of a novel lipopolysaccharide-inducible gene with key features of both A kinase anchor proteins and chs1/beige proteins. 2001. *J Immunol* 166, 4586-95). CHS is characterized by severe immunodeficiency and premature mortality (Faigle, et al., Deficient peptide loading and MHC class II endosomal sorting in a human genetic immunodeficiency disease: the Chediak-Higashi syndrome. 1998. *J Cell Biol* 141, 1121-34; Barrat, et al., Defective CTLA-4 cycling pathway in Chediak-Higashi syndrome: a possible mechanism for deregulation of T lymphocyte activation. 1999. *Proc Natl Acad Sci USA* 96, 8645-50). LRBA and LYST may have similar functions, as they have high similarity of protein structure. Three independent papers show that absence of LRBA, resulting from homozygous mutations or deletions, causes autosomal recessive diseases of severe immunodeficiency (defective B-cell differentiation, hypogammaglobulinemia, recurrent infections), autoimmunity (idiopathic thrombocytopenic purpura (ITP), autoimmune hemolytic anemia and inflammatory bowel disease) (Lopez-Herrera, et al., Deleterious mutations in LRBA are associated with a syndrome of immune deficiency and autoimmunity 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2), and inflammatory cell infiltration (Lopez-Herrera, et al., Deleterious mutations in LRBA are associated with a syndrome of immune deficiency and autoimmunity 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2; Faigle, et al., Deficient peptide loading and MHC class II endosomal sorting in a human genetic immunodeficiency disease: the Chediak-Higashi syndrome. 1998. *J Cell Biol* 141, 1121-34; Barrat, et al., Defective CTLA-4 cycling pathway in Chediak-Higashi syndrome: a possible mechanism for deregulation of T lymphocyte activation. 1999. *Proc Natl Acad Sci USA* 96, 8645-50; Alangari, et al., LPS-responsive beige-like anchor (LRBA) gene mutation in a family with inflammatory bowel disease and combined immunodeficiency. 2012. *J Allergy Clin Immunol* 130, 481-8 e2). Another analogue, rg interacts with 14 genes, including multiple components of EGFR, Notch, RAS and MAPK pathways (Shamloula, et al., rugose (rg), a *Drosophila* A kinase Anchor Protein, Is Required for Retinal Pattern Formation and Interacts Genetically With Multiple Signaling Pathways. 2002. *Genetics* 161, 693-710). LRBA interacts with the EGFR pathway (Wang, et al., Deregulated expression of LRBA facilitates cancer cell growth. 2004. *Oncogene* 23, 4089-97).

The GC is now viewed as headquarters for signal transduction and cell-fate decisions, in addition to its "classic role" of cargo sorting/processing and metabolism (Wilson, C. et al. The Golgi apparatus: an organelle with multiple complex functions. *Biochem J* 433, 1-9; Wilson, C. et al. The Golgi apparatus: an organelle with multiple complex functions. *Biochem J* 433, 1-9). For example, internalized LPS and Toll-like receptor-4 (TLR-4) are found in GC (Hornef, M. W., Frisan, T., Vandewalle, A., Normark, S. & Richter-Dahlfors, A. Toll-like receptor 4 resides in the Golgi apparatus and colocalizes with internalized lipopolysaccharide in intestinal epithelial cells. *J Exp Med* 195, 559-70 (2002)). Activation of the proto-oncogene Ras on the Golgi can lead to cell transformation (Bivona, T. G. et al. Phospholipase Cgamma activates Ras on the Golgi apparatus by means of RasGRP1. *Nature* 424, 694-8 (2003); Tracey, K. J. et al. Anti-cachectin/TNF monoclonal antibodies prevent septic shock during lethal bacteraemia. *Nature* 330, 662-4 (1987)). The proto-oncogenes Ras and Src are activated on the GC (Pulvirenti, et al., A traffic-activated Golgi-based signalling circuit coordinates the secretory pathway. *Nat Cell Biol* 10, 912-22 (2008); Bivona, T. G. et al. Phospholipase Cgamma activates Ras on the Golgi apparatus by means of RasGRP1. *Nature* 424, 694-8 (2003); Pulvirenti, et al., A traffic-activated Golgi-based signalling circuit coordinates the secretory pathway. *Nat Cell Biol* 10, 912-22 (2008)). Membrane trafficking is crucial in transducing signals to GC and other cellular locations (Kholodenko, Four-dimensional organization of protein kinase signaling cascades: the roles of diffusion, endocytosis and molecular motors. *J Exp Biol* 206, 2073-82 (2003)), as simple diffusion has a limited role in intracellular transport of signaling complexes (Kholodenko, Four-dimensional organization of protein kinase signaling cascades: the roles of diffusion, endocytosis and molecular motors. *J Exp Biol* 206, 2073-82 (2003)). Thus the endomembrane system has critical role in signal transduction, which is not yet appreciated enough. LRBA may be important in GC's function, as LRBA is extensively co-localized with GC proteins and an abnormally high number of GCs is found in LRBA deficient B cells (Lopez-Herrera, et al., Deleterious mutations in LRBA are associated with a syndrome of immune deficiency and autoimmunity. *Am J Hum Genet* 90, 986-1001 (2012)). It is extensively associated with the endomembrane system and vesicle trafficking. Vesicle trafficking is essential for deposition, secretion and signal transduction of immune effectors.

Taken together, LRBA appears to be critical in vesicle trafficking involving deposition of membrane proteins, endocytosis of signal transduction complex and protein secretion, and thus a crucial regulator of these proteins including the other CVID proteins, TLRs and antibodies, involved in multiple pathways and cellular processes such as growth, apoptosis, autophagy, membrane dynamics, receptor signaling, and cell differentiation (Wang, et al., Identification of a novel lipopolysaccharide-inducible gene with key features of both A kinase anchor proteins and chs1/beige proteins. 2001. *J Immunol* 166, 4586-95). Deficiency of LRBA may cause vesicle trafficking defects and affect many membrane or secreted immune effectors, resulting in broader and severer problems, even death (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2).

A well characterized LRBA polyclonal antibody and organelle-specific antibodies were used in the present study to detect endogenous proteins and study their co-localizations. The results show that LRBA is extensively associated with the endomembrane system, including the Golgi complex, endosomes, lysosomes, plasma membranes, nucleus, pseudopodia and microtubules, and vesicle trafficking, which is responsive to LPS stimulation. These results suggest that LRBA plays a role in vesicle trafficking and signal transduction essential for the immune system (Burns, et al., LRBA gene deletion in a patient presenting with autoimmunity without hypogammaglobulinemia. 2012. *J Allergy Clin Immunol* 130, 1428-32).

It is proposed that LRBA functions as a converging node for multiple pathways through vesicle trafficking and plays a fundamental role in the immune system. This concept is supported by data showing LRBA may interact with multiple important signal transduction pathways (Shamloula, et al. rugose (rg), a *Drosophila* A kinase Anchor Protein, Is Required for Retinal Pattern Formation and Interacts Genetically With Multiple Signaling Pathways. 2002. *Genetics* 161, 693-710); mutations of LRBA cause severe immunodeficiency and autoimmunity (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2); depletion of LRBA results in significant cell growth inhibition, and sensitizes cells to apoptosis (Lopez-Herrera, et al., Deleterious mutations in LRBA are associated with a syndrome of immune deficiency and autoimmunity 2012. *Am J Hum Genet* 90, 986-1001; Wang, et al., Deregulated expression of LRBA facilitates cancer cell growth. 2004. *Oncogene* 23, 4089-97); LRBA is important for cell proliferation, apoptosis and autophagy (Lopez-Herrera, et al., Deleterious mutations in LRBA are associated with a syndrome of immune deficiency and autoimmunity. 2012. *Am J Hum Genet* 90, 986-1001; Wang, et al., Deregulated expression of LRBA facilitates cancer cell growth. 2004. *Oncogene* 23, 4089-97); and deficiency of LRBA results in fewer cells positive for three CVID proteins: CD19, CD20 and B cell-activating factor receptor (BAFFR). This suggests that it may regulate these genes, and may cause immunodeficiency at least partially through these genes (Lopez-Herrera, et al., Deleterious mutations in LRBA are associated with a syndrome of immune deficiency and autoimmunity. 2012. *Am J Hum Genet* 90, 986-1001).

LRBA appears to regulate cytokines. LRBA-deficient patients have immunodeficiency, and defective cytokines are known to cause immunodeficiency (Leonard, Cytokines and immunodeficiency diseases. 2001. *Nat Rev Immunol* 1, 200-8). LRBA paralogue, FAN (Factor associated with neutral sphingomyelinase activation) is a TNF adaptor protein and is required for the TNF-induced expression of cytokines, such as IL-6 and CXCL-2 (Adam-Klages, et al., FAN, a novel WD-repeat protein, couples the p55 TNF-receptor to neutral sphingomyelinase. 1996. *Cell* 86, 937-47; Montfort, et al., FAN stimulates TNF(alpha)-induced gene expression, leukocyte recruitment, and humoral response. 2009. *J Immunol* 183, 5369-78). LYST is required for LPS induction of inflammatory cytokines (Cheng, et al., Novel functions of a regulator of lysosomal trafficking, LYST in TLR4 signal transduction. 2012. *Immunology* 137, 299-300).

These findings demonstrate that LRBA is essential for proper functioning of the immune system. However, the underlying cellular and molecular mechanisms are most unknown. LRBA may be an effective therapeutic target for inflammatory diseases. For example, RA is a severe, often destructive, chronic inflammatory disease of peripheral joints. Anti-TNF therapy has revolutionized the treatment of RA and other inflammatory diseases (Tracey, et al., Tumor necrosis factor antagonist mechanisms of action: a comprehensive review. 2008. *Pharmacol Ther* 117, 244-79). However, anti-TNF therapy is not effective in about one-third of RA patients and most of other inflammatory diseases, and patients may become refractory to the treatment. It may have severe side effects, and can also cause or increase heart failure (Ambrosi, & Lafforgue, [The cardiologist and immunosuppressive therapy]. 2012. *Presse Med* 41, 655-61; Nicola, et al., The risk of congestive heart failure in rheumatoid arthritis: a population-based study over 46 years. 2005. *Arthritis Rheum* 52, 412-20). New therapeutic strategies, based on a large number of cytokines, for these patients unresponsive to anti-TNF therapy have been explored, but the results are disappointing in most cases. The trials using IL-5 antagonists are disappointing (Commins, et al., Immunologic messenger molecules: cytokines, interferons, and chemokines. 2010. *J Allergy Clin Immunol* 125, S53-72). This may reflect that the cytokine cascade is highly redundant, and an inflammatory disease is often a complex disease, multiple cytokines may be involved in the inflammation (Holgate, S. T. Novel targets of therapy in asthma. *Curr Opin Pulm Med* 15, 63-71 (2009)). Inhibition of a single cytokine may not be sufficient, whereas blocking many cytokines with multiple agents would be impractical. Targeting a crucial gene that regulates multiple cytokines is desirable. LRBA may be one of such genes, as it may be a crucial regulator of multiple immune effectors including secreted cytokines through vesicle trafficking.

LRBA appears to regulate TLR4, as TLR4/LPS complex rapidly cycles between the cell membrane, the GC and endosomes (Latz, et al., Lipopolysaccharide rapidly traffics to and from the Golgi apparatus with the toll-like receptor 4-MD-2-CD14 complex in a process that is distinct from the initiation of signal transduction. 2002. *J Biol Chem* 277, 47834-43; Thieblemont & Wright, Transport of bacterial lipopolysaccharide to the golgi apparatus. 1999. *J Exp Med* 190, 523-34), and can activate signaling pathways at endo-lysosome (Cheng, et al., Novel functions of a regulator of lysosomal trafficking, LYST in TLR4 signal transduction. 2012. *Immunology* 137, 299-300), indicating vesicle-mediated localization and trafficking of TLR4 are required for its activation. Lyst deficient cells exhibit defective TLR signaling, specifically in TLR4 pathways (Cheng, et al., Novel functions of a regulator of lysosomal trafficking, LYST in TLR4 signal transduction. 2012. *Immunology* 137, 299-300). Recurrent bacterial infections in LRBA-deficient patients indicates impaired TLR4/LPS pathway. In summary, LRBA may interact with multiple important signal transduction pathways, including epidermal growth factor receptor (EGFR), Notch, PKA, Ras, E2F1, p53, MAPK, NF-κB LPS, cytokines and TLRs (Schreiber, et al., Genetic screen for modifiers of the rough eye phenotype resulting from overexpression of the Notch antagonist hairless in *Drosophila*. 2002. *Genesis* 33, 141-52; Shamloula, et al., rugose (rg), a *Drosophila* A kinase Anchor Protein, Is Required for Retinal Pattern Formation and Interacts Genetically With Multiple Signaling Pathways. 2002. *Genetics* 161, 693-710; de Souza, et al., SEL-2, the *C. elegans* neurobeachin/LRBA homolog, is a negative regulator of lin-12/Notch activity and affects endosomal traffic in polarized epithelial cells. 2007. *Development* 134, 691-702; Wang, et al., Deregulated expression of LRBA facilitates cancer cell growth. 2004. *Oncogene* 23, 4089-97). This concept is supported by information showing LRBA is highly conserved throughout the eukaryotic kingdom; LRBA interacts with multiple important signal transduction pathways, including those of epidermal growth factor receptor (EGFR), Notch, PKA, Ras, E2F1, p53 and NF-κB (Schreiber, et al., Genetic screen for modifiers of the rough eye phenotype resulting from overexpression of the Notch antagonist hairless in *Drosophila*. 2002. *Genesis* 33, 141-52; Shamloula, et al., rugose (rg), a *Drosophila* A kinase Anchor Protein, Is Required for Retinal Pattern Formation and Interacts Genetically With Multiple Signaling Pathways. 2002. *Genetics* 161, 693-710; de Souza, et al., SEL-2, the *C. elegans* neurobeachin/LRBA homolog, is a negative regulator of lin-12/Notch activity and affects endosomal traffic in polarized epithelial cells. 2007. *Development* 134, 691-702; Wang, et al., Deregulated expression of LRBA facilitates cancer cell growth. 2004. *Oncogene* 23, 4089-97; mutations of LRBA cause severe immunodeficiency and autoimmunity (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, A. et al. LPS-responsive beige-like anchor (LRBA) gene mutation in a family with inflammatory bowel disease and combined immunodeficiency. 2012. *J Allergy Clin Immunol* 130, 481-8 e2); depletion of LRBA results in significant cell growth inhibition, and sensitizes cells to apoptosis (Wang, et al., Deregulated expression of LRBA facilitates cancer cell growth. 2004. *Oncogene* 23, 4089-97; Lopez-Herrera, et al., Deleterious mutations in LRBA are associated with a syndrome of immune deficiency and autoimmunity. 2012. *Am J Hum Genet* 90, 986-1001); LRBA is important for cell proliferation, apoptosis and autophagy (Wang, et al., Deregulated expression of LRBA facilitates cancer cell growth. 2004. *Oncogene* 23, 4089-97; Lopez-Herrera, et al., Deleterious mutations in LRBA are associated with a syndrome of immune deficiency and autoimmunity. 2012. *Am J Hum Genet* 90, 986-1001) and deficiency of LRBA causes less cells positive for at least three CVID proteins: CD19, CD20 and BAFFR, suggesting that LRBA may regulate these genes (Lopez-Herrera, et al., Deleterious mutations in LRBA are associated with a syndrome of immune deficiency and autoimmunity. 2012. *Am J Hum Genet* 90, 986-1001).

SUMMARY OF THE INVENTION

LRBA is found present in the blood stream (Liu, et al., High dynamic range characterization of the trauma patient plasma proteome. 2006. *Mol Cell Proteomics* 5, 1899-913; Qian, et al., Quantitative proteome analysis of human plasma following in vivo lipopolysaccharide administration using 160/180 labeling and the accurate mass and time tag approach. 2005. *Mol Cell Proteomics* 4, 700-9). It is one of the genes critical for inflammation, which include the inflammatory bottle-neck kinase (NFκB, AKT and MAPK), cytokines (TNFα and IL-10), Toll-like receptor 4 (TLR4), and CVID (common variable immunodeficiency) genes (CD19, CD20, CD21, BAFFR and TACI). The plasma presence of LRBA provides a feasible way to therapeutically modulate LRBA levels. The most potent inducer of TNF is LPS (Tracey, et al., Anti-cachectin/TNF monoclonal antibodies prevent septic shock during lethal bacteraemia. 1987. *Nature* 330, 662-4), which also induces LRBA (this study) (Burns, et al., LRBA gene deletion in a patient presenting with autoimmunity without hypogammaglobulinemia. 2012. *J Allergy Clin Immunol* 130, 1428-32; Kerr, et al., Analysis of lipopolysaccharide-response genes in B-lineage cells demonstrates that they can have differentiation stage-restricted expression and contain SH2 domains. 1996. *Proc Natl Acad Sci USA* 93, 3947-52; Wang, et al., Identification of a novel lipopolysaccharide-inducible gene with key features of both A kinase anchor proteins and chs1/beige proteins. 2001. *J Immunol* 166, 4586-95). TNF is an autocrine growth factor for normal human B cells (Boussiotis, et al., Tumor necrosis factor alpha is an autocrine growth factor for normal human B cells. *Proc Natl Acad Sci USA* 91, 7007-11 (1994)). Anti-TNF therapy inhibits the immune system, such as inhibition of memory B cells and susceptibility to infections (Anolik, J. H. et al. Cutting edge: anti-tumor necrosis factor therapy in rheumatoid arthritis inhibits memory B lymphocytes via effects on lymphoid germinal centers and follicular dendritic cell networks. *J Immunol* 180, 688-92 (2008)). The same phenotype is present in LRBA deficient patients. LRBA deficient patients have very low levels of memory B cells (Lopez-Herrera, G. et al. Deleterious mutations in LRBA are associated with a syndrome of immune deficiency and autoimmunity. *Am J Hum Genet* 90, 986-1001 (2012)), suggesting that TNF may be repressed due to deficient LRBA. These data suggests that LRBA may be involved in TNF pathway and can be explored as a better therapeutic target for inflammatory diseases.

Moreover, as LRBA is found in the blood, and LRBA levels in healthy controls and patients with controlled symptoms are undetectable or much lower, LRBA can be used as a convenient noninvasive biomarker for inflammatory diseases such as asthma exacerbation, rheumatoid arthritis, ulcerative colitis and sepsis. Deficiency of LRBA causes immunodeficiency and autoimmunity.

As such, LRBA therapies are used to target immunodeficiency and autoimmunity. Most of the current biologics are based on cytokines. For example, anti-TNF therapy has revolutionized the treatment of RA (Tracey, et al., Tumor necrosis factor antagonist mechanisms of action: a comprehensive review. 2008. *Pharmacol Ther* 117, 244-79). However, anti-TNF therapy is not effective in about one-third of RA subjects and in most other inflammatory diseases, and patients may eventually become refractory to it. New therapeutic strategies, based on a large number of cytokines, for patients unresponsive to anti-TNF, have been explored, in most cases, the results were disappointing (Commins, et al., Immunologic messenger molecules: cytokines, interferons, and chemokines. 2010. *J Allergy Clin Immunol* 125, S53-72). This may indicate that the cytokine cascade is highly redundant, for RA and other immune-based diseases, and an inflammatory disease, more often than not, is a complex one involving multiple cytokines (Holgate, Novel targets of therapy in asthma. 2009. *Curr Opin Pulm Med* 15, 63-71). Inhibition of a single cytokine may not be sufficient, whereas blocking many cytokines with multiple agents is impractical and treatment resistance can develop (Sfikakis, P. P. The first decade of biologic TNF antagonists in clinical practice: lessons learned, unresolved issues and future directions. *Curr Dir Autoimmun* 11, 180-210 (2010)). Targeting a vital gene that regulates multiple cytokines is desirable. Targeting a master regulator that is a crucial connection node for multiple inflammatory pathways will lead to a more effective therapy. However, until the present invention, no such gene(s) have been identified.

Anti-LRBA therapy was tested for safety and efficacy using model mice. LRBA is present in the blood stream (Liu, et al., High dynamic range characterization of the trauma patient plasma proteome. 2006. *Mol Cell Proteomics* 5, 1899-913; Qian, et al., Quantitative proteome analysis of human plasma following in vivo lipopolysaccharide administration using 160/180 labeling and the accurate mass and time tag approach. 2005. *Mol Cell Proteomics* 4, 700-9), providing a feasible way for therapeutic modulation. The absence of LRBA in humans is not lethal (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2), suggesting that temporarily blocking it will not cause significant toxicity. This parallels with anti-TNF therapy, which is well tolerated (Grijalva, et al., Initiation of tumor necrosis factor-alpha antagonists and the risk of hospitalization for infection in patients with autoimmune diseases. 2011. *JAMA* 306, 2331-9). The development in TNF knockout mice is normal (Pasparakis, et al., Immune and inflammatory responses in TNF alpha-deficient mice: a critical requirement for TNF alpha in the formation of primary B cell follicles, follicular dendritic cell networks and germinal centers, and in the maturation of the humoral immune response. 1996. *J Exp Med* 184, 1397-411), and anti-TNF therapy is well tolerated (Grijalva, et al., Initiation of tumor necrosis factor-alpha antagonists and the risk of hospitalization for infection in patients with autoimmune diseases. 2011. *JAMA* 306, 2331-9). The LRBA knockout mice are also viable, and absence of LRBA in humans is not lethal (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2). This mirrors the anti-TNF therapy and suggests that temporarily blocking LRBA may not cause intolerable toxicity.

Cardiovascular disease (CVD) is a complex chronic inflammatory disease (Ross, Atherosclerosis—an inflammatory disease. 1999. *N Engl J Med* 340, 115-26), and pro-inflammatory cytokines play a key role in its pathophysiology (Charalambous, et al., Role of bacterial endotoxin in chronic heart failure: the gut of the matter. 2007. *Shock* 28, 15-23). Heart failure was reported in a LRBA deficient patient (Lopez-Herrera, et al., Deleterious mutations in LRBA are associated with a syndrome of immune deficiency and autoimmunity. 2012. *Am J Hum Genet* 90, 986-1001). LRBA may be directly involved in CVD inflammation, and an effective CVD therapeutic target. As noted above, most current biologics are based on cytokines. LRBA is implied to be a master regulator of inflammatory effectors including pro-inflammatory cytokines through vesicle trafficking. Mutations of LRBA cause immunodeficiency and autoimmunity inflammation. Heart failure was observed in an LRBA deficient patient (Lopez-Herrera, G. et al. Deleterious mutations in LRBA are associated with a syndrome of immune deficiency and autoimmunity. *Am J Hum Genet* 90, 986-1001 (2012)). LRBA is highly expressed in the heart: its levels rank at above 90% percentile in all genes examined (Dufour, C. R. et al. Genome-wide orchestration of cardiac functions by the orphan nuclear receptors ERRalpha and gamma. *Cell Metab* 5, 345-56 (2007)). Those data show that LRBA and CVD may be closely related. Moreover, LRBA can be secreted into plasma at high levels (up to 6.7 µg/L) upon LPS stimulation and high in asthmatic inflammation. LRBA may be directly involved in CVD inflammation, and an effective CVD therapeutic target.

LRBA can be used as a therapeutic through intravenous injection of protein LRBA or genome-editing technology to replenish or correct LRBA deficiency or mutation in the patients who lack functional LRBA, or mutations of LRBA can be corrected through genome-editing technology. On another hand, when LRBA is overexpressed in the patients and contribute to the pathogenesis, we may use LRBA antibody or LRBA dominant negative mutants (DNM) to block LRBA function, or other technologies such as siRNA and shRNA knockdown technologies to knockdown LRBA.

BRIEF DESCRIPTION OF THE DRAWINGS

For a fuller understanding of the invention, reference should be made to the following detailed description, taken in connection with the accompanying drawings, in which.

0.36891260097958145 Costes' randomization based colocalization: Parameters: Nb of randomization rounds: 1000, Resolution (bin width): 0.0010 r (original)=0.154 r (randomized)=0.0±0.0010 (calculated from the fitted data) P-value=100.0% (calculated from the fitted data) Results for fitting the probability density function on a Gaussian (Probability=a+(b-a)exp(-(R-c)^2/(2d^2))): Formula: y=a+(b-a)*exp(-(x-c)*(x-c)/(2*d*d)) Status: Success Number of completed minimizations: 2 Number of iterations: 184 (max: 4000) Time: 3 ms Sum of residuals squared: 0.00045802 Standard deviation: 0.0059357 R^2: 0.99305 Parameters: a=0.0017604 b=0.19444 c=−0.00015210 d=0.0019903 FWHM=0.0040.

FIGS. 13(A)-(D) are montages of time-lapse videos of live macrophage cells. The BEACH-WD domain of mouse Lrba gene was cloned into pEGFP-N1 vector as described previously (Wang, et al., Identification of a novel lipopolysaccharideinducible gene with key features of both A kinase anchor proteins and chs1/beige proteins. 2001. *J Immunol* 166: 4586-4595). RAW264.7 macrophage cells were stably transfected with LRBA (BEACH-WD)-GFP and were stimulated with (top panel) or without LPS (bottom panel). The time-lapse video was taken at one picture per second using the Leica TCS SP2 laser scanning inverted confocal microscope with a mini cell culture chamber at 37° C. and 5% CO2. The GFP fluorescence shows cell membrane, Golgi and vesicle locations of LRBA, and the dynamic activities of LRBA associated vesicles moving from GC to the membrane. The pictures were ordered sequentially as the original video and labeled accordingly. The smaller numbers indicate vesicle paths.

FIGS. 13E-H are montages of time-lapse videos of live macrophage cells. The BEACH-WD domain of mouse Lrba gene was cloned into pEGFP-N1 vector as described previously (Wang, et al., Identification of a novel lipopolysaccharideinducible gene with key features of both A kinase anchor proteins and chs1/beige proteins. 2001. *J Immunol* 166: 4586-4595). RAW264.7 macrophage cells were stably transfected with LRBA (BEACH-WD)-GFP and were stimulated with (top panel) or without LPS (bottom panel). The time-lapse video was taken at one picture per second using the Leica TCS SP2 laser scanning inverted confocal microscope with a mini cell culture chamber at 37° C. and 5% CO2. The GFP fluorescence shows cell membrane, Golgi and vesicle locations of LRBA, and the dynamic activities of LRBA associated vesicles moving from GC to the membrane. The pictures were ordered sequentially as the original video and labeled accordingly. The smaller numbers indicate vesicle paths.

Figure 13A:
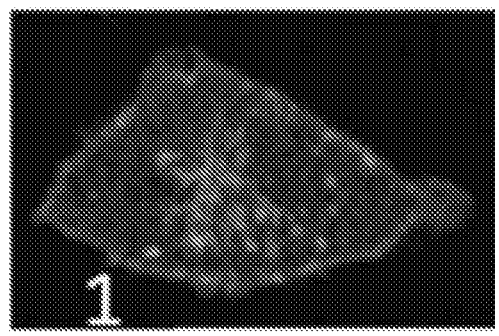
Figure 13B:
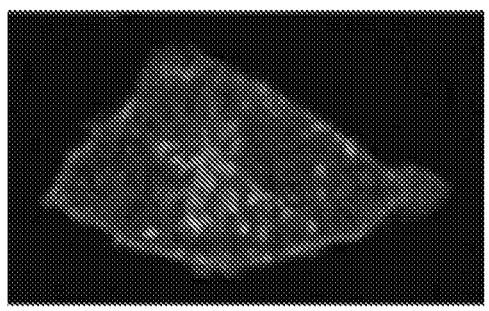
Figure 13C:
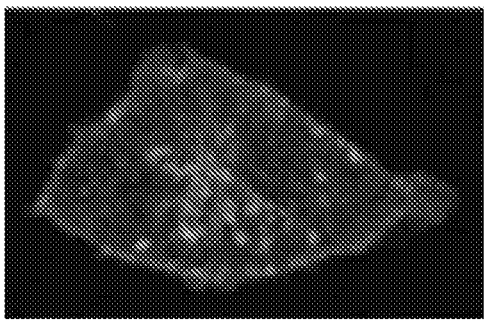
Figure 13D:
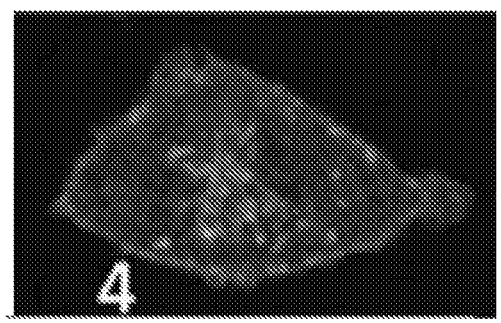
Figure 13E:
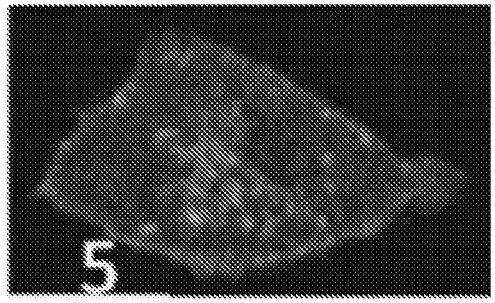
Figure 13F:
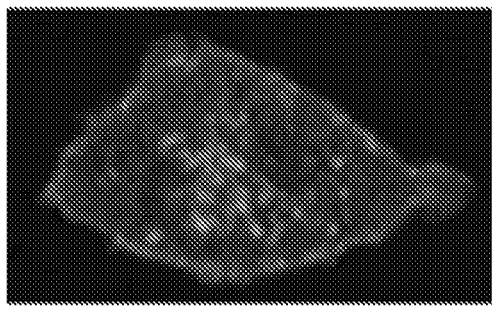
Figure 13G:
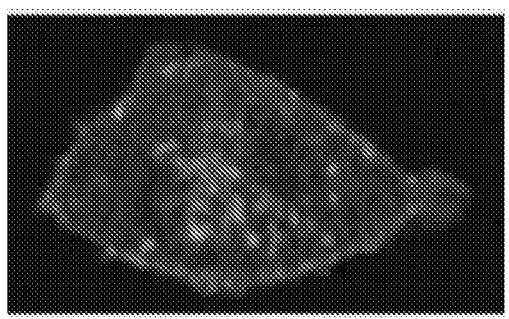
Figure 13H:
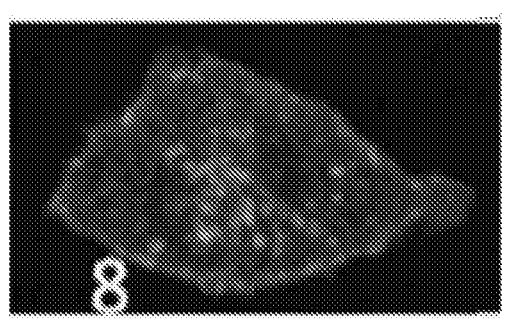
Figure 13I:
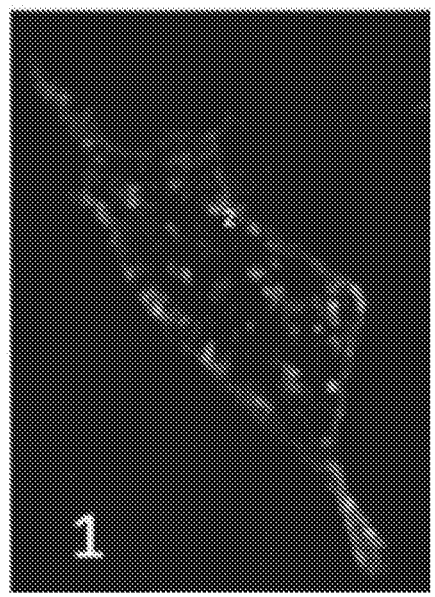
Figure 13J:
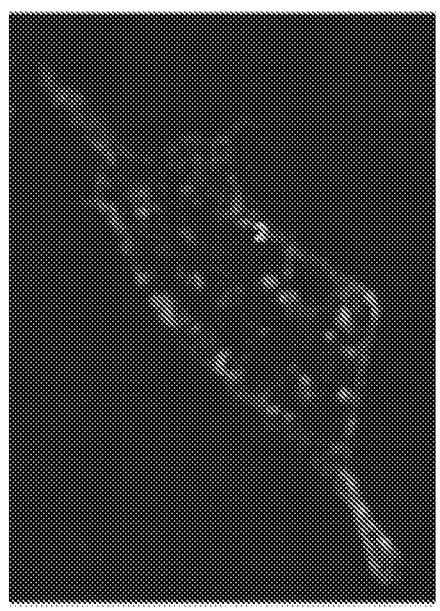

FIGS. 13I-J are montages of time-lapse videos of live macrophage cells. The BEACH-WD domain of mouse Lrba gene was cloned into pEGFP-N1 vector as described previously (Wang, et al., Identification of a novel lipopolysaccharideinducible gene with key features of both A kinase anchor proteins and chs1/beige proteins. 2001. *J Immunol* 166: 4586-4595). RAW264.7 macrophage cells were stably transfected with LRBA (BEACH-WD)-GFP and were stimulated with (top panel) or without LPS (bottom panel). The time-lapse video was taken at one picture per second using the Leica TCS SP2 laser scanning inverted confocal microscope with a mini cell culture chamber at 37° C. and 5% CO2. The GFP fluorescence shows cell membrane, Golgi and vesicle locations of LRBA, and the dynamic activities of LRBA associated vesicles moving from GC to the membrane. The pictures were ordered sequentially as the original video and labeled accordingly. The smaller numbers indicate vesicle paths.

Figure 13K:
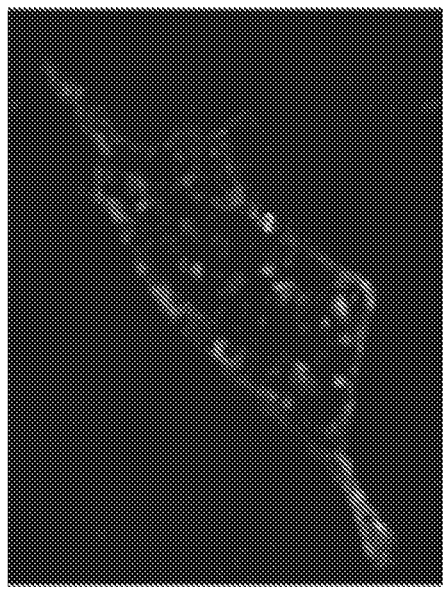
Figure 13L:
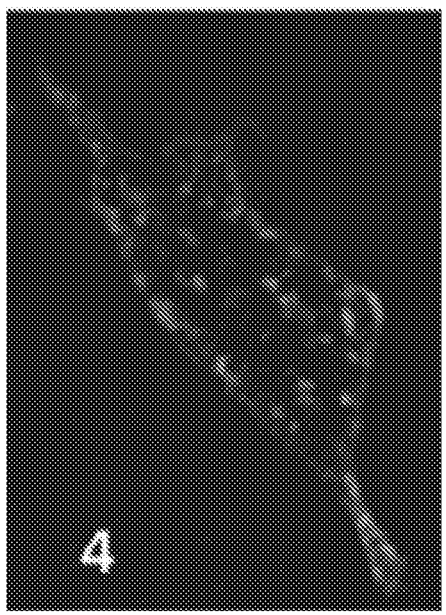

FIGS. 13K-L are montages of time-lapse videos of live macrophage cells. The BEACH-WD domain of mouse Lrba gene was cloned into pEGFP-N1 vector as described previously (Wang, et al., Identification of a novel lipopolysaccharideinducible gene with key features of both A kinase anchor proteins and chs1/beige proteins. 2001. *J Immunol* 166: 4586-4595). RAW264.7 macrophage cells were stably transfected with LRBA (BEACH-WD)-GFP and were stimulated with (top panel) or without LPS (bottom panel). The time-lapse video was taken at one picture per second using the Leica TCS SP2 laser scanning inverted confocal microscope with a mini cell culture chamber at 37° C. and 5% CO2. The GFP fluorescence shows cell membrane, Golgi and vesicle locations of LRBA, and the dynamic activities of LRBA associated vesicles moving from GC to the membrane. The pictures were ordered sequentially as the original video and labeled accordingly. The smaller numbers indicate vesicle paths.

Figure 13M:
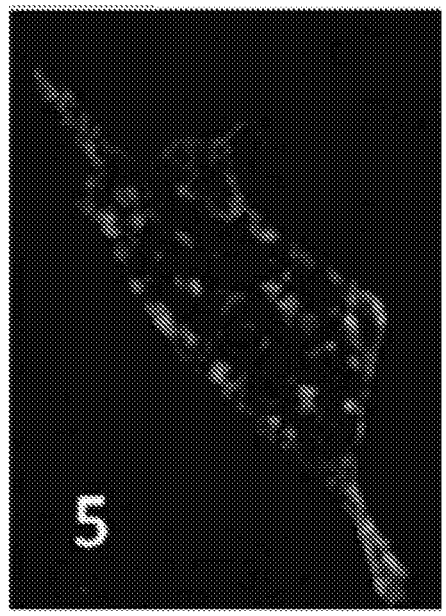
Figure 13N:
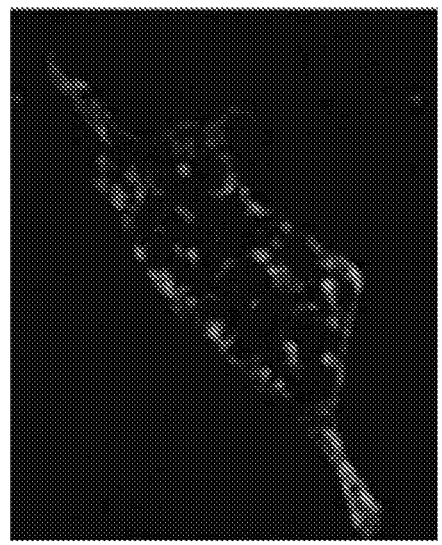

FIGS. 13M-N are montages of time-lapse videos of live macrophage cells. The BEACH-WD domain of mouse Lrba gene was cloned into pEGFP-N1 vector as described previously (Wang, et al., Identification of a novel lipopolysaccharideinducible gene with key features of both A kinase anchor proteins and chs1/beige proteins. 2001. *J Immunol* 166: 4586-4595). RAW264.7 macrophage cells were stably transfected with LRBA (BEACH-WD)-GFP and were stimulated with (top panel) or without LPS (bottom panel). The time-lapse video was taken at one picture per second using the Leica TCS SP2 laser scanning inverted confocal microscope with a mini cell culture chamber at 37° C. and 5% CO2. The GFP fluorescence shows cell membrane, Golgi and vesicle locations of LRBA, and the dynamic activities of LRBA associated vesicles moving from GC to the membrane. The pictures were ordered sequentially as the original video and labeled accordingly. The smaller numbers indicate vesicle paths.

Figure 13O:
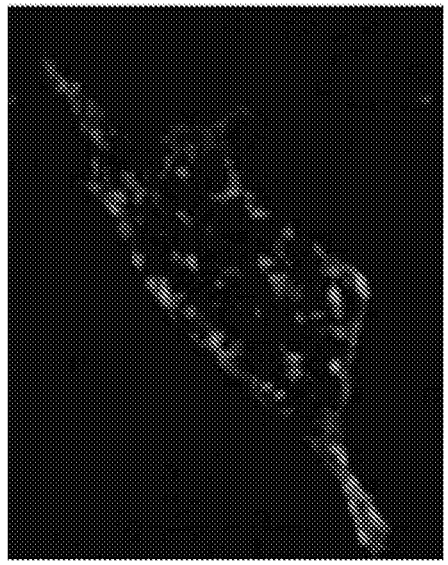
Figure 13P:
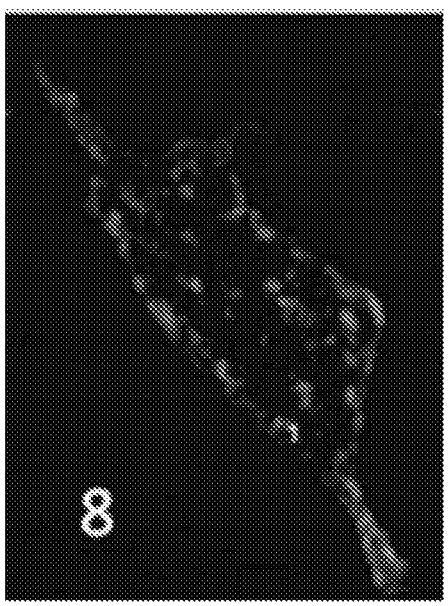

FIGS. 13O-P are montages of time-lapse videos of live macrophage cells. The BEACH-WD domain of mouse Lrba gene was cloned into pEGFP-N1 vector as described previously (Wang, et al., Identification of a novel lipopolysaccharideinducible gene with key features of both A kinase anchor proteins and chs1/beige proteins. 2001. *J Immunol* 166: 4586-4595). RAW264.7 macrophage cells were stably transfected with LRBA (BEACH-WD)-GFP and were stimulated with (top panel) or without LPS (bottom panel). The time-lapse video was taken at one picture per second using the Leica TCS SP2 laser scanning inverted confocal microscope with a mini cell culture chamber at 37° C. and 5% CO2. The GFP fluorescence shows cell membrane, Golgi and vesicle locations of LRBA, and the dynamic activities of LRBA associated vesicles moving from GC to the membrane. The pictures were ordered sequentially as the original video and labeled accordingly. The smaller numbers indicate vesicle paths.

Figure 14A:
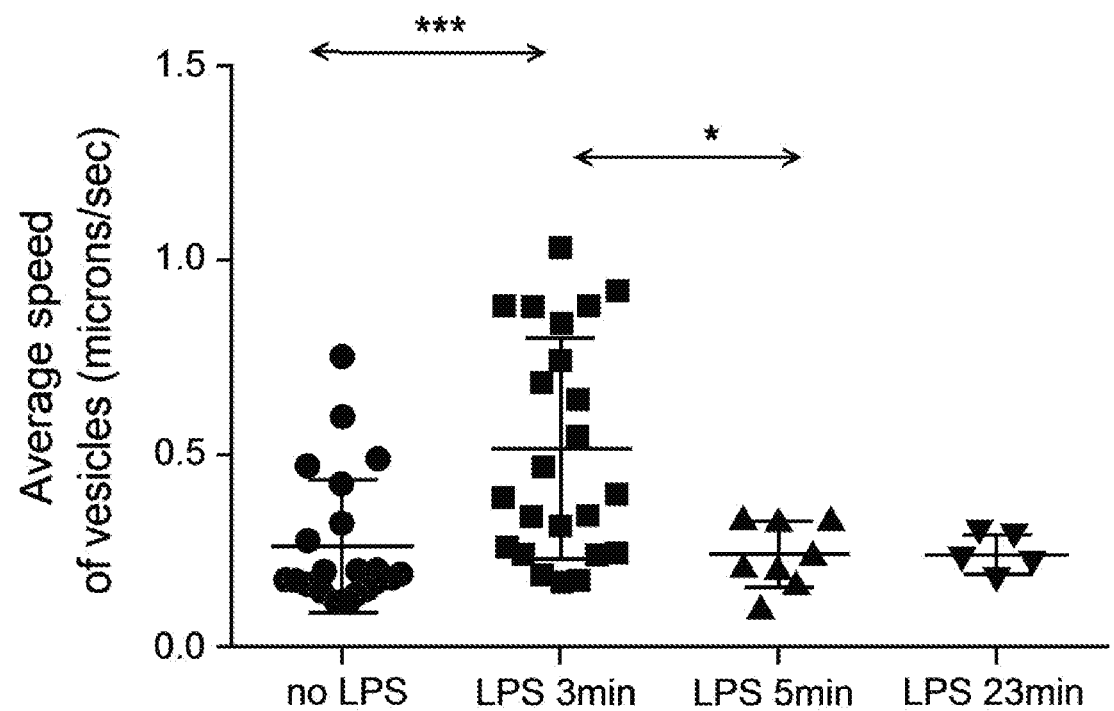
Figure 14B:
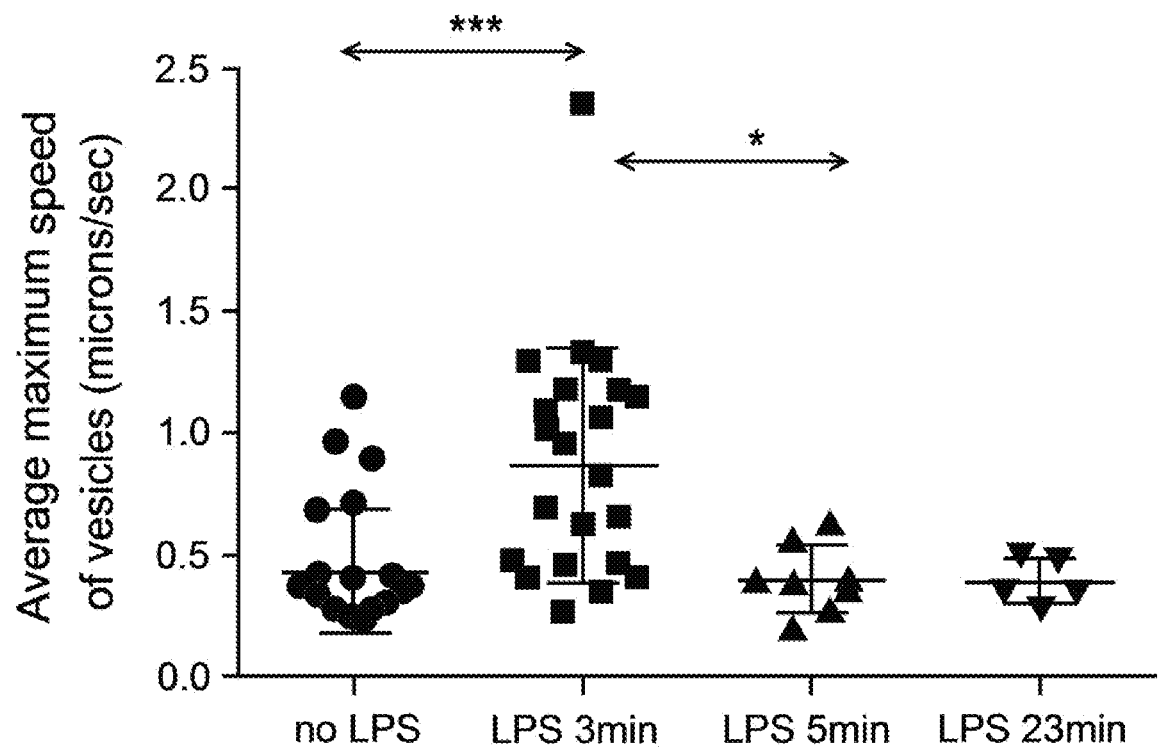

FIGS. 14(A) and (B) are graphs showing LPS stimulates LRBA-positive vesicles movements. RAW264.7 macrophage cells stably transfected with pBWEGFP were cultured in a glass bottom dish and put into the culture chamber. LPS was added at final concentration of 100 ng/ml. The time-lapse video of four living cells was taken at one picture per second using the Leica TCS SP2 laser scanning inverted confocal microscope with a mini cell culture chamber at 37° C. and 5% CO2. (A) Average speed of LRBA-associated vesicles; (B) Average maximum speed of LRBA-associated vesicles; The two tails and unpaired T test p values: ***$p<0.001$; *$p<0.0138$ (A); ***$p<0.0005$; *$p<0.0117$ (B).

LPS 3 min indicates that the measurements were obtained 3 min after adding LPS into the media.

Figure 15A:
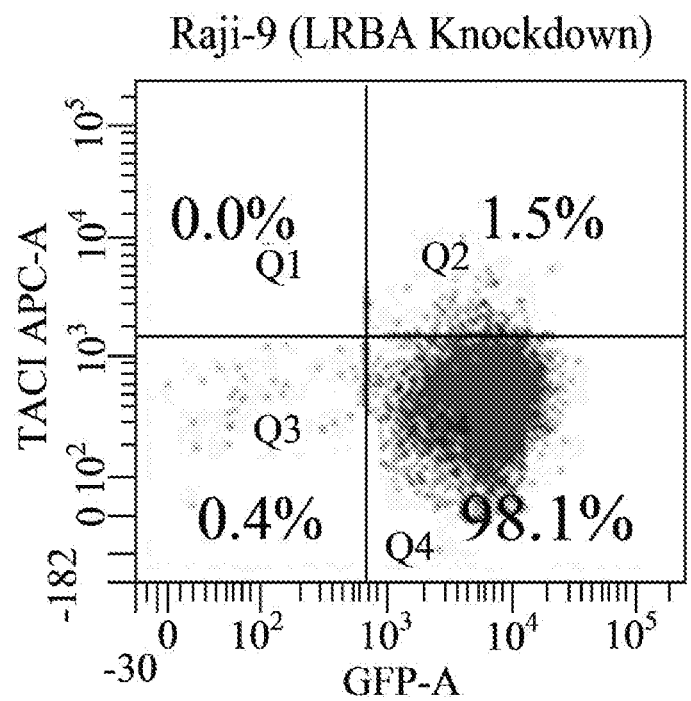
Figure 15B:
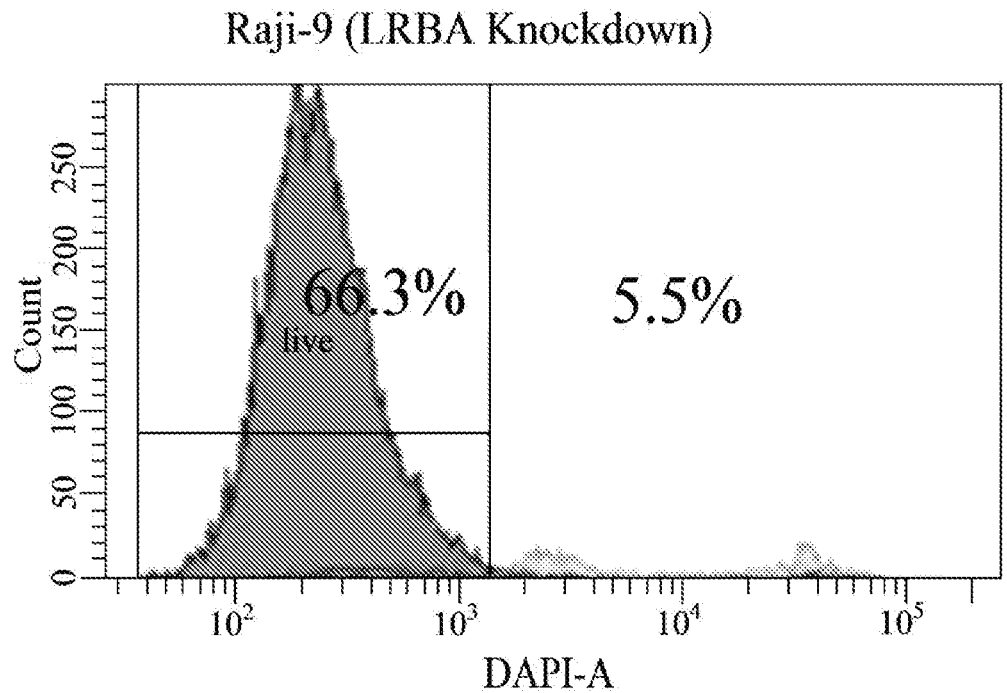
Figure 15C:
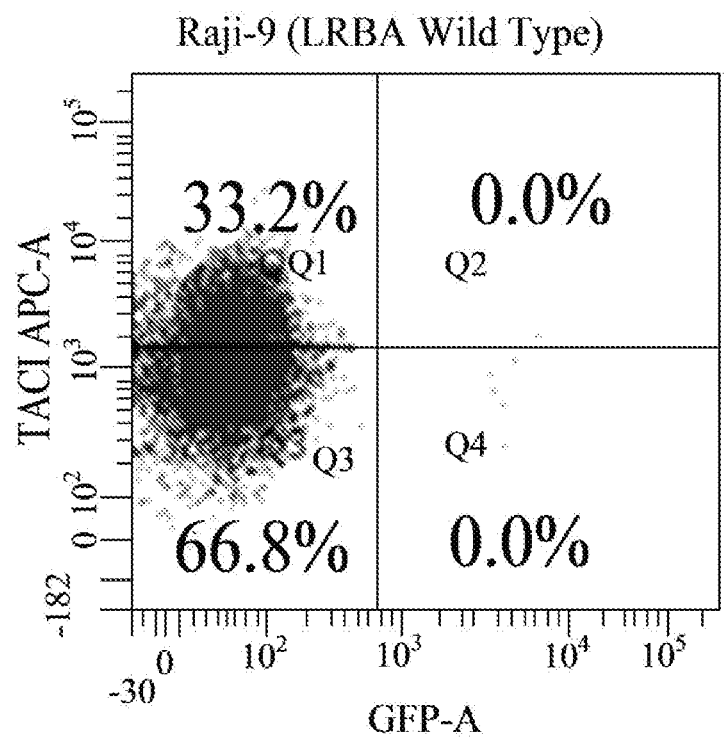
Figure 15D:
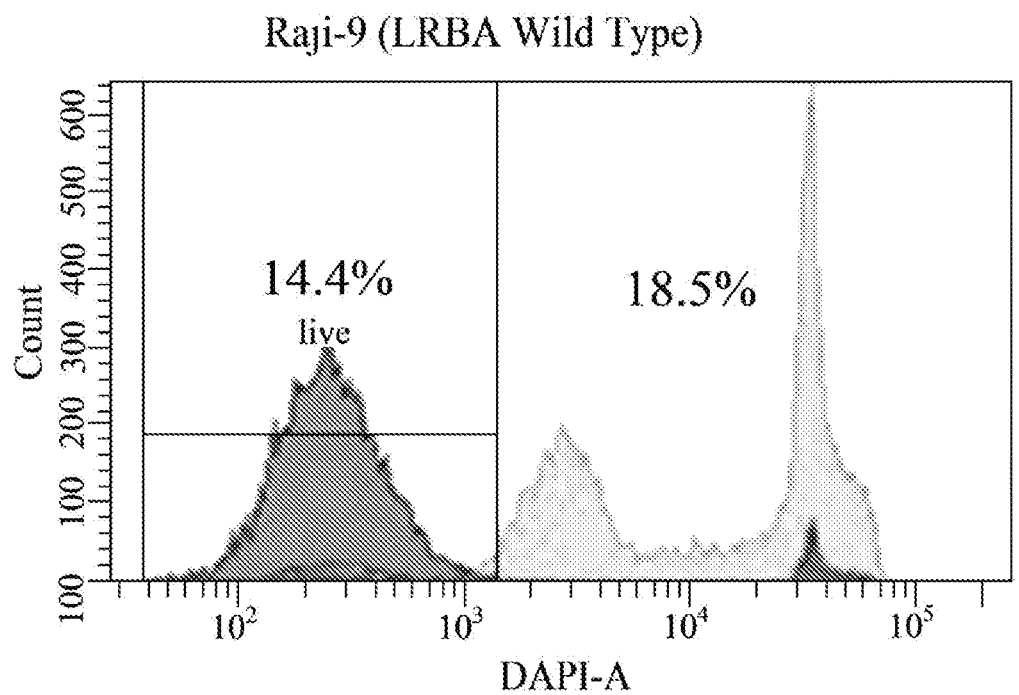

FIGS. 15(A)-(B) are a series of graphs showing knockdown of LRBA decreases the TACI levels on B cells. Raji B cells and Raji-9 (stably transfected with shRNA plasmid against LRBA) B cells were stained with TACI antibody (Hu CD267 APC 1A1-K21-M22, BD BioSciences) and DAPI for dead/live discrimination. A, B. Raji-9 (LRBA Knockdown);

FIGS. 15C-D are a series of graphs showing knockdown of LRBA decreases the TACI levels on B cells. Raji B cells and Raji-9 (stably transfected with shRNA plasmid against LRBA) B cells were stained with TACI antibody (Hu CD267 APC 1A1-K21-M22, BD BioSciences) and DAPI for dead/live discrimination. C, D. Raji (LRBA Wild Type).

Figure 15E:
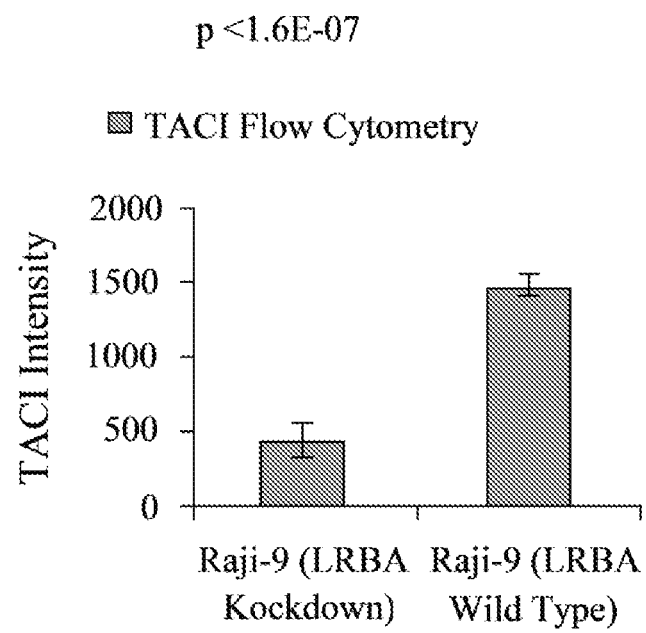
Figure 15F:
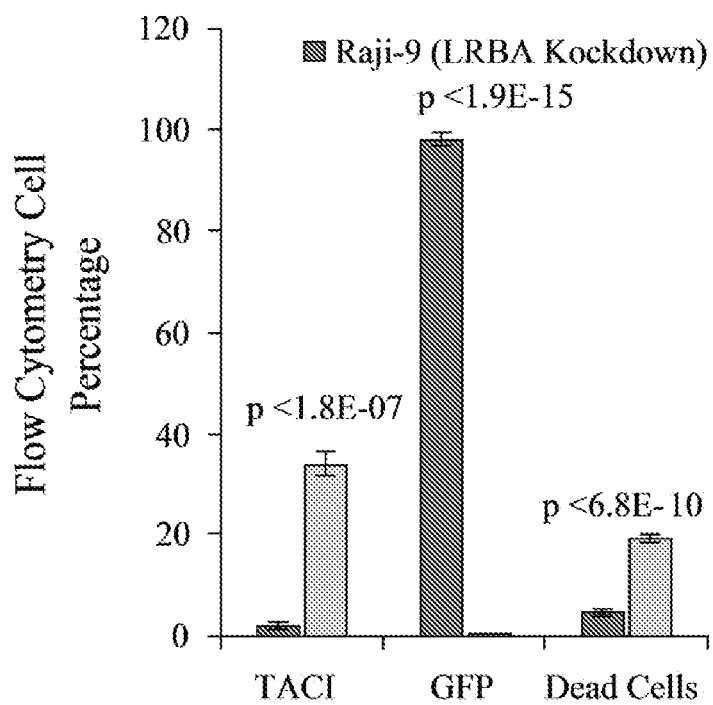

FIGS. 15E-F are a series of graphs showing knockdown of LRBA decreases the TACI levels on B cells. Raji B cells and Raji-9 (stably transfected with shRNA plasmid against LRBA) B cells were stained with TACI antibody (Hu CD267 APC 1A1-K21-M22, BD BioSciences) and DAPI for dead/live discrimination. E, Average expression levels of TACI on B cells. F. Flow Cytometry Cell Percentage.

FIGS. 16(A)-(C) are a series of graphs showing knockdown of LRBA decreases the surface levels of TLR4, CD21 and TACI on B cells. Raji B cells and Raji-9 (stably transfected with shRNA plasmid against LRBA) B cells were stained with TLR4, CD21 and TACI antibody (BD BioSciences) and DAPI or 7AAD for dead/live discrimination.

Figure 16D:
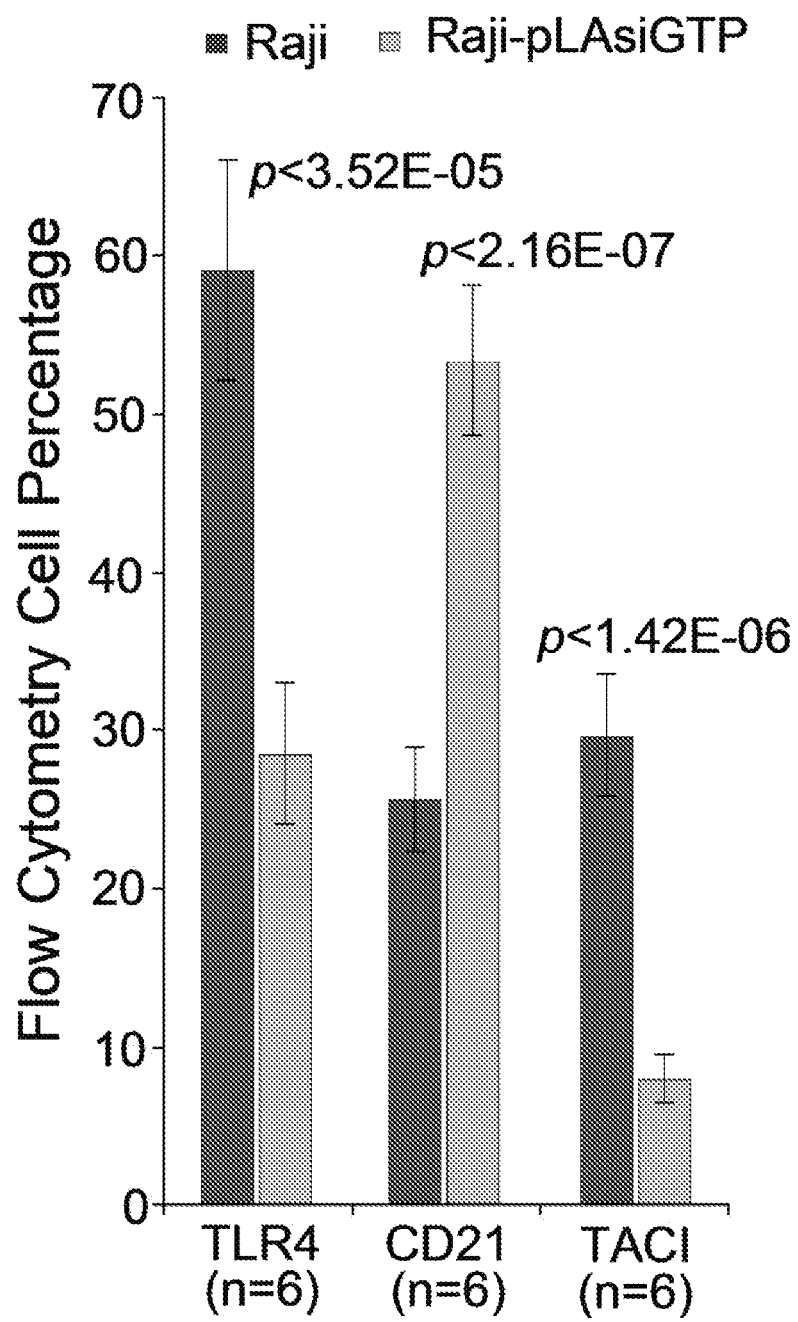

FIG. 16D is a graph showing knockdown of LRBA decreases the surface levels of TLR4, CD21 and TACI on B cells. Raji B cells and Raji-9 (stably transfected with shRNA plasmid against LRBA) B cells were stained with TLR4, CD21 and TACI antibody (BD BioSciences) and DAPI or 7AAD for dead/live discrimination.

Figure 17A:
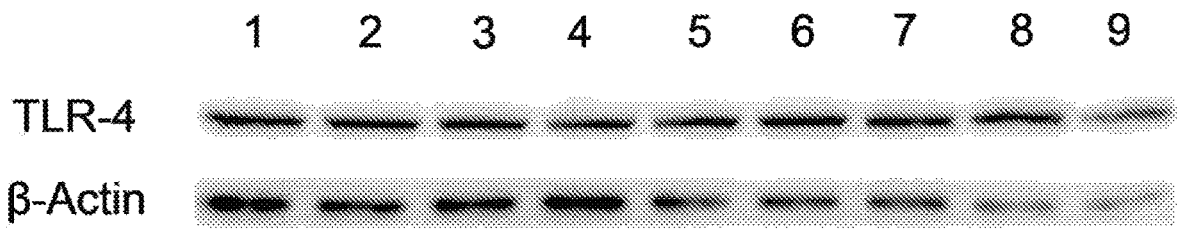
Figure 17B:
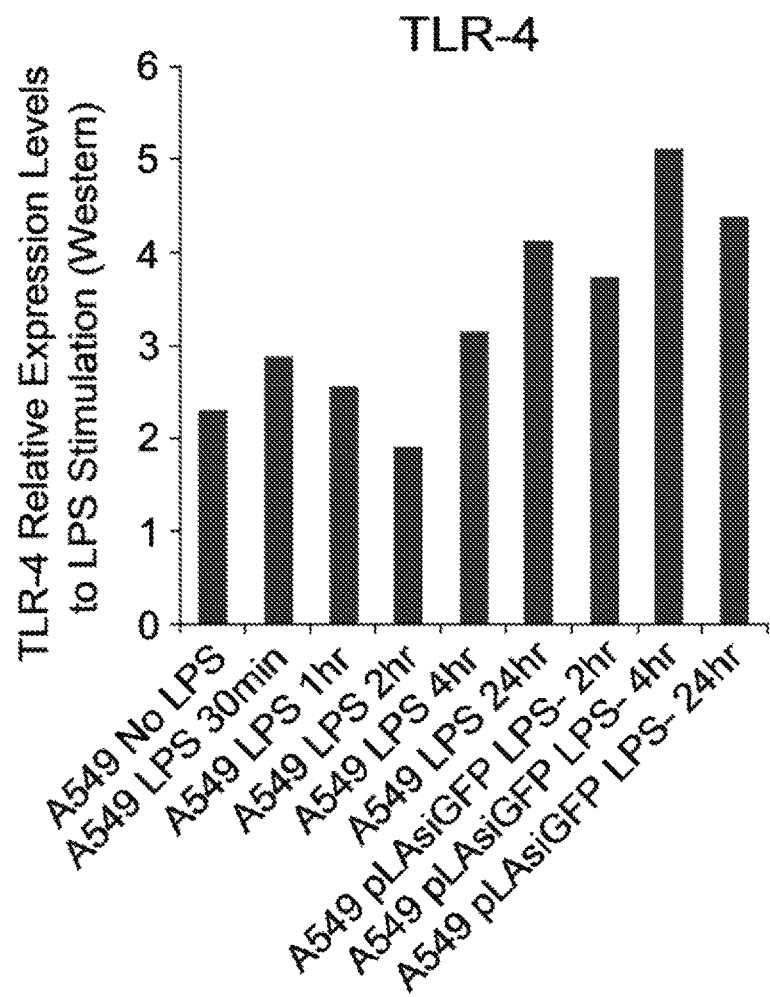

FIG. 17(A)-(B) are a series of graphs showing knockdown of LRBA increases the TLR4 levels in A549 cells. A549 cells and A549 pLAsiGFP cells (stably transfected with shRNA plasmid against LRBA) were treated with LPS (1 μg/ml). The TLR4 concentrations were detected by Western blot. Cells were cultured in 6-well plates and stimulated with LPS (1 μg/ml) for different time as shown, then lysed with RIPA buffer. Western blots were carried out. TLR4 antibody (sc-1351. Santa Cruz Biotechnology, Santa Cruz, USA) was used at 1:500 ratio and incubated at 4° C. overnight. BioRad ChemiDoc XRS and Quantity One software were used to acquire gel image and measure band relative intensity. (A) Western blot. 1. A549 No LPS, 2. A549 LPS 30 min, 3. A549 LPS 1 hr, 4. A549 LPS 2 h, 5. A549 LPS 4 h, 6. A549 LPS 24 h, 7. A549 pLAsiGFP LPS 2 h, 8. A549 pLAsiGFP LPS 4 h, 9. A549 pLAsiGFP LPS 24 h. (B) Band intensity quantification from A.

Figure 17C:
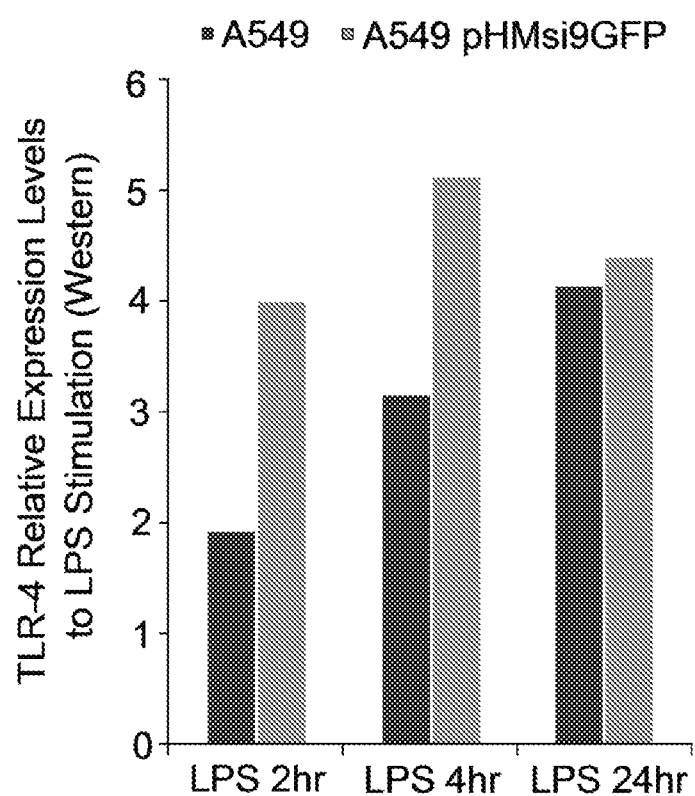

FIG. 17C is a graph showing knockdown of LRBA increases the TLR4 levels in A549 cells. A549 cells and A549 pLAsiGFP cells (stably transfected with shRNA plasmid against LRBA) were treated with LPS (1 μg/ml). The TLR4 concentrations were detected by Western blot. Cells were cultured in 6-well plates and stimulated with LPS (1 μg/ml) for different time as shown, then lysed with RIPA buffer. Western blots were carried out. TLR4 antibody (sc-1351. Santa Cruz Biotechnology, Santa Cruz, USA) was used at 1:500 ratio and incubated at 4° C. overnight. BioRad ChemiDoc XRS and Quantity One software were used to acquire gel image and measure band relative intensity. (C) TNFα levels in A549 and A549 pLAsiGFP cells were compared side by side.

Figure 18A:
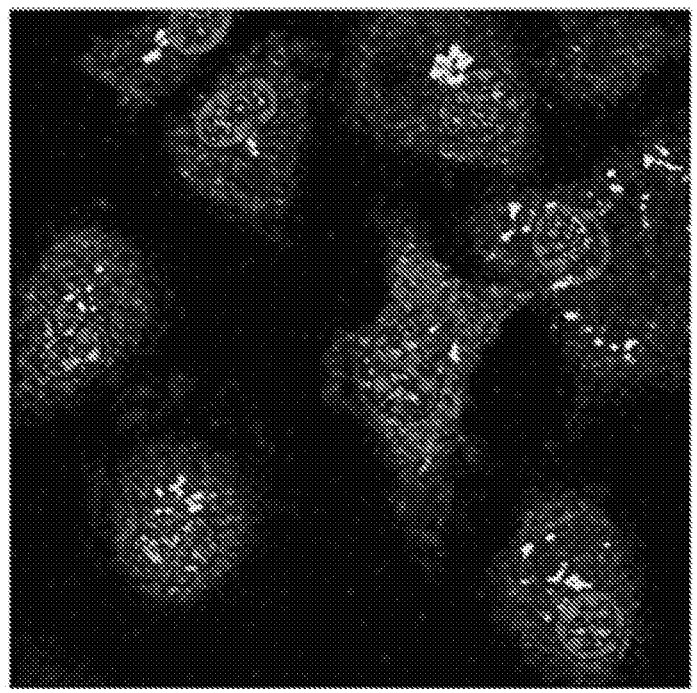

FIGS. 18(A) and (B) are a series of images showing LRBA translocates to the nucleus upon LPS stimulation. Mouse (C57BL/6J) bone marrow stromal cells were cultured on glass cover slips with (A) or without (B) LPS (1 μg/ml) stimulation for 3 hours, then fixed, permeabilized, and stained following the immuno-fluorescence staining protocol from the Human Protein Atlas Project (Sigma). The LRBA Prestige antibodies and three Golgi protein primary antibodies from BD Biosciences were used at 1:500 (volume to volume dilution). The anti-mouse IgG-Alexa Fluor® 555, and anti-rabbit IgG-Alexa Fluor 488 (Invitrogen) secondary antibodies were used at 1:400. The images were acquired with an Olympus FV1000 scanning confocal microscope by sequential scanning with 0.5 μm per slice. Green=LRBA; Red=GM130; Blue=Nucleus.

Figure 19A:
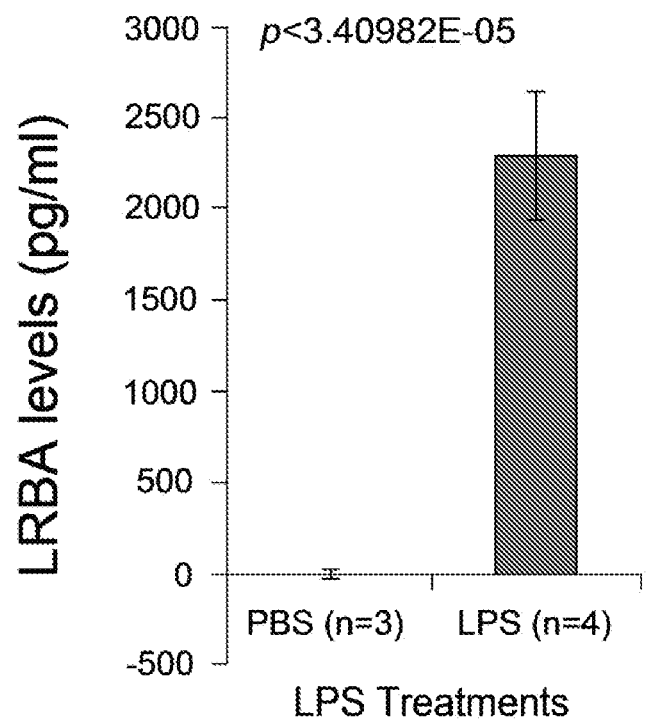
Figure 19B:
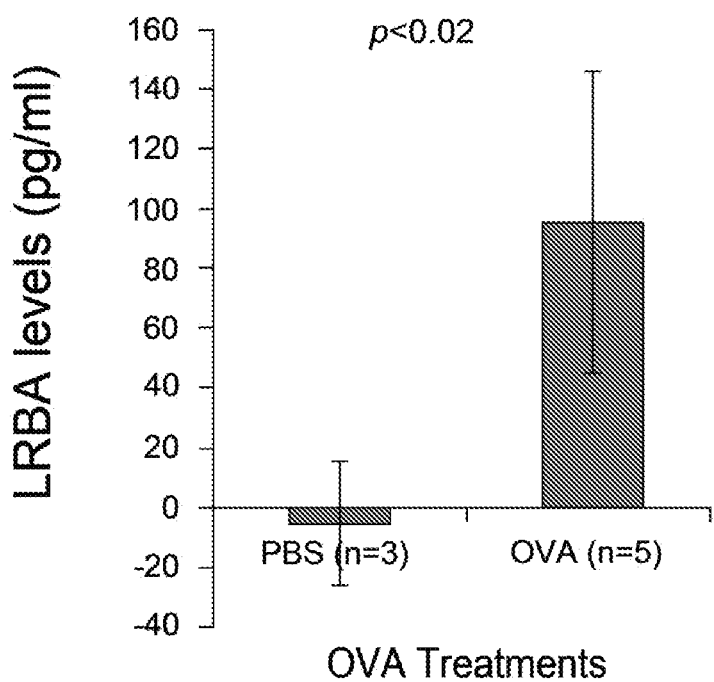

FIGS. 19(A)-(B) are graphs showing plasma or extracellular LRBA levels are increased significantly in inflammation. (A) Mice stimulated with LPS (1 μg/g body weight) for 6 hours. (B) OVA induced asthma mouse model.

Figure 19C:
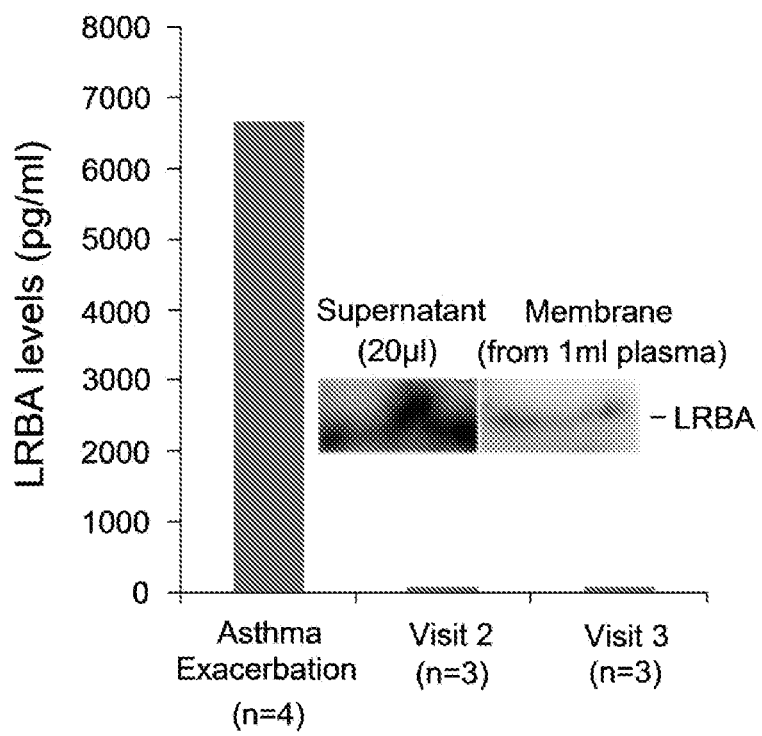
Figure 19D:
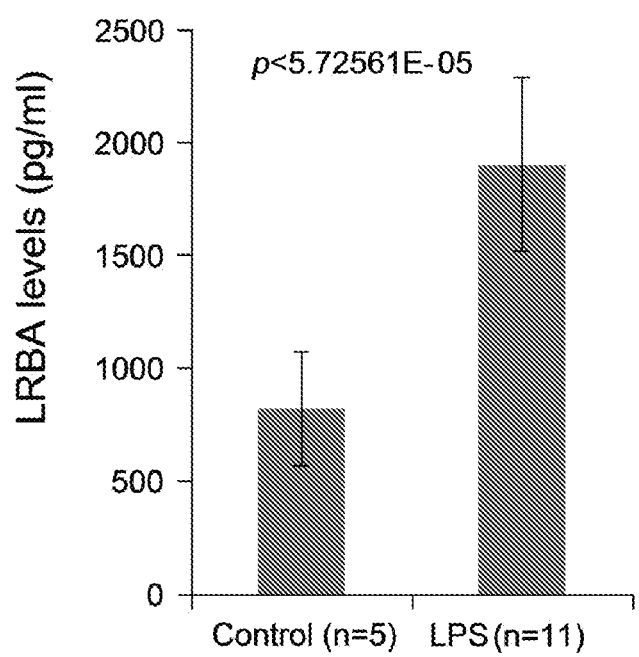

FIGS. 19C-D are graphs showing plasma or extracellular LRBA levels are increased significantly in inflammation. (C) Asthma patients with an exacerbation or controlled symptoms; (D) Human mononuclear leukocytes stimulated with LPS (1 μg/ml). LPS was derived from *Escherichia coli* 0111:B4 (Sigma, St. Louis, Mo.). LRBA levels were determined by LRBA ELISA Kit using 100 μl of plasma or conditioned media in each well, following the manufacturer's protocol.

Figure 20:
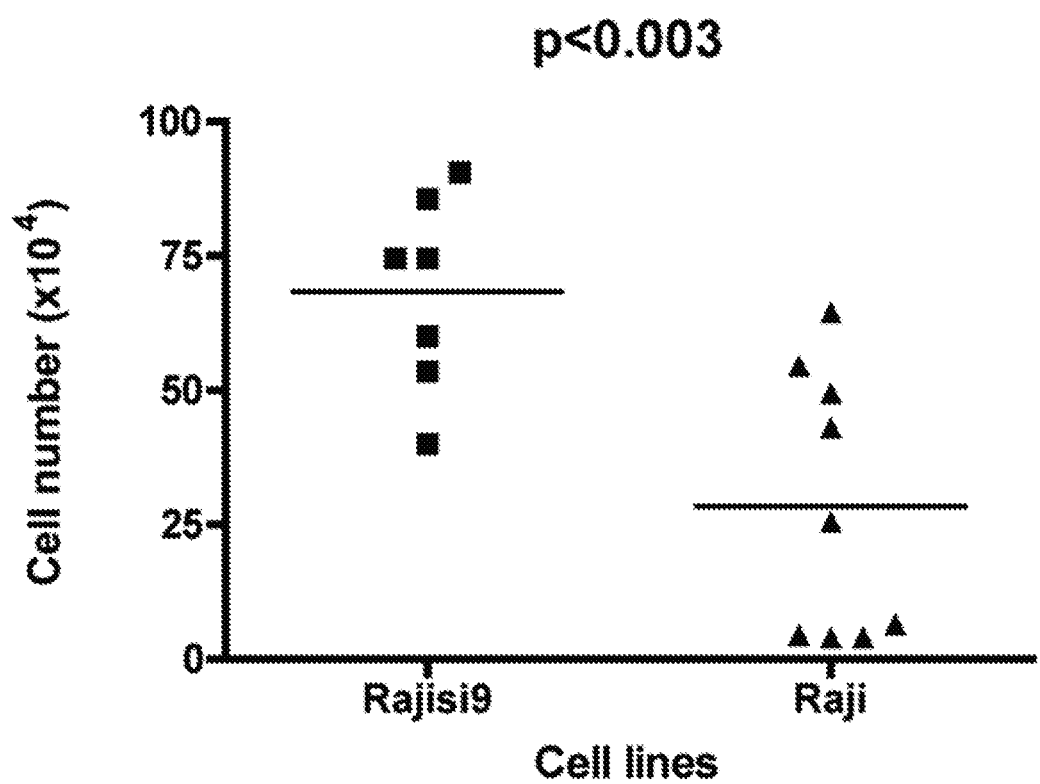

FIG. 20 is a graph showing knockdown of LRBA promotes B cell proliferations. Raji B cells and Rajisi9 B cells (Raji B cells stably transfected with shRNA plasmid against LRBA) were culture on a 96 well plate with 10 cells per well for 11 days. Viable cells were counted by the Trypan blue live/dead discrimination method with a Hemocytometer.

Figure 21:
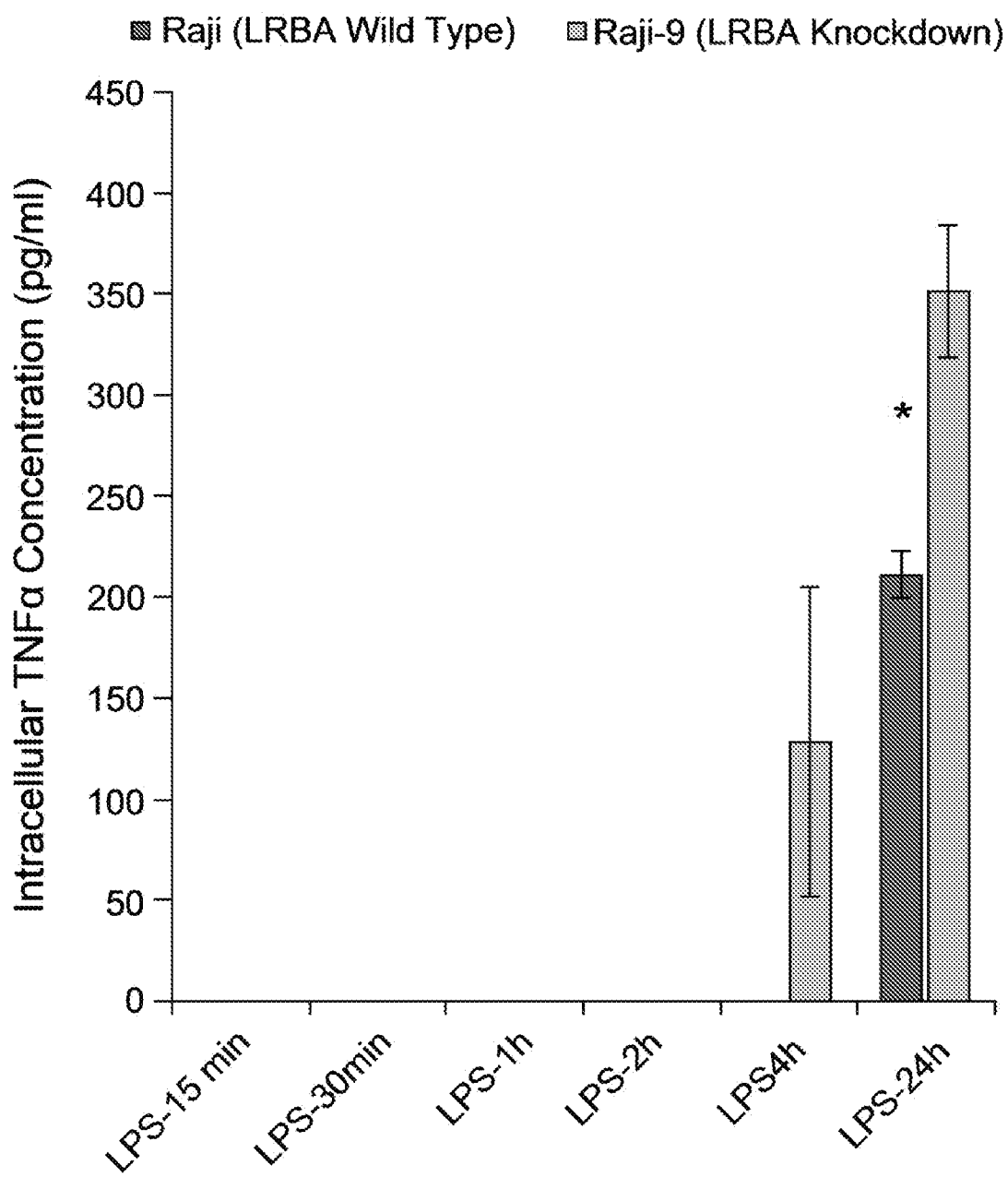

FIG. 21 are graphs showing knockdown of LRBA increases the TNFα levels in Raji B (Burkitt's lymphoma) cells. Raji B cells and Raji-9 (stably transfected with shRNA plasmid against LRBA) B cells were treated with LPS (1 μg/ml). The TNFa concentrations were measured by Human TNFα DuoSet ELISA kit (R&D) following the manufacture's instruction. A. Culture supernatant; B. Cell lysate. #=p<0.07, *=p<0.05, **=p<0.005.

Figure 22:
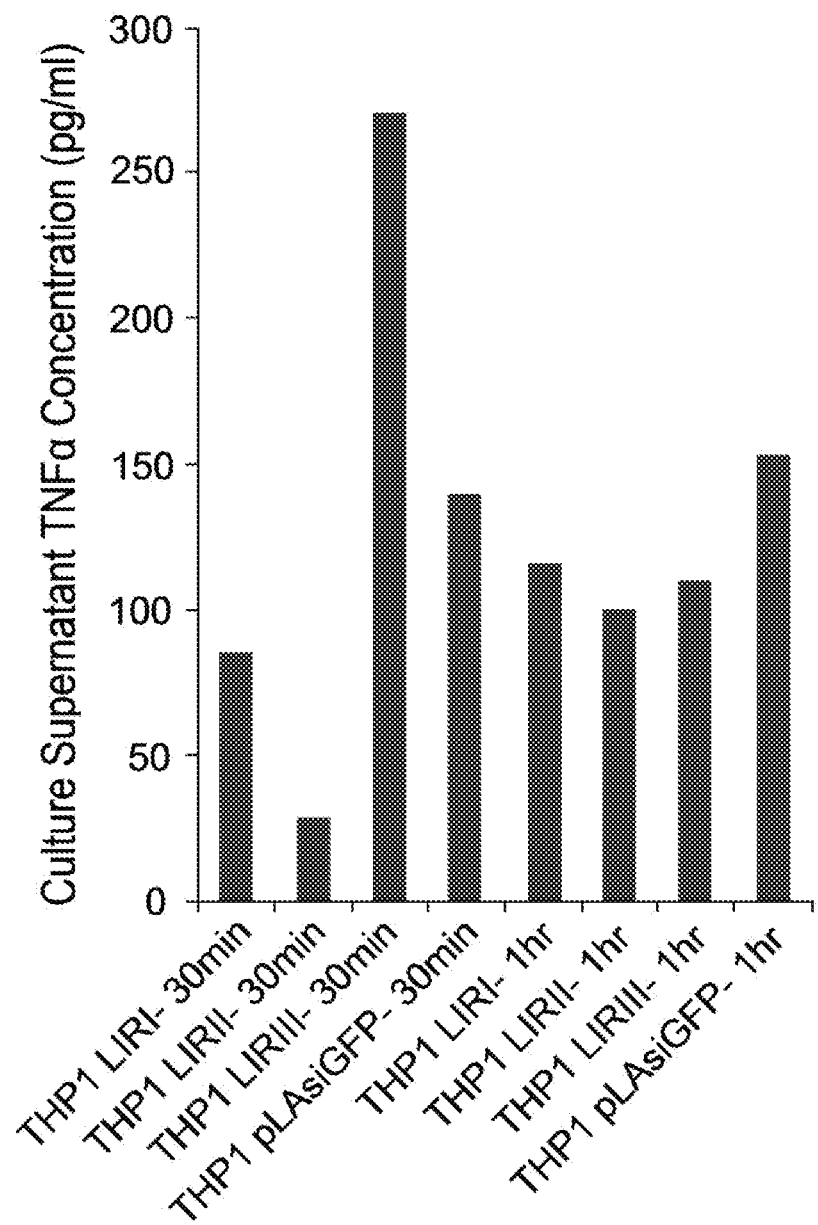

FIG. 22 is a graph showing dominant negative mutants of LRBA decrease the TNFα levels in THP1 cells (Human acute monocytic leukemia cell line). THP1 cells were transfected with LRBA dominant negative constructs with different domains. LIR1=LRBA-VHSLIR1, LIRII=LRBA-VHS and LIRIII=LRBA-LIR3; PhmsiGFP is the construct that expresses shRNA described in the text. After 24 hrs transfection, cells were stimulated with LPS at 1 μg/ml for deferent time periods. TNFα levels in the cell culture supernatant were measured as in FIG. 21.

Figure 23A:
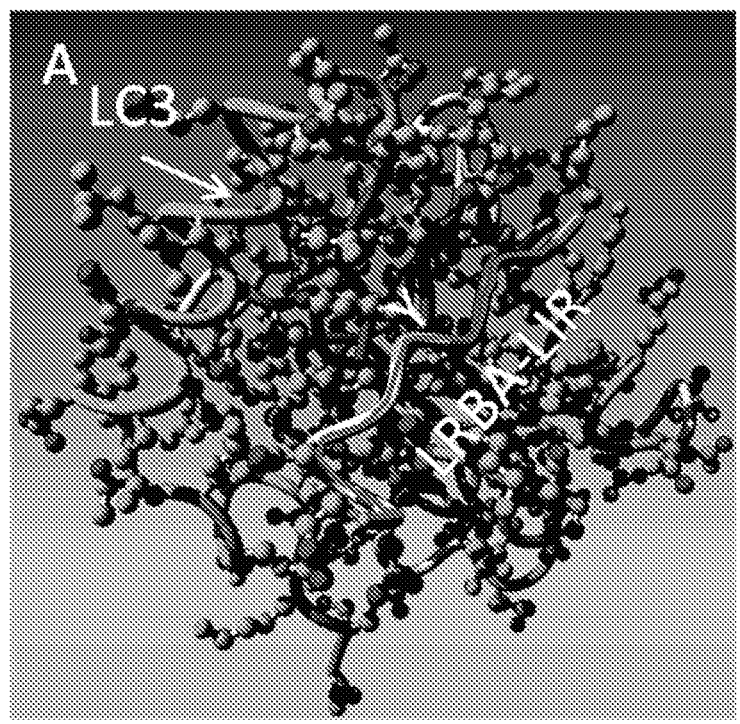
Figure 23B:
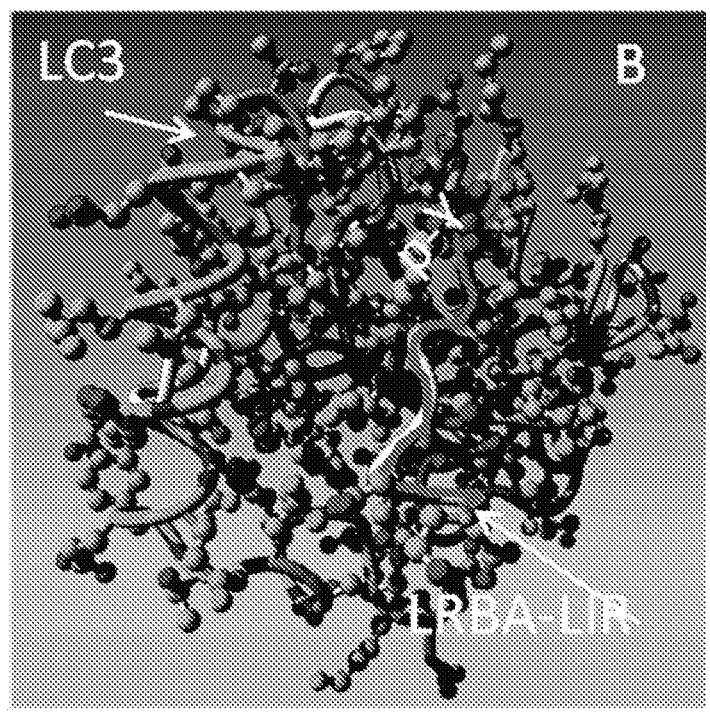
Figure 23C:
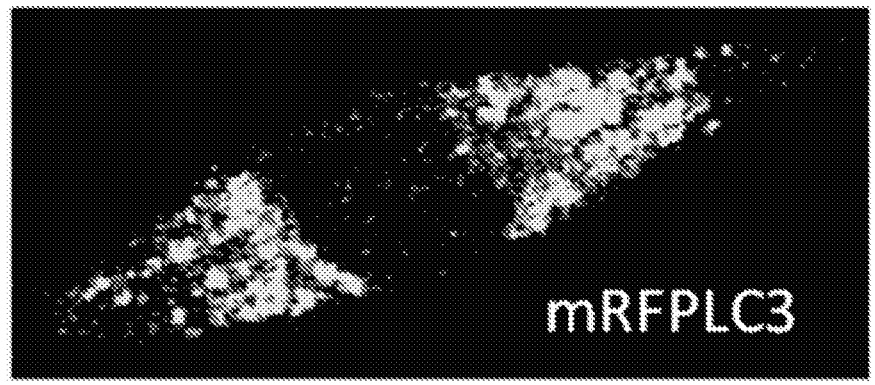
Figure 23D:
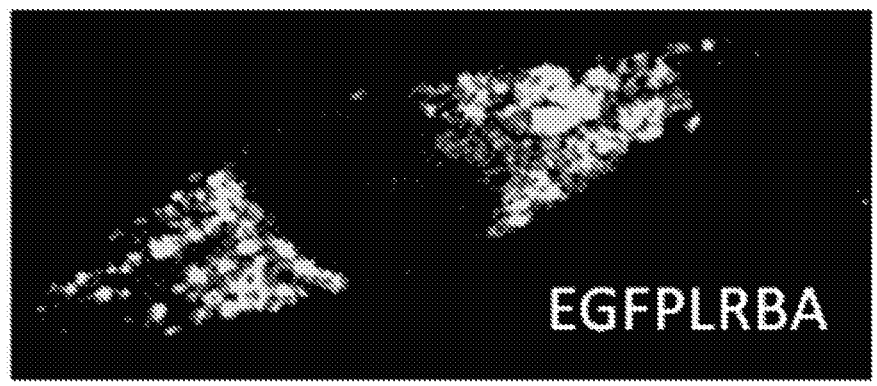
Figure 23E:
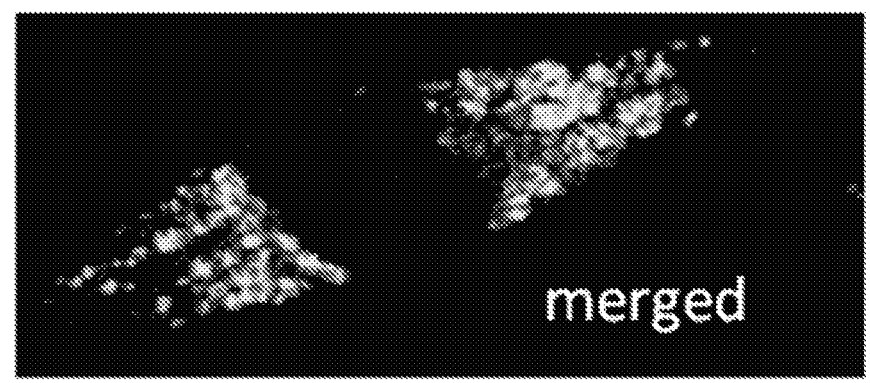

FIGS. 23(A)-(B) are three-dimensional structure remodeling shows that the LIR can form a complex with LC3 more stable than that of p62, a known LC3 binding protein. Tyrosine is in the hydrophobic pocket (A) and phosphorylation of the tyrosine in the LIR destabilizes the complex (B). Confocal microscopy confirmed the interaction FIGS. 23C-E are three-dimensional structure remodeling shows that the LIR can form a complex with LC3 more stable than that of p62, a known LC3 binding protein. Tyrosine is in the hydrophobic pocket. (C). Green (GFP) and red (RFP) fluorescent protein genes were fused with LRBA and LC3 genes, respectively, and co-transfected into HeLa cervical cancer, A549 adenocarcinomic alveolar basal epithelial and HEK293 embryonic kidney human cells, and Raw264.7 macrophage tumor mouse cells. Three-dimensional structure remodeling, confocal microscopy, and immunofluorescence assays (IFA) were utilized. Representative images of LC3 expression (C), LRBA expression (D), and both LC3 and LRBA (D) were shown.

FIGS. 24(A) and (B) are a three-dimensional structure remodeling of LIR and LIC3 interaction. (A) The LIR (dark gray) from LRBA is predicted to form a complex with LC3 (light gray) more stable than that of p62, a known LC3 binding protein. Tyrosine is in a hydrophobic pocket. (B) Phosphorylation of the tyrosine in the LIR destabilizes the complex. Phospho-Tyrosine is hydrophibic. Its side chain is away from the hydrophobic pocket and the LC3.

Figure 25:
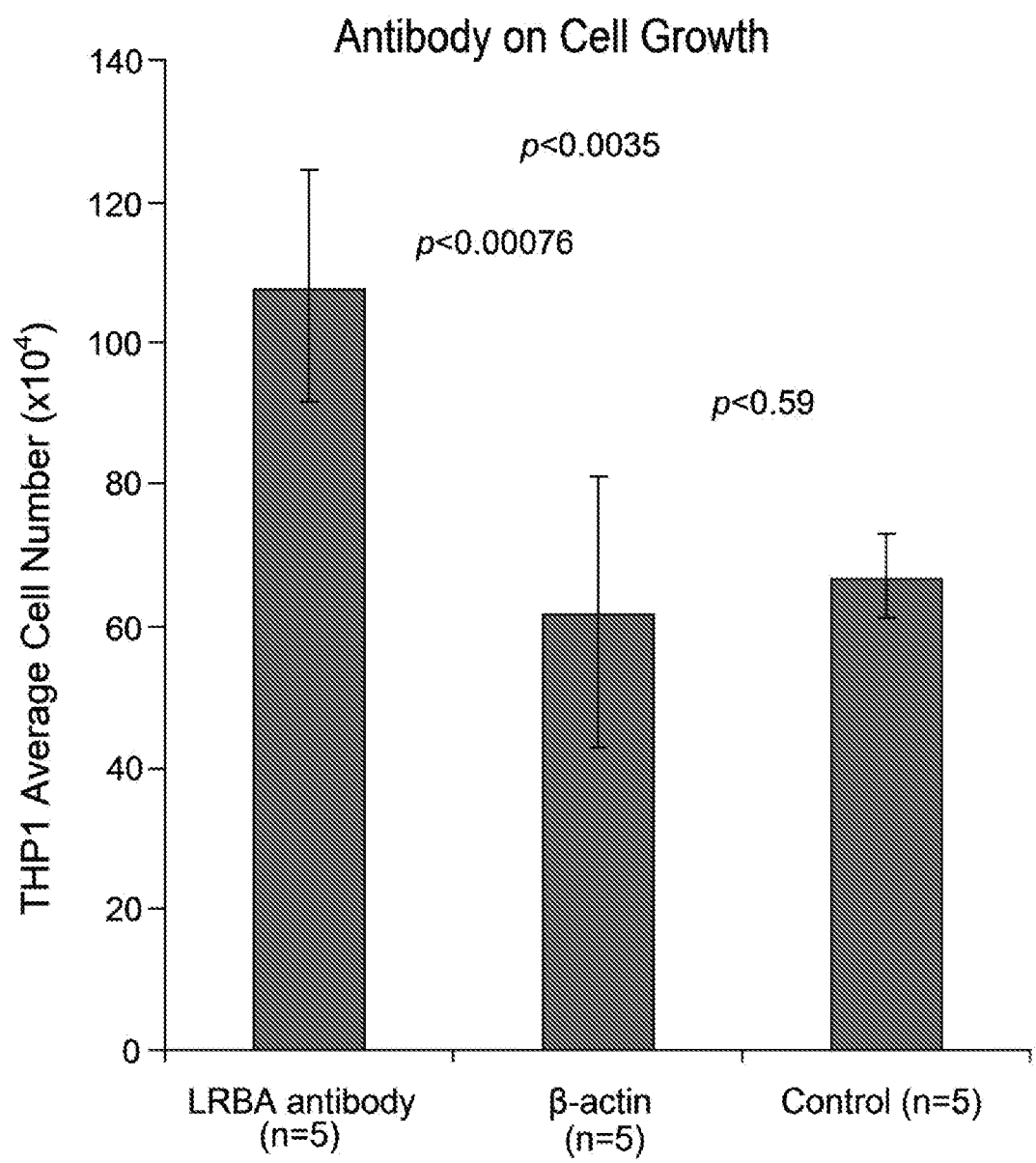

FIG. 25 is a graph showing blockage of LRBA promotes THP1 cell proliferations. THP1 cells (Human acute monocytic leukemia cell line) were cultured in 100 µl of RPMI1640 media with or without human LRBA polyclonal IgG antibody (Novus Biologicals, Littleton, USA. NBP1-90764) at 0.67 □g/ml or same amount of human Actin polyclonal IgG antibody (Santa Cruz Biotechnology, Santa Cruz, USA. SC-1616) on a 96 well plate with 10 cells per well for 9 days. Viable cells were counted by the Trypan blue live/dead discrimination method with a Hemocytometer.

Figure 26A:
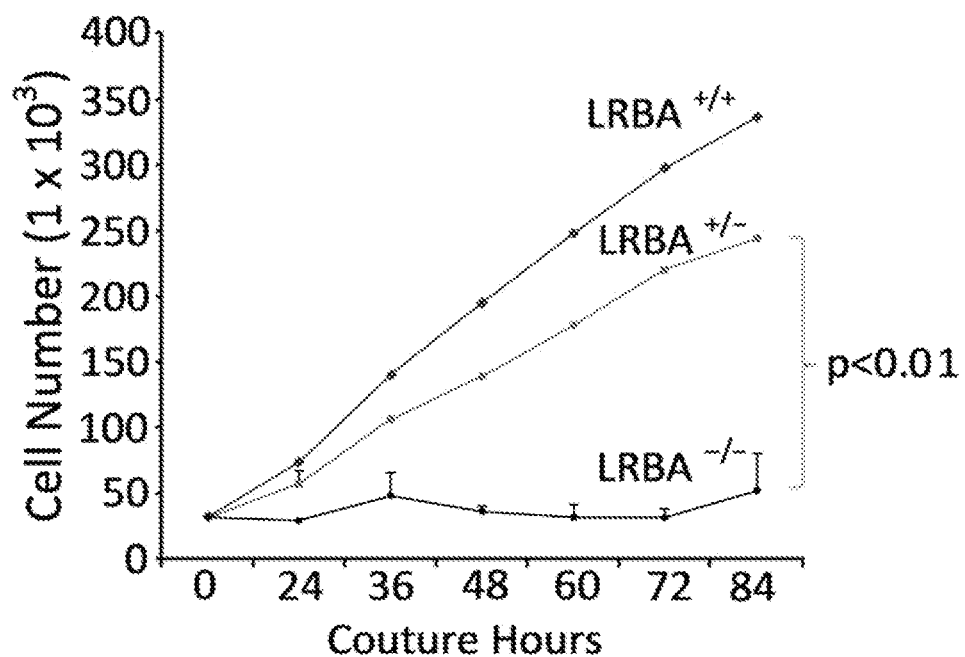
Figure 26B:
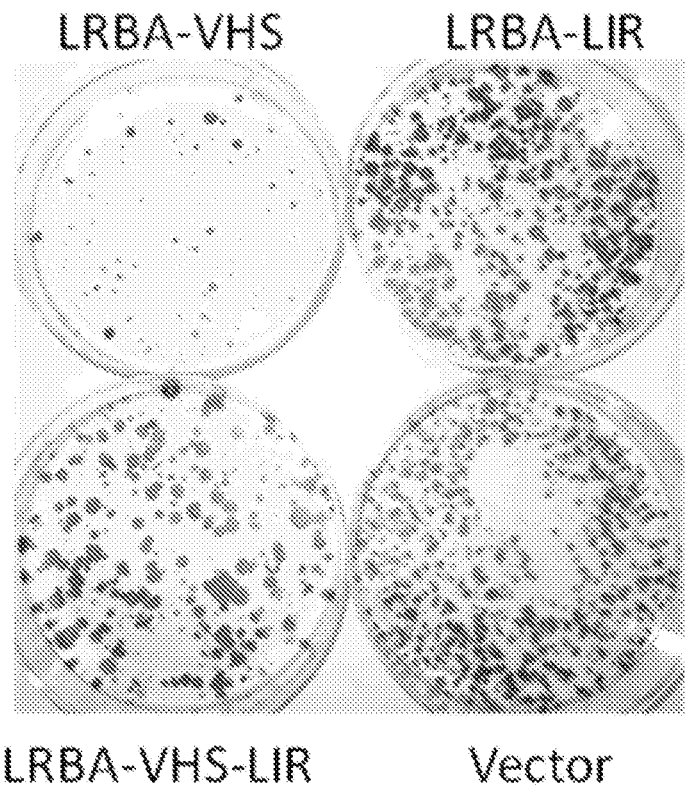

FIGS. 26(A)-(B) show LRBA is important for cell growth. A. Knockout of LRBA inhibits cell growth in mouse ES cells. LRBA double knockout (KO) ES cell clones were obtained by culturing LRBA single KO cells with 1 mg/ml G418 for about two weeks and confirmed by PCR genotyping. 4000 cells of LRBA$^{+/+}$, LRBA$^{+/-}$ and LRBA$^{-/-}$ were plated into each well of a 96-well plate. Cell numbers were counted by Trypan blue staining every 12 hours for 3.5 days using a hemocytometer. Each time point had three wells. B. Colony-forming assay (CFA) of HEK293 cells transfected with LRBA dominant negative constructs with different domains. One million cells were plated and 400 µg/ml of G418 was used to select positive clones for about 20 days. Then, the clone numbers were counted.

Figure 26C:
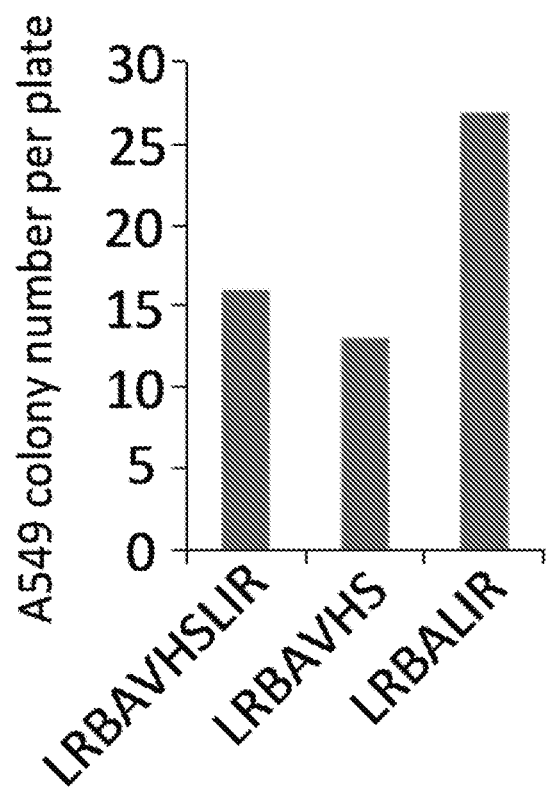
Figure 26D:
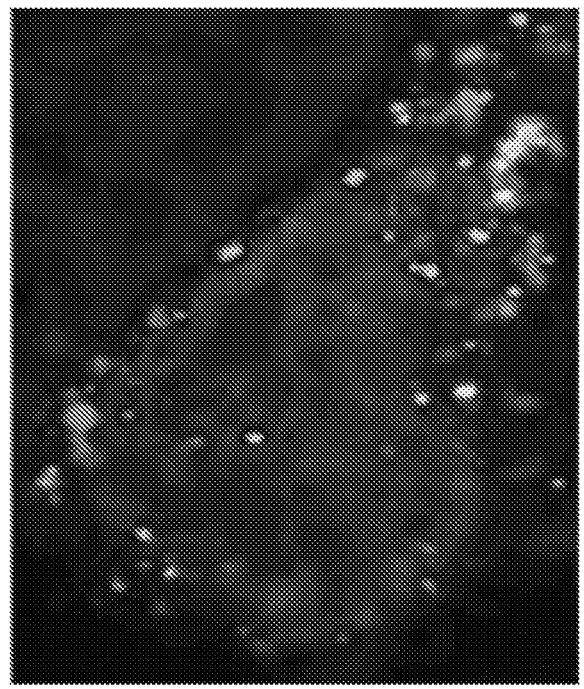

FIGS. 26C-D show LRBA is important for cell growth. C. The full length of murine LRBA coding sequence was cloned into pEGFP-C1. A positive clone (pmLRBAGFP) was identified by EcoRI and BamHI digestion and sequencing. D. The pmLRBAGFP plasmid DNA was transfected into H293 cells. Stable clones were selected with 500 µg/ml of G418 for 25 days.

Figure 26E:
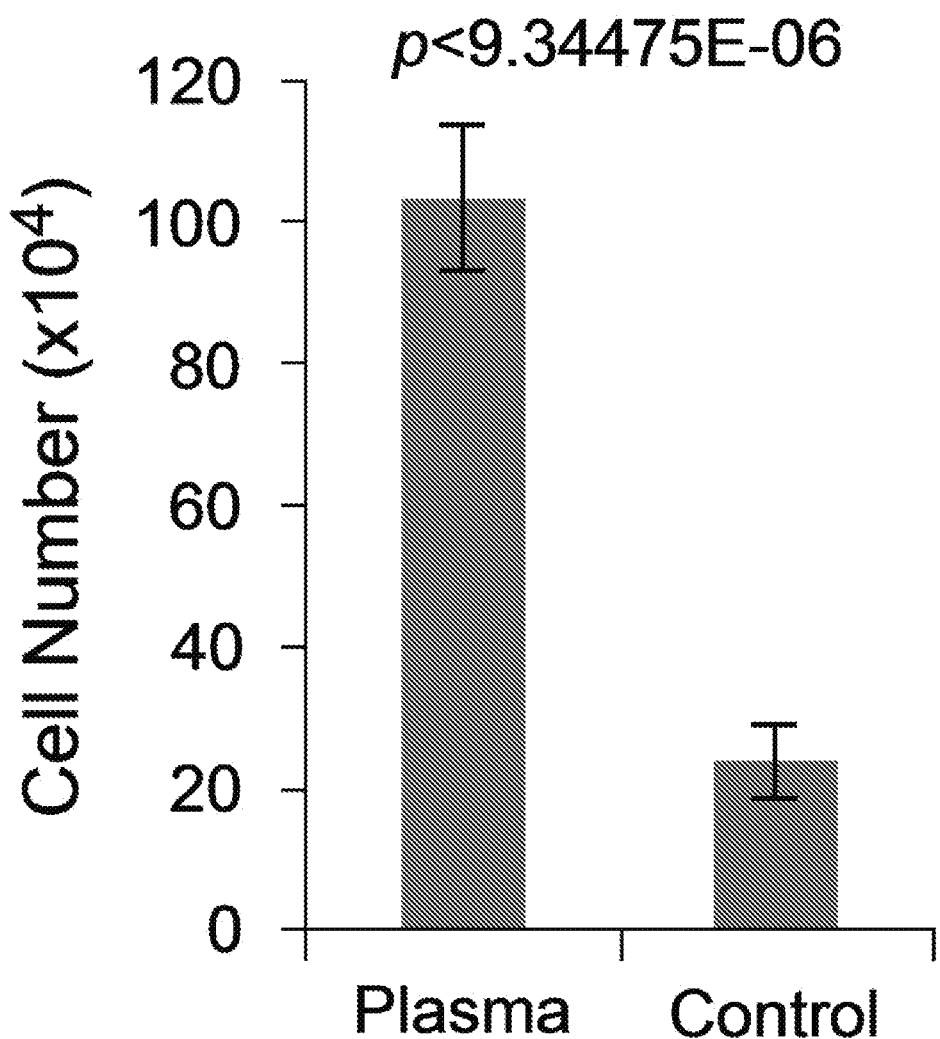
Figure 28A:
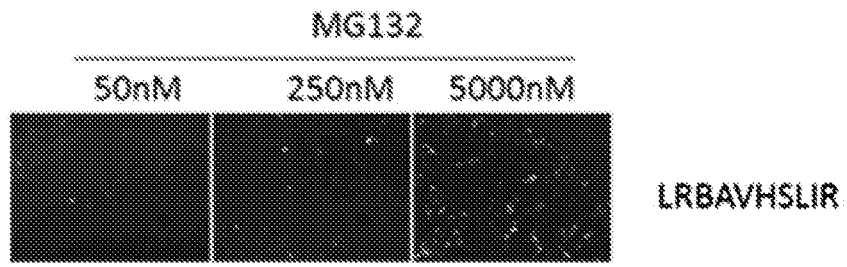
Figure 28B:
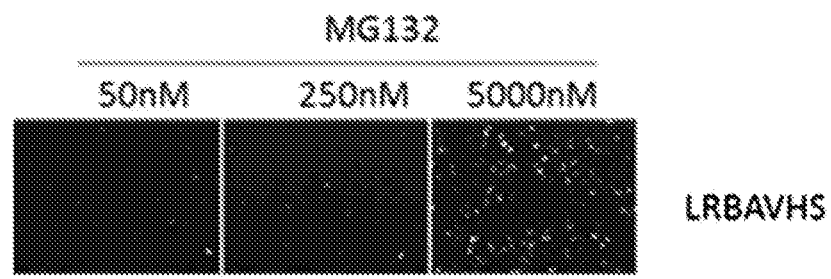
Figure 28C:
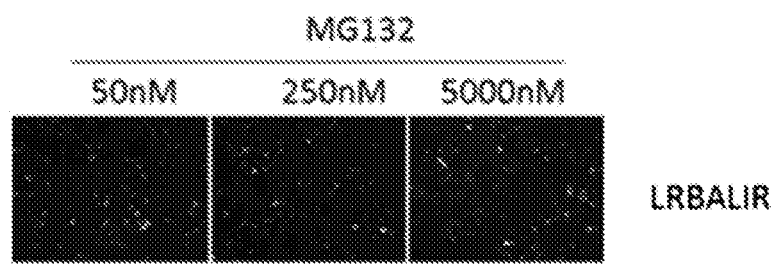
Figure 28D:
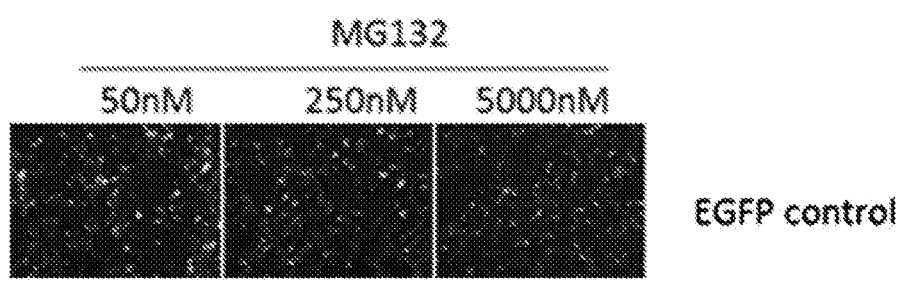
Figure 28E:
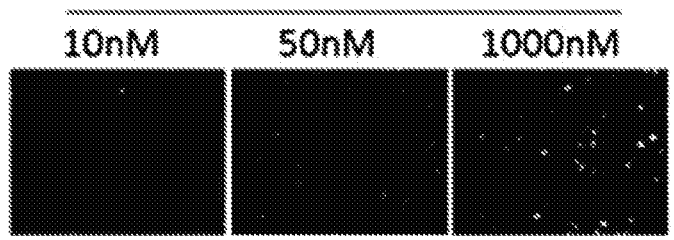
Figure 28F:
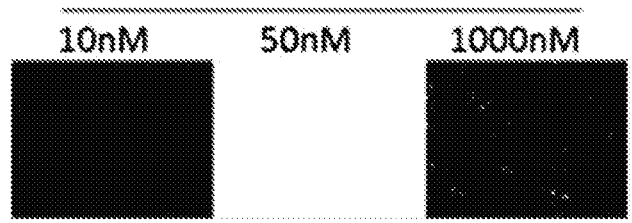
Figure 28G:
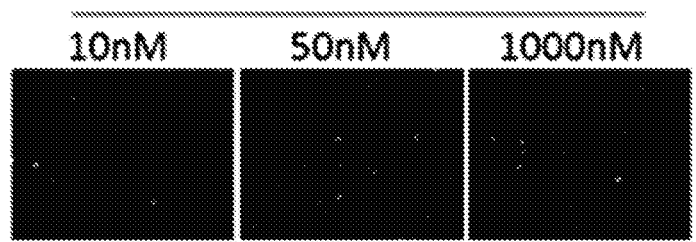
Figure 28H:
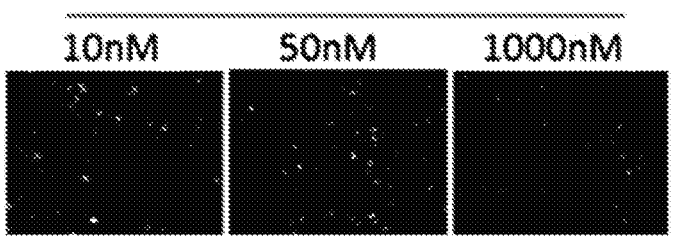

FIG. 26E shows that LRBA is important for cell growth. E. CFA of A549 was obtained from the same experiments as in B.

FIG. 27 shows LRBA promoter region of −438 to +43 (relative to the translation start codon as boxed). Putative binding sites for NF-κB and p53 factors are shown. The two NFκB binding sites are highly homologous to the B element (GGGACTTTCC) at 90% and 80%, respectively, and conserved in mouse and human. The arrows indicate the mutations are created in reporter constructs. Luciferase gene are fused in-frame with LRBA 5' coding sequence as shown.

FIGS. 28(A)-(D) are a series of images showing LRBA is regulated by Ubiquitin-dependent protein degradation system. HEK293 (Human embryo kidney) cells were seeded in 24 well plates at 4×10$^5$ per well overnight, then transfected with 0.8 ng of the following plasmid DNAs per well with Lipofectamine-2000 following the manufacturer's instruction: (A) MG132-treated cells transfected with pLRBA-VHSLIR, (B) MG132-treated cells transfected with pLRBA-VHS, (C) MG132-treated cells transfected with pLRBA-LIR and (D) MG132-treated cells transfected with cloning vector pEGFP-C3;

FIGS. 28E-H are a series of images showing LRBA is regulated by Ubiquitin-dependent protein degradation system. HEK293 (Human embryo kidney) cells were seeded in 24 well plates at 4×10$^5$ per well overnight, then transfected with 0.8 ng of the following plasmid DNAs per well with Lipofectamine-2000 following the manufacturer's instruction: (E) PS341-treated cells transfected with pLRBA-VHS-LIR, (F) PS341-treated cells transfected with pLRBA-VHS, (G) PS341-treated cells transfected with pLRBA-LIR and (H) PS341-treated cells transfected with cloning vector pEGFP-C3. After 24 hours, media were changed and cells were treated with MG132 and PS341 at the concentration indicated in the figure and microscopy pictures were taken after overnight.

Figure 29A:
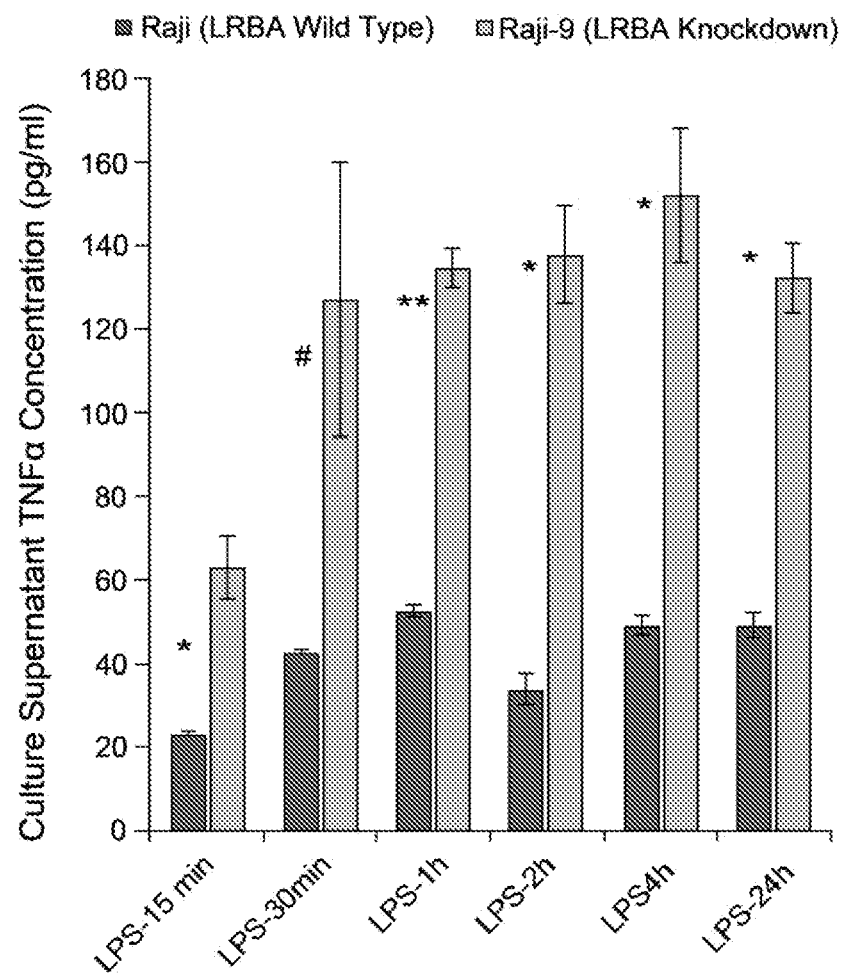
Figure 29B:
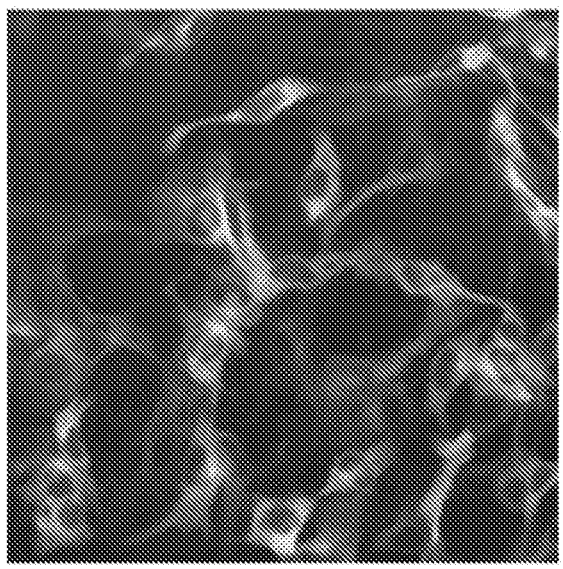

FIGS. 29(A) and (B) are images showing whole length of LRBA gene is fused with EGFP then transfected into H293 cells. Stable clones were screened with 500 µg/ml of G418 for 25 days. The GFP fluorescence pattern of LRBA GFP fusion is similar to that of tubulin. Filaments are seen. The explanation for this that there are many LRBA/GFP associated vesicles traveling along the cytoskeleton filaments.

FIG. 30(A) is an alignment showing LRBA is regulated by microRNAs. (A) Human and mouse LRBA have miR-150 site.

FIG. 30B is an alignment showing LRBA is regulated by microRNAs. (B) Human, mouse and other 21 vertebrate LRBA genes have miR-181 sites.

| Hsa | Human | Homo sapiens |
|---|---|---|
| Ptr | Chimpanzee | Pan troglodytes |
| Mnnl | Rhesus | Macaca mulatta |
| Oga | Bushbaby | Otolemur garnetti |
| Tbe | Treeshrew | Tupaia belangeri |
| Mnnu | Mouse | Mus musculus |
| Rno | Rat | Rattus norvegicus |
| Cpo | Guinea pig | Cavia porcellus |
| Ocu | Rabbit | Oryctolagus cuniculus |
| Sar | Shrew | Sorex araneus |
| Eeu | Hedgehog | Erinaceus europaeus |
| Cfa | Dog | Canis fanniliaris |
| Fca | Cat | Felis catus |
| Eca | Horse | Equus caballus |
| Bta | Cow | Bos taurus |
| Dno | Armadillo | Dasypus novenncinctus |
| Laf | Elephant | Loxodonta africana |
| Ete | Tenrec | Echinops telfairi |
| Mdo | Opossum | Monodelphis donnestica |
| Oan | Platypus | Ornithorhynchus anatinus |
| Aca | Lizard | Anolis carolinensis |
| Gga | Chicken | Gallus gallus |
| Xtr | Frog | Xenopus tropicalis |

Figure 30C:
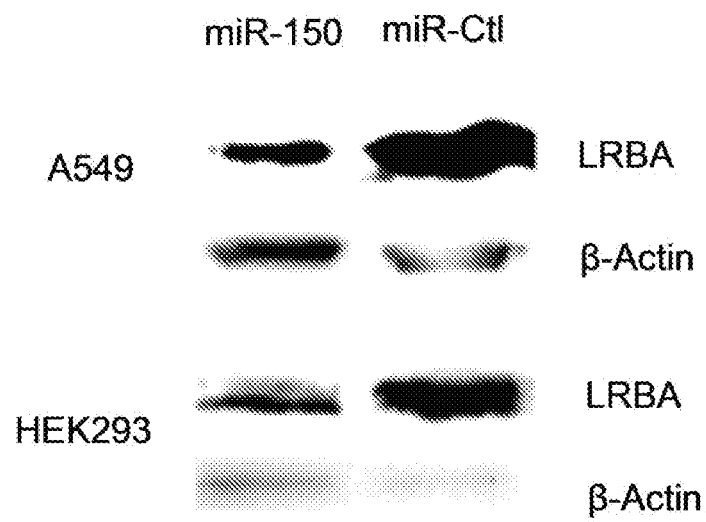
Figure 30D:
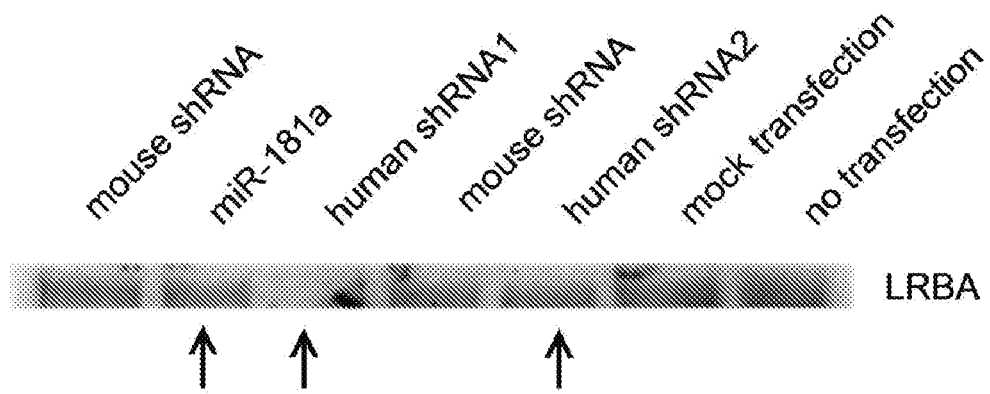

FIGS. 30C-D is a series of blots showing LRBA is regulated by microRNAs. (C). Western blot results show LRBA is downregulated by overexpression miR-150. (D) Western blot results show LRBA is downregulated by overexpression miR-181.

Figure 31A:
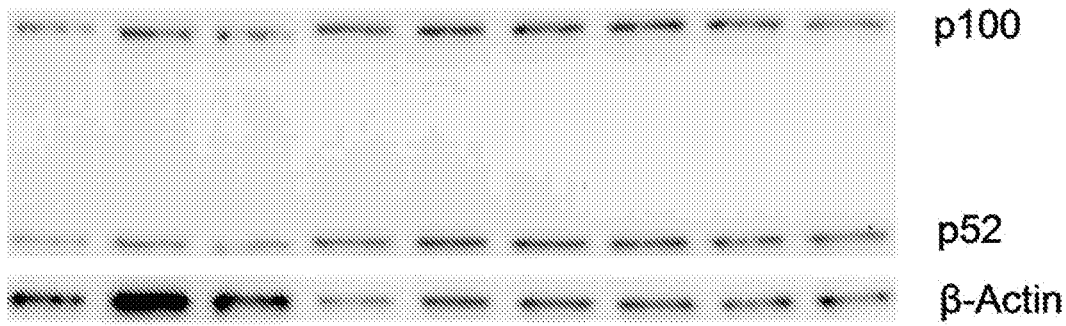
Figure 31B:
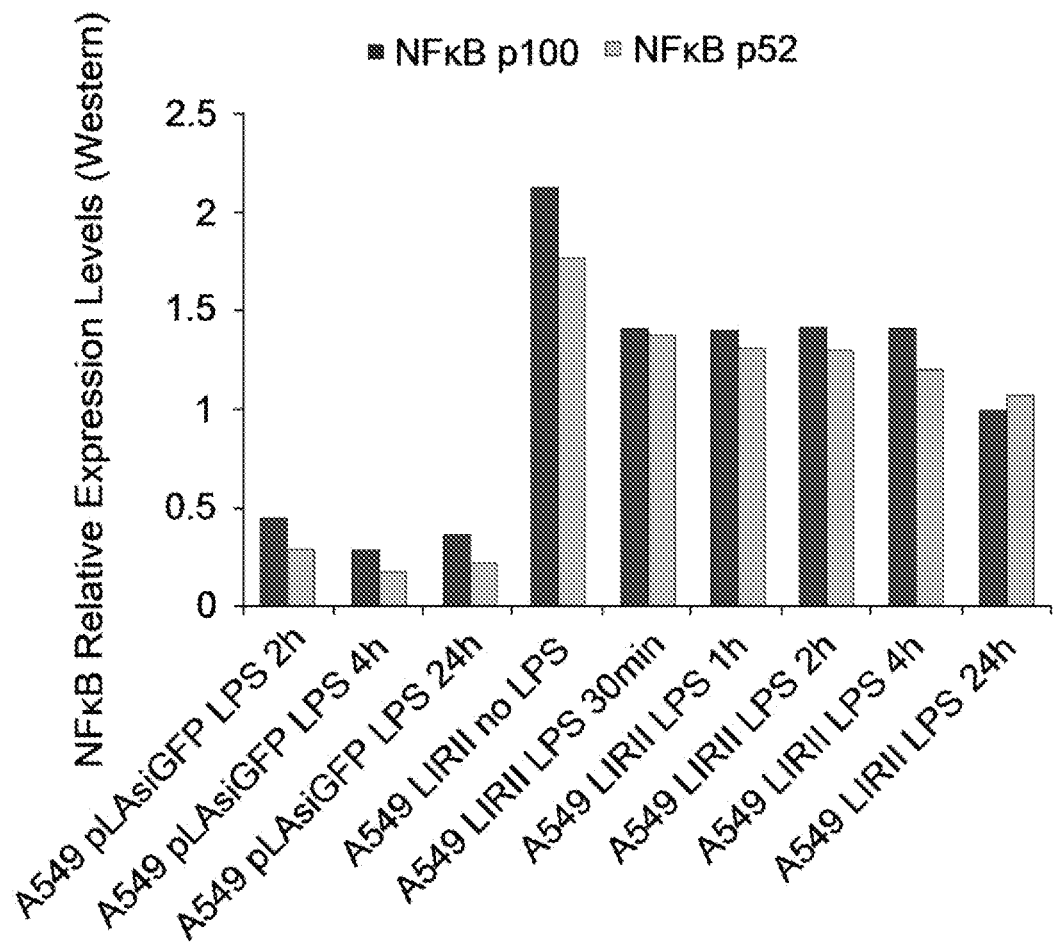

FIGS. 31(A) and (B) are a blot and graph showing knockdown of LRBA decreases the total NFκB levels in A549 cells. A549 LIRII cells (stably transfected with pLRBA-VHS) and A549 pLAsiGFP cells (stably transfected with shRNA plasmid against LRBA) were treated with LPS (1 µg/ml). The NFκB concentrations were detected by Western blot. Cells were cultured in 6-well plates and stimulated with LPS (1 µg/ml) for different time as shown, then lysed with RIPA buffer. Western blots were carried out. NF-κB2 p100/p52 Antibody #4882 (Cell Signaling Technology, Danvers, Mass., USA) was used at 1:500 ratio and incubated at 4° C. overnight. BioRad ChemiDoc XRS and Quantity One software were used to acquire gel image and measure band relative intensity. A. Western blot. B. Band intensity quantification from A.

Figure 32A:
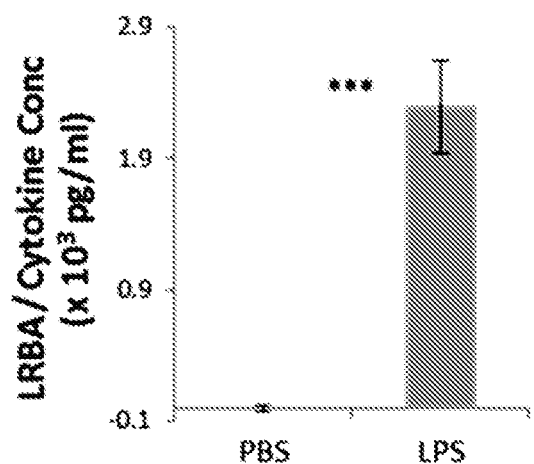
Figure 32B:
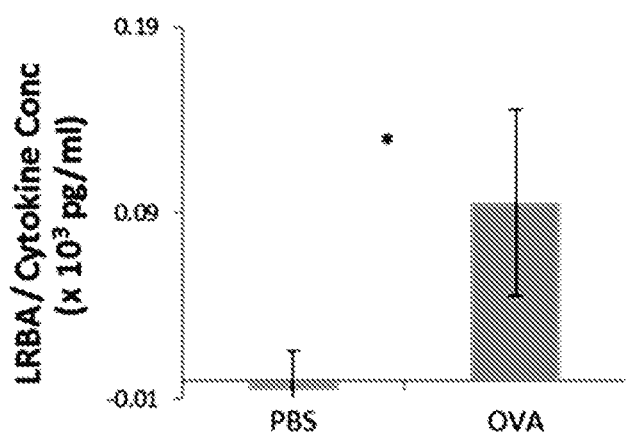
Figure 32C:
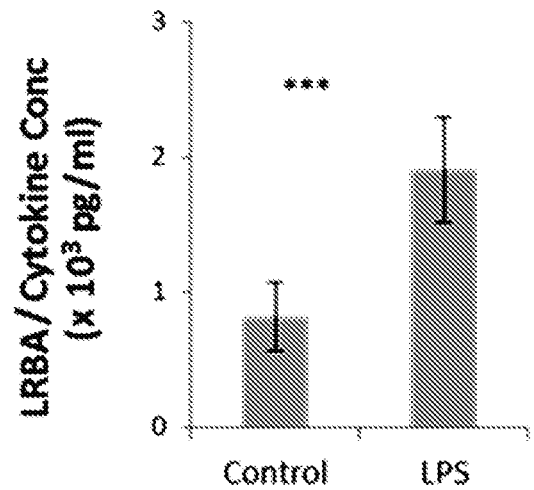

FIG. 32(A)-(C) are graphs showing plasma or extracellular LRBA levels are increased significantly in inflammation. LRBA levels are increased significantly in plasma from mice stimulated with LPS (A, n=3, 4) or OVA (B, n=3, 5), in culture media of human mononucleocytes stimulated with LPS (C, n=5,11)

Figure 32D:
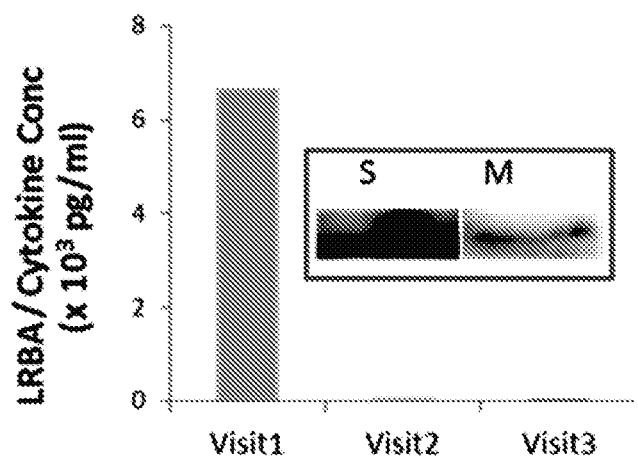

FIG. 32D is a graph showing plasma or extracellular LRBA levels are increased significantly in inflammation. In plasma from subjects at first visit (D, n=4) compared to the second and third (with controlled symptoms, n=2, 2) visits (inset: LRBA Western blot, plasma supernatant (S) & membrane (M) fractions from ultracentrifugation).

Figure 32E:
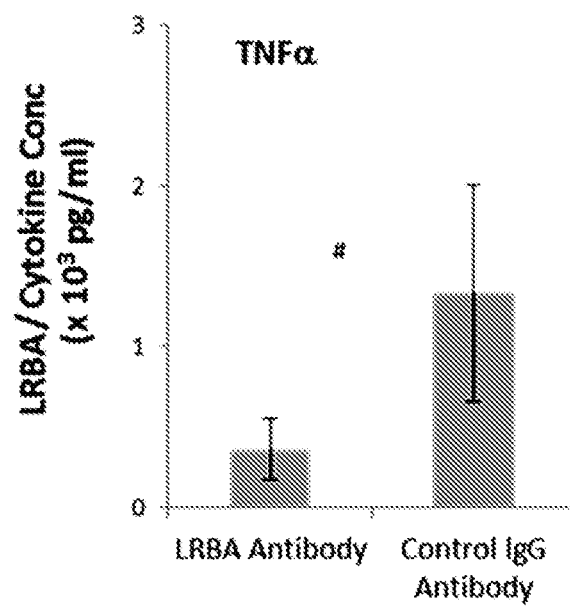

FIG. 32E is a graph showing proinflammatory cytokine TNFa levels are decreased in plasma of mice contacted with LRBA antibody as compared to those contacted with control IgG antibody.

Figure 32F:
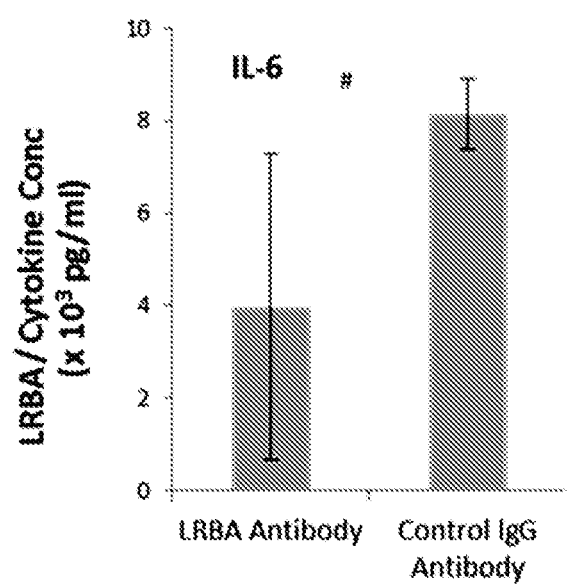

FIG. 32F is a graph showing proinflammatory cytokine IL-6 levels are decreased in plasma of mice contacted with LRBA antibody as compared to those contacted with control IgG antibody.

Figure 33A:
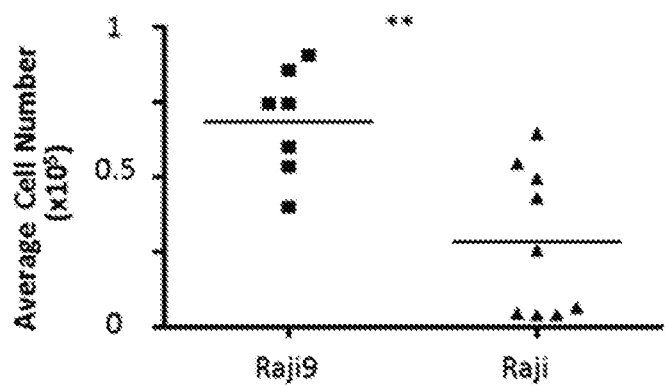
Figure 33B:
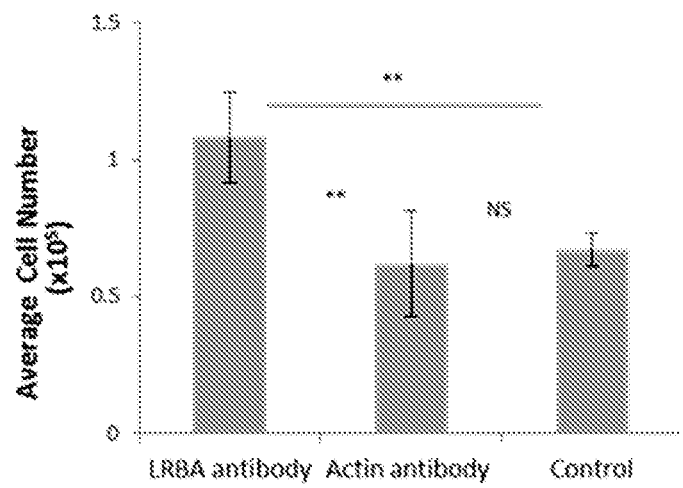
Figure 33C:
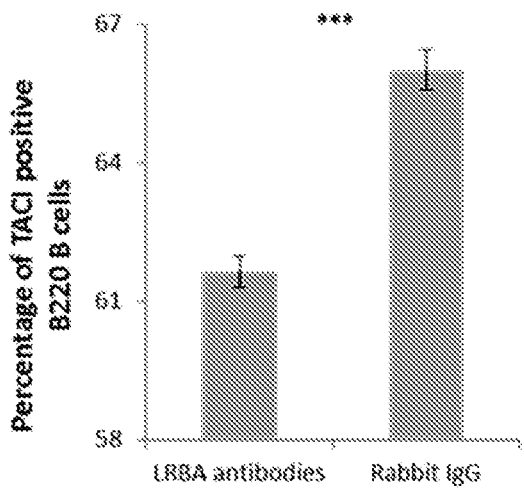

FIGS. 33(A)-(C) are a series of graphs showing a mouse model and LRBA antibodies treatment. Asthma patients with an exacerbation or controlled symptoms. Cell survival is increased by knockdown (A) or antibody blockage (B) seen in THP1 cells (n=5) of LRBA. (C) Two million splenocytes from C57BL/6J mice were culture in 24-well plate with 500 µl culture media, with 2 µg/ml LRBA antibodies (9415) or anti-rabbit IgG control antibodies for 24 hours under LPS (1 µg/ml) stimulation. Anti-mouse TACI antibodies were used to detect TACI.

Figure 34A:
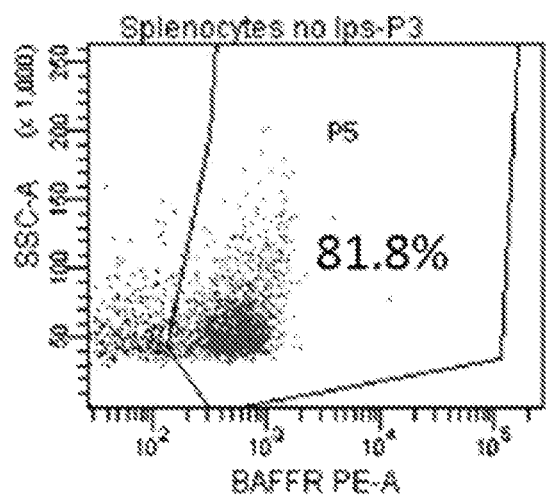
Figure 34B:
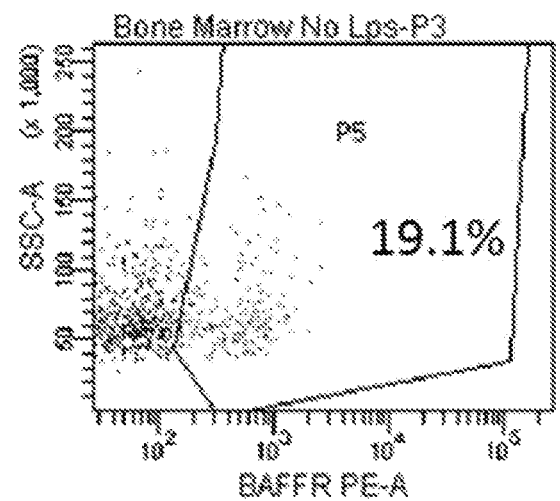

FIG. 34(A)-(B) are graphs showing LPS regulates BAFFR in vivo and in vitro. C57BL/6J mice of 2-month age were injected intraperitoneally with LPS (5 µg/g body weight) or PBS (control). For in vitro LPS stimulation, cells from mouse spleen or bone marrow were cultured with or without LPS (1 µg/ml) for 24 hr. Cells were stained with fluorophores-conjugated BAFFR and TACI antibodies and DAPI for dead/live discrimination and analyzed with cytometry. (A) Spleocytes without LPS-P3, (B) bone marrow cells without LPS-P3. Negative gating was based on B220 negative cells, which are negative for BAFFR and TACI. Numbers other than percentage are arbitrary MFI units. All experiments were done in triplicate for in the vitro experiment and data shown is representative of two separate experiments.

Figure 34C:
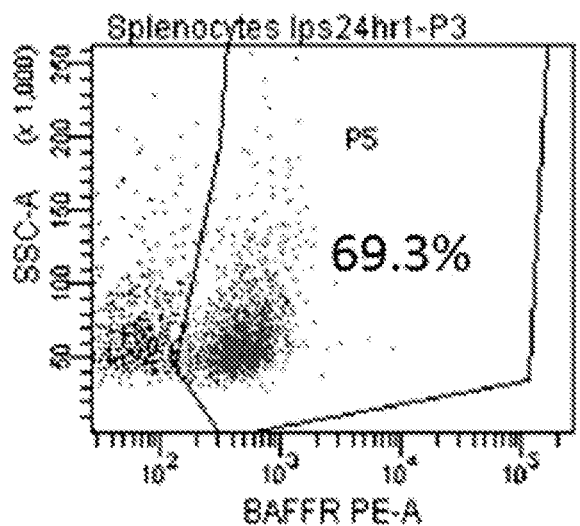
Figure 34D:
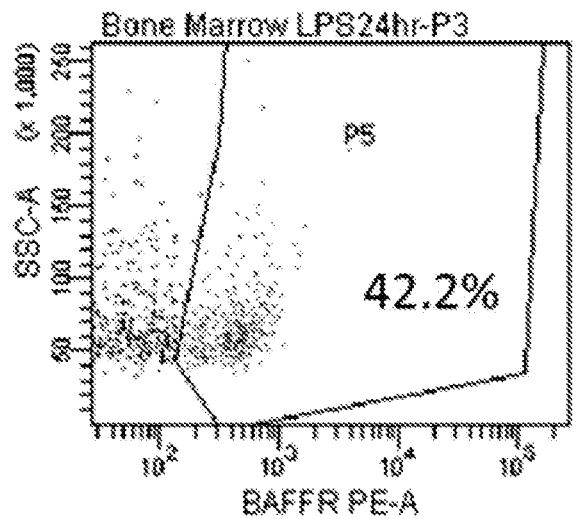

FIGS. 34C-D are graphs showing LPS regulates BAFFR in vivo and in vitro. C57BL/6J mice of 2-month age were injected intraperitoneally with LPS (5 µg/g body weight) or PBS (control). For in vitro LPS stimulation, cells from mouse spleen or bone marrow were cultured with or without LPS (1 µg/ml) for 24 hr. Cells were stained with fluorophores-conjugated BAFFR and TACI antibodies and DAPI for dead/live discrimination and analyzed with cytometry. (C) spleocytes with LPS for 24 hours, (D) bone marrow cells with LPS for 24 hours. Negative gating was based on B220 negative cells, which are negative for BAFFR and TACI. Numbers other than percentage are arbitrary MFI units. All experiments were done in triplicate for in the vitro experiment and data shown is representative of two separate experiments.

Figure 34E:
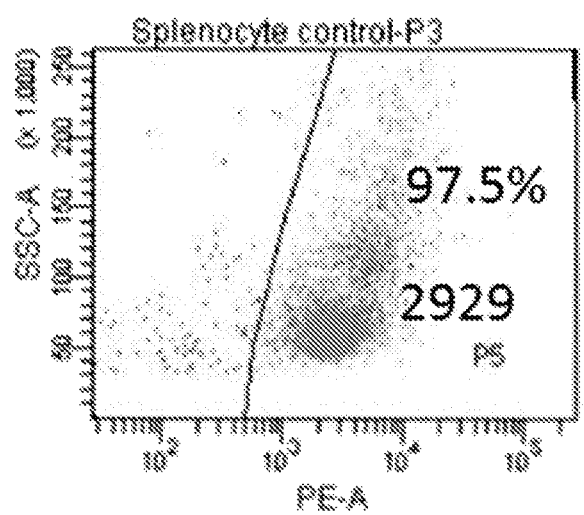
Figure 34F:
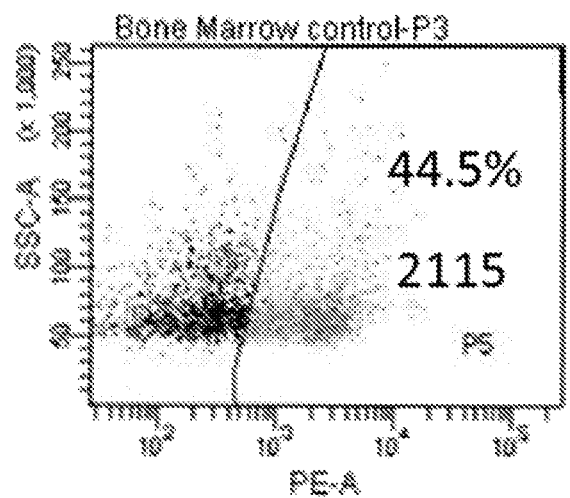

FIGS. 34E-F are graphs showing LPS regulates BAFFR in vivo and in vitro. C57BL/6J mice of 2-month age were injected intraperitoneally with LPS (5 µg/g body weight) or PBS (control). For in vitro LPS stimulation, cells from mouse spleen or bone marrow were cultured with or without LPS (1 µg/ml) for 24 hr. Cells were stained with fluorophores-conjugated BAFFR and TACI antibodies and DAPI for dead/live discrimination and analyzed with cytometry. (E) spleocytes control, (F) bone marrow cell control. Negative gating was based on B220 negative cells, which are negative for BAFFR and TACI. Numbers other than percentage are arbitrary MFI units. All experiments were done in triplicate for in the vitro experiment and data shown is representative of two separate experiments.

Figure 34G:
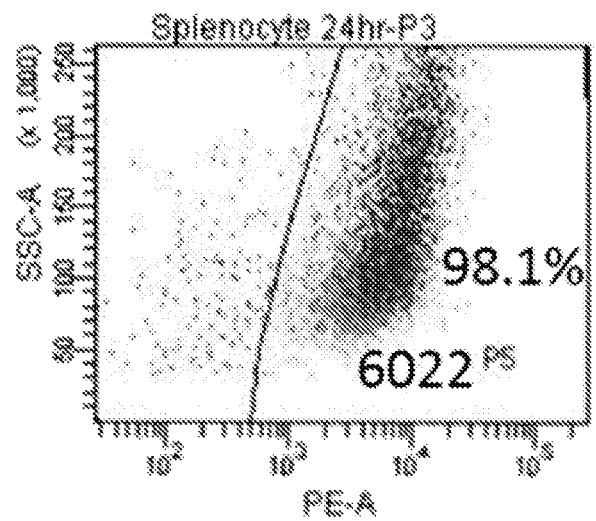
Figure 34H:
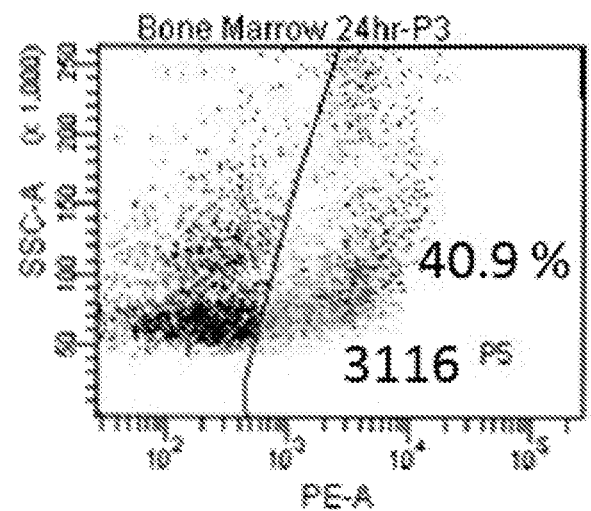

FIGS. 34G-H are graphs showing LPS regulates BAFFR in vivo and in vitro. C57BL/6J mice of 2-month age were injected intraperitoneally with LPS (5 µg/g body weight) or PBS (control). For in vitro LPS stimulation, cells from mouse spleen or bone marrow were cultured with or without LPS (1 µg/ml) for 24 hr. Cells were stained with fluorophores-conjugated BAFFR and TACI antibodies and DAPI for dead/live discrimination and analyzed with cytometry. (G) splenocyte control at 24 hours in PBS, and (H) bone marrow cell control at 24 hours in PBS. TACI is upregulated by LPS in vivo (n=3 for each group) and in vitro in both tissues. Negative gating was based on B220 negative cells, which are negative for BAFFR and TACI. Numbers other than percentage are arbitrary MFI units. All experiments were done in triplicate for in the vitro experiment and data shown is representative of two separate experiments.

Figure 35A:
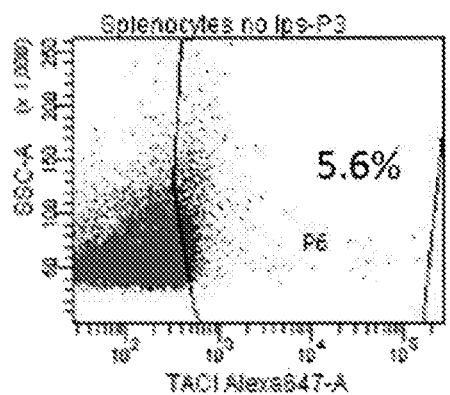
Figure 35B:
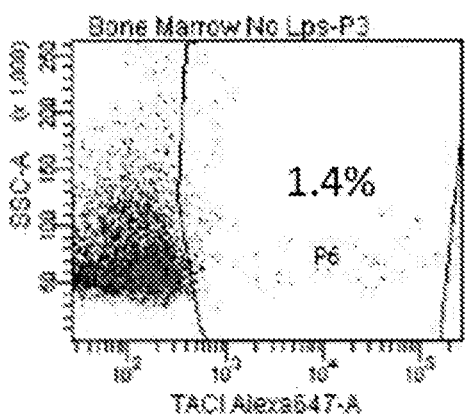
Figure 35C:
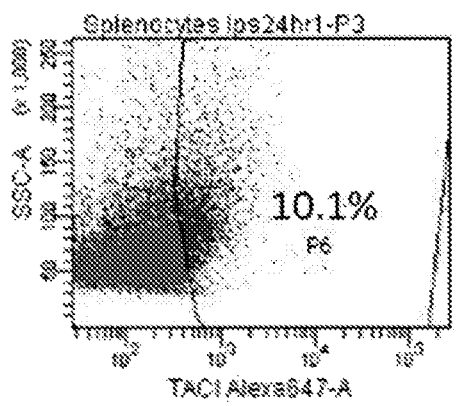

FIG. 35(A)-(C) are graphs showing LPS regulates TACI in vivo and in vitro. C57BL/6J mice of 2 month age were injected intraperitoneally with LPS (5 µg/g body weight) or PBS (upper panels). For in vitro LPS stimulation, cells from mouse spleen or bone marrow were cultured with or without LPS (1 µg/ml) (lower panels) for 24 hr. Cells were stained with fluorophores-conjugated BAFFR and TACI antibodies and DAPI for dead/live discrimination and analyzed with cytometry. TACI is upregulated by LPS in vivo (n=3 for each group) and in vitro in both tissues. Negative gating was based on B220 negative cells, which are negative for BAFFR and TACI. (A) in vivo splenocytes treated with PBS; (B) in vivo bone marrow cells treated with PBS; (C) in vivo splenocytes treated with LPS; Numbers other than percentage are arbitrary MFI units. All experiments were done in triplicate for in the vitro experiment and data shown is representative of two separate experiments.

Figure 35D:
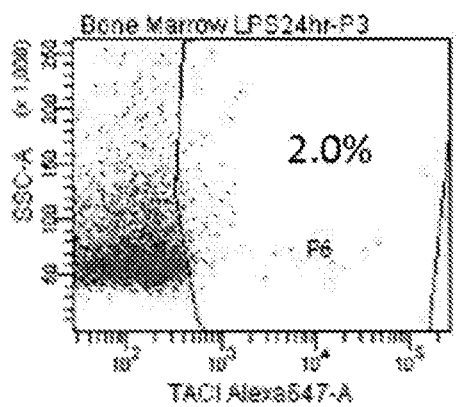
Figure 35E:
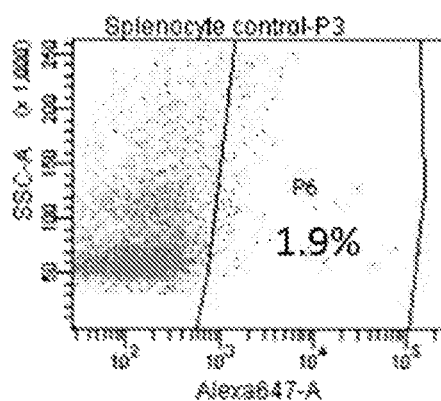
Figure 35F:
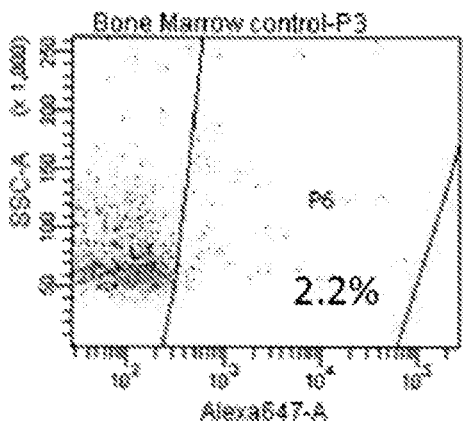

FIG. 35D-F are graphs showing LPS regulates TACI in vivo and in vitro. C57BL/6J mice of 2 month age were injected intraperitoneally with LPS (5 µg/g body weight) or PBS (upper panels). For in vitro LPS stimulation, cells from mouse spleen or bone marrow were cultured with or without LPS (1 µg/ml) (lower panels) for 24 hr. Cells were stained with fluorophores-conjugated BAFFR and TACI antibodies and DAPI for dead/live discrimination and analyzed with cytometry. TACI is upregulated by LPS in vivo (n=3 for each group) and in vitro in both tissues. Negative gating was based on B220 negative cells, which are negative for BAFFR and TACI. (D) in vivo bone marrow cells treated with LPS; (E) in vitro splenocytes treated with PBS; (F) in vitro bone marrow cells treated with PBS; Numbers other than percentage are arbitrary MFI units. All experiments were done in triplicate for in the vitro experiment and data shown is representative of two separate experiments.

Figure 35G:
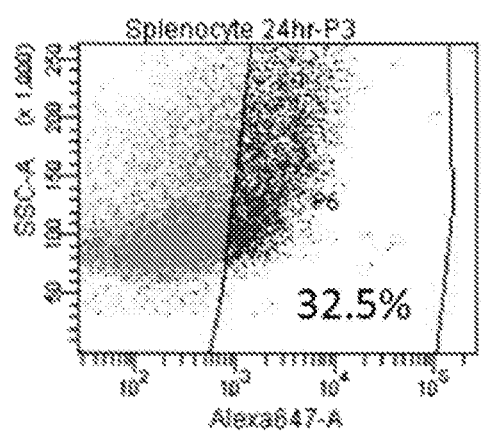
Figure 35H:
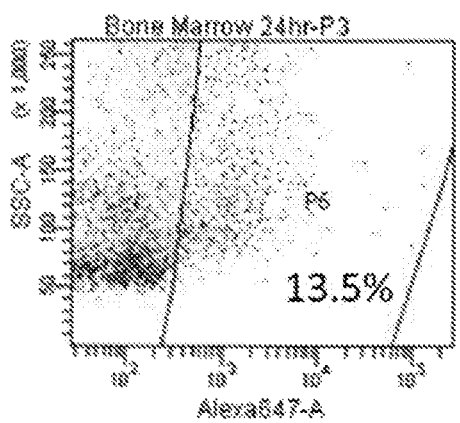

FIG. 35G-H are graphs showing LPS regulates TACI in vivo and in vitro. C57BL/6J mice of 2 month age were injected intraperitoneally with LPS (5 µg/g body weight) or PBS (upper panels). For in vitro LPS stimulation, cells from mouse spleen or bone marrow were cultured with or without LPS (1 µg/ml) (lower panels) for 24 hr. Cells were stained with fluorophores-conjugated BAFFR and TACI antibodies and DAPI for dead/live discrimination and analyzed with cytometry. TACI is upregulated by LPS in vivo (n=3 for each group) and in vitro in both tissues. Negative gating was based on B220 negative cells, which are negative for BAFFR and TACI. (G) in vitro splenocytes treated with LPS; (H) in vitro bone marrow wells treated with LPS. Numbers other than percentage are arbitrary MFI units. All experiments were done in triplicate for in the vitro experiment and data shown is representative of two separate experiments.

Figure 36A:
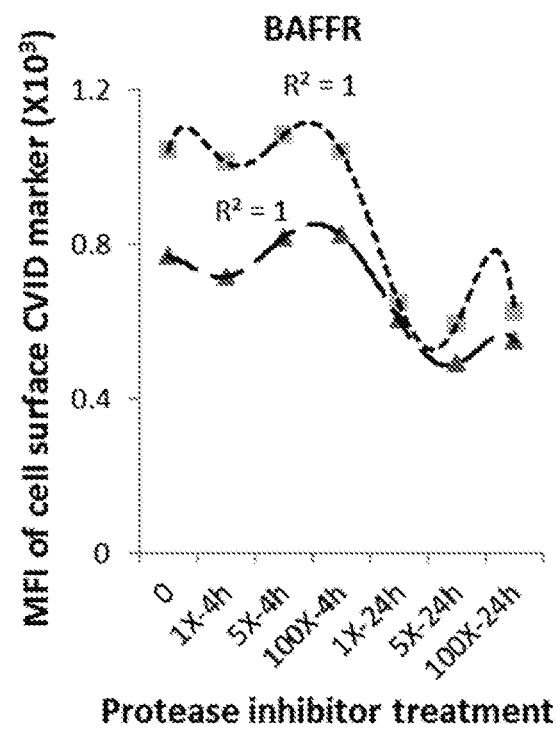
Figure 36B:
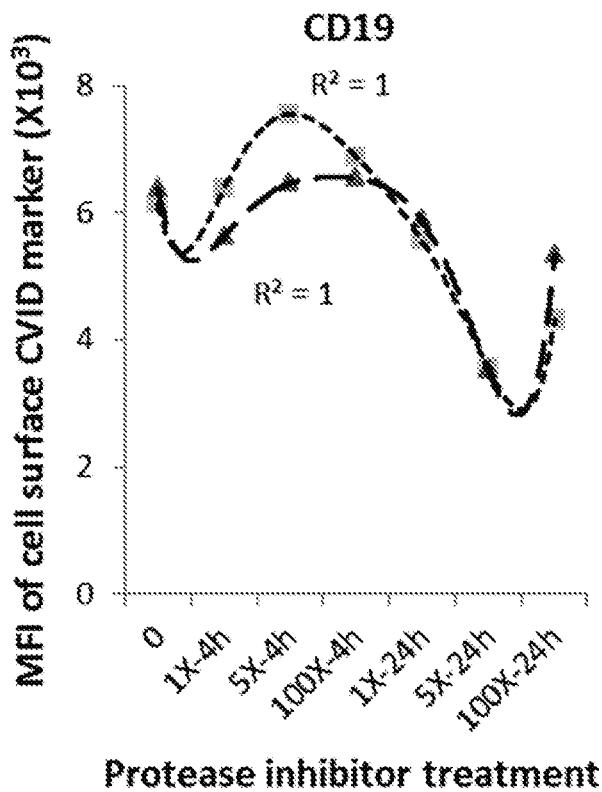

FIGS. 36(A)-(B) are graphs showing repression of LRBA by shRNA knockdown influences the levels of TLR4, multiple CVID receptors. Raji B cells were transfected with LRBA shRNA plasmid and control plasmid and stable clones were obtained by G418 selection. Cells were treated with LPS (1 μg/ml) for 15 min (1), 30 min (2), 1 h (3), 2 h (4), 4 h (5), 24 h (6). Cells were stained with fluorophores-conjugated Cells were stained for CVID antibodies and DAPI for dead/live discrimination and analyzed with cytometry. CVID antibodies were BAFFR (A), CD19 (B), and TACI (C). A. Median fluorescence intensity (MFI): LRBA WT(●), LRBA KD (x); B. Percentage:): LRBA WT (■), LRBA KD (▲). Data are representative of 2 to 3 separate experiments. MG132 was used.

Figure 36C:
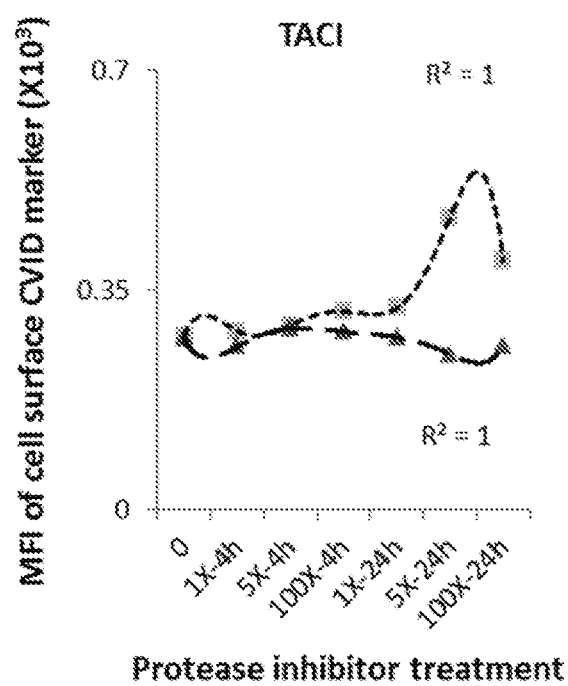

FIG. 36C is a graph showing repression of LRBA by shRNA knockdown influences the levels of TLR4, multiple CVID receptors. Raji B cells were transfected with LRBA shRNA plasmid and control plasmid and stable clones were obtained by G418 selection. Cells were treated with LPS (1 μg/ml) for 15 min (1), 30 min (2), 1 h (3), 2 h (4), 4 h (5), 24 h (6). Cells were stained with fluorophores-conjugated Cells were stained for CVID antibodies and DAPI for dead/live discrimination and analyzed with cytometry. CVID antibodies were BAFFR (A), CD19 (B), and TACI (C). A. Median fluorescence intensity (MFI): LRBA WT(●), LRBA KD (x); B. Percentage:): LRBA WT (■), LRBA KD (▲). Data are representative of 2 to 3 separate experiments. MG132 was used.

Figure 37A:
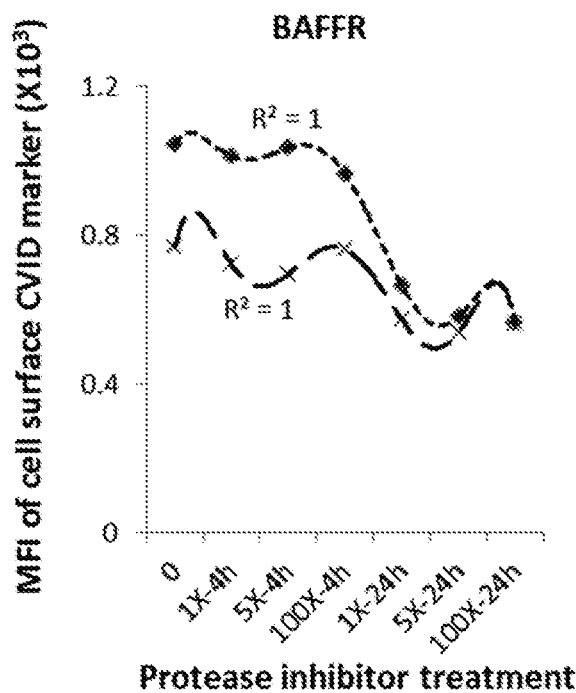
Figure 37B:
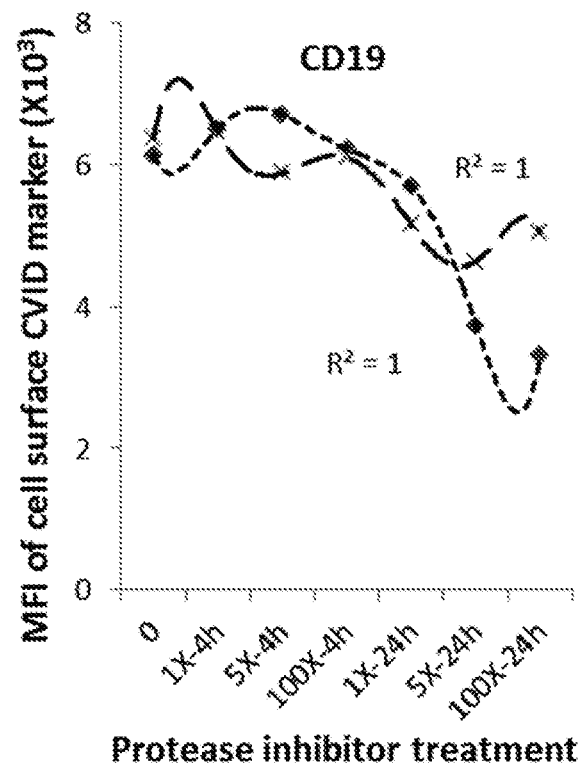

FIGS. 37(A)-(B) are graphs showing repression of LRBA by shRNA knockdown influences the levels of TLR4, multiple CVID receptors. Raji B cells were transfected with LRBA shRNA plasmid and control plasmid and stable clones were obtained by G418 selection. Cells were treated with LPS (1 μg/ml) for 15 min (1), 30 min (2), 1 h (3), 2 h (4), 4 h (5), 24 h (6). Cells were stained with fluorophores-conjugated CVID antibodies and DAPI for dead/live discrimination and analyzed with cytometry. CVID antibodies were BAFFR (A), CD19 (B), and TACI (C). A. Median fluorescence intensity (MFI): LRBA WT(●), LRBA KD (x); B. Percentage:): LRBA WT (■), LRBA KD (▲). Data are representative of 2 to 3 separate experiments. PS341 was used.

Figure 37C:
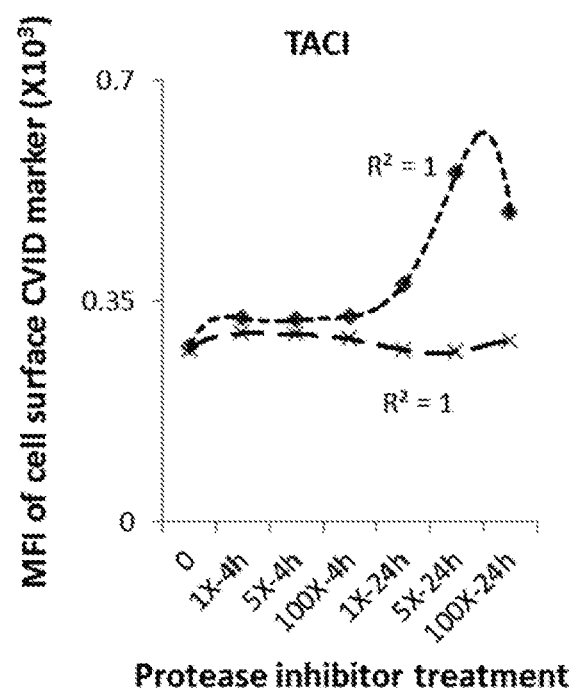

FIG. 37C is a graph showing repression of LRBA by shRNA knockdown influences the levels of TLR4, multiple CVID receptors. Raji B cells were transfected with LRBA shRNA plasmid and control plasmid and stable clones were obtained by G418 selection. Cells were treated with LPS (1 μg/ml) for 15 min (1), 30 min (2), 1 h (3), 2 h (4), 4 h (5), 24 h (6). Cells were stained with fluorophores-conjugated CVID antibodies and DAPI for dead/live discrimination and analyzed with cytometry. CVID antibodies were BAFFR (A), CD19 (B), and TACI (C). A. Median fluorescence intensity (MFI): LRBA WT(●), LRBA KD (x); B. Percentage:): LRBA WT (■), LRBA KD (▲). Data are representative of 2 to 3 separate experiments. PS341 was used.

FIG. 38(A)-(F) are graphs showing the effects of LRBA knockdown using dominant negative influences the levels of multiple CVID receptors. LRBA WT and LRBA KD Raji cells were stimulated with LPS, and the cell surface levels of CVID receptors and TLR4 were analyzed by flow cytometry. Raji B cells were electroporated with different LRBA DNMs: 1. LRBA-VHSLIR, 2. LRBA-VHS, 3. LRBA-LIR and 4. LRBA-BEACH. Blues: GFP positive; Red: GFP negatives. Cells were stained with fluorophores-conjugated CVID antibodies and DAPI for dead/live discrimination and analyzed with cytometry. A GFP marker was used to distinguish transfected and untransfected Raji cells. Cells were treated with LPS (1 μg/ml) for 24 h. CVID probes were CD19 (A), CD20 (B), BAFFR (C), TACI (D), CD21 (E), and TLR4 (F). Median fluorescence intensity (MFI). LRBA DNM: first column in each series. LRBA WT: second column in each series.

FIG. 39(A)-(F). Repression of LRBA with dominant negative influences the levels of multiple CVID receptors. Raji B cells were electroporated with different LRBA DNMs: 1. LRBA-VHSLIR, 2. LRBA-VHS, 3. LRBA-LIR and 4. LRBA-BEACH. Blues: GFP positive; Red: GFP negatives. Cells were stained with fluorophores-conjugated CVID antibodies and DAPI for dead/live discrimination and analyzed with cytometry. A GFP marker was used to distinguish transfected and untransfected Raji cells. Cells were treated with LPS (1 μg/ml) for 24 h. CVID probes were CD19 (A), CD20 (B), BAFFR (C), TACI (D), CD21 (E), and TLR4 (F). Percentage of positive cells were measured.

FIG. 40(A)-(D). LRBA potential dominant negative mutants (DNM) fused with green fluorescent protein (GFP) were constructed from BEACH (Beige and Chediak-Higashi), VHS-LIR [VPS (vacuolar protein sorting), Hrs (hepatocyte growth factor-regulated tyrosine kinase substrate) and STAM (signal transducing adaptor molecule), LC3 (light chain 3) Interacting Region], VHS and LIR domains and transfected into Raji cells. CVID and TLR4 receptors were analyzed in the GFP positive and negative populations. CVID probes were CD21 (A), CD20 (B), TACI (C), and BAFFR (D).

FIGS. 41(A)-(D). LRBA potential dominant negative mutants and wild type were transfected into Raji cells. CVID and TLR4 receptors were analyzed in the GFP positive and negative populations. CVID probes were CD21 (A), CD20 (B), TACI (C), and BAFFR (D).

Figures 42A, 42B:
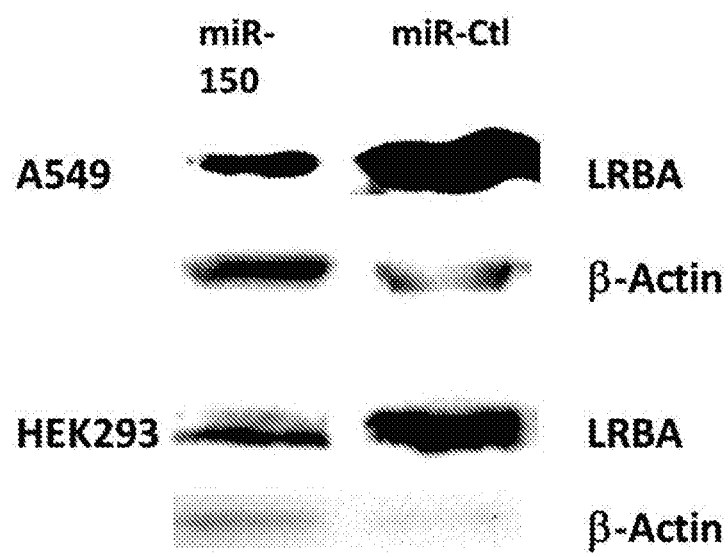

FIGS. 42(A) and (B). (A) Overexpression of miR-150 down-regulates LRBA. A549 and HEK293 cells transfected with the vectors that overexpress miR-150 or a control miRNA. After 48 hours, cell lysates were prepared and subjected to Western blotting with LRBA antibody. (B) a comparison of LRBA is different species compared to miR-150.

Figure 43A:
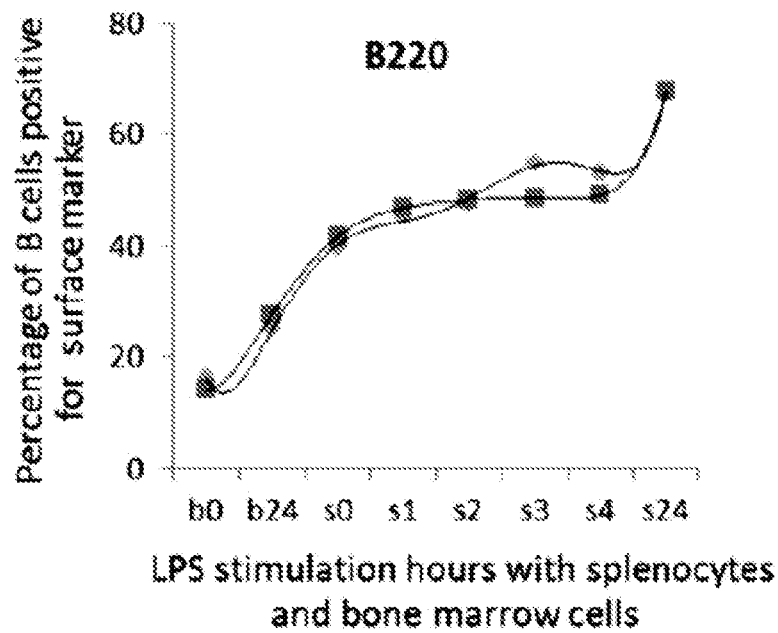
Figure 43B:
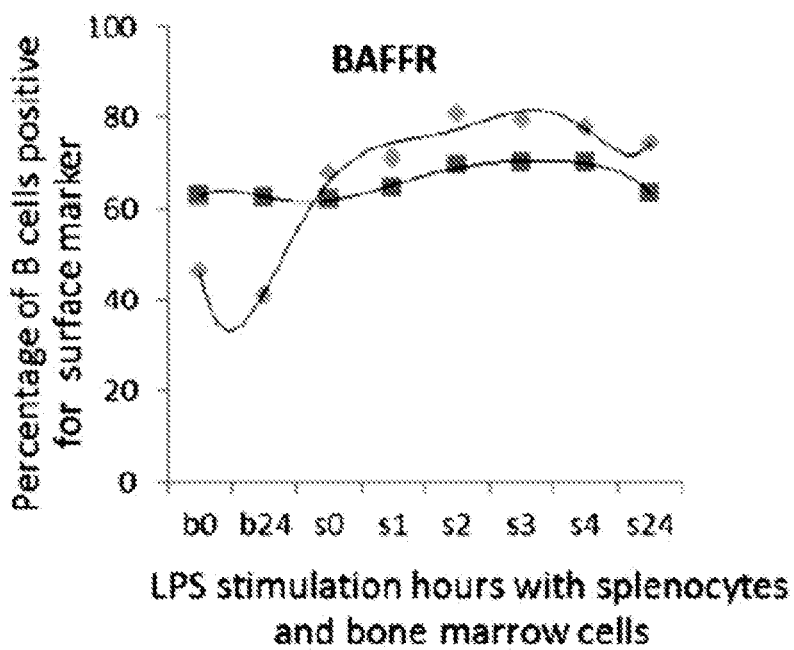

FIG. 43(A)-(B). Proteasome inhibitors decrease the levels of BAFFR and CD19 but increased the levels of TACI. Raji and Raji9 cells were treated with NFkB inhibitors MG-132 and PS-341 at different doze (for MG-132 1x=50 nM, 5x=250, 100x=5000 nM; PS-341: 10 nM, 50, 1000 nM). Raji/MG-132(■), Raji/PS-341(♦), Raji9/MG-132(▲) Raji9/PS-341(x). All samples were stimulated with LPS at 1 mg/ml. Trend lines with short dash are for Raji cells, while trend lines with long dash are for Raji9 cells. Probes were conducted for (A) B220, (B) BAFFR.

Figure 43C:
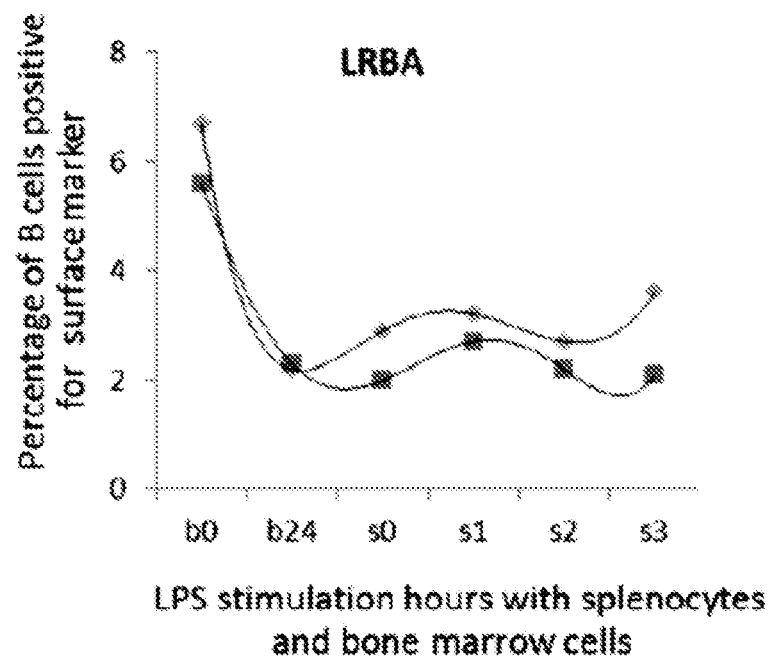
Figure 43D:
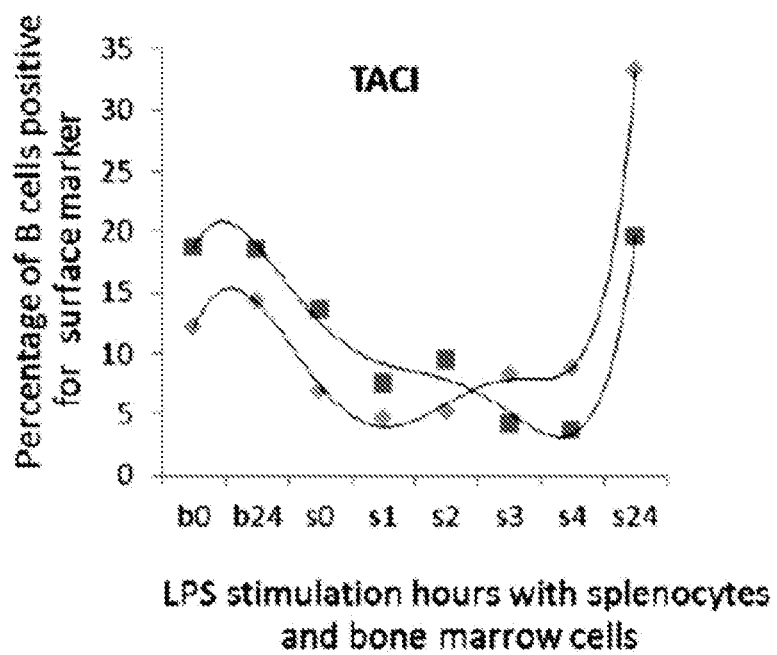

FIG. 43C-D. Proteasome inhibitors decrease the levels of BAFFR and CD19 but increased the levels of TACI. Raji and Raji9 cells were treated with NFkB inhibitors MG-132 and PS-341 at different doze (for MG-132 1x=50 nM, 5x=250, 100x=5000 nM; PS-341: 10 nM, 50, 1000 nM). Raji/MG-132(■), Raji/PS-341(♦), Raji9/MG-132(▲), Raji9/PS-341(x). All samples were stimulated with LPS at 1 mg/ml. Trend lines with short dash are for Raji cells, while trend lines with long dash are for Raji9 cells. Probes were conducted for (C) LRBA, and (D) TACI.

Figure 44A:
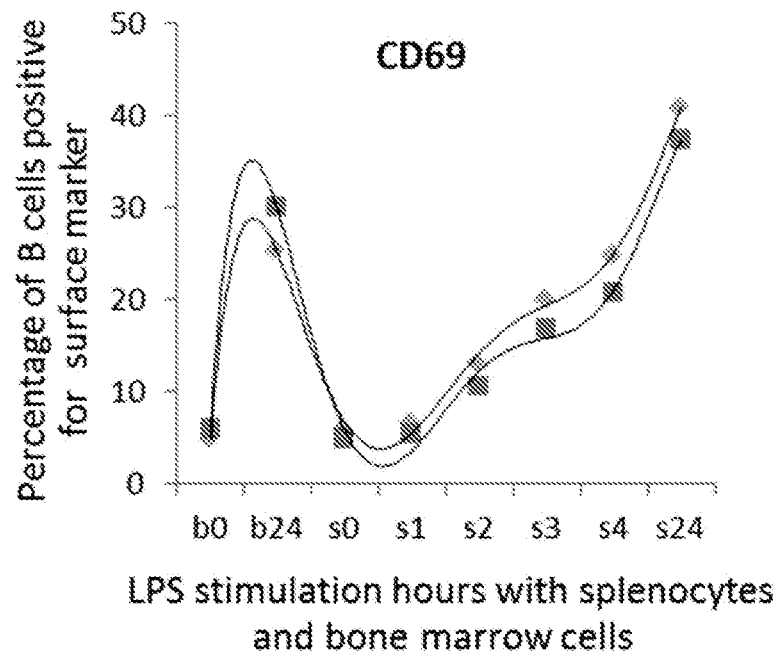

FIGS. 44(A) and (B). Proteasome inhibitors have minor effect on the levels of CVID CD69 and TLR4. Raji and Raji9 cells were treated with NFkB inhibitors MG-132 and PS-341 at different doze (for MG-132 1×=50 nM, 5×=250, 100×=5000 nM; PS-341: 10 nM, 50, 1000 nM). Raji/MG-132(■), Raji/PS-341(♦), Raji9/MG-132(▲), Raji9/PS-341(x). All samples were stimulated with LPS at 1 mg/ml. Trend lines with short dash are for Raji cells, while trend lines with long dash are for Raji9 cells. Probes were for CD69 (A) and TLR4 (B).

FIG. 45A-D. Knockdown of LRBA deregulates NFκB. (A) Knockdown of LRBA increases NFκB luciferase activity. An NFκB luciferase reporter was used to measure the NFκB transcription activity. The data are shown as scatter with bar graph of mean with standard error of mean (SEM). (B) Knockdown of LRBA increases phospho-NFκB. The Phosflow kit including Cytofix Fixation Buffer, Phosflow Perm Buffer III and Stain Buffer (BD) and phospho-antibodies, NFκB p65 (pS529) PE-Cy7 were used for the intracellular staining following the company's instruction. For each samples, 50,000 cells were recorded for the FACS assay. (C) A549 cells were stably transfected with LRBA shRNA knockdown plasmid and several clones were picked up. Half million of cells were seeded in a well of a 24 well plate and incubated overnight, then stimulated with LPS (10 μg/ml) for certain time. Luciferase assay Biotium. NFκB luciferase activity is inversely dose-dependent on the LRBA levels in A549 cells with different levels of LRBA knockdown judged by the GFP levels of the cells stably transfected with the LRBA shRNA/GFP construct. (D) LRBA KD#3, LRBA KD#4 and LRBA KD#5 clones express different levels of GFP expression from low to high. The GFP expression levels can be an indicator of shRNA expression levels and are inversely related to the levels of LRBA. The trend line equations are $y=-1.9597x^6+47.904x^5-462.33x^4+2225.6x^3-5526.7x^2+6530.5x-2560$ for LRBA KD; $y=-2.1153x^6+51.396x^5-492.3x^4+2354.3x^3-5846.6x^2+7013.3x-2870$ for LRBA WT. All experiments are representative of 2 to 5 separate experiments.

FIGS. 46(A) and (B). Knockdown of LRBA deregulates NFκB. (A) Time course study. 2 million, Raji cells transfected 2 mg Secreted luciferase plasmid nucleofector 4D, put 96 well plate with 0.5 Clontech were stimulated with LPS for time period as indicated. NFκB luciferase activity was measured at each time point for both cell lines as in A. RLU: Relative Light Units. (B) Trend lines obtained by polynomial fitting at order of 6 from E. The R2 values for both curves are 1. The trend line equations are $y=-1.9597x^6+47.904x^5-462.33x^4+2225.6x^3-5526.7x^2+6530.5x-2560$ for LRBA KD; $y=-2.1153x^6+51.396x^5-492.3x^4+2354.3x^3-5846.6x^2+7013.3x-2870$ for LRBA WT. All experiments are representative of 2 to 5 separate experiments FIGS. 47(A) and (B). Knockdown of LRBA deregulates MAPKs. Knockdown of LRBA upregulates p38 and JNK but downregulates p42/44. Half million of Raji or Raji9 cells were put in a well in a 6 well plate. After 24 hr, cells were treated with or without LPS for the time as indicated. 200 μl RIPA buffer with protease inhibitors and PMSF. (A) Western blot of cells was performed. 30 μl of cell extracts were loaded to ach well. Phosphorylated protein levels were normalized to β-Actin shown as the numbers between the two blots. (B) curves based on the Western blots. Quantity One software was used to quantify the levels.

FIGS. 48(A)-(I). Knockdown of LRBA influences the levels of cytokines. A. Raji cells (LRBA WT or KD) were seeded in a 24 well plate wells and stimulated with LPS for 15 min (1), 30 min (2) and 1 hr (3) with 0.26 million cells in each well or for 2 h (4), 4 h (5) and 24 h (6) with 0.2 million cells in each well, 0.2 million of cells were plated in each well. ELISA and CBA assays of TNFα and IL-10. Cells were treated as in A. 0.2×10^6 cells, timepoint. 500 uL total volume medium. Duoset ELISA human TNF-a kit protocol was followed for cell culture supernatant. Blues: Raji (♦); Red: Raji9 (■). Data are representative of 2 to 5 separate experiments.

Figure 49A:
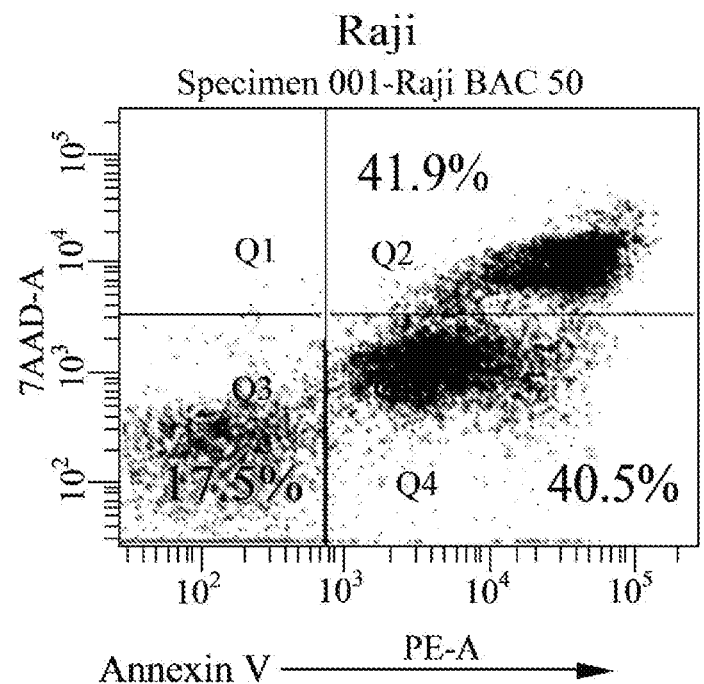
Figure 49B:
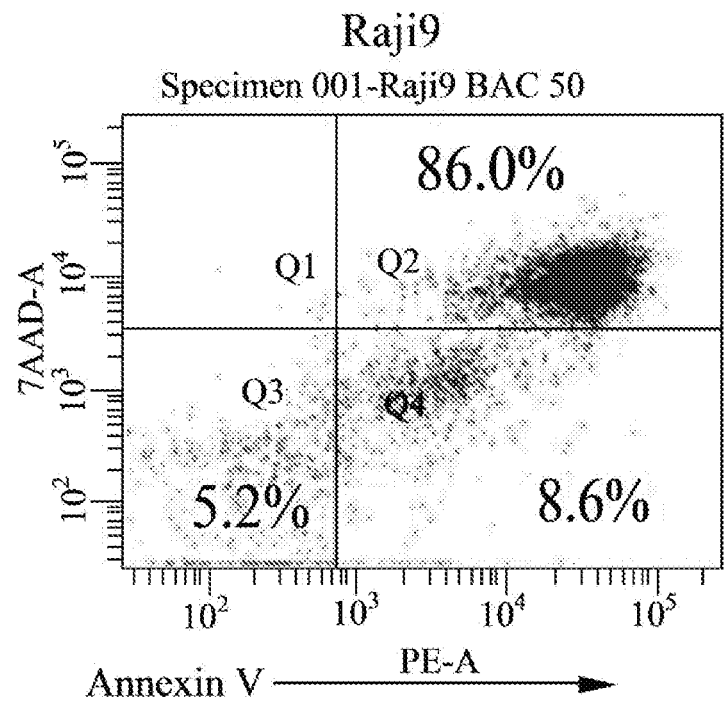

FIGS. 49(A) through (B) are graphs showing cells with LRBA knockdown cannot fight viral and bacterial infections efficiently. Half million of Raji and Raji9 cells were infected with adenoviruses at 100 multiplicity of infection (MOI) or 50 μl of Gram-negative bacteria from overnight culture. After 24 hours of incubation at 37° C., Apoptosis was detected by Annexin V-PE and 7-AAD. Cells that were double negative (left lower quadrant) were viable, Annexin only positive cells (right lower quadrant) were early phase of apoptosis or other cell death, and double positive cells (right upper quadrant) were end stage apoptosis or dead. ****p<9E-05, *p<0.007.

Figure 49C:
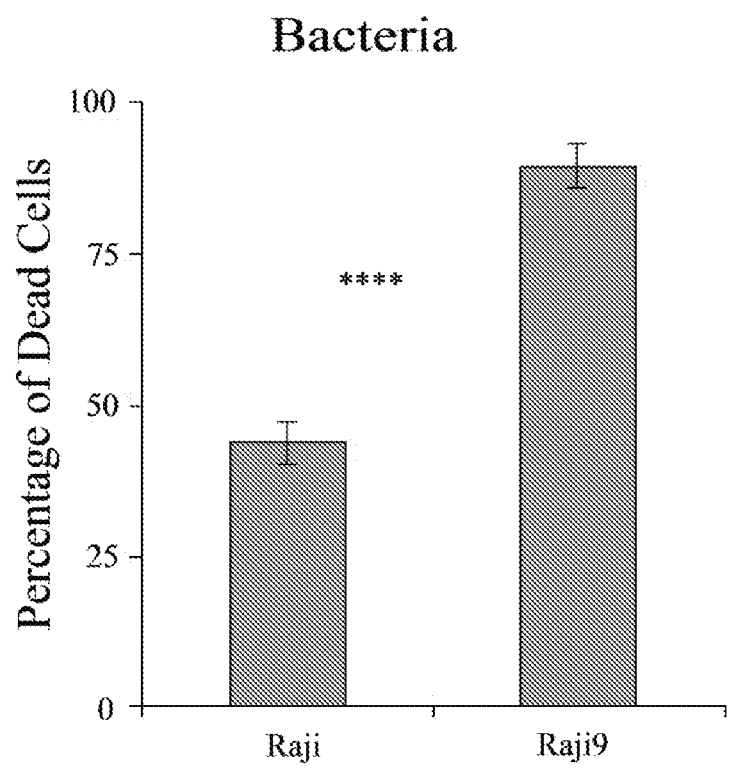
Figure 49D:
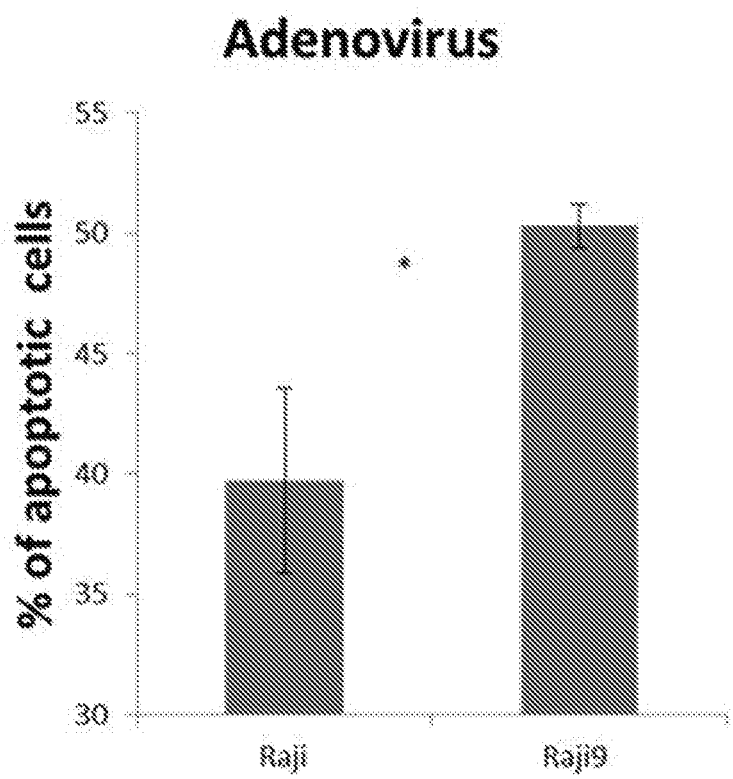

FIGS. 49(C) through (D) are graphs showing cells with LRBA knockdown cannot fight viral and bacterial infections efficiently. Half million of Raji and Raji9 cells were infected with adenoviruses at 100 multiplicity of infection (MOI) or 50 μl of Gram-negative bacteria from overnight culture. After 24 hours of incubation at 37° C., Apoptosis was detected by Annexin V-PE and 7-AAD. Cells that were double negative (left lower quadrant) were viable, Annexin only positive cells (right lower quadrant) were early phase of apoptosis or other cell death, and double positive cells (right upper quadrant) were end stage apoptosis or dead. ****p<9E-05, *p<0.007.

Figure 50:
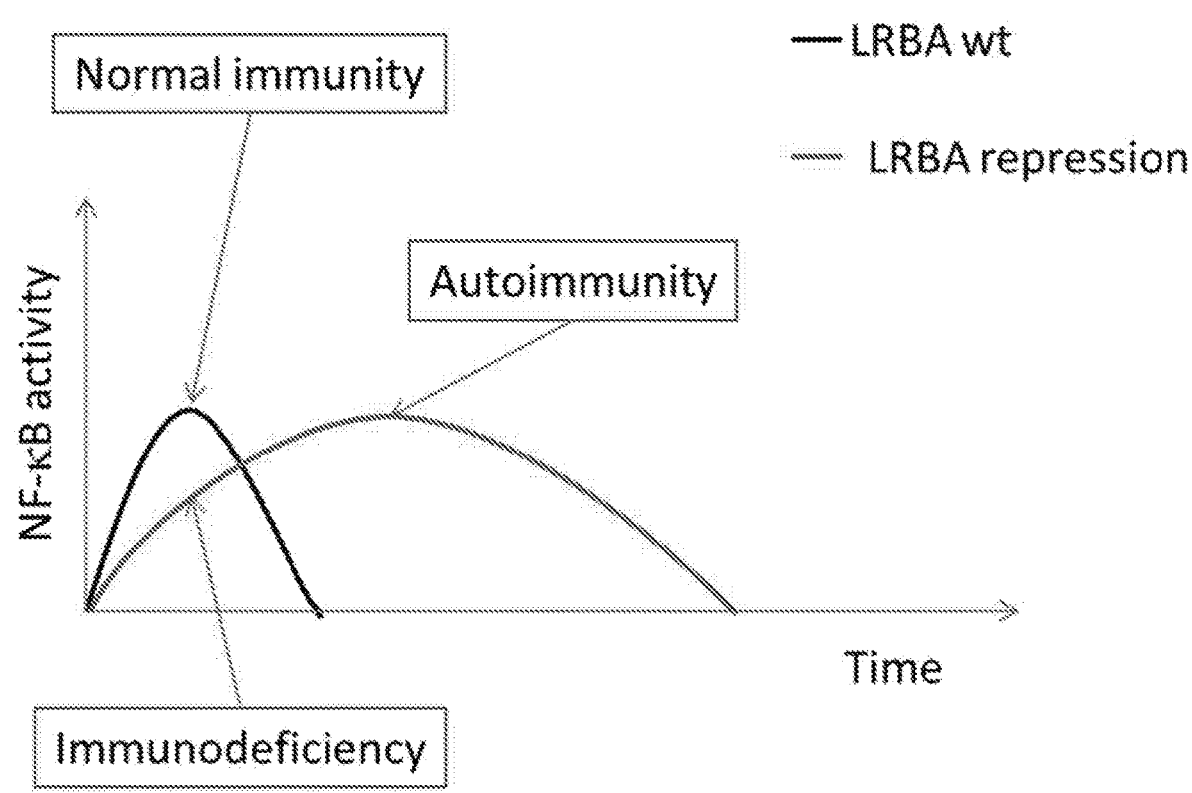

FIG. 50 is graph showing the effect of LRBA expression on immune system function, plotted against NF-κβ activity and time.

DETAILED DESCRIPTION OF THE PREFERRED EMBODIMENT

LRBA and its paralogues are proposed to be involved in vesicle trafficking (Shamloula, et al., rugose (rg), a *Drosophila* A kinase Anchor Protein, Is Required for Retinal Pattern Formation and Interacts Genetically With Multiple Signaling Pathways. 2002. *Genetics* 161, 693-710; Montfort, et al., FAN stimulates TNF(alpha)-induced gene expression, leukocyte recruitment, and humoral response. 2009. *J Immunol* 183, 5369-78) in immune cells. This finding permits use of LRBA for diagnostics, such as biomarkers, and as a treatment methodology.

As used herein, "treat", "treatment", "treating", and the like refer to acting upon a condition, such as autoimmune disease or immunotolerance, with an agent, like anti-LRBA antibodies or LRBA protein, depending on the desired effect, to affect the condition by improving or altering it. The improvement or alteration may include an improvement in symptoms or an alteration in the physiologic pathways associated with the condition. "Treatment," as used herein, covers one or more treatments of a condition in a host (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c)

relieving the condition, e.g., causing regression of the condition and/or relieving one or more condition symptoms (e.g., reduce inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as antibodies or other agents which are effective for producing an intended result, including preventing further autoimmune disease or immunotolerance, or treating an autoimmune disease, such as rheumatoid arthritis and asthma, or immunotolerance, such as cancer. Compositions according to the present invention may be used to effect a favorable change on immune cells, whether that change is an improvement, such as stopping or reversing the immune disease, or relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" refers to introducing an agent of the present disclosure into a patient. One preferred route of administration of the agent is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the term "subject," "patient," or "organism" includes humans and mammals (e.g., mice, rats, pigs, cats, dogs, and horses). Typical patients to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Reagents: Monoclonal antibodies against the following proteins were purchased from BD Biosciences (San Jose, Calif., USA): Annexin II, BiP/GRP78, b-Catenin, Caveolin 1, Connexin-43, EEA1, GM130, CD49b (Integrin a2), Lamp-1, MAP2B, Bcl-2, Nucleoporin p62, Paxillin, ZO-1 (Organelle Sampler Kit, 612740, BD Pharmingen™); AKAP79, AKAP95, AKAP149, AKAP220, AKAP-KL, MAP2B, PKAC, PKARI, PKARIa, PKARIIa, PKARIIb (PKA Sampler Kit, 611420 BD Transduction Laboratories™); GM130, Golgin-84, GS15, GS27, GS28, p115, p230 trans Golgi, Rab8, Syntaxin 6, Vti1a, Vti1b (Golgi Sampler Kit, 611434, BD Transduction Laboratories™) and Adaptin a, Adaptin b, Adaptin g, Adaptin d, Amphiphysin, AP180, Clathrin Heavy Chain, EEA1, eps15, b-NAP, Rab4 (Coated Vesicle Sampler Kit, 611424, BD Transduction Laboratories™). The LRBA Prestige antibodies (NBP1-90764) were purchased from Novus Biologicals (Littleton, Colo., USA). The Alexa Fluor Conjugated secondary antibodies: anti-mouse IgG-Alexa Fluor® 555, and anti-rabbit IgG-Alexa Fluor® 488 were purchased from Life Technologies (Grand Island, N.Y., USA).

Statistical Analysis

Each experiment is repeated at least three times independently, and each sample assayed in at least triplicate wells or plates to provide statistically meaningful data, and to avoid false data introduced by errors during each experiment. The statistical significance of the experimental results are calculated by using a two tailed unpaired T-test at 95% confidence intervals. $P<0.05$ will be considered to be statistically significant.

Example 1

Human and mouse LRBA genes were cloned and sequenced (Wang, et al., Deregulated expression of LRBA facilitates cancer cell growth. 2004. *Oncogene* 23, 4089-97; Barrat, et al., Defective CTLA-4 cycling pathway in Chediak-Higashi syndrome: a possible mechanism for deregulation of T lymphocyte activation. 1999. *Proc Natl Acad Sci USA* 96, 8645-50), contributing seven LRBA sequences to GenBank, as seen in NM006726, AF216648, AF188507, AF188506, AF187731, AF188505, AF188504.

Figure 2:
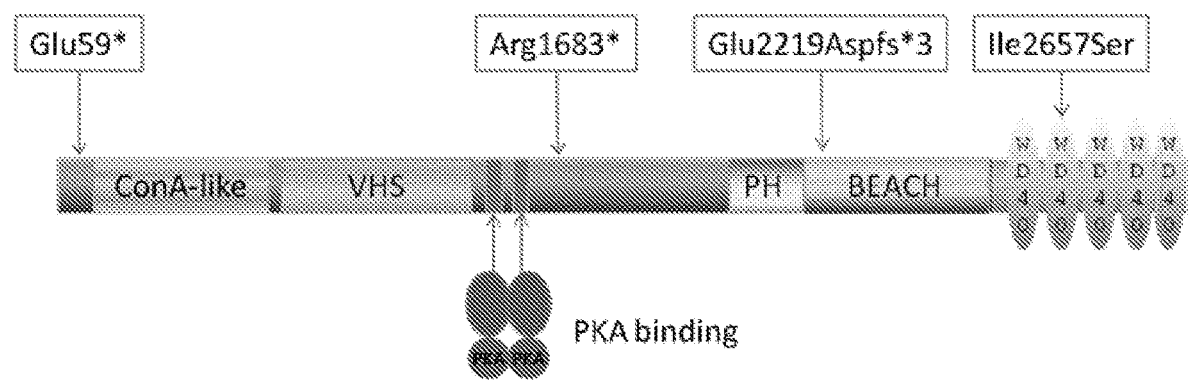
FIG. 2 is an illustration showing LRBA protein structure. The LRBA peptide has a highly conserved WBW [WDL (WD-like)-BEACH-WD40] multi-domain structure at the C-terminal end, two PKA binding sites, a VHS domain that may bind ubiquitin domains, and a ConA-like domain, which generally bind oligosaccharides. The mutations that cause diseases are shown in the boxes. *=stop codon; fs*3=3 frame-shift codons then stop codon.
Figure 3A:
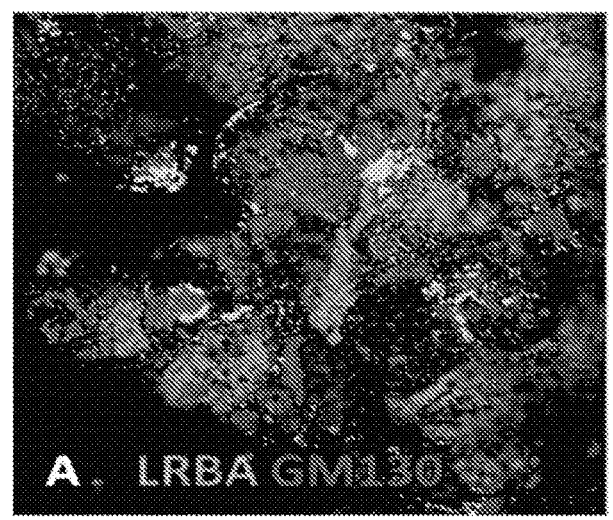
FIG. 3A is an image showing LRBA is co-localized with GC protein, dynamically involved in vesicle trafficking. HEK293 cells cultured on glass cover slips were fixed, permeabilized, and stained following the immuno-fluorescence staining protocol from the Human Protein Atlas Project (Sigma). The LRBA Prestige antibodies and three Golgi protein primary antibodies from BD biosciences were used at 1:500 (volume to volume dilution). The anti-mouse IgG-Alexa Fluor® 555, and anti-rabbit IgG-Alexa Fluor® 488 (Invitrogen) secondary antibodies were used at 1:400. The images were acquired with an Olympus FV1000 scanning confocal microscope with 0.5 μm of per slice by sequential scanning.
Figure 3B:
FIGS. 3B-C are a series of images depicting LRBA is co-localized with GC proteins, dynamically involved in vesicle trafficking. HEK293 cells cultured on glass cover slips were fixed, permeabilized, and stained following the immuno-fluorescence staining protocol from the Human Protein Atlas Project (Sigma). The LRBA Prestige antibodies and three Golgi protein primary antibodies from BD biosciences were used at 1:500 (volume to volume dilution). The anti-mouse IgG-Alexa Fluor® 555, and anti-rabbit IgG-Alexa Fluor® 488 (Invitrogen) secondary antibodies were used at 1:400. The images were acquired with an Olympus FV1000 scanning confocal microscope with 0.5 μm of per slice by sequential scanning.
Figure 3C:
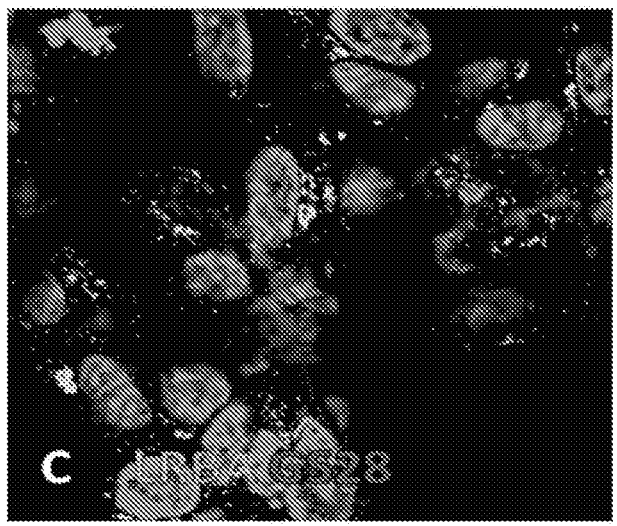
Figure 3D:
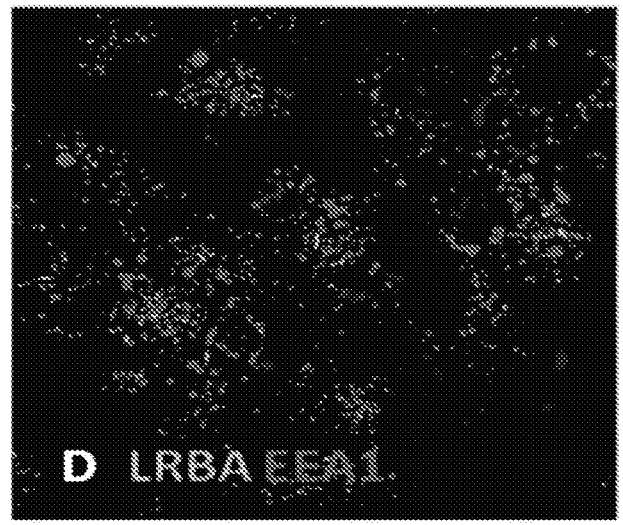
FIG. 3D is an image depicting LRBA is co-localized with early endosome protein, dynamically involved in vesicle trafficking. HEK293 cells cultured on glass cover slips were fixed, permeabilized, and stained following the immuno-fluorescence staining protocol from the Human Protein Atlas Project (Sigma). The LRBA Prestige antibodies and three Golgi protein primary antibodies from BD biosciences were used at 1:500 (volume to volume dilution). The anti-mouse IgG-Alexa Fluor® 555, and anti-rabbit IgG-Alexa Fluor® 488 (Invitrogen) secondary antibodies were used at 1:400. The images were acquired with an Olympus FV1000 scanning confocal microscope with 0.5 μm of per slice by sequential scanning.
Figure 3E:
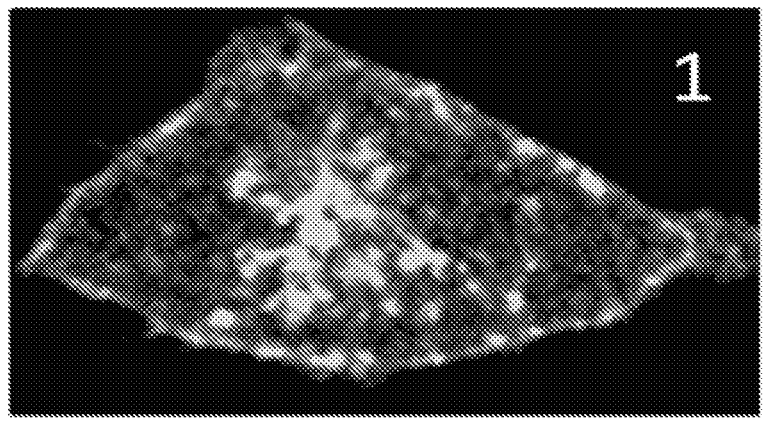
FIGS. 3E-G are a series of images depicting three time lapse video representative sequential captures of live RAW264.7 macrophage cells stably transfected with LRBA-GFP, showing cell membrane and Golgi locations, dynamic activities of vesicles moving from Golgi to the membrane, acquired from Leica TCS SP2 laser scanning confocal microscope. LRBA Prestige antibodies and primary antibodies from BD biosciences at a concentration of 1:500 against endogenous proteins.
Figure 3F:
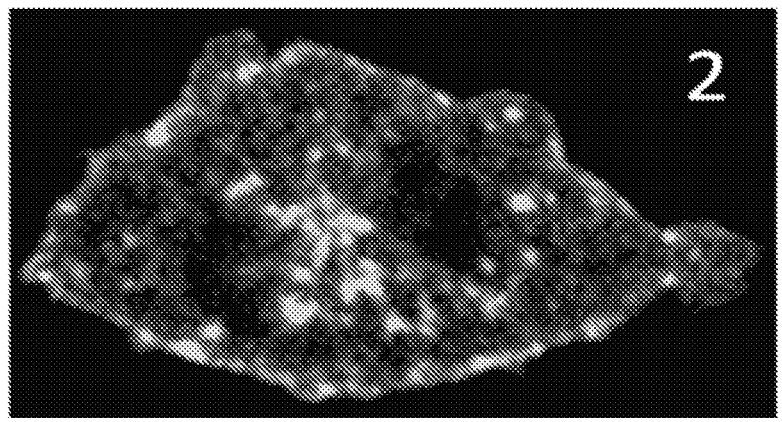
Figure 3G:
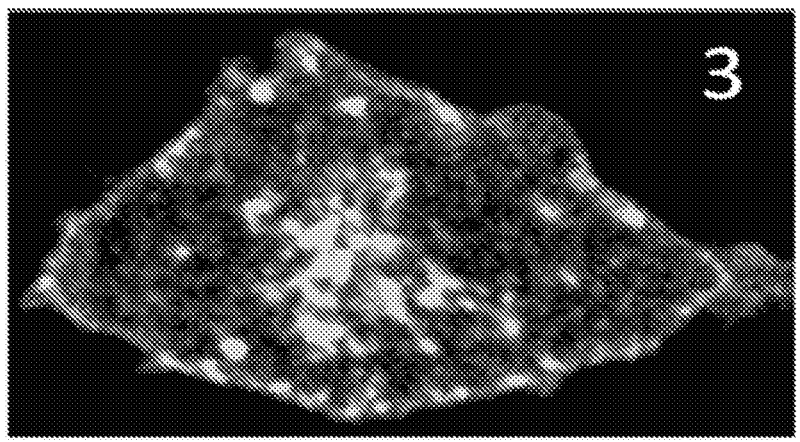

LRBA (Seq ID No. 1) is composed of multiple domains, as seen in FIG. 2. The Concanavalin A-like (ConA) lectin binding domain (Burgess, et al., A concanavalin A-like lectin domain in the CHS1/LYST protein, shared by members of the BEACH family 2009. Bioinformatics 25: 1219-1222), VHS (Bradshaw, et al., HMMer Thread: detecting remote, functional conserved domains in entire genomes by combining relaxed sequence-database searches with fold recognition. 2011. *PloS one* 6: e17568) [VPS (vacuolar protein sorting)] (Fearon, et al., Regulation of B lymphocyte responses to foreign and self-antigens by the CD19/CD21 complex. 2000. *Annu Rev Immunol* 18, 393-422), Hrs (hepatocyte growth factor-regulated tyrosine kinase substrate) domain and STAM (signal transducing adaptor molecule)], RII binding motifs and WBW super domain. The molecular weight of LRBA predicted from the largest open reading frame (ORF) of LRBA cDNA is 319 KD and similar size of protein was detected by Western blot (Lopez-Herrera, et al., Deleterious Mutations in LRBA Are Associated with a Syndrome of Immune Deficiency and Autoimmunity. *Am J Hum Genet* 90, 986-1001 (2012).). The three-dimensional structure of the WDLBEACH of LRBA has been determined (Gebauer, et al., Crystal structure of the PH-BEACH domains of human LRBA/BGL. 2004. *Biochemistry* 43: 14873-14880).

Human LRBA protein sequence (Seq ID No. 1):
MASEDNRVPSPPPTGDDGGGGGREETPTEGGALSLKPGLPIRGIRMKFAV

LTGLVEVGEVSNRDIVETVFNLLVGGQFDLEMNFIIQEGESINCMVDLLE

```
KCDITCQAEVWSMFTAILKKSIRNLQVCTEVGLVEKVLGKIEKVDNMIAD

LLVDMLGVLASYNLTVRELKLFFSKLQGDKGRWPPHAGKLLSVLKHMPQK

YGPDAFFNFPGKSAAAIALPPIAKWPYQNGFTFHTWLRMDPVNNINVDKD

KPYLYCFRTSKGLGYSAHFVGGCLIVTSIKSKGKGFQHCVKFDFKPQKWY

MVTIVHIYNRWKNSELRCYVNGELASYGEITWFVNTSDTFDKCFLGSSET

ADANRVFCGQMTAVYLFSEALNAAQIFAIYQLGLGYKGTFKFKAESDLFL

AEHHKLLLYDGKLSSAIAFTYNPRATDAQLCLESSPKDNPSIFVHSPHAL

MLQDVKAVLTHSIQSAMHSIGGVQVLFPLFAQLDYRQYLSDEIDLTICST

LLAFIMELLKNSIAMQEQMLACKGFLVIGYSLEKSSKSHVSRAVLELCLA

FSKYLSNLQNGMPLLKQLCDHVLLNPAIWIHTPAKVQLMLYTYLSTEFIG

TVNIYNTIRRVGTVLLIMHTLKYYYWAVNPQDRSGITPKGLDGPRPNQKE

MLSLRAFLLMFIKQLVMKDSGVKEDELQAILNYLLTMHEDDNLMDVLQLL

VALMSEHPNSMIPAFDQRNGLRVIYKLLASKSEGIRVQALKAMGYFLKHL

APKRKAEVMLGHGLFSLLAERLMLQTNLITMTTYNVLFEILIEQIGTQVI

HKQHPDPDSSVKIQNPQILKVIATLLRNSPQCPESMEVRRAFLSDMIKLF

NNSRENRRSLLQCSVWQEWMLSLCYFNPKNSDEQKITEMVYAIFRILLYH

AVKYEWGGWRVWVDTLSITHSKVTFEIHKENLANIFREQQGKVDEEIGLC

SSTSVQAASGIRRDINVSVGSQQPDTKDSPVCPHFTTNGNENSSIEKTSS

LESASNIELQTTNTSYEEMKAEQENQELPDEGTLEETLTNETRNADDLEV

SSDIIEAVAISSNSFITTGKDSMTVSEVTASISSPSEEDASEMPEFLDKS

IVEEEEDDDYVELKVEGSPTEEANLPTELQDNSLSPAASEAGEKLDMFGN

DDKLIFQEGKPVTEKQTDTETQDSKDSGIQTMTASGSSAMSPETTVSQIA

VESDLGQMLEEGKKATNLTRETKLINDCHGSVSEASSEQKIAKLDVSNVA

TDTERLELKASPNVEAPQPHRHVLEISRQHEQPGQGIAPDAVNGQRRDSR

STVFRIPEFNWSQMHQRLLTDLLFSIETDIQMWRSHSTKTVMDFVNSSDN

VIFVHNTIHLISQVMDNMVMACGGILPLLSAATSATHELENIEPTQGLSI

EASVTFLQRLISLVDVLIFASSLGFTEIEAEKSMSSGGILRQCLRLVCAV

AVRNCLECQQHSQLKTRGDKALKPMHSLIPLGKSAAKSPVDIVTGGISPV

RDLDRLLQDMDINRLRAVVFRDIEDSKQAQFLALAVVYFISVLMVSKYRD

ILEPQNERHSQSCTETGSENENVSLSEITPAAFSTLTTASVEESESTSSA

RRRDSGIGEETATGLGSHVEVTPHTAPPGVSAGPDAISEVLSTLSLEVNK

SPETKNDRGNDLDTKATPSVSVSKNVNVKDILRSLVNIPADGVTVDPALL

PPACLGALGDLSVEQPVQFRSFDRSVIVAAKKSAVSPSTFNTSIPTNAVS

VVSSVDSAQASDMGGESPGSRSSNAKLPSVPTVDSVSQDPVSNMSITERL

EHALEKAAPLLREIFVDFAPFLSRTLLGSHGQELLIEGTSLVCMKSSSSV

VELVMLLCSQEWQNSIQKNAGLAFIELVNEGRLLSQTMKDHLVRVANEAE

FILSRQRAEDIHRHAEFESLCAQYSADKREDEKMCDHLIRAAKYRDHVTA

TQLIQKIINILTDKHGAWGNSAVSRPLEFWRLDYWEDDLRRRRRFVRNPL

GSTHPEATLKTAVEHVCIFKLRENSKATDEDILAKGKQSIRSQALGNQNS

ENEILLEGDDDTLSSVDEKDLENLAGPVSLSTPAQLVAPSVVVKGTLSVT

SSELYFEVDEEDPNFKKIDPKILAYTEGLHGKWLFTEIRSIFSRRYLLQN

TALEIFMANRVAVMFNFPDPATVKKVVNYLPRVGVGTSFGLPQTRRISLA

SPRQLFKASNMTQRWQHREISNFEYLMFLNTIAGRSYNDLNQYPVFPWVI

TNYESEELDLTLPTNFRDLSKPIGALNPKRAAFFAERYESWEDDQVPKFH

YGTHYSTASFVLAWLLRIEPFTTYFLNLQGGICPDHADRTFSSISRAWRN

SQRDTSDIKELIPEFYYLPEMFVNFNNYNLGVMDDGTVVSDVELPPWAKT

SEEFVHINRLALESEFVSCQLHQWIDLIFGYKQQGPEAVRALNVFYYLTY

EGAVNLNSITDPVLREAVEAQIRSFGQTPSQLLIEPHPPRGSAMQVSPLM

FTDKAQQDVIMVLKFPSNSPVTHVAANTQPGLATPAVITVTANRLFAVNK

WHNLPAHQGAVQDQPYQLPVEIDPLIASNTGMHRRQITDLLDQSIQVHSQ

CFVITSDNRYILVCGFWDKSFRVYSTDTGRLIQVVFGHWDVVTCLARSES

YIGGNCYILSGSRDATLLLWYWNGKCSGIGDNPGSETAAPRAILTGHDYE

VTCAAVCAELGLVLSGSQEGPCLIHSMNGDLLRTLEGPENCLKPKLIQAS

REGHCVIFYENGLFCTFSVNGKLQATMETDDNIRAIQLSRDGQYLLTGGD

RGVVVVRQVSDLKQLFAYPGCDAGIRAMALSYDQRCIISGMASGSIVLFY

NDFNRWHHEYQTRY
```

The ConA-like lectin domain was proposed to bind oligosaccharide associated with protein traffic and sorting, especially in relation with the vesicle fusion machinery (Burgess, et al., A concanavalin A-like lectin domain in the CHS1/LYST protein, shared by members of the BEACH family 2009. *Bioinformatics* 25: 1219-1222). The ConA domain was predicted in LRBA and other four LRBA paralogues (Burgess, et al., A concanavalin A-like lectin domain in the CHS1/LYST protein, shared by members of the BEACH family 2009. *Bioinformatics* 25, 1219-2).

The VHS domain is considered to have a general membrane targeting/cargo recognition role in vesicular trafficking by binding sorting receptors that move and transfer cargo between the trans-Golgi network and the endosomal compartment (Lohi, et al., VHS domain—a longshoreman of vesicle lines. 2002. *FEBS letters* 513: 19-23; Misra, et al., Structure of the VHS domain of human Tom1 (target of myb 1): insights into interactions with proteins and membranes. 2000. *Biochemistry* 39, 11282-90). LRBA contains two potential RII binding sites for anchoring PKA through the RII subunits (Wang, et al., Identification of a novel lipopolysaccharide-inducible gene with key features of both A kinase anchor proteins and chs1/beige proteins. 2001. *J Immunol* 166, 4586-95; Hou, et al., Prediction of peptides binding to the PKA RIIalpha subunit using a hierarchical strategy. 2011. *Bioinformatics* 27, 1814-21).

The WBW super-domain at the C-terminal is composed of a WDL and BEACH domain and five WD40 repeats. This same super-domain C-terminal architecture is shared by various large proteins which define the WBW family. The WDL is structurally similar to the pleckstrin homology (PH) domain and strongly interacts with the BEACH domains. The interface between WDL and BEACH two domains form a prominent groove which may be used to recruit binding partners (Gebauer, et al., Crystal structure of the PH-BEACH domains of human LRBA/BGL. 2004. *Biochemistry* 43, 14873-14880; Jogl, et al., Crystal structure of the BEACH domain reveals an unusual fold and extensive association with a novel PH domain. 2002. *Embo Journal* 21, 4785-4795). LRBA GFP fusion protein is associated with vesicles, suggesting that BEACH and/or WD40 domains are involved in vesicle-binding or can form a dimer with LRBA or other proteins including WBW proteins (Wang, et al., Identification of a novel lipopolysaccharide-inducible gene with key features of both A kinase anchor proteins and chs1/beige proteins. 2001. *J Immunol* 166, 4586-95).

LRBA also contains a microtubule-associated protein 1 light chain 3 (LC3) interaction region LC3 interaction region (LIR), which is shared in both human and murine LRBA. The LIR consensus sequence is [DE]-[DE]-[DE]-[WFY]-X-X-[LIV] (Birgisdottir, et al., The LIR motif—crucial for selective autophagy. 2013. *J Cell Sci* 126, 3237-47; Seq ID No. 2). The DDDYVEL (Seq ID No. 3) sequence from LRBA has high homology with LIR from TP53INP1 (similarity is 92%) and TP53INP249, as seen in Table 2.

TABLE 2

The potential LIR of LRBA has high homology with two known LIR motifs

| Seq ID No. | Gene | LIR sequence | Length |
|---|---|---|---|
| 4 | LIR-TP53INP1 | EKEDDEWILVDFI | 13 |
| 2 | LIR-LRBA | EEEDDDYVELKVE | 13 |
| 5 | LIR-TP53INP2 | EDEVGDWLIIDLP | 13 |
|  | homology | *.* .: :: :.. |  |

Three dimensional structure remodeling (YASARA v12.7.16) shows that the LIR forms a complex with LC3 which is more stable than with p62, a known LC3 binding protein, as seen in FIGS. 23(A) and 24.

Interestingly, mutated LRBA proteins cannot be detected in LRBA deficient patients by Western blot (Lopez-Herrera, et al., Deleterious Mutations in LRBA Are Associated with a Syndrome of Immune Deficiency and Autoimmunity. 2012. *Am J Hum Genet* 90, 986-1001; Burns, et al., LRBA gene deletion in a patient presenting with autoimmunity without hypogammaglobulinemia. *J Allergy Clin Immunol* 130, 1428-32 (2012). Alangari, A. et al., LPS-responsive beige-like anchor (LRBA) gene mutation in a family with inflammatory bowel disease and combined immunodeficiency. 2012. *J Allergy Clin Immunol* 130, 481-8 e2).

It was previously suggested that LRBA is involved in vesicle trafficking for polarized secretion and/or membrane deposition of immune effector molecules, as seen by LRBA's subcellular localizations obtained by over-expressing a part of Lrba (the BEACH-WD40 super-domain) fused with the EGFP gene (BWGFP). The BWGFP fusion protein was colocalized with the vesicular system, including the Golgi complex, lysosomes, ER, plasma membrane, and perinuclear ER demonstrated by GFP fluorescence confocal microscopy and Immunoelectron microscopy. (Wang, et al., Identification of a novel lipopolysaccharide-inducible gene with key features of both A kinase anchor proteins and chs1/beige proteins. 2001. Journal of immunology (Baltimore, Md.: 1950) 166, 4586-4595) However, as the BWGFP fusion protein can interfere with the function of the endogenous LRBA, (Wang, J. W., Gamsby, J. J., Highfill, S. L., Mora, L. B., Bloom, G. C., Yeatman, T. J., Pan, T. C., Ramne, A. L., Chodosh, L. A., Cress, W. D., et al. (2004). Deregulated expression of LRBA facilitates cancer cell growth. Oncogene 23, 4089-4097) and GFP tag also interferes with protein function, (Yewdell, J. W., Lacsina, J. R., Rechsteiner, M. C., and Nicchitta, C. V. (2011). Out with the old, in with the new? Comparing methods for measuring protein degradation. Cell biology international 35, 457-462) and only a part of LRBA gene is used for the colocalization study. Moreover, the organelle-specific antibodies were not used in the previous study. (Wang, J. W., Howson, J., Haller, E., and Kerr, W. G. (2001). Identification of a novel lipopolysaccharide-inducible gene with key features of both A kinase anchor proteins and chs1/beige proteins. Journal of immunology (Baltimore, Md.: 1950) 166, 4586-4595). The LysoTracker Red used in the previous study can be photoconverted to a green fluorescent molecule. (Freundt, E. C., Czapiga, M., and Lenardo, M. J. (2007). Photoconversion of Lysotracker Red to a green fluorescent molecule. Cell research 17, 956-958). Therefore, it is still not clear whether the subcellular localization of the fusion protein is the same as that of the endogenous LRBA protein.

Subcellular LRBA colocalization was analyzed against known organelle proteins using immunofluorescence staining and confocal microscopy to better understand the cellular and molecular mechanisms by which LRBA functions in the cell.

RAW264.7, A549, and HEK293 cell lines (American Type Culture Collection, Manassas, Va., USA) at concentration of $5 \times 10^6$/ml were plated on glass coverslips in Dulbecco's modified minimum essential medium (D-MEM) supplemented with 10% fetal calf serum (Gemini Bio-Products, West Sacramento, Calif.), penicillin and streptomycin, according to ATCC instructions in Dulbecco's modified minimum essential medium (DMEM) or RPMI1640 supplemented with 10% FBS and penicillin-streptomycin (5,000 IU/ml penicillin and 5,000 µg/ml streptomycin). BMMs were obtained by the protocol described by Weischenfeldt, et al. (Weischenfeldt & Porse, Bone Marrow-Derived Macrophages (BMM): Isolation and Applications. 2008. *CSH Protoc* 2008, pdb prot5080). Bone marrow cells were obtained by flushing the femurs and tibias from 8-12-week-old C57BL/6 wild type mice and LRBA$^{-/-}$ mice, and the bone marrow cells plated in 10-cm bacteriological plastic plates at $2 \times 10^6$ cells/mL with 10% FCS in RPMI 1640 supplemented with 100 ng/ml of recombinant murine M-CSF. On day 7, BMMs were plated at $1 \times 10^5$ cells/ml in 24-well plates and cultured with or without 100 ng/ml of LPS for 7 h (Nagai, et al., Essential role of MD-2 in LPS responsiveness and TLR4 distribution. 2002. *Nat Immunol* 3, 667-72).

After 24 h of stimulation, cells were fixed, permeabilized, and stained following the immuno-fluorescence staining protocol from the Human Protein Atlas Project (Sigma). Briefly, growth medium was removed and the cells were washed in 1×PBS, the cells were fixed for 15 minutes in ice cold 4% paraformaldehyde pH 7.2-7.3 in growth medium supplemented with 10% fetal bovine serum (FBS). The cells were permeabilized 3 times for 5 minutes each with 0.1% TRITON® X-100 in PBS. The cells were washed with 1×PBS and incubated overnight at 4° C. with the primary antibodies, disclosed above, in 1×PBS supplemented with 4% FBS. The following day the cells were washed 4 times for 10 minutes each with 1×PBS and incubated for 1.5 hours at room temperature with the secondary antibodies in 1×PBS supplemented with 4% FBS. The cells were counterstained for 4 minutes with the nuclear stain DAPI (0.6 µM in 1×PBS). The cells were washed 4 times for 10 minutes with 1×PBS and then mounted in glycerol+10% 10×PBS. The LRBA antibodies and three Golgi protein primary antibodies were used at 1:500 (volume to volume dilution). The anti-mouse IgG-Alexa Fluor® 555, and anti-rabbit IgG-Alexa Fluor® 488 secondary antibodies were used at 1:400. The confocal imaging was acquired with an Olympus FV1000 MPE multiphoton laser scanning microscope using 60× objective (U Plan APO 1.42 N.A. oil) and sequential scanning with 0.5 µm per slice. Colocalization analysis for dual stained samples was carried out using JACop and FV10-ASW software.

Colocalization analysis for dual stained samples was carried out using JACop and FV10-ASW software. JACoP (Just Another Colocalization Plugin) integrates current global statistic methods and a novel object-based approach (Bolte, et al., A guided tour into subcellular colocalization analysis in light microscopy. 2006. *Journal of microscopy* 224: 213-232). All of the following features were used: Calculating a set of commonly used co-localization indicators: Pearson's coefficient, Overlap coefficient, k1 & k2 coefficients, Manders' coefficient, Cytofluorogram for generating commonly used visualizations, Costes' automatic threshold, Costes' randomization, Li's intensity correlation coefficient, and two objects based methods: distances between centers and center-particle coincidence. The calculated P-value of 100% based on the Costes' randomization colocalization in the JACoP suggests that colocalization in the regions masked in white is highly probable (Bolte, et al., A guided tour into subcellular colocalization analysis in light microscopy. 2006. *Journal of microscopy* 224: 213-232).

LRBA is mainly localized to the GC, as demonstrated by the co-localization of LRBA with three Golgi proteins; two golgins (GM-130 and P-230) and another GC protein (GS-28), as seen in FIGS. 7-11. The GC is a central organelle in the endomembrane system, and viewed as the "headquarters" for signal transduction and cell-fate decisions, controlling mitotic entry, cytoskeleton organization and dynamics, calcium homoeostasis, and plasma membrane receptor-initiated and organelle-autochthonous signaling events, in addition to its "classic role" of cargo sorting/processing and metabolism (Wilson, et al., The Golgi apparatus: an organelle with multiple complex functions. 2011. *Biochem J* 433: 1-9).

Figure 4A:
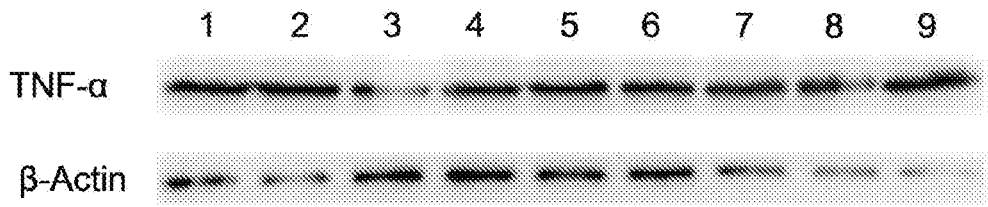
FIGS. 4A-B are a blot and graph showing knockdown of LRBA increases the TNFα levels in A549 cells (adenocarcinomic human alveolar basal epithelial cells). A549 cells and A549 pLAsiGFP cells (stably transfected with shRNA plasmid against LRBA) were treated with LPS (1 μg/ml). The TNFα concentrations were detected by Western blot. Cells were cultured in 6-well plates and stimulated with LPS (1 μg/ml) for different time as shown, then lysed with RIPA buffer. Western blots were carried out. TNFα antibody (sc-1351. Santa Cruz Biotechnology, Santa Cruz, USA) was used at 1:500 ratio and incubated at 4° C. overnight. BioRad ChemiDoc XRS and Quantity One software were used to acquire gel image and measure band relative intensity. (A) Western blot. 1. A549 No LPS, 2. A549 LPS 30 min, 3. A549 LPS 1 hr, 4. A549 LPS 2 h, 5. A549 LPS 4 h, 6. A549 LPS 24 h, 7. A549 pLAsiGFP LPS 2 h, 8. A549 pLAsiGFP LPS 4 h, 9. A549 pLAsiGFP LPS 24 h. (B) Band intensity quantification from A.
Figure 4B:
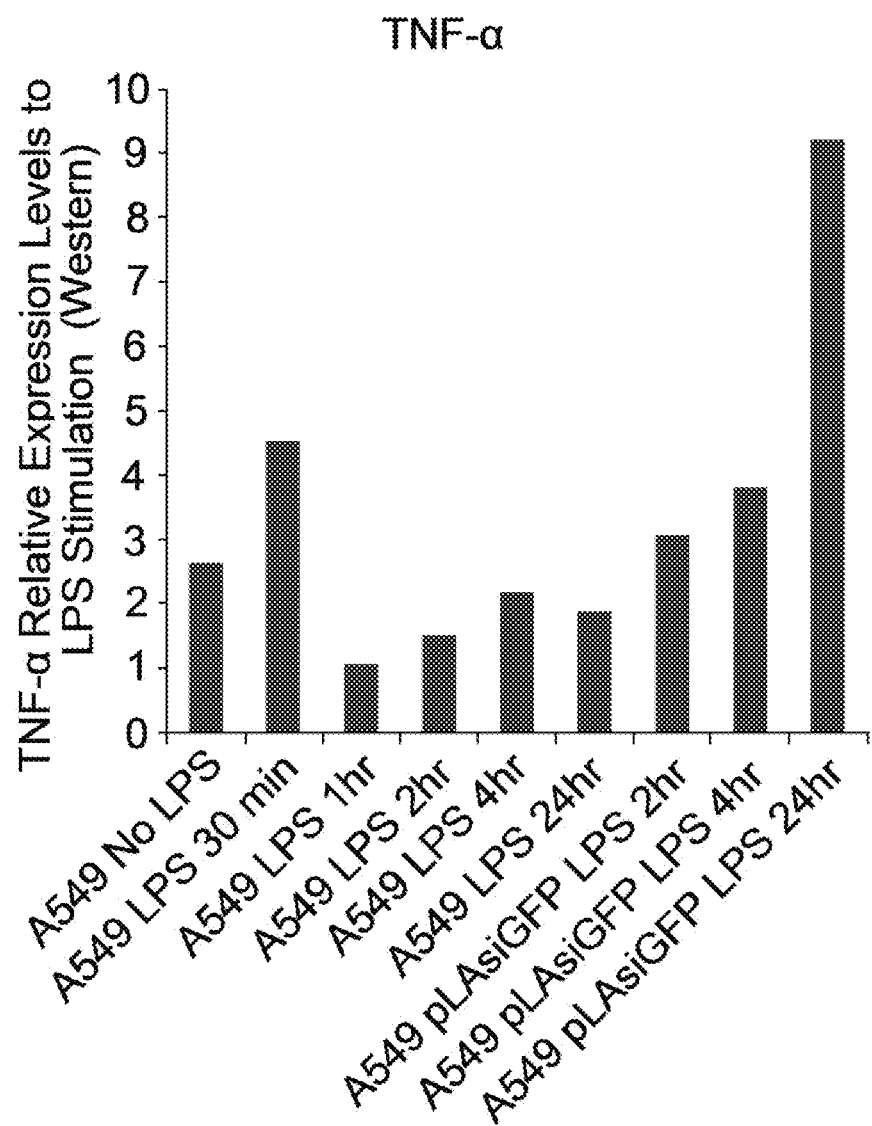
Figure 4C:
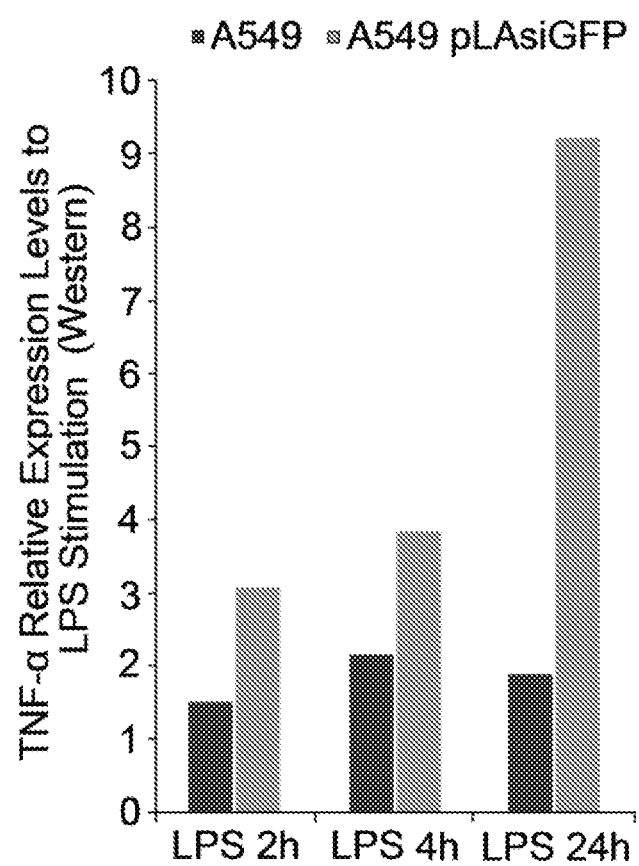
FIG. 4C is a graph showing knockdown of LRBA increases the TNFα levels in A549 cells (adenocarcinomic human alveolar basal epithelial cells). A549 cells and A549 pLAsiGFP cells (stably transfected with shRNA plasmid against LRBA) were treated with LPS (1 μg/ml). The TNFα concentrations were detected by Western blot. Cells were cultured in 6-well plates and stimulated with LPS (1 μg/ml) for different time as shown, then lysed with RIPA buffer. Western blots were carried out. TNFα antibody (sc-1351. Santa Cruz Biotechnology, Santa Cruz, USA) was used at 1:500 ratio and incubated at 4° C. overnight. BioRad ChemiDoc XRS and Quantity One software were used to acquire gel image and measure band relative intensity. (C) TNFα levels in A549 and A549 pLAsiGFP cells were compared side by side.
Figure 5A:
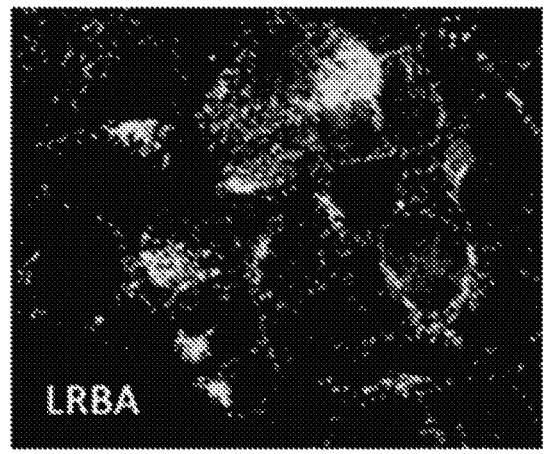
FIGS. 5A-C are a series of confocal images showing LRBA is co-localized with GC proteins demonstrated by confocal microscopy and JACoP software. HEK293 cells cultured on glass cover slips were fixed, permeabilized, and stained following the immuno-fluorescence staining protocol from the Human Protein Atlas Project (Sigma). The LRBA Prestige antibodies and three Golgi protein primary antibodies from BD Biosciences were used at 1:500 (volume to volume dilution). The anti-mouse IgG-Alexa Fluor® 555, and anti-rabbit IgG-Alexa Fluor® 488 (Invitrogen) secondary antibodies were used at 1:400. The images were acquired with an Olympus FV1000 scanning confocal microscope by sequential scanning with 0.5 μm per slice. 1, 2 & 3: Three representative sequential captures from a time-lapse video of live RAW264.7 macrophage cells stably transfected with LRBA-GFP, showing cell membrane and Golgi locations, dynamic activities of vesicles moving from GC to the membrane (Leica TCS SP2 laser scanning confocal microscope). GM130: Pearson's Coefficient: r=0.562 Overlap Coefficient: r=0.674 r^2=k1×k2: k1=0.71 k2=0.639 Using thresholds (thrA=11 and thrB=26) Overlap Coefficient: r=0.782 r^2=k1×k2: k1=0.926 k2=0.661 Manders' Coefficients (original): M1=0.853 (fraction of A overlapping B) M2=0.968 (fraction of B overlapping A) Manders' Coefficients (using threshold value of 11 for imgA and 26 for imgB): M1=0.674 (fraction of A overlapping B) M2=0.916 (fraction of B overlapping A) Costes' automatic threshold set to 2 for imgA & 16 for imgB Pearson's Coefficient: r=0.385 (0.0 below thresholds) M1=0.999 & M2=0.977 Van Steensel's Cross-correlation Coefficient between H293LRBAgreenframes.tif and H293GM130redframes.tif: CCF min.: 0.377 (obtained for dx=−20) CCF max.: 0.562 (obtained for dx=0) Results for fitting CCF on a Gaussian (CCF=a+(b−a)exp(−(xshift−c)^2/(2d^2))): Formula: y=a+(b−a)*exp(−(x−c)*(x−c)/(2*d*d)) Status: Success Number of completed minimizations: 2 Number of iterations: 93 (max: 4000) Time: 4 ms Sum of residuals squared: 0.0021718 Standard deviation: 0.0073685 R^2: 0.98178 Parameters: a=0.38178 b=0.55472 c=−0.45801 d=9.31510 FWHM=21.935 pixels Cytofluorogram's parameters: a: 0.612 b: 15.267 Correlation coefficient: 0.562 Li's Intensity correlation coefficient: ICQ: 0.28053263239399306 Costes' randomization based colocalization: Parameters: Nb of randomization rounds: 1000, Resolution (bin width): 0.0010 r (original)=0.56 r (randomized)=0.0±−0.0030 (calculated from the fitted data) P-value=100.0% (calculated from the fitted data) Results for fitting the probability density function on a Gaussian (Probability=a+(b−a)exp(−(R−c)^2/(2d^2))): Formula: y=a+(b−a)*exp(−(x−c)*(x−c)/(2*d*d)) Status: Success Number of completed minimizations: 2 Number of iterations: 160 (max: 4000) Time: 4 ms Sum of residuals squared: 0.00086502 Standard deviation: 0.0062705 R^2: 0.97303 Parameters: a=0.0013404 b=0.10599 c=−0.00010744 d=−0.0036972 FWHM=0.0080 Colocalization based on distance between centres of mass Threshold for Image A=11; Image B=26 Particles size between 0 & 245385 Image A: 10 centre(s) colocalizing out of 98 Image B: 12 centre(s) colocalizing out of 168 Colocalization based on centres of mass-particles coincidence Threshold for Image A=11; Image B=26 Particles size between 0 & 245385 Image A: 4 centre(s) colocalizing out of 98 Image B: 1 centre(s) colocalizing out of 168.
Figure 5B:
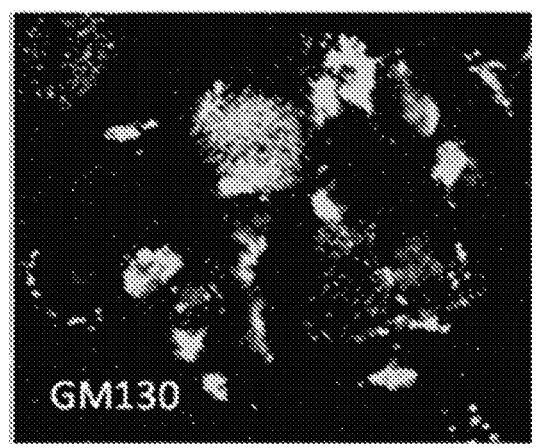
Figure 5C:
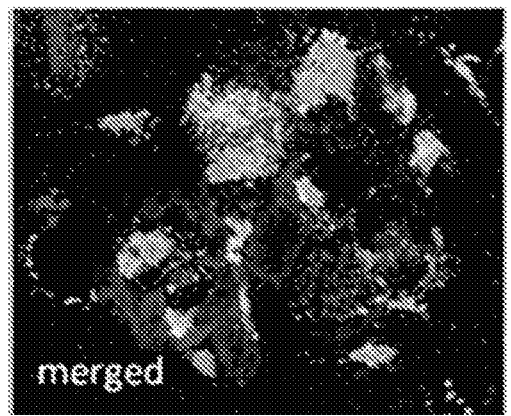
Figure 5D:
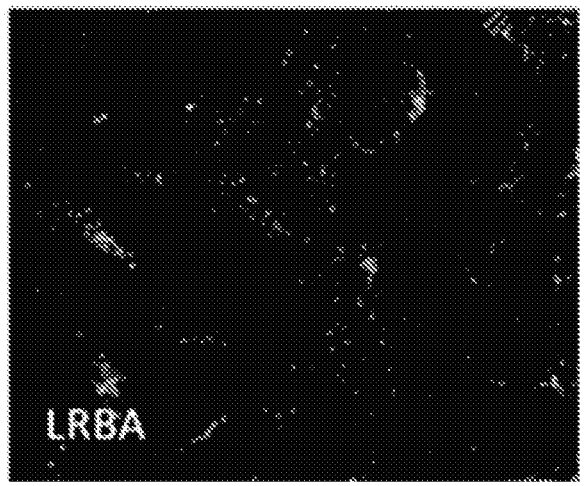
FIGS. 5D-F are a series of confocal images showing LRBA is co-localized with GC proteins demonstrated by confocal microscopy and JACoP software. HEK293 cells cultured on glass cover slips were fixed, permeabilized, and stained following the immuno-fluorescence staining protocol from the Human Protein Atlas Project (Sigma). The LRBA Prestige antibodies and three Golgi protein primary antibodies from BD Biosciences were used at 1:500 (volume to volume dilution). The anti-mouse IgG-Alexa Fluor® 555, and anti-rabbit IgG-Alexa Fluor® 488 (Invitrogen) secondary antibodies were used at 1:400. The images were acquired with an Olympus FV1000 scanning confocal microscope by sequential scanning with 0.5 μm per slice. 1, 2 & 3: Three representative sequential captures from a time-lapse video of live RAW264.7 macrophage cells stably transfected with LRBA-GFP, showing cell membrane and Golgi locations, dynamic activities of vesicles moving from GC to the membrane (Leica TCS SP2 laser scanning confocal microscope). P230: Pearson's Coefficient: r=0.443 Overlap Coefficient: r=0.469 r^2=k1×k2: k1=0.734 k2=0.3 Using thresholds (thrA=74 and thrB=27) Overlap Coefficient: r=0.846 r^2=k1×k2: k1=0.915 k2=0.782 Manders' Coefficients (original): M1=0.933 (fraction of A overlapping B) M2=0.288 (fraction of B overlapping A) Manders' Coefficients (using threshold value of 74 for imgA and 27 for imgB): M1=0.758 (fraction of A overlapping B) M2=0.29 (fraction of B overlapping A) Costes' automatic threshold set to 2 for imgA & 8 for imgB Pearson's Coefficient: r=0.248 (0.0 below thresholds) M1=0.999 & M2=0.943 Van Steensel's Cross-correlation Coefficient between H293LRBAgreenp230red1Cropped.tif.frames (red) and H293LRBAgreenp230red1Cropped.tif.frames (green): CCF min.: 0.07 (obtained for dx=20) CCF max.: 0.443 (obtained for dx=0) Results for fitting CCF on a Gaussian (CCF=a+(b−a)exp(−(xshift−c)^2/(2d^2))): Formula: y=a+(b−a)*exp(−(x−c)*(x−c)/(2*d*d)) Status: Success Number of completed minimizations: 2 Number of iterations: 107 (max: 4000) Time: 4 ms Sum of residuals squared: 0.010757 Standard deviation: 0.016399 R^2: 0.97905 Parameters: a=0.097205 b=0.41277 c=0.33764 d=6.60137 FWHM=15.545 pixels Cytofluorogram's parameters: a: 0.669 b: 7.406 Correlation coefficient: 0.443 Li's Intensity correlation coefficient: ICQ: 0.33931448608371684 Costes' randomization based colocalization: Parameters: Nb of randomization rounds: 1000, Resolution (bin width): 0.0010 r (original)=0.442 r (randomized)=0.0±0.0020 (calculated from the fitted data) P-value=100.0% (calculated from the fitted data) Results for fitting the probability density function on a Gaussian (Probability=a+(b−a)exp(−(R−c)^2/(2d^2))): Formula: y=a+(b−a)*exp(−(x−c)*(x−c)/(2*d*d)) Status: Success Number of completed minimizations: 2 Number of iterations: 155 (max: 4000) Time: 4 ms Sum of residuals squared: 0.0019026 Standard deviation: 0.012098 R^2: 0.96178 Parameters: a=−0.0030523 b=0.16637 c=6.67246E-5 d=0.0024017 FWHM=0.0050.
Figure 5E:
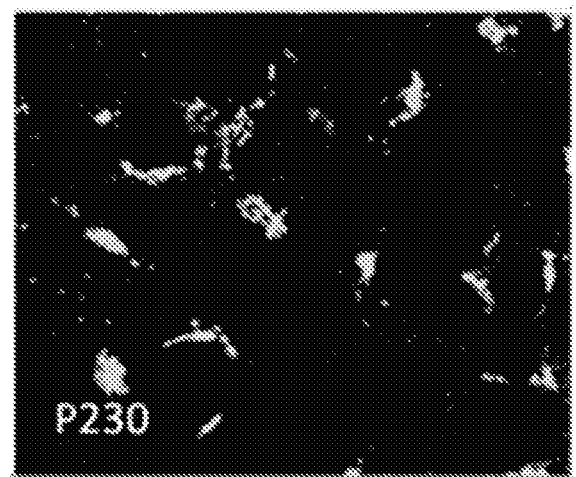
Figure 5F:
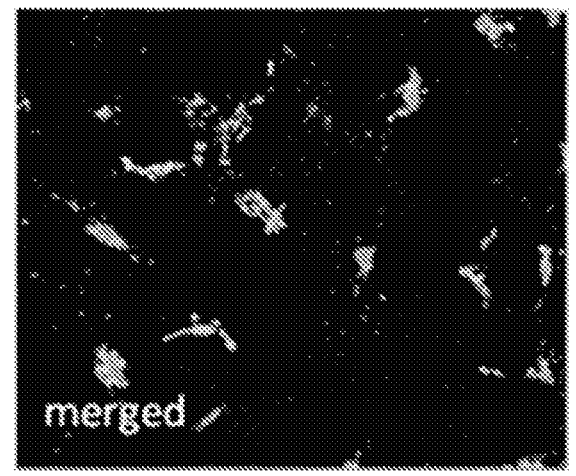
Figure 5G:
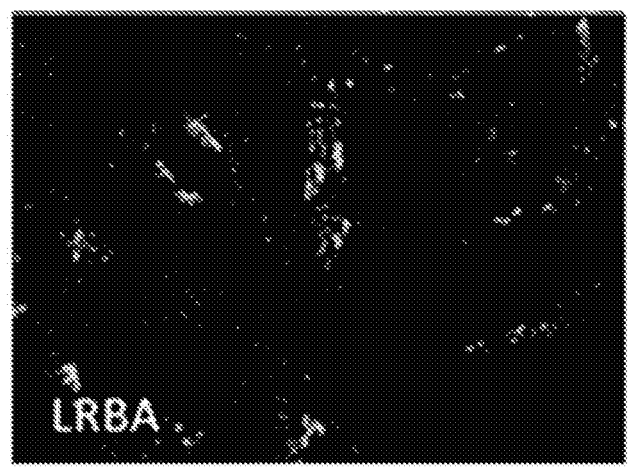
FIGS. 5G-I are a series of confocal images showing LRBA is co-localized with GC proteins demonstrated by confocal microscopy and JACoP software. HEK293 cells cultured on glass cover slips were fixed, permeabilized, and stained following the immuno-fluorescence staining protocol from the Human Protein Atlas Project (Sigma). The LRBA Prestige antibodies and three Golgi protein primary antibodies from BD Biosciences were used at 1:500 (volume to volume dilution). The anti-mouse IgG-Alexa Fluor® 555, and anti-rabbit IgG-Alexa Fluor® 488 (Invitrogen) secondary antibodies were used at 1:400. The images were acquired with an Olympus FV1000 scanning confocal microscope by sequential scanning with 0.5 μm per slice. 1, 2 & 3: Three representative sequential captures from a time-lapse video of live RAW264.7 macrophage cells stably transfected with LRBA-GFP, showing cell membrane and Golgi locations, dynamic activities of vesicles moving from GC to the membrane (Leica TCS SP2 laser scanning confocal microscope). GS-28: Pearson's Coefficient: r=0.366 Overlap Coefficient: r=0.381 r^2=k1×k2: k1=0.851 k2=0.17 Using thresholds (thrA=63 and thrB=44) Overlap Coefficient: r=0.883 r^2=k1×k2: k1=1.084 k2=0.72 Manders' Coefficients (original): M1=0.782 (fraction of A overlapping B) M2=0.259 (fraction of B overlapping A) Manders' Coefficients (using threshold value of 63 for imgA and 44 for imgB): M1=0.676 (fraction of A overlapping B) M2=0.173 (fraction of B overlapping A) Costes' automatic threshold set to 2 for imgA & 7 for imgB Pearson's Coefficient: r=0.176 (0.0 below thresholds) M1=0.999 & M2=0.987 Van Steensel's Cross-correlation Coefficient between H293GS28red(red).tif and H293LRBA(green).tif: CCF min.: 0.0080 (obtained for dx=20) CCF max.: 0.366 (obtained for dx=0) Results for fitting CCF on a Gaussian (CCF=a+(b−a)exp(−(xshift−c)^2/(2d^2))): Formula: y=a+(b−a)*exp(−(x−c)*(x−c)/(2*d*d)) Status: Success Number of completed minimizations: 2 Number of iterations: 112 (max: 4000) Time: 4 ms Sum of residuals squared: 0.011774 Standard deviation: 0.017157 R^2: 0.97313 Parameters: a=0.047265 b=0.34334 c=0.32362 d=4.48046 FWHM=10.55 pixels. Cytofluorogram's parameters: a: 0.802 b: 5.927 Correlation coefficient: 0.366 Li's Intensity correlation coefficient: ICQ: 0.4039760078011444 Costes' randomization based colocalization: Parameters: Nb of randomization rounds: 1000, Resolution (bin width): 0.0010 r (original)=0.367 r (randomized)=0.0±−0.0020 (calculated from the fitted data) P-value=100.0% (calculated from the fitted data) Results for fitting the probability density function on a Gaussian (Probability=a+(b−a)exp(−(R−c)^2/(2d^2))): Formula: y=a+(b−a)*exp(−(x−c)*(x−c)/(2*d*d)) Status: Success Number of completed minimizations: 2 Number of iterations: 508 (max: 4000) Time: 12 ms Sum of residuals squared: 0.00041598 Standard deviation: 0.0049467 R^2: 0.99252 Parameters: a=−0.00013085 b=0.15664 c=1.21787E-5 d=−0.0025101 FWHM=0.0050.
Figure 5H:
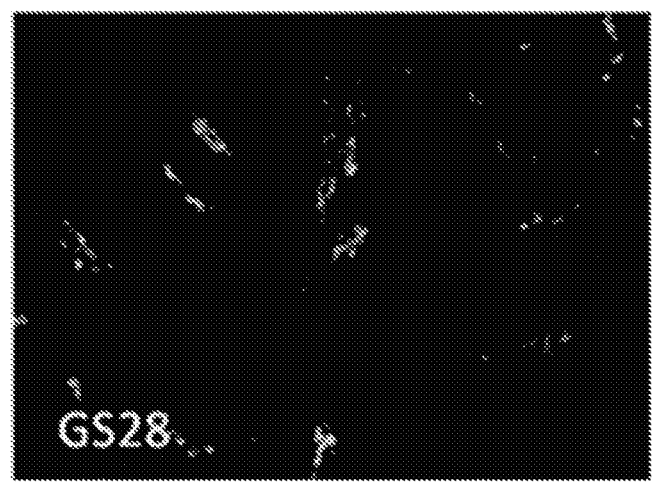
Figure 5I:
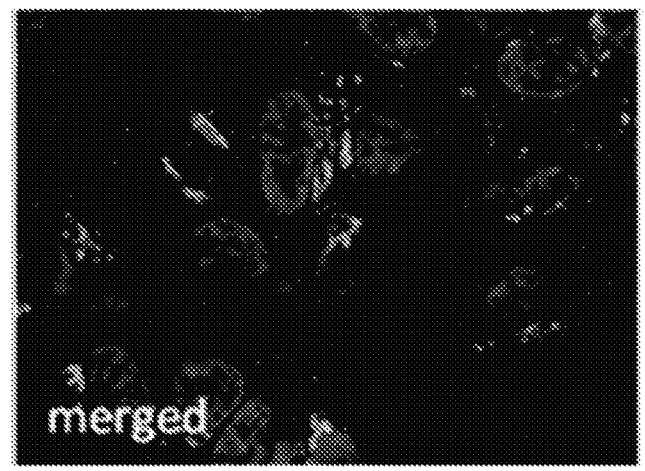

Immunofluorescent confocal microscopy indicated endogenous LRBA colocalized with Golgi proteins (GM-130, P-230, and GS-28) and with EEA1, an early endosome marker. The overlap between LRBA and GM-130 is 62% in one million cells, seen in FIG. 4. GM-130 is a coiled-coil protein associated with the Golgi matric necessary for tethering events in membrane fusion and has a role in maintaining cis-Golgi structure (Barr, & Short, Golgins in the structure and dynamics of the Golgi apparatus. 2003. *Current opinion in cell biology* 15: 405-413; (Nakamura, et al., Characterization of a cis-Golgi matrix protein, GM130. 1995. *The Journal of cell biology* 131: 1715-1726; (Puthenveedu, et al., GM130 and GRASP65-dependent lateral cisternal fusion allows uniform Golgi-enzyme distribution. 2006. Nature cell biology 8: 238-248). P-230 is associated with vesicles budding from the trans-Golgi network (Gleeson, et al., p230 is associated with vesicles budding from the trans-Golgi network. 1996. *Journal of cell science* 109 (Pt 12): 2811-2821) and required for the regulated secretion of TNF (Lieu, et al., A trans-Golgi network golgin is required for the regulated secretion of TNF in activated macrophages in vivo. 2008. *Proceedings of the National Academy of Sciences of the United States of America* 105: 3351-3356)). GS28 is a 28-kDa membrane protein that plays an essential role in mammalian endoplasmic reticulum (ER)-Golgi or intra-Golgi vesicle transport (Subramaniam, et al., GS28, a 28-kilodalton Golgi SNARE that participates in ER-Golgi transport. 1996. *Science* 272: 1161-1163), found to protect p53 from degradation (Sun, et al., Golgi-SNARE GS28 potentiates cisplatin-induced apoptosis by forming GS28-MDM2-p53 complexes and by preventing the ubiquitination and degradation of p53. 2012. *The Biochemical journal* 444: 303-314).

Figure 11A:
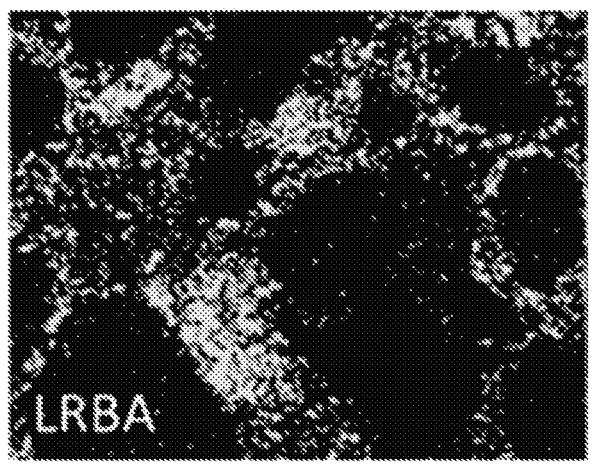
FIGS. 11(A)-(C) are a series of confocal images showing LRBA is co-localized with β-Adaptin demonstrated by confocal microscopy and JACoP software. Pearson's Coefficient: r=0.234 Overlap Coefficient: r=0.345 r^2=k1×k2: k1=0.171 k2=0.694 Using thresholds (thrA=84 and thrB=30) Overlap Coefficient: r=0.798 r^2=k1×k2: k1=0.492 k2=1.294 Manders' Coefficients (original): M1=0.541 (fraction of A overlapping B) M2=0.693 (fraction of B overlapping A) Manders' Coefficients (using threshold value of 84 for imgA and 30 for imgB): M1=0.226 (fraction of A overlapping B) M2=0.303 (fraction of B overlapping A) Costes' automatic threshold set to 2 for imgA & 5 for imgB Pearson's Coefficient: r=0.061 (0.0 below thresholds) M1=0.999 & M2=0.979 Van Steensel's Cross-correlation Coefficient between H293adaptinb(red).tif and H293LRBA(green).tif: CCF min.: 0.076 (obtained for dx=20) CCF max.: 0.234 (obtained for dx=0) Results for fitting CCF on a Gaussian (CCF=a+(b−a)exp(−(xshift-c)^2/(2d^2))): Formula: y=a+(b−a)*exp(−(x−c)*(x−c)/(2*d*d)) Status: Success Number of completed minimizations: 2 Number of iterations: 93 (max: 4000) Time: 1 ms Sum of residuals squared: 0.0050619 Standard deviation: 0.011249 R^2: 0.92969 Parameters: a=0.074437 b=0.20971 c=−2.50994 d=10.06241 FWHM=23.695 pixels Cytofluorogram's parameters: a: 0.123 b: 5.619 Correlation coefficient: 0.234 Li's Intensity correlation coefficient: ICQ: 0.24554066463945545 Costes' randomization based colocalization: Parameters: Nb of randomization rounds: 1000, Resolution (bin width): 0.0010 r (original)=0.234 r (randomized)=0.0±−0.0010 (calculated from the fitted data) P-value=100.0% (calculated from the fitted data) Results for fitting the probability density function on a Gaussian (Probability=a+(b−a)exp(−(R-c)^2/(2d^2))): Formula: y=a+(b−a)*exp(−(x−c)*(x−c)/(2*d*d)) Status: Success Number of completed minimizations: 2 Number of iterations: 214 (max: 4000) Time: 2 ms Sum of residuals squared: 0.00014031 Standard deviation: 0.0041879 R^2: 0.99885 Parameters: a=−0.0011198 b=0.32906 c=−0.00010102 d=−0.0011592 FWHM=0.0020.
Figure 11B:
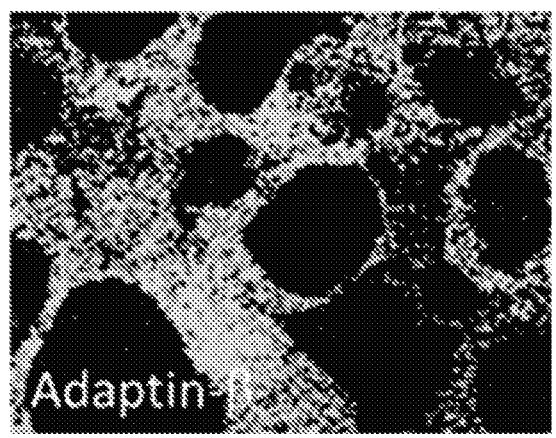
Figure 11C:
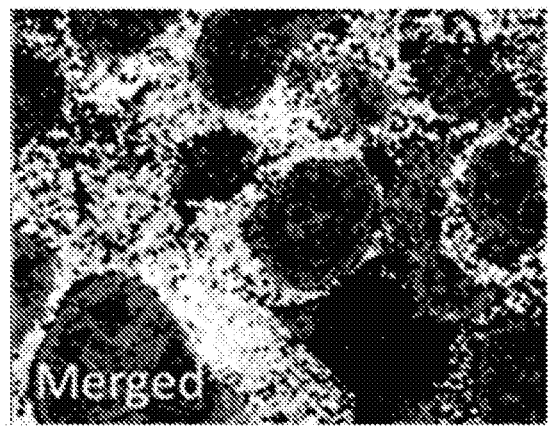
Figure 12A:
FIGS. 12(A)-(C) are a series of confocal images showing LRBA is co-localized with early endosome protein EEA1 demonstrated by confocal microscopy and JACoP software. Pearson's Coefficient: r=0.153 Overlap Coefficient: r=0.193 r^2=k1×k2: k1=0.353 k2=0.106 Using thresholds (thrA=10 and thrB=19) Overlap Coefficient: r=0.801 r^2=k1×k2: k1=1.358 k2=0.472 Manders' Coefficients (original): M1=0.448 (fraction of A overlapping B) M2=0.262 (fraction of B overlapping A) Manders' Coefficients (using threshold value of 10 for imgA and 19 for imgB): M1=0.215 (fraction of A overlapping B) M2=0.185 (fraction of B overlapping A) Costes' automatic threshold set to 2 for imgA & 3 for imgB Pearson's Coefficient: r=0.05 (0.0 below thresholds) M1=0.993 & M2=0.968 Van Steensel's Cross-correlation Coefficient between H293LRBAgreenframes.tif and H293EEA1red1mcropped2frames.tif: CCF min.: 0.048 (obtained for dx=−20) CCF max.: 0.153 (obtained for dx=0) Results for fitting CCF on a Gaussian (CCF=a+(b−a)exp(−(xshift-c)^2/(2d^2))): Formula: y=a+(b−a)*exp(−(x−c)*(x−c)/(2*d*d)) Status: Success Number of completed minimizations: 2 Number of iterations: 104 (max: 4000) Time: 4 ms Sum of residuals squared: 0.0030669 Standard deviation: 0.0087563 R^2: 0.91752 Parameters: a=0.058253 b=0.13982 c=−0.46218 d=5.72505 FWHM=13.481 pixels Cytofluorogram's parameters: a: 0.277 b: 3.149 Correlation coefficient: 0.153 Li's Intensity correlation coefficient: ICQ.
Figure 12B:
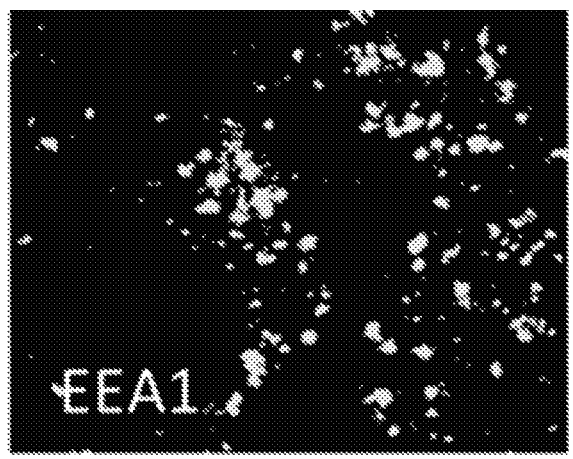
Figure 12C:
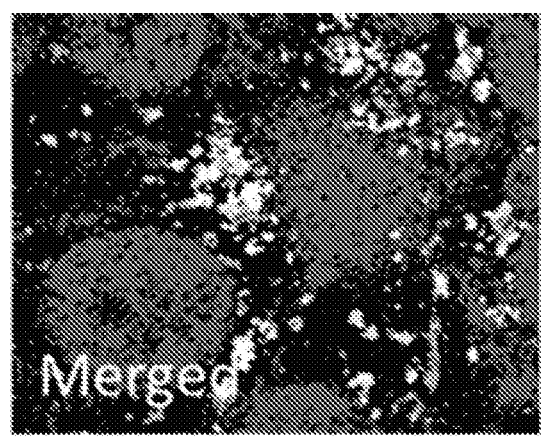

The immunofluorescence confocal microscopy results show that LRBA also colocalized with EEA1, Clathrin, Rab4 and Adaptin-β, FIGS. 5(A) through (I), 6(A) through (C), 7(A) through (C), 8(A) through (C), 9(A) through (C), 10(A) through (C), 11(A) through (C). EEA1 is an early endosome marker; Clathrin is a vesicle coating protein, shown in FIGS. 12(A) through (C), and Adaptin-β, seen in FIGS. 11(A) through (C), is an adaptor protein that mediates the formation of vesicles by Clathrin-coated pits, through interaction with membrane-bound receptors. Rab4 a member of the RAB family of RAS-related GTP-binding proteins, important regulators of vesicular transport and are located in specific intracellular compartments. Rab4A is a master regulator of receptor recycling from endocytic compartments to the plasma membrane (Goueli, et al., TBC1D16 is a Rab4A GTPase activating protein that regulates receptor recycling and EGF receptor signaling. 2012. *Proceedings of the National Academy of Sciences of the United States of America* 109: 15787-15792). Vesicle trafficking is required for homeostasis (deposition, recycling and degradation) of cell membrane proteins.

Figure 8A:
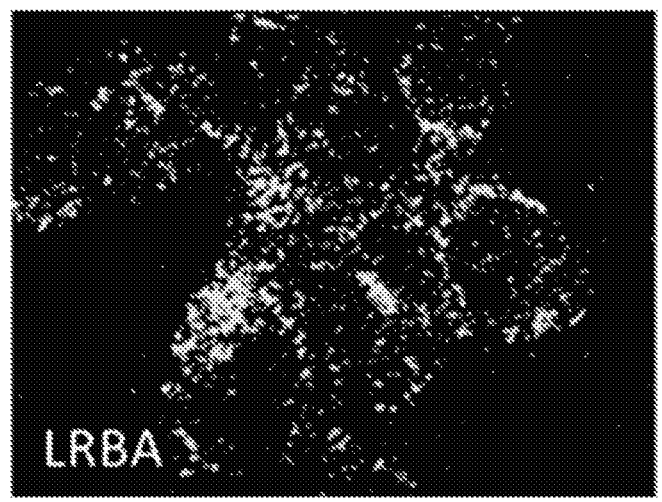
FIGS. 8(A)-(C) are a series of confocal images showing LRBA is co-localized with β-tubulin demonstrated by confocal microscopy and JACoP software. Pearson's Coefficient: r=0.171 Overlap Coefficient: r=0.207 r^2=k1×k2: k1=0.134 k2=0.32 Using thresholds (thrA=33 and thrB=42) Overlap Coefficient: r=0.753 r^2=k1×k2: k1=0.945 k2=0.599 Manders' Coefficients (original): M1=0.216 (fraction of A overlapping B) M2=0.713 (fraction of B overlapping A) Manders' Coefficients (using threshold value of 33 for imgA and 42 for imgB): M1=0.089 (fraction of A overlapping B) M2=0.362 (fraction of B overlapping A) Costes' automatic threshold set to 5 for imgA & 2 for imgB Pearson's Coefficient: r=0.044 (0.0 below thresholds) M1=0.986 & M2=0.997 Van Steensel's Cross-correlation Coefficient between H293LRBAgreentubulinred(1)cropped.tif.frames (red) and H293LRBAgreentubulinred(1)cropped.tif.frames (green): CCF min.: 0.043 (obtained for dx=20) CCF max.: 0.171 (obtained for dx=0) Results for fitting CCF on a Gaussian (CCF=a+(b−a)exp(−(xshift−c)^2/(2d^2))): Formula: y=a+(b−a)*exp(−(x−c)*(x−c)/(2*d*d)) Status: Success Number of completed minimizations: 2 Number of iterations: 104 (max: 4000) Time: 4 ms Sum of residuals squared: 0.0013469 Standard deviation: 0.0058028 R^2: 0.97500 Parameters: a=0.053279 b=0.15896 c=−0.17761 d=7.69119 FWHM=18.111 pixels Cytofluorogram's parameters: a: 0.115 b: 1.507 Correlation coefficient: 0.171 Li's Intensity correlation coefficient: ICQ: 0.3429955832151942 Costes' randomization based colocalization: Parameters: Nb of randomization rounds: 1000, Resolution (bin width): 0.0010 r (original)=0.17 r (randomized)=0.0±−0.0010 (calculated from the fitted data) P-value=100.0% (calculated from the fitted data) Results for fitting the probability density function on a Gaussian (Probability=a+(b−a)exp(−(R−c)^2/(2d^2))): Formula: y=a+(b−a)*exp(−(x−c)*(x−c)/(2*d*d)) Status: Success Number of completed minimizations: 2 Number of iterations: 176 (max: 4000) Time: 2 ms Sum of residuals squared: 0.00020366 Standard deviation: 0.0053939 R^2: 0.99794 Parameters: a=−0.0024953 b=0.31261 c=−2.90146E-5 d=−0.0012107 FWHM=0.0020.
Figure 8B:
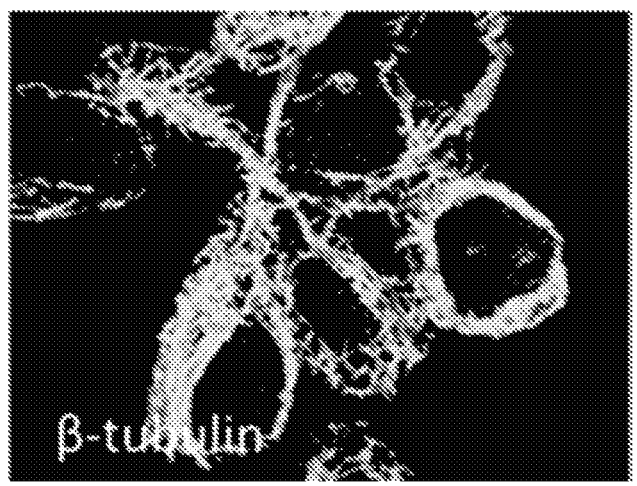
Figure 8C:
Figure 9A:
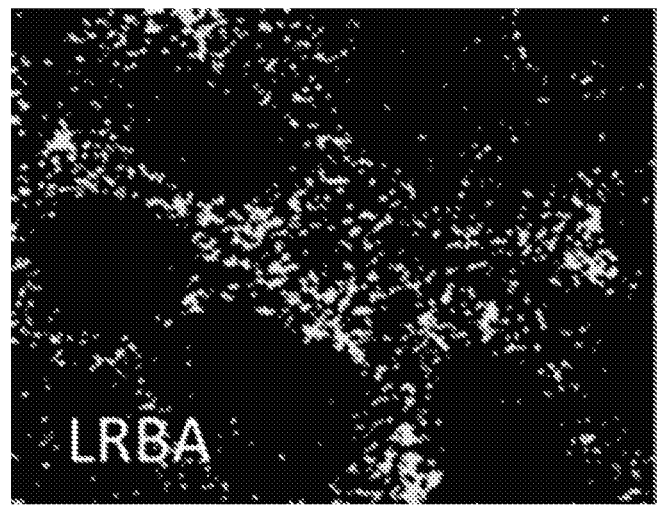
FIGS. 9(A)-(C) are a series of confocal images showing LRBA is co-localized with Clathrin demonstrated by confocal microscopy and JACoP software. Pearson's Coefficient: r=0.363 Overlap Coefficient: r=0.403 r^2=k1×k2: k1=0.329 k2=0.495 Using thresholds (thrA=21 and thrB=19) Overlap Coefficient: r=0.704 r^2=k1×k2: k1=0.696 k2=0.711 Manders' Coefficients (original): M1=0.51 (fraction of A overlapping B) M2=0.799 (fraction of B overlapping A) Manders' Coefficients (using threshold value of 21 for imgA and 19 for imgB): M1=0.402 (fraction of A overlapping B) M2=0.621 (fraction of B overlapping A) Costes' automatic threshold set to 2 for imgA & 3 for imgB Pearson's Coefficient: r=0.151 (0.0 below thresholds) M1=0.998 & M2=0.997 Van Steensel's Cross-correlation Coefficient between H293LRBAgreenframes.tif and H293Clathrinredrames.tif: CCF min.: 0.0050 (obtained for dx=−20) CCF max.: 0.363 (obtained for dx=0) Results for fitting CCF on a Gaussian (CCF=a+(b−a)exp(−(xshift−c)^2/(2d^2))): Formula: y=a+(b−a)*exp(−(x−c)*(x−c)/(2*d*d)) Status: Success Number of completed minimizations: 2 Number of iterations: 103 (max: 4000) Time: 4 ms Sum of residuals squared: 0.018832 Standard deviation: 0.021698 R^2: 0.95013 Parameters: a=0.016205 b=0.30867 c=2.92049 d=9.06131 FWHM=21.337 pixels Cytofluorogram's parameters: a: 0.301 b: 2.932 Correlation coefficient: 0.363 Li's Intensity correlation coefficient: ICQ: 0.3826994110012978 Costes' randomization based colocalization: Parameters: Nb of randomization rounds: 1000, Resolution (bin width): 0.0010 r (original)=0.363 r (randomized)=0.0±−0.0050 (calculated from the fitted data) P-value=100.0% (calculated from the fitted data) Results for fitting the probability density function on a Gaussian (Probability=a+(b−a)exp(−(R-c)^2/(2d^2))): Formula: y=a+(b−a)*exp(−(x−c)*(x−c)/(2*d*d)) Status: Success Number of completed minimizations: 2 Number of iterations: 165 (max: 4000) Time: 5 ms Sum of residuals squared: 0.00065865 Standard deviation: 0.0048501 R^2: 0.96764 Parameters: a=−0.0049276 b=0.074079 c=−0.00016016 d=−0.0058440 FWHM=0.013 Colocalization based on distance between centres of mass Threshold for Image A=21; Image B=19 Particles size between 0 & 80136 Image A: 15 centre(s) colocalizing out of 67 Image B: 19 centre(s) colocalizing out of 109 Colocalization based on centres of mass-particles coincidence Threshold for Image A=21; Image B=19 Particles size between 0 & 80136 Image A: 5 centre(s) colocalizing out of 67 Image B: 2 centre(s) colocalizing out of 109.
Figure 9B:
Figure 9C:
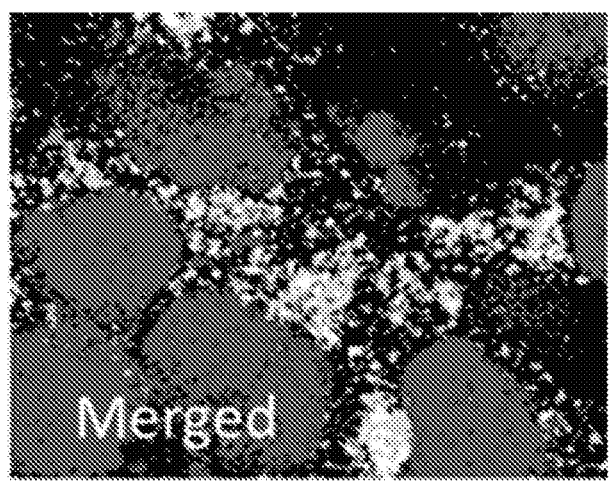
Figure 10A:
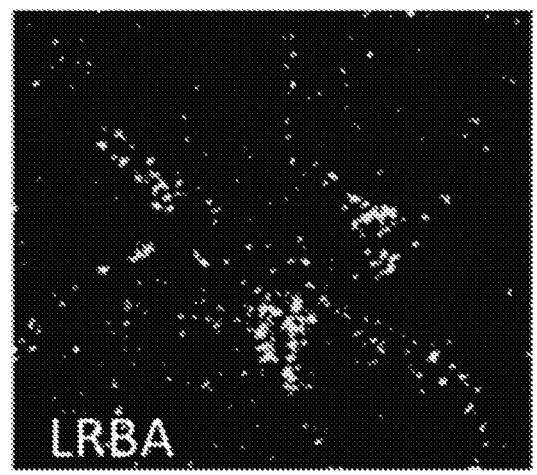
FIGS. 10(A)-(C) are a series of confocal images showing LRBA is co-localized with Rab4 demonstrated by confocal microscopy and JACoP software. Pearson's Coefficient: r=0.395 Overlap Coefficient: r=0.46 r^2=k1×k2: k1=0.735 k2=0.288 Using thresholds (thrA=3 and thrB=12) Overlap Coefficient: r=0.596 r^2=k1×k2: k1=0.954 k2=0.372 Manders' Coefficients (original): M1=0.764 (fraction of A overlapping B) M2=0.806 (fraction of B overlapping A) Manders' Coefficients (using threshold value of 3 for imgA and 12 for imgB): M1=0.638 (fraction of A overlapping B) M2=0.728 (fraction of B overlapping A) Costes' automatic threshold set to 2 for imgA & 7 for imgB Pearson's Coefficient: r=0.172 (0.0 below thresholds) M1=0.988 & M2=0.984 Van Steensel's Cross-correlation Coefficient between H293LRBAgreenframes.tif and H293Rab4red(1)frames.tif: CCF min.: 0.259 (obtained for dx=20) CCF max.: 0.395 (obtained for dx=0) Results for fitting CCF on a Gaussian (CCF=a+(b−a)exp(−(xshift-c)^2/(2d^2))): Formula: y=a+(b−a)*exp(−(x−c)*(x−c)/(2*d*d)) Status: Success Number of completed minimizations: 2 Number of iterations: 92 (max: 4000) Time: 1 ms Sum of residuals squared: 0.0051683 Standard deviation: 0.011367 R^2: 0.90661 Parameters: a=0.26934 b=0.36942 c=0.68039 d=6.78003 FWHM=15.965 pixels Cytofluorogram's parameters: a: 0.627 b: 6.485 Correlation coefficient: 0.395 Li's Intensity correlation coefficient: ICQ: 0.3393714371437143 Costes' randomization based colocalization: Parameters: Nb of randomization rounds: 1000, Resolution (bin width): 0.0010 r (original)=0.395 r (randomized)=0.0±−0.0030 (calculated from the fitted data) P-value=100.0% (calculated from the fitted data) Results for fitting the probability density function on a Gaussian (Probability=a+(b−a)exp(−(R-c)^2/(2d^2))): Formula: y=a+(b−a)*exp(−(x−c)*(x−c)/(2*d*d)) Status: Success Number of completed minimizations: 2 Number of iterations: 155 (max: 4000) Time: 1 ms Sum of residuals squared: 0.00064254 Standard deviation: 0.0055315 R^2: 0.98428 Parameters: a=5.76543E-5 b=0.12117 c=−7.94034E-5 d=−0.0032634 FWHM=0.0070 Colocalization based on distance between centres of mass Threshold for Image A=3; Image B=12 Particles size between 0 & 213312 Image A: 351 centre(s) colocalizing out of 996 Image B: 251 centre(s) colocalizing out of 455 Colocalization based on centres of mass-particles coincidence Threshold for Image A=3; Image B=12 Particles size between 0 & 213312 Image A: 9 centre(s) colocalizing out of 996 Image B: 5 centre(s) colocalizing out of 455.
Figure 10B:
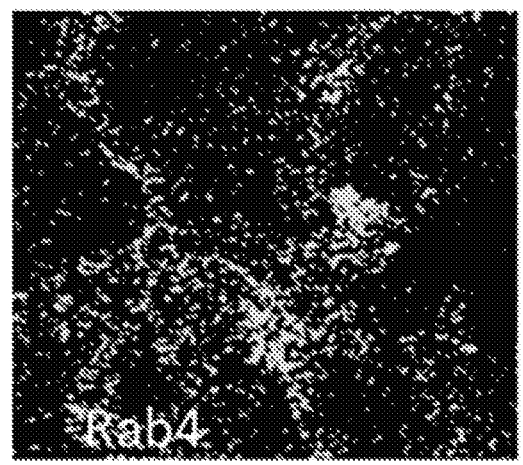
Figure 10C:
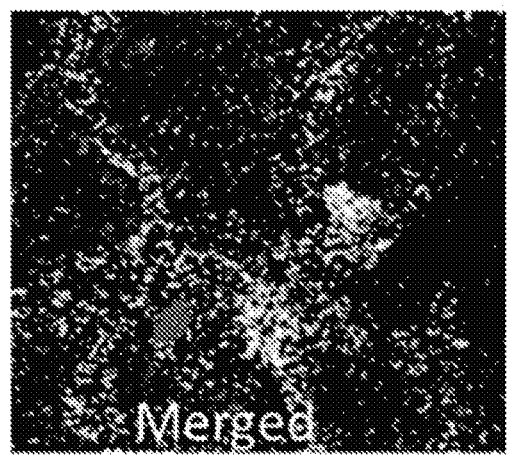

Immunofluorescence confocal microscopy results also demonstrated that LRBA colocalized with tubulin in the microtubules, as seen in FIGS. 8(A)-(C). The results also were supported by the H293 cells stably transfected with a plasmid that overexpresses the full length of Lrba tagged with EGFP at the C-terminal. Cell skeleton association of the Lrba/EGFP fusion protein is demonstrated.

LRBA was predicted to have two RII binding motifs (Wang, et al., Identification of a novel lipopolysaccharideinducible gene with key features of both A kinase anchor proteins and chs1/beige proteins. 2001. *J Immunol* 166: 4586-4595) and its orthologue in *Drosophila rugose* (rg) is an A kinase anchor protein (AKAP) (Han, et al., Molecular characterization of a novel A kinase anchor protein from *Drosophila melanogaster*. 1997. *The Journal of biological chemistry* 272: 26611-26619). PKA, also known as cAMP-dependent protein kinase, functions based on its location or its anchor protein and is involved in various membrane trafficking events including the generation of vesicles at the trans-Golgi network (TGN) for both constitutive and regulated secretion (Ohashi & Huttner, An elevation of cytosolic protein phosphorylation modulates trimeric G-protein regulation of secretory vesicle formation from the trans-Golgi network. 1994. *The Journal of biological chemistry* 269: 24897-24905; Muniz, et al., Protein kinase A activity is required for the budding of constitutive transport vesicles from the trans-Golgi network. 1997. *Proceedings of the National Academy of Sciences of the United States of America* 94: 14461-14466). LRBA contains two potential RII binding motifs for anchoring PKA through the type II regulatory subunits (RII) (Wang, et al., Identification of a novel lipopolysaccharideinducible gene with key features of both A kinase anchor proteins and chs1/beige proteins. 2001. J Immunol 166: 4586-4595). A computer program, which has over 80 percent accuracy to predict RII binding motifs, predicted one of the two potential RII binding motifs (Hou, et al., Prediction of peptides binding to the PKA RIIalpha subunit using a hierarchical strategy. 2011. *Bioinformatics* 27: 1814-1821). A previous study suggests that LRBA may not bind the RII subunit (Wang, et al., Neurobeachin: A protein kinase A-anchoring, beige/Chediak-higashi protein homolog implicated in neuronal membrane traffic. 2000. *The*

Figure 6A:
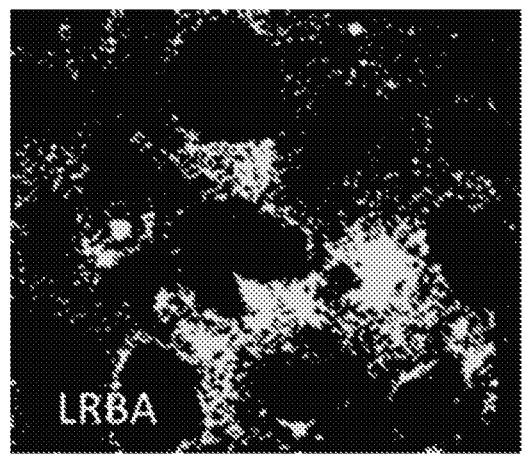
FIG. 6(A)-(C) is a series of confocal images showing LRBA is co-localized with PKA RIIβ subunits demonstrated by confocal microscopy and JACoP software. The colocalization was evaluated by the Pearson's Coefficient: r=0.225; Overlap Coefficient: r=0.257; r^2=k1×k2: k1=0.351; k2=0.189 using thresholds (thrA=12 and thrB=8): Overlap Coefficient: r=0.802; r^2=k1×k2; k1=0.802; k2=0.802 Manders' Coefficients (original): M1=0.407 (fraction of A overlapping B) M2=0.348 (fraction of B overlapping A) Manders' Coefficients (using threshold value of 12 for imgA and 8 for imgB): M1=0.338 (fraction of A overlapping B) M2=0.162 (fraction of B overlapping A) Costes' automatic threshold set to 3 for imgA & 2 for imgB Pearson's Coefficient: r=0.111 (0.0 below thresholds) M1=0.958 & M2=0.99 Van Steensel's Cross-correlation Coefficient between H293LRBAgreenframes.tif and H293PKARIIbredframes.tif: CCF min.: 0.048 (obtained for dx=−20) CCF max.: 0.225 (obtained for dx=0) Results for fitting CCF on a Gaussian (CCF=a+(b−a)exp(−(xshift−c)^2/(2d^2))): Formula: y=a+(b−a)*exp(−(x−c)*(x−c)/(2*d*d)) Status: Success Number of completed minimizations: 2 Number of iterations: 98 (max: 4000) Time: 3 ms Sum of residuals squared: 0.00081518 Standard deviation: 0.0045144 R^2: 0.99369 Parameters: a=0.042353 b=0.21464 c=−0.17572 d=8.50897 FWHM=20.037 pixels Cytofluorogram's parameters: a: 0.304 b: 1.322 Correlation coefficient: 0.225 Li's Intensity correlation coefficient: ICQ: 0.3859623903228554 Costes' randomization based colocalization: Parameters: Nb of randomization rounds: 1000, Resolution (bin width): 0.0010 r (original)=0.225 r (randomized)=0.0±0.0 (calculated from the fitted data) P-value=100.0% (calculated from the fitted data) Results for fitting the probability density function on a Gaussian (Probability=a+(b−a)exp(−(R−c)^2/(2d^2))): Formula: y=a+(b−a)*exp(−(x−c)*(x−c)/(2*d*d)) Status: Success Number of completed minimizations: 2 Number of iterations: 178 (max: 4000) Time: 4 ms Sum of residuals squared: 0.00016703 Standard deviation: 0.0057798 R^2: 0.99891 Parameters: a=0.0048521 b=0.45306 c=−1.33088E-5 d=0.00077178 FWHM=0.0010.
Figure 6B:
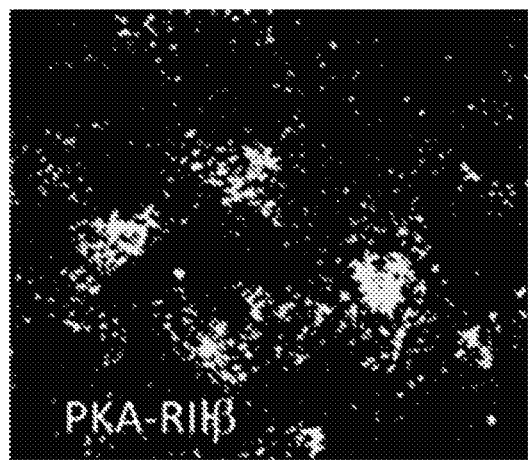
Figure 6C:
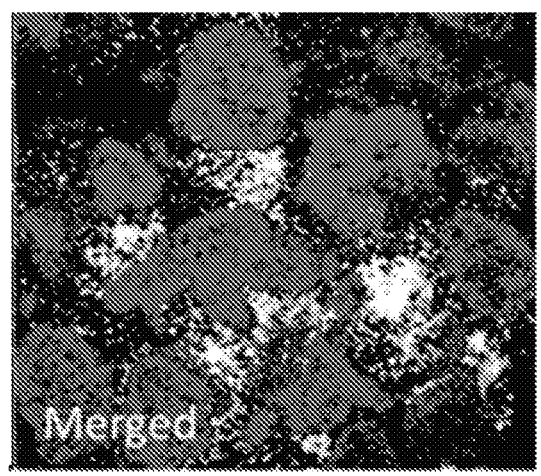
Figure 7A:
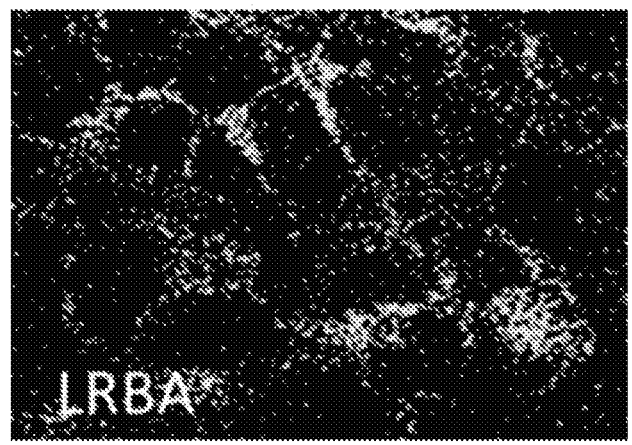
FIGS. 7(A)-(C) are a series of confocal images showing LRBA is co-localized with PKA catalytic subunits demonstrated by confocal microscopy and JACoP software. Pearson's Coefficient: r=0.197 Overlap Coefficient: r=0.261 r^2=k1×k2: k1=0.232 k2=0.295 Using thresholds (thrA=44 and thrB=68) Overlap Coefficient: r=0.821 r^2=k1×k2: k1=1.02 k2=0.66 Manders' Coefficients (original): M1=0.307 (fraction of A overlapping B) M2=0.681 (fraction of B overlapping A) Manders' Coefficients (using threshold value of 44 for imgA and 68 for imgB): M1=0.121 (fraction of A overlapping B) M2=0.243 (fraction of B overlapping A) Costes' automatic threshold set to 2 for imgA & 4 for imgB Pearson's Coefficient: r=0.092 (0.0 below thresholds) M1=0.994 & M2=0.995 Van Steensel's Cross-correlation Coefficient between H293LRBAgreen.tif and H293PKAcred.tif: CCF min.: 0.029 (obtained for dx=−20) CCF max.: 0.197 (obtained for dx=0) Results for fitting CCF on a Gaussian (CCF=a+(b−a)exp(−(xshift−c)^2/(2d^2))): Formula: y=a+(b−a)*exp(−(x−c)*(x−c)/(2*d*d)) Status: Success Number of completed minimizations: 2 Number of iterations: 99 (max: 4000) Time: 4 ms Sum of residuals squared: 0.0024994 Standard deviation: 0.0079048 R^2: 0.97523 Parameters: a=0.041320 b=0.18057 c=0.094024 d=6.44875 FWHM=15.185 pixels Cytofluorogram's parameters: a: 0.18 b: 3.989 Correlation coefficient: 0.197 Li's Intensity correlation coefficient: ICQ: 0.2826960483630244 Costes' randomization based colocalization: Parameters: Nb of randomization rounds: 1000, Resolution (bin width): 0.0010 r (original)=0.197 r (randomized)=0.0±−0.0010 (calculated from the fitted data) P-value=100.0% (calculated from the fitted data) Results for fitting the probability density function on a Gaussian (Probability=a+(b−a)exp(−(R−c)^2/(2d^2))): Formula: y=a+(b−a)*exp(−(x−c)*(x−c)/(2*d*d)) Status: Success Number of completed minimizations: 2 Number of iterations: 172 (max: 4000) Time: 3 ms Sum of residuals squared: 0.00063475 Standard deviation: 0.0079671 R^2: 0.99365 Parameters: a=0.0025887 b=0.27547 c=−9.38343E-5 d=−0.0013731 FWHM=0.0030.
Figure 7B:
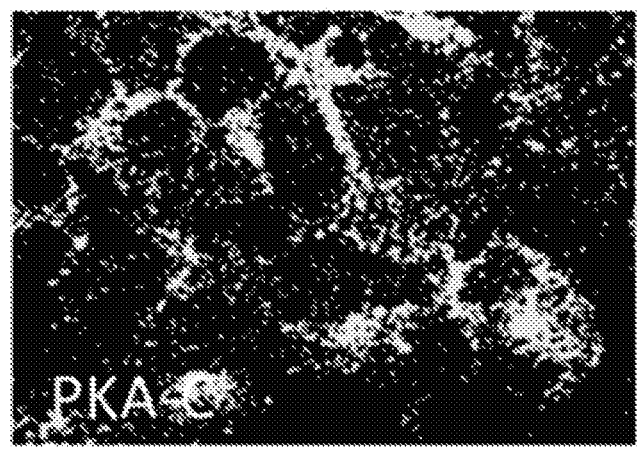
Figure 7C:
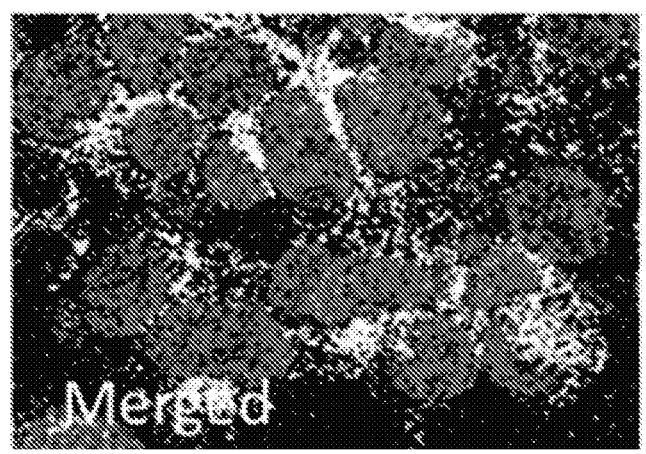

Journal of neuroscience: the official journal of the Society for Neuroscience 20: 8551-8565). However, LRBA was found to colocalized with the RIIβ, RIIα and RIIc subunits of PKA, as seen in FIGS. 6(A)-(C), contradicting the previous study and indicating it binds to PKA directly.

LRBA also colocalized with nucleus in mouse bone marrow cells, shown in FIGS. 4-11 and colocalized with Lysosome-associated membrane glycoprotein (Lamp) in A549 cells (Data not shown).

Time lapse video was taken for living macrophage cells. RAW264.7 macrophage cells stably transfected with pBWEGFP were cultured in a glass bottom dish and put into the mini cell culture chamber at 37° C. and 5% $CO_2$ in a Leica TCS SP2 laser scanning inverted confocal microscope. LPS was added at final concentration of 100 ng/ml. The time-lapse video of four living cells was taken at one picture per second using the Avg. timelapse interval: 1000.05 ms (1.0 Hz) (+/−8.9 ms); Initial SAC Position: 1700; Objective: 100× (magnification: 100.00×); Mag. changer: EMCCD (magnification: 1.00×); 8 inning: 1×1; Channel 1: c488em at 50 ms. Gain: 3 Intensification: 700 ND: 60 [Independent]. The time-lapse video was taken at one picture per second using the Leica TCS SP2 laser scanning inverted confocal microscope with a mini cell culture chamber at 37° C. and 5% $CO_2$.

Snapshots from a time lapse video of a live cell show that LRBA-positive vesicles are budding from Golgi and moving to cell membrane. These processes accelerate within minutes of LPS stimulation, seen in FIGS. 5(A)-(I). These data strongly correlate with previous information (Wang, et al., Identification of a novel lipopolysaccharide-inducible gene with key features of both A kinase anchor proteins and chs1/beige proteins. 2001. *J Immunol* 166: 4586-4595) and the data from Human Protein Atlas Project (Fagerberg, et al., Contribution of Antibody-based Protein Profiling to the Human Chromosome-centric Proteome Project (C-HPP). 2012. *Journal of proteome research* 12(6):2439-48). This indicates that LRBA is dynamically involved in vesicle trafficking.

The RAW 264.7 cells were stably transfected with a plasmid expressing LRBA BEACH-WD/EGFP fusion protein to study the subcellular localizations of LRBA as described (Wang, et al., Identification of a novel lipopolysaccharide-inducible gene with key features of both A kinase anchor proteins and chs1/beige proteins. 2001. *J Immunol* 166: 4586-4595). Confocal time lapse video was used to observe vesicle trafficking. The results show that LRBA-associated vesicles are isolated from Golgi area, traveling along cytoskeleton, towards cell membrane and fused with the cell membrane. LRBA-associated vesicles forming at the cell membrane were also observed, seen in FIGS. 13(A)-(H). The uneven distribution of LRBA-GFP on the cell membrane and vesicles were observed, indicating that LRBA may not be a component of these structures, rather a regulator of these structures, seen in FIGS. 13(I) to (P). The results confirm the data obtained by IF that LRBA is located at the Golgi, vesicle and cell membrane. LRBA associated vesicles are very active in the pseudopodia. The vesicle movements respond to LPS stimulation quickly: the average speed of vesicles doubles 3 min after adding LPS into the media, but slows down to original levels after 5 and 23 min, as seen in FIGS. 14(A) and (B), Table 3.

TABLE 3

Path Movement Statistics of LRBA-Associated Vesicles (Manual Path).

| Path | Average Speed (microns/sec) | Maximum Speed (microns/sec) | Total Displacement (microns) | Path duration (time points) | Path duration (sec) |
|---|---|---|---|---|---|
| No LPS | | | | | |
| 0 | 0.1669 | 0.2947 | 3.17 | 20 | 19 |
| 1 | 0.1794 | 0.35 | 3.404 | 20 | 19 |
| 2 | 0.7541 | 0.9724 | 1.504 | 3 | 1.99 |
| 3 | 0.1378 | 0.2832 | 5.648 | 42 | 41 |
| 4 | 0.1823 | 0.3607 | 5.286 | 30 | 29 |
| 5 | 0.1947 | 0.3451 | 5.841 | 31 | 30 |
| 6 | 0.1991 | 0.412 | 3.983 | 21 | 20 |
| 7 | 0.4725 | 1.15 | 1.413 | 4 | 2.99 |
| 8 | 0.2055 | 0.4228 | 2.875 | 15 | 14 |
| 9 | 0.1795 | 0.34 | 1.795 | 11 | 10 |
| 10 | 0.1755 | 2.99 | 1.93 | 12 | 11 |
| 11 | 0.2019 | 03402 | 1.817 | 10 | 9 |
| 12 | 0.4894 | 0.7241 | 2.44 | 6 | 4.98 |
| 13 | 0.1128 | 0.2282 | 2.597 | 24 | 23 |
| 14 | 0.153 | 0.2674 | 4.59 | 31 | 30 |
| 15 | 0.2782 | 0.3785 | 0.8321 | 4 | 2.99 |
| 16 | 0.3228 | 0.3782 | 0.6436 | 3 | 1.99 |
| 17 | 0.1191 | 0.2674 | 2.62 | 23 | 22 |
| 18 | 0.1472 | 0.2282 | 1.765 | 13 | 12 |
| 19 | 0.4228 | 0.4228 | 0.4215 | 2 | 0.997 |
| 20 | 0.1521 | 0.299 | 3.648 | 25 | 24 |
| 21 | 0.5979 | 0.8969 | 1.192 | 3 | 1.99 |
| LPS (100 ng/ml) 3 min | | | | | |
| 0 | 0.838 | 1.183 | 1.684 | 3 | 2.01 |
| 1 | 0.2647 | 0.3559 | 1.056 | 5 | 3.99 |
| 2 | 0.8811 | 1.302 | 1.757 | 3 | 1.99 |
| 3 | 0.2441 | 0.4091 | 3.421 | 15 | 14 |
| 4 | 0.4695 | 1.09 | 3.291 | 8 | 7.01 |
| 5 | 0.1914 | 0.467 | 2.105 | 12 | 11 |
| 6 | 0.9217 | 1.185 | 6.46 | 8 | 7.01 |
| 7 | 0.314 | 0.4174 | 1.888 | 7 | 6.01 |
| 8 | 0.1812 | 0.4847 | 2.535 | 15 | 14 |
| 9 | 0.6408 | 0.8366 | 1.917 | 4 | 2.99 |
| 10 | 0.1748 | 0.2694 | 1.051 | 7 | 6.01 |
| 11 | 0.3406 | 0.4748 | 1.698 | 6 | 4.98 |
| 12 | 0.5446 | 1.07 | 2.715 | 6 | 4.99 |
| 13 | 0.2439 | 0.4224 | 2.439 | 11 | 10 |
| 14 | 0.3444 | 0.7056 | 2.404 | 8 | 6.98 |
| 15 | 0.6841 | 1.15 | 3.41 | 6 | 4.98 |
| 16 | 0.2469 | 0.6685 | 1.977 | 9 | 8.01 |
| 17 | 0.8842 | 1.304 | 3.553 | 5 | 4.02 |
| 18 | 0.3985 | 0.6356 | 1.589 | 5 | 3.99 |
| 19 | 0.7431 | 0.9641 | 1.482 | 3 | 1.99 |
| 20 | 1.034 | 2.365 | 4.153 | 5 | 4.02 |
| 21 | 0.3936 | 1.017 | 3.543 | 10 | 9 |
| 22 | 0.8833 | 1.338 | 3.523 | 5 | 3.99 |
| LPS (100 ng/ml) 5 min | | | | | |
| 0 | 0.216 | 0.3656 | 1.514 | 8 | 7.01 |
| 1 | 0.338 | 0.5667 | 4.728 | 15 | 14 |
| 2 | 0.2072 | 0.4058 | 3.105 | 16 | 15 |
| 3 | 0.3326 | 0.406 | 2.994 | 10 | 9 |
| 4 | 0.3394 | 0.6398 | 4.409 | 14 | 13 |
| 5 | 0.1072 | 0.2006 | 0.855 | 9 | 7.98 |
| 6 | 0.2481 | 0.3905 | 5.456 | 23 | 22 |
| 7 | 0.1717 | 0.2832 | 3.263 | 20 | 19 |
| LPS (100 ng/ml) 23 min | | | | | |
| 0 | 0.1798 | 0.36 | 1.081 | 7 | 6.01 |
| 1 | 0.2899 | 0.4821 | 3.188 | 12 | 11 |
| 2 | 0.2219 | 0.2832 | 2.219 | 11 | 10 |
| 3 | 0.2321 | 0.3555 | 4.179 | 19 | 18 |
| 4 | 0.2982 | 0.5082 | 4.171 | 15 | 14 |

Membrane trafficking is crucial to the transduction of signaling complexes to the GC and other cellular locations (Kholodenko, Four-dimensional organization of protein kinase signaling cascades: the roles of diffusion, endocytosis and molecular motors. 2003. *The Journal of experimental* biology 206: 2073-2082). Thus the endomembrane system plays a critical role in signal transduction. Previous data show that LRBA regulates two cell membrane receptors: epidermal growth factor receptor (EGFR) and NOTCH (Wang, et al., Deregulated expression of LRBA facilitates cancer cell growth. 2004. *Oncogene* 23: 4089-4097; Volders, et al., *Drosophila* rugose is a functional homolog of mammalian Neurobeachin and affects synaptic architecture, brain morphology, and associative learning. 2012. *The Journal of neuroscience: the official journal of the Society for Neuroscience* 32: 15193-15204; Yatim, et al., NOTCH1 nuclear interactome reveals key regulators of its transcriptional activity and oncogenic function. 2012. *Molecular cell* 48: 445-45), and regulates CVID receptors (Lopez-Herrera, et al., Mutations in LRBA are Associated with a Syndrome of Immune Deficiency and Autoimmunity. 2012. *Journal of Clinical Immunology* 32: 363-364).

The data show that LRBA is co-localized to several components of PKA: the catalyst unit, RIIβ and RIIα, supporting that LRBA is an AKAP and can phosphorylate substrate proteins such as NFκβ (Gao, et al., Neddylation of a breast cancer-associated protein recruits a class III histone deacetylase that represses NFkappaB-dependent transcription. 2006. *Nature cell biology* 8: 1171-1177), which is central to the immune system. The Golgi complex and TGN are major subcellular locations of RII (De Camilli, et al., Heterogeneous distribution of the cAMP receptor protein RII in the nervous system: evidence for its intracellular accumulation on microtubules, microtubule-organizing centers, and in the area of the Golgi complex. 1986. *The Journal of cell biology* 103: 189-203; Griffiths, et al., Ultrastructural localization of the regulatory (RII) subunit of cyclic AMP-dependent protein kinase to subcellular compartments active. 1990. *J Cell Sci.* 96 (Pt 4):691-703).

Well characterized LRBA polyclonal antibody and organelle-specific antibodies were used to detect endogenous proteins and study their co-localizations to LRBA. LRBA appears imperative to the GC's function, as LRBA is highly co-localized with GC proteins and LRBA-deficient B cells show an abnormally high number of GCs (Lopez-Herrera, et al., Deleterious Mutations in LRBA Are Associated with a Syndrome of Immune Deficiency and Autoimmunity. 2012. *American journal of human genetics* 90: 986-1001).

Endogenous LRBA is co-localized with multiple endomembrane proteins including Golgi proteins (GM-130, P-230, and GS-28), EEA1, PKA Rub and RIIc subunits, Tubulin, Clathrin, Rab4 and Adaptin, seen in FIGS. 6(A)-11(C). LRBA appears to be involved in endocytosis based on co-localization staining results. EEA1 is an early endosome marker, Clathrin is a vesicle coating protein, and Adaptin-B is an adaptor protein. Adaptins are proteins that mediate the formation of vesicles by Clathrin-coated pits, through interaction with membrane-bound receptors.

Additionally, Golgi co-localization of LRBA was demonstrated by in primary mouse cultured adherent bone marrow cells, as seen in FIGS. 6(A)-12(C). This shows that LRBA is mainly localized to the GC and dynamically involved in vesicle trafficking. LRBA associated vesicles are very active in the pseudopodia, indicating that LRBA may be involved in forming and growth of pseudopodia membrane.

Figure 1:
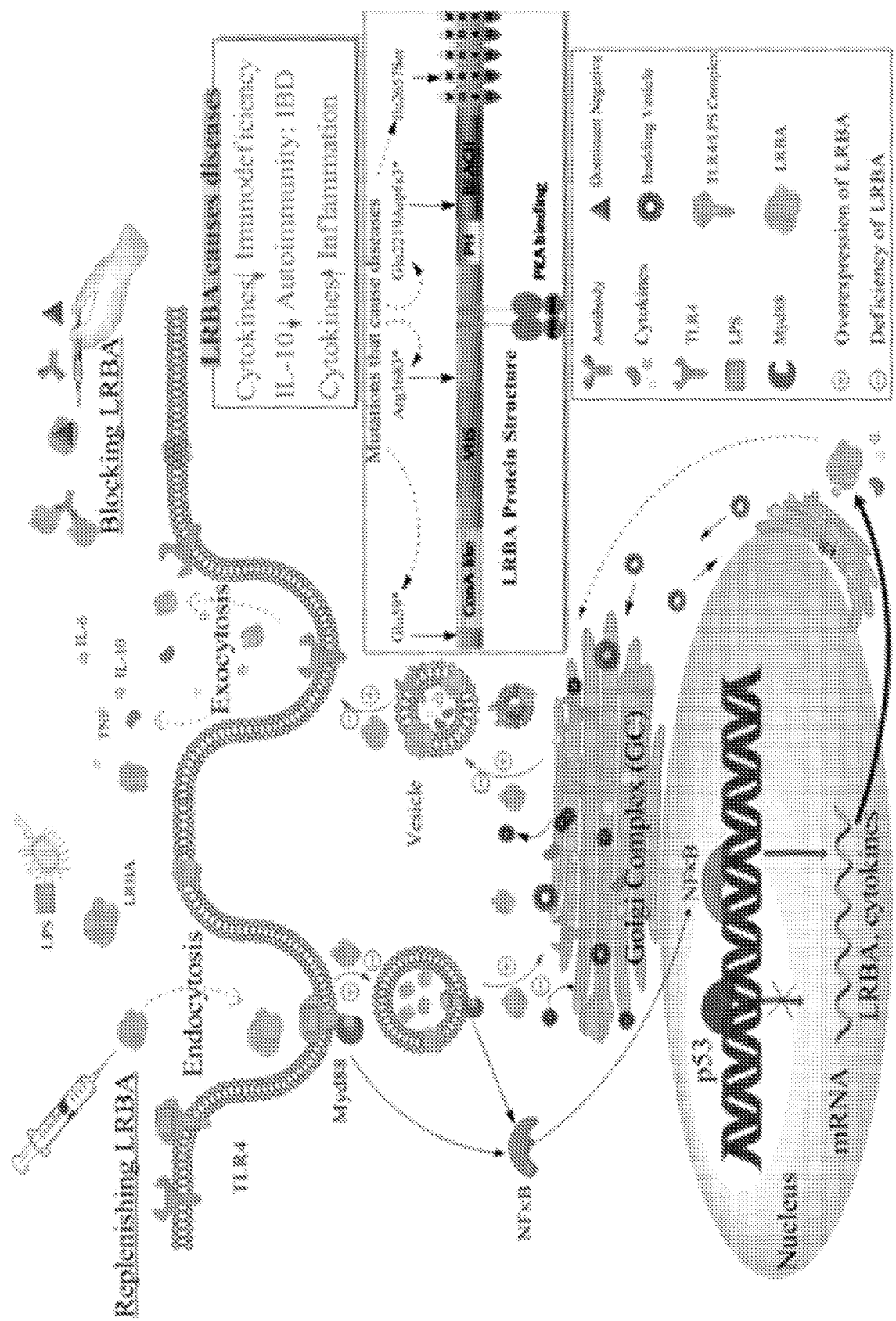
FIG. 1 is an image showing LRBA is a crucial regulator for cytokine secretion and TLR4 activation. Overexpression of LRBA enhances cytokine secretion and TLR4 activation, while depletion of LRBA inhibits these two processes. The plasma presence of LRBA provides a way to feasibly modulate LRBA: intravenously, LRBA can be replenished when down-regulated or blocked with antibody or dominant negative mutants (DNMs) when over-expressed to treat inflammatory diseases. A remote, functional conserved domain related to VHS[64] (Vps-27, Hrs and STAM) domain was identified in LRBA.[63] *=stop codon; fs*3=3 frame-shift codons then stop codon. For more details, please see the text.

The data support a two-stimulation model of vesicle trafficking for WBW proteins using LRBA as a prototype, as seen in FIG. 1, which was modified from a previous model (Wang, et al., Identification of a novel lipopolysaccharide-inducible gene with key features of both A kinase anchor proteins and chs1/beige proteins. 2001. *J Immunol* 166: 4586-4595). It suggests that two stimulations are required for LRBA function: the first stimulation is required to recruit LRBA to the membrane structure, such as GC and plasma membrane; while the second stimulation involves cAMP production and is required to activate the PKA anchored by LRBA. After the first stimulation of an immune cell, LRBA binds to the GC, plasma membrane or ER, and is involved in the sorting of cargo proteins, forming vesicles containing proteins for secretion or deposition on the plasma membrane. LRBA also may be involved in vesicle movements along microtubules to the plasma membrane where the PKA anchored by LRBA may be activated by the second messenger cyclic adenosine monophosphate (cAMP). PKA then phosphorylates the intracellular sequences of the membrane receptor/ligand complexes.

The WD domain of LRBA binds to the phosphorylated sequences to mediate the fusion of the vesicles with the membrane to release the cargo proteins or deposit membrane proteins on the plasma membrane of immune cells.

LRBA plays a role in membrane/vesicle trafficking and signal transduction required for the regulation and function of many immune molecules. The co-localization results show that LRBA is extensively associated with the endomembrane/vesicle trafficking system, including Golgi complex, endosome, lysosome and plasma membrane, indicating that LRBA is involved in membrane/vesicle trafficking, and LRBA deficiency may cause defective trafficking and signaling of immune effector molecules, resulting in immunodeficiency and autoimmunity diseases. (Kovanen, P. E., and Leonard, W. J. (2004). Cytokines and immunodeficiency diseases: critical roles of the gamma(c)-dependent cytokines interleukins 2, 4, 7, 9, 15, and 21, and their signaling pathways. Immunol Rev 202, 67-83).

Example 2

Lipopolysaccharide (LPS)-responsive beige-like anchor (LRBA) critical in cell proliferation and survival. LRBA was initially identified as an LPS-upregulated gene, with structural similarity to lysosomal trafficking regulator (LYST in human; beige in mouse) and A-kinase anchoring proteins (AKAPs). (Fagerberg, et al., Contribution of Antibody-based Protein Profiling to the Human Chromosome-centric Proteome Project (C-HPP). 2012. J proteome res.; 12(6):2439-48; Freundt, et al., Photoconversion of Lysotracker Red to a green fluorescent molecule. 2007. Cell research 17, 956-958). LRBA deficiency, resulting from homozygous deletion or mutations in LRBA gene, causes common variable immunodeficiency (CVID8) and autoimmunity. LRBA-deficient patients have an array of serious symptoms including hypogammaglobulinemia, antibody deficiency, recurrent bacterial infections, defective B-cell differentiation, decreased or absent antibody production, recurrent infections particularly respiratory infections, variable autoimmune disorders (idiopathic thrombocytopenic purpura autoimmune hemolytic anemia, inflammatory bowel disease). Death can occur from complication. The underlying cellular and molecular mechanisms are mostly unknown.

Additionally, knockdown of LRBA resulted in significant growth inhibition in multiple cell lines and sensitized cells to apoptosis; and LRBA upregulation is found in multiple cancer types including breast cancer, cervical cancer, epidermal carcimona, renal cancer, pancreatic cancer, colorectal cancer, and lung cancer. E2F and p53 transcription factors up- and down-regulate LRBA, respectively.

Thus far, mutations in 7 genes are associated with or cause CVID (common variable immunodeficiency), as seen in Table 4. LRBA is the 8th gene, the newest gene, mutations of which causes CVID, thus the name CVID8. Deficiency of LRBA results in fewer cells positive for three CVID proteins: CD19, CD20 and B cell-activating factor receptor (BAFFR) (Lopez-Herrera, et al., Deleterious mutations in LRBA are associated with a syndrome of immune deficiency and autoimmunity. 2012. *American journal of human genetics* 90:986-1001). Knockdown of LRBA decreases the TACI (transmembrane activator and calcium modulator and cyclophilin ligand interactor) levels on B cells. TACI controls T cell-independent B cell antibody responses, isotype switching, and B cell homeostasis, as seen in FIGS. 15(A) through (F). LRBA and TLR4 co-localized at GC and endosome or cell membrane, providing direct evidence that LRBA is involved in TLR4 activation. Knockdown of LRBA also decreases the surface levels of Toll-like receptor 4 (TLR4) and CD21 on B cells, seen in FIGS. 16(A) through 17.

CD21 is also known as complement component (3d/Epstein Barr virus) receptor 2(CR2), is a protein involved in the complement system. It binds to iC3b (inactive derivative of C3b), C3dg, or C3d. B cells have CR2 receptors on their surfaces, allowing the complement system to play a role in B-cell activation and maturation. These results indicate that LRBA is a master regulator of other CVID genes, and that its deficiency's causing immunodeficiency is at least partially through deregulation of these genes. Thus, deficiency of LRBA causes more severe and broader symptoms in patients due to that LRBA is a master regulator of multiple important genes.

TABLE 4

Comparison of eight CVID genes.

| CVID genes | Molecular weight (kD) | Subcellular localization | Function | Diseases |
|---|---|---|---|---|
| ICOS: inducible costimulator | 27 | T Cell Surface | CD28 and CTLA-4 cell-surface receptor family, germinal center formation, isotype class switching, and the development of memory B cells. Cell-cell signaling, immune response, and regulation of cell proliferation. | CVID26 |
| TACI: transmembrane activator and calcium modulator and cyclophilin ligand interactor. Receptor | 32 | B Cell Surface | Mutations impair the development of IgA- and IgG-secreting plasma cells and promote lymphoproliferation. Antibody class switching autoimmunity. Negative regulator of B-cell. Activation of the transcription factors NFAT, AP1, and NF-κB, humoral immunity by interacting with TNF ligand | Significantly reduced IgA levels mutated in 5%-10% of CVID patients Common variable immunodeficiency and IgA deficiency |
| CD19 | 61 | B Cell Surface | B cell co-receptor in conjunction with CD21 and CD81. | CVID 19, |
| BAFFR: B-cell activating factor receptor | 19 | B Cell Surface | B-lymphocyte survival (BAFF-R deficiency blocks B-cell development at the stage of transitional B cells, The most important B cell survival signals. Major B-cell-activating factor receptor. | An adult-onset antibody deficiency syndrome24 High levels of BAFF in mice, lead to an autoimmune disease similar to SLE75 |
| CD81 | 26 | B Cell Surface | Regulation of cell development, activation, growth and motility. | CVID21 |
| CD21 | 145 | B Cell Surface | Receptor for Epstein-Barr virus (EBV) binding on B and T lymphocytes Expansion of CD21lo in CVID patients has been clearly associated with a higher incidence of splenomegaly and more recently with autoimmune cytopenia | CVID 20 |
| CD20 | 35 | B Cell Surface | Impaired T cell-independent antibody responses markedly | Impaired T cell-independent antibody |

TABLE 4-continued

Comparison of eight CVID genes.

| CVID genes | Molecular weight (kD) | Subcellular localization | Function | Diseases |
|---|---|---|---|---|
| LRBA | 320 | Golgi apparatus, nucleus, plasma membrane, and cytoplasm. | augment antigen presentation and the B-cell receptor response to antigen development and differentiation of B-cells into plasma cells Master vesicle trafficking regulator required for other CVID genes. | responses22 Expansion of CD21lo has been found in patients with SLE76 and CVID77 Switched memory B cells are low 4, 8, 38 Disrupting BAFFR signaling causes a dramatic drop in B cell numbers 30 More CD20 positive B cells and respond to anti-CD20 therapy 4, 8, 9 |

LRBA is co-localized with GC proteins including p230, seen in FIGS. 3(A) through (D), which is required for the regulated secretion of TNF (Lieu, et al., A trans-Golgi network golgin is required for the regulated secretion of TNF in activated macrophages in vivo. 2008. *Proc Natl Acad Sci USA* 105, 3351-6). FAN is required for the TNF-induced expression of cytokines (Adam-Klages, et al. FAN, a novel WD-repeat protein, couples the p55 TNF-receptor to neutral sphingomyelinase. 1996. *Cell* 86, 937-47; Montfort, et al., FAN stimulates TNF(alpha)-induced gene expression, leukocyte recruitment, and humoral response. 2009. *J Immunol* 183, 5369-78). LYST is required for inflammatory cytokine production in response to LPS (Cheng, et al., Novel functions of a regulator of lysosomal trafficking, LYST in TLR4 signal transduction. 2012. Immunology 137, 299-300). One of the most common symptoms in LRBA-deficient patients is diarrhea associated with autoimmunity, probably due to a reduction in or absence of IL10 secretion. IL10 knockout mice develop fetal diarrhea (Kuhn, et al., Interleukin-10-deficient mice develop chronic enterocolitis. 1993. *Cell* 75, 263-74). These data along with the subcellular localization of LRBA and the dynamic involvement of LRBA in vesicle trafficking, all point to LRBA being required for cytokine secretion in response to LPS stimulation. Absence of LRBA may inhibit pro-inflammatory cytokine secretion and causes immunodeficiency.

Example 3

Testing was undertaken to determine if absence of LRBA inhibit pro-inflammatory cytokine secretion. The immunodeficiency caused by LRBA deficiency may result from defective cytokine signaling pathways (Leonard, Cytokines and immunodeficiency diseases. 2001. *Nat Rev Immunol* 1, 200-8; Kovanen, & Leonard, Cytokines and immunodeficiency diseases: critical roles of the gamma(c)-dependent cytokines interleukins 2, 4, 7, 9, 15, and 21, and their signaling pathways. 2004. *Immunol Rev* 202, 67-83), indicating LRBA is involved in cytokine regulation and TLR activation. Moreover, data show that LRBA is involved in the LPS pathway and most likely serves to facilitate transportation and secretion of cytokines through vesicle trafficking.

Figure 18B:
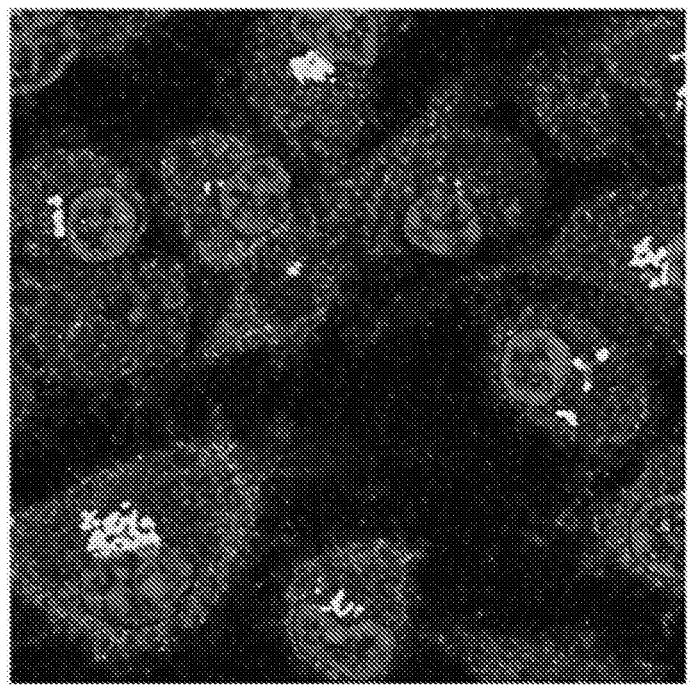

Testing has shown LRBA is involved transcription regulation through translocation to the nucleus upon LPS stimulation, as seen in FIG. 18. LRBA is found to bind NOTCH1 in the nucleus (Yatim, A., Benne, C., Sobhian, B., Laurent-Chabalier, S., Deas, O., Judde, J. G., Lelievre, J. D., Levy, Y., and Benkirane, M. (2012). NOTCH1 nuclear interactome reveals key regulators of its transcriptional activity and oncogenic function. Molecular cell 48, 445-458). In humans, plasma or extracellular LRBA levels are increased significantly in inflammation induced by LPS, or asthma patients (C) with an exacerbation, as seen in FIGS. 19(A) through (D). LRBA is present in the human plasma in mainly membrane-free fraction, with the presence of LRBA in the plasma confirmed by Western blot. The results show that LRBA is mainly present in vesicle-free plasma. Since LRBA is present in the plasma it can be used as a noninvasive biomarker alone or combined with other genes.

Mouse models and primary cell culture models were tested to determine if LRBA is crucial in LPS-induced inflammation.: $LRBA^{-/-}$ patients suffer from recurrent infections (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2), indicating that the LPS pathway is impaired, as an impaired LPS pathway often causes more bacteria infections (Hoshino, et al., Cutting edge: Toll-like receptor 4 (TLR4)-deficient mice are hyporesponsive to lipopolysaccharide: evidence for TLR4 as the Lps gene product. 1999. *J Immunol* 162, 3749-52). LPS/sepsis mouse models were used for in vivo tests. As males develop sepsis more easily than females (Aoyama, et al., Gender difference in granulocyte dynamics and apoptosis and the role of IL-18 during endotoxin-induced systemic inflammation. 2009. Shock 32, 401-9), the male C57BL/6J littermates ($LRBA^{+/+}$, $LRBA^{+/-}$ and $LRBA^{-/-}$, 6-8 weeks, n=5 each genotype) were intraperitoneally injected with a 200 μl single sub-lethal dose of lipopolysaccharide (LPS) from *E. coli* (1 mg/kg) in sterile saline or 200 µl saline using a 26 gauge needle (Haziot, et al., Resistance to endotoxin shock and reduced dissemination of gram-negative bacteria in CD14-deficient mice. 1996. *Immunity* 4, 407-14). The induced pro-inflammatory cytokines have the highest levels 2 h after injection (Haziot, et al., Resistance to endotoxin shock and reduced dissemination of gram-negative bacteria in CD14-deficient mice. 1996. Immunity 4, 407-14). At that time point, blood samples (150 µl per 20 gram body weight) were collected into BD Microtainer EDTA tubes by submandibular venipuncture procedure, and immediately placed on ice and processed within 1 h. Plasma was centrifuged twice, the first time at 1,000×g for 10 minutes and the second time at 2,000×g for 15 minutes at 4° C., then assayed immediately or stored at −80° C. until assayed. Cytokine assays were conducted as described above.

LRBA plasma levels in the mice challenged with LPS increased dramatically from undetectable levels. LRBA was also detected by mass spectrometry in the plasma from subjects stimulated with LPS. These data suggest that LRBA is involved in LPS induced inflammation in vivo. LPS induces three pro-inflammatory cytokines, TNFα, IFNβ, and IL-6, which induce acute phase response and systemic inflammation. The murine endotoxin model has dramatically improved the understanding of the inflammation (Steer, et al., Glucocorticoids suppress tumor necrosis factor-alpha expression by human monocytic THP-1 cells by suppressing transactivation through adjacent NF-kappa B and c-Jun-activating transcription factor-2 binding sites in the promoter. 2000. *J Biol Chem* 275, 18432-40; MacRedmond, et al., Respiratory epithelial cells require Toll-like receptor 4 for induction of human beta-defensin 2 by lipopolysaccharide. 2005. *Respir Res* 6, 116). Injecting endotoxin into mice led to the discovery of TNF (Carswell, et al., An endotoxin-induced serum factor that causes necrosis of tumors. 1975. *Proc Natl Acad Sci USA* 72, 3666-70).

Example 4

Because LRBA deficiency causes diseases of immunodeficiency and autoimmunity, NFκB was analyzed to determine if it activates LRBA promoter activity upon LPS stimulation. LRBA mRNA levels are 34% lower in the Crohn's group and 45% lower in the ulcerative colitis group compared to healthy controls (McKinley, et al., LPS-responsive beige-like anchor (LRBA): A novel gene with a potential role in the pathophysiology of inflammatory bowel disease. 2008. *Gastroenterology* 134, A461-A461).

Briefly, human LRBA promoter including the two NFκB sites were cloned into a promoterless firefly luciferase vector, seen in FIG. 27, using SLIC technology (Li & Elledge, Harnessing homologous recombination in vitro to generate recombinant DNA via SLIC. 2007. *Nat Methods* 4, 251-6). The positive clones were identified by digestion and sequencing, and then transfected into A549 cells, which are LPS responsive. Promoter assay using LPS stimulation was conducted as described (Steer, et al., Glucocorticoids suppress tumor necrosis factor-alpha expression by human monocytic THP-1 cells by suppressing transactivation through adjacent NF-kappa B and c-Jun-activating transcription factor-2 binding sites in the promoter. 2000. *J Biol Chem* 275, 18432-40; MacRedmond, et al., Respiratory epithelial cells require Toll-like receptor 4 for induction of human beta-defensin 2 by lipopolysaccharide. 2005. *Respir Res* 6, 116). To determine, whether upregulation of LRBA by LPS is through NFκB, the two potential NFκB binding sites (consensus NFκB binding sequence: gggRNNYYCC (Seq ID No. 6), R=purine Y=pyrimidine) were mutated to ggTRNNYYAC (Seq ID No. 7) separately or in combination. In all experiments, the NF-κB reporter positive control is used to monitor NF-κB activity.

LRBA is regulated by NF-κB, a pivotal inflammatory transcription factor (Edwards, et al., Targeting the NF-kappaB pathway in asthma and chronic obstructive pulmonary disease. 2009. *Pharmacol Ther* 121, 1-13), as its promoter has two NFκB binding sites highly homologous to the κB element and is conserved in mouse and human, seen in FIG. 27. The two potential NFκB binding sites in the LRBA sequence are true NFκB binding sites, and the mutations, seen in FIG. 27, abolished NFκB activation, confirming that LRBA is an NFκB downstream gene, and LPS activates NFκB, which, in turn, upregulates LRBA.

EBV immortalized LRBA deficient and LRBA positive control B cell lines were cultured in T25 culture flasks at $10^6$ cells/ml for 24 h. Media was changed and $10^5$ cells seeded in each well with 100 µl culture media in 96 well plates 2 h before LPS treatment. Serial concentrations of LPS were used (0.1-10 µg) to stimulate B cells. After 0.5 to 18 h, the levels of secreted and intracellular TNF, IL-6 and IFN from 100 µl of culture supernatants and all cell lysates made from 100 µl of RIPA buffer, respectively, were measured using ELISA kits following the manufacturer's protocols. The intracellular cytokine ELISA results was confirmed by Western blots, flow cytometry, immunofluorescence (IF) staining. LRBA levels are significantly increased in inflammation induced by LPS, seen in FIGS. 32(A) & (D), or ovalbumin (OVA), seen in FIG. 32(B), and in asthma patients, seen in FIG. 32(C), with an exacerbation. The presence of LRBA in the plasma was confirmed by Western blots, seen in FIG. 32(C), inset). LRBA in the plasma from subjects stimulated with LPS (Qian, et al., Quantitative proteome analysis of human plasma following in vivo lipopolysaccharide administration using 160/180 labeling and the accurate mass and time tag approach. 2005. *Mol Cell Proteomics* 4, 700-9) or from trauma patients was also detected using mass spectrometry (Liu, et al., High dynamic range characterization of the trauma patient plasma proteome. 2006. *Mol Cell Proteomics* 5, 1899-913). Data indicate that plasma LRBA levels are significantly increased in asthma patients with an exacerbation and in mouse asthma models, seen in FIG. 32(C), suggesting that overexpression of LRBA is associated with inflammatory diseases.

Example 5

The B cell is one of most affected cell types in LRBA deficient patients, while monocytes are highly resposive to LPS stimulation. Accordingly, these two cell types were used to examine LRBA and test the effectiveness of LRBA treatment. B cells are responsive to LPS stimulation and secret various cytokines including IL-6 (Dumont, et al., Increased secretion of hyperimmune antibodies following lipopolysaccharide stimulation of CD40-activated human B cells in vitro. 2009. *Immunology* 126, 588-95) and TNFα (Boussiotis, et al., Tumor necrosis factor alpha is an autocrine growth factor for normal human B cells. 1994. *Proc Natl Acad Sci USA* 91, 7007-11; Frasca, et al., A molecular mechanism for TNF-alpha-mediated downregulation of B cell responses. 2012. *J Immunol* 188, 279-86).

EBV immortalized LRBA-deficient and LRBA-positive control B cell lines were used (Alangari, et al., LPS-responsive beige-like anchor (LRBA) gene mutation in a family with inflammatory bowel disease and combined immunodeficiency. 2012. *J Allergy Clin Immunol* 130, 481-8 e2). The LRBA⁻/⁻ B cell lines were obtained from patients with a homozygous deletion or mutations, in LRBA gene (Lopez-Herrera, et al., Deleterious mutations in LRBA are associated with a syndrome of immune deficiency and autoimmunity. 2012. *Am J Hum Genet* 90, 986-1001; Alangari, et al., LPS-responsive beige-like anchor (LRBA) gene mutation in a family with inflammatory bowel disease and combined immunodeficiency. 2012. *J Allergy Clin Immunol* 130, 481-8 e2). These cell lines were cultured in T25 culture flasks at $10^6$ cells/ml for 24 h. The "loss of function" and "gain of function" strategies are used to determine whether LRBA plays a crucial role in key cytokine production and TLR4 activation induced by LPS in cell culture and mouse models. For "gain of function" strategy, whole length LRBA was successfully overexpressed.

TLRs (TLR4, input signal) and cytokines (TNF, IL6 and IFN output signal) are two of most critical components of inflammation mediated by LPS, thus are examined TLR4 detects lipopolysaccharide from Gram-negative bacteria and is thus important in the activation of the innate immune system. Internalized LPS and TLR4 are found in the GC (Hornef, et al., Toll-like receptor 4 resides in the Golgi apparatus and colocalizes with internalized lipopolysaccharide in intestinal epithelial cells. 2002. *The Journal of experimental medicine* 195: 559-570). Proto-oncogenes Ras and Src are activated on the GC (Bivona, et al., Phospholipase C gamma activates Ras on the Golgi apparatus by means of RasGRP1. 2003. *Nature* 424: 694-698; Pulvirenti, et al., A traffic-activated Golgi-based signaling circuit coordinates the secretory pathway. 2008. *Nature cell biology* 10: 912-922). LRBA deficiency appears to impair TLR4 activation by interfering with TLR4 trafficking between cell membrane and GC.

The shRNA knockdown of LRBA increases the TLR4 levels in A549 cells at 2 h and 4 h after LPS stimulation, when compared to untransfected A549 cells, evidencing that LRBA regulates TLR4 in these cells. TLR4 levels have no difference in the two cell lines at 24 h, seen in FIGS. 17(A) through (C).

Intracellular and secreted TNF, IL-6 and IFNβ are significantly reduced in the LRBA deficient B cells compared to LRBA positive control B cells, because LRBA is involved in more than the secretion of cytokines, such as signal transductions that are required for de novo production of cytokines started from transcription by NFκB transcription factor. Three Raji B cell lines stably transfected with LRBA shRNA that knockdown LRBA over 90% were generated, along with RAW246.7 mouse cell lines stably transfected with a LRBA DNM.

The DNA sequence used to express DNM was SEQ ID No. 8:

```
AGGCTCATGCTTCAGACAAATTTAATCACAATGACCACATATAATGTGC

TGTTTGAGATTCTTATAGAACAGATTGGTACTCAGGTGATACATAAACA

GCATCCAGATCCTGATTCTTCAGTGAAGATACAAAACCCTCAGATACTA

AAAGTAATTGCGACCCTACTTCGAAATTCTCCCCAGTGCCCAGAGAGCA

TGGAGGTTCGCAGAGCCTTTCTTTCTGACATGATTAAACTTTTTAATAA

CAGTAGAGAAACAGGAGGAGCTTGCTACAATGCTCTGTGTGGCAAGAA

TGGATGCTTTCTCTCTGCTATTTTAATCCTAAGAATTCAGATGAGCAAA

AGATAACAGAAATGGTATACGCCATATTCAGAATCCTGCTTTAC.
```

This sequence was used to produce the LRBA-VHS peptide described in the figures.

Cloning of LRBA Dominant Negative Mutant:

The LRBA dominant negative mutants were amplified using the following primers and cloned into the pEGFP-C3 vector using the Gibson cloning method: (Seq ID No. 9) GFPLRBAF, TGTACAAGTACTCAGATCGGCTCATGCTTCAGACAAATTTAATC; GFPVHSR, (Seq ID No. 10) AGTTATCTAGATCCGGTGGTAAAGCAGGATTCTGAATATG; The GFP gene was fused at the C-terminal of every one of these LRBA fragments and expressed as LRBA GFP fusion proteins. The cloned sequence of the LRBA domain is (Seq ID No. 11)

```
QTNLITMTTYNVLFEILIEQIGTQVIHKQHPDPDSSVKIQNPQILKVIAT

LLRNSPQCPESMEVRRAFLSDMIKLFNNSRENRRSLLQCSVWQEWMLSLC

YFNPKNSDEQKITEMVYAIFRIL.
```

LRBA knockdown showed that LRBA regulates both extracellular and intracellular TNFα levels in Raji B cells (Burkitt's lymphoma), A549 cells and THP1 cells. Knockdown of LRBA significantly increased the TNFα levels in Raji B cells in the cell culture supernatants and in cells lysates during LPS stimulation for 15 min to 24 h, when compared to untransfected Raji B cells, seen in FIG. 21. This data agrees with that of Western blot results with A549 cells stably transfected with the same shRNA plasmid against LRBA, seen in FIG. 4. Two LRBA dominant negative mutants (LRBA-VHSLIR1, LRBA-VHS) but not LRBA-LIR3 decrease TNFα levels in the cell culture supernatants, seen in FIG. 22.

LRBA-VHS peptide (Seq ID No. 12):
```
QTNLITMTTYNVLFEILIEQIGTQVIHKQHPDPDSSVKIQNPQILKVIATL

LRNSPQCPESMEVRRAFLSDMIKLFNNSRENRRSLLQCSVWQEWMLSLCYF

NPKNSDEQKITEMVYAIFRIL
```

LRBA-LIR3 (Seq ID No. 13):
```
GWRVWVDTLSITHSKVTFEIHKENLANIFREQQGKVDEEIGLCSSTSVQAA

SGIRRDINVSVGSQQPDTKDSPVCPHFTTNGNENSSIEKTSSLESASNIEL

QTTNTSYEEMKAEQENQELPDEGTLEETLTNETRNADDLEVSSDIIEAVAI

SSNSFITTGKDSMTVSEVTASISSPSEEDASEMPEFLDKSIVEEEEDDDYV

ELKVEGSPTEEANLHRI
```

LRBA-VHSLIR1 (Seq ID No. 14):
```
RLMLQTNLITMTTYNVLI-BILIEQIGTQVIHKQHPDPDSSVKIQNPQILK

VIATLLRNSPQCPESMEVRRAFLSDMIKLFNNSRENRRSLLQCSVWQEWML

SLCYFNPKNSDEQKITEMVYAIFRILLYHAVKYEWGGWRVWVDTLSITHSK

VTFEIHKENLANIFREQQGKVDEEIGLCSSTSVQAASGIRRDINVSVGSQQ

PDTKDSPVCPHFTTNGNENSSIEKTSSLESASNIELQTTNTSYEEMKAEQE

NQELPDEGTLEETLTNETRNADDLEVSSDIIEAVAISSNSFITTGKDSMTV

SEVTASISSPSEEDASEMPEFLDKSIVEEEEDDDYVELKVEGSPTEEANLP

TELQDNSLSPAASEAGEKLDMFGNDDKLIFQEGKPVTEKQTDTETQDSKDS

GIQTMTASGSSAMSPETTVSQIAVESDLGQMLEEGKKATNLTRETKLINDC
```

-continued

HGSVSEASSEQKIAKLDVSNVATDTERLELKASPNVEAPQPHRHVLEISRQ

HEQPGQGIAPDAVNGQRRDSRSTVFRIPEF

The impact on these intracellular cytokines likely represents de novo synthesis. These results confirm that LRBA is crucial in cytokine secretion and signal transduction, which leads to increased cytokine production in inflammation.

Example 6

LRBA deficiency suppresses autophagy by more than 50% and accumulates more autophagosome and Golgi apparatuses, suggesting that LRBA is critical for autophagy. Autophagy is involved in almost all facets of innate and adaptive immunity. LRBA has a LC3 interaction region (LIR). A microtubule-associated protein 1 light chain 3 (LC3) interaction region LC3 interaction region (LIR) motif in both human and murine LRBA. The LIR consensus sequence is [DE]-[DE]-[DE]-[WFY]-X-X-[LIV]+(Birgisdottir, et al., The LIR motif—crucial for selective autophagy. 2013. *J Cell Sci* 126, 3237-47; Seq ID No. 2). The DDDYVEL (Seq ID No. 3) sequence from LRBA has high homology with LIR from TP53INP1 (similarity is 92%) and TP53INP249. Three dimensional structure remodeling (YASARA v12.7.16) shows that the LIR forms a complex with LC3 which is more stable than with p62, a known LC3 binding protein, as seen in FIG. 23(A). Tyrosine phosphorylation in the LIR destabilizes this complex, seen in FIG. 23(B).

Co-localization microscopy and LRBA has a potential LC3 interaction region (LIR) and ubiquitin binding domain (UBD). Confocal microscopy and IFA show that LRBA is highly co-localized with LC3, as seen in FIGS. 23(C) through (E), and show LRBA co-localized with autophagosomes. Dominant-negatives containing UBD and/or LIR inhibit and/or LIR inhibit cell growth.

Structural analysis of LRBA indicated that the protein contains an LC3 interaction region (LIR) region and ubiquitin binding domain (UBD). The interaction energy between LC3 and LIRs of LRBA and three known LC3 binding proteins, the phosphorylated LIR of LRBA and the alanine scan were calculated using Foldx50, seen in Table 5. These findings demonstrate that LRBA serves as an adaptor for ubiquitinized proteins destined for degradation through association with LC3 and ubiquitin by LIR and UBD respectively during autophagy. Tyrosine phosphorylation may impede LRBA binding with LC3, inhibit autophagy, but favor cell growth, in agreement with the hypothesis that LIR is phosphorylated in several cancer types, such as lung, breast, bladder, kidney, gastric cancers and leukemia. Moreover, overexpression of LRBA has been observed in several types of cancer cells, such as breast cancer, cervical cancer, epidermal carcimona, renal cancer, pancreatic cancer, colorectal cancer, and lung cancer (Wang, et al., Deregulated expression of LRBA facilitates cancer cell growth. 2004. *Oncogene* 23, 4089-97). LRBA may also contribute to the following cancers: adrenal cancer, anal cancer, Bile Duct Cancer, Bladder Cancer, Bone Cancer, Brain/CNS Tumors In Adults, Brain/CNS Tumors In Children, Breast Cancer In Men, Cancer in Adolescents, Cancer in Children, Cancer in Young Adults, Cancer of Unknown Primary, Castleman Disease, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Leukemia—Acute Lymphocytic (ALL) in Adults, Leukemia—Acute Myeloid (AML), Leukemia—Chronic Lymphocytic (CLL), Leukemia—Chronic Myeloid (CML), Leukemia—Chronic Myelomonocytic (CMML), Leukemia in Children, Liver Cancer, Lung Cancer—Non-Small Cell, Lung Cancer—Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Skin Cancer—Basal and Squamous Cell, Skin Cancer—Melanoma, Skin Cancer—Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, Wilms Tumor. Of note, LRBA expression is correlated to that of estrogen receptor (Wang, et al., Deregulated expression of LRBA facilitates cancer cell growth. 2004. *Oncogene* 23, 4089-97). These results provide a molecular mechanism for clinical intervention of autophagy and cell growth related to human diseases.

TABLE 5

Calculated interaction energy between LC3 and LIRs of other proteins using Foldx.

|  | LRBA-LIR | p62-LIR | LRBA-LIR-p | TP53INP1-LIR | TP53INP2-LIR | Alanine Scan |
| --- | --- | --- | --- | --- | --- | --- |
| Interaction energy with LC3 (kcal/mol) | −15.19 | −13.89 | −13.22 | −18.35 | −15.13 | −3.76 |
| Interaction | ++ predicted | + experimental | + predicted | +++ experimental | ++ experimental | − predicted |

In agreement with these findings, blockage of LRBA by antibody against LRBA or using LRBA dominant negative mutants promotes cell proliferations in THP1 cells, as seen in FIG. 25, and RAW264.7 cells (data not shown), and Raji B cells (Burkitt's lymphoma), seen in FIG. 20.

These data suggest that LRBA expression levels are closely related to chronic diseases such as ALS (Lou Gehrig's Disease), Alzheimer's Disease and other Dementias; Arthritis, Asthma, Chronic Obstructive Pulmonary Disease (COPD), Cystic Fibrosis, Diabetes, End Stage Renal Disease, Heart Disease, Obesity and Related Conditions, in addition to cancer, immunodeficiency and autoimmunity, and must be tightly regulated. The transcription is the first and most important control step for gene expression.

Example 7

Overexpression of LRBA has been observed in several types of cancer cells, such as cervical cancer, breast cancer, lung cancer, and epidemral cancer (Wang, et al., Deregulated expression of LRBA facilitates cancer cell growth. 2004. *Oncogene* 23, 4089-97). Data show that plasma LRBA levels are significantly increased in asthma patients with an exacerbation and in mouse asthma models, seen in FIG. 32(C), suggesting that overexpression or up-regulation of LRBA facilitates vesicle trafficking of cytokines and is associated with inflammatory diseases. Accordingly, absence or repression of LRBA inhibits cytokine secretion.

Next, blocking of LRBA using dominant negative mutant (DN-VHS) was tested as a therapeutic strategy to treat inflammatory diseases. HEK293, RAW264.7 and A549 cell lines (American Type Culture Collection, Manassas, Va., USA) were maintained according to the ATCC's instructions. Stable cell lines comprising RAW264.7, H293 and A549 cells, transfected with LRBA DNM or shRNA, and tested for impaired growth as discussed above. The mutated or truncated LRBA protein cannot be detected in the cells from LRBA-deficient patients (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2), suggesting that these mutated LRBA proteins could serve as DNMs and are harmful to the body and must be degraded. When over-expressed in the cells, DN-VHS greatly suppresses cell growth, as seen in FIGS. 26(B) & (E), indicating that it can serve as a DMN to inhibit LRBA function. DN-VHS associated vesicles were motionless, data not shown, suggesting that the vesicle trafficking is blocked. This provides direct evidence that LRBA is crucial for vesicle trafficking. Moreover, the VHS domain of LRBA is a small 14 kD peptide, which may be easier to deliver into cells. Taken together, DN-VHS is a promising peptide to be developed into a biologic to treat inflammatory diseases.

HEK293 cell lines (American Type Culture Collection, Manassas, Va., USA) were cultured in Dulbecco's modified minimum essential medium (DMEM) or RPMI1640 supplemented with 10% FBS and penicillin-streptomycin (5,000 IU/ml penicillin and 5,000 µg/ml streptomycin) as provided by ATCC. Three constructs of LRBA fragments fused with EGFP were generated and successfully expressed in HEK293 cells. To explore if LRBA DN-VHS is useful as a biologic to treat inflammatory diseases, its effects on pro-inflammatory cytokine secretion were examined as disclosed above. To this end, the three constructs are transfected into Raw246.7 cells and stable clones selected with G418. The proinflammatory cytokine (TNF and IL-6) production induced by LPS stimulation was compared in the three cell lines: RAW246.7 (Wt control), RAW$^{LRBA-GFP}$ (LRBA-VHS-EGFP, LRBA-LIR-EGFP, LRBA-VHS and LIR-EGFP) and RAW$^{GFP}$ (vector control).

The inhibitory effects on the proinflammatory cytokines by the three LRBA DNMs is similar to that of their growth inhibitions, seen in FIGS. 26(B) & (E), i.e. the order of cytokine inhibitory effects is VHS-EGFP>VHSLIR-EGFP>LIR-EGFP. This suggests that the functions of LRBA on cell growth and cytokine production are related, and VHS domain is a promising target to treat inflammatory diseases.

Both absence of LRBA and defective cytokines can cause immunodeficiency. LRBA$^{-/-}$ may first inhibit the production and secretion of cytokines, resulting in defective cytokines, the latter then cause immunodeficiency.

LRBA was tested for its effect on cell growth. For the "loss of function" strategy, EBV immotalized LRBA-deficient B cell lines were generated from LRBA deficient patients, and dominant negative LRBA mutants (DNM) and knockout mouse models. The LRBA sequence targeted by the shRNA used was SEQ ID No. 15;

```
GGGATATTGTAGAAACTGTCTTT,
``` which is 100% conserved in mouse and human LRBA. Determination of shRNAs can be performed by those skilled in the art. For example, a possible shRNA is shown in SEQ ID No. 43 for the top strand;

```
GGGATATTGTAGAAACTGTCTTTTTCAAGAGAAAAGACAGTTTCTACAA
TATCCCTTTTTT
``` and SEQ ID No. 44 for the bottom strand;

```
CCCTATAACATCTTTGACAGAAAAGTTCTCTTTTCTGTCAAAGATGTTA
TAGGGAAAAAA
```

The DNA sequence used to express DNM was SEQ ID No. 8:

```
AGGCTCATGCTTCAGACAAATTTAATCACAATGACCACATATAATGTGC
TGTTTGAGATTCTTATAGAACAGATTGGTACTCAGGTGATACATAAACA
GCATCCAGATCCTGATTCTTCAGTGAAGATACAAAACCCTCAGATACTA
AAAGTAATTGCGACCCTACTTCGAAATTCTCCCCAGTGCCCAGAGAGCA
TGGAGGTTCGCAGAGCCTTTCTTTCTGACATGATTAAACTTTTTAATAA
CAGTAGAGAAAACAGGAGGAGCTTGCTACAATGCTCTGTGTGGCAAGAA
TGGATGCTTTCTCTCTGCTATTTTAATCCTAAGAATTCAGATGAGCAAA
AGATAACAGAAATGGTATACGCCATATTCAGAATCCTGCTTTAC.
```

This sequence was used to produce the LRBA-VHS peptide described in the figures, and shown as SEQ ID No. 11;

```
QTNLITMTTYNVLFEILIEQIGTQVIHKQHPDPDSSVKIQNPQILKVIAT
LLRNSPQCPESMEVRRAFLSDMIKLFNNSRENRRSLLQCSVWQEWMLSLC
YFNPKNSDEQKITEMVYAIFRIL.
```

Knockout of LRBA (LRBA$^{-/-}$) greatly suppresses cell growth in mouse embryo stem (ES) cells, as seen in FIG. 26(A). The results from HEK293 cells, seen in FIGS. 26(B), and A549 cells, seen in FIG. 26(C), are very similar, indicating that the data are reliable and LRBA likely plays the same role in different types of cells. The cells transfected with LRBA-VHS, seen in FIG. 2, an LRBA dominant negative mutation (DNM), produced fewer and smaller colonies, seen in FIG. 26(B). LRBA-VHS is associated with membranous vesicles, as seen in FIG. 26(D). Live cell microscopy shows no movement of LRBA-VHS-EGFP vesicles and some directional movement of mRFP-LC3 vesicles. This suggests that these vesicles have defects caused by the LRBA DNM.

These findings correspond well to the studies showing that LRBA-deficient patients had retarded growth (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. *J Allergy Clin Immunol* 130, 481-8 e2), T-cell proliferation to Phytohaemagglutinin (PHA) and anti-CD3 mAb was markedly reduced in the absence of LRBA (Alangari, et al., LPS-responsive beige-like anchor (LRBA) gene mutation in a family with inflammatory bowel disease and combined immunodeficiency. 2012. *J Allergy Clin Immunol* 130, 481-8 e2).The growth inhibition by a LRBA DNM can be overridden by plasma from mice stimulated with LPS, as seen in FIG. 27(G).

LRBA is regulated by Ubiquitin-dependent protein degradation system. LRBA protein has 11 ubiquitination sites (Oshikawa, K., Matsumoto, M., Oyamada, K., and Nakayama, K. I. (2012). Proteome-wide identification of ubiquitylation sites by conjugation of engineered lysine-less ubiquitin. Journal of proteome research 11, 796-807). The EGFP levels of LRBA-EGFP fusion proteins expressed by the plasmids pLRBA-VHSLIR-EGFP and pLRBA-VHS-EGFP are much lower than that expressed by the plasmids pLRBA-LIR and the control pEGFP-C3. LRBA peptides VHSLIR and VHS contain two and one ubiquitination sites respectively. LIR does not contain any ubiquitination site. MG132, a specific, potent, reversible, and cell-permeable proteasome inhibitor, can increase the expression levels of LRBA-EGFP fusion proteins expressed by the plasmids pLRBA-VHSLIR-EGFP and pLRBA-VHS-EGFP, but not that of LRBA-EGFP fusion proteins expressed by the plasmid pLRBA-LIR. The effects of MG132 on the expression levels of LRBA-EGFP fusion proteins are dose dependent, seen in FIG. 18(A). The similar results were obtained with PS341, seen in FIG. 18(B), which is a proteasome inhibitor, FDA-approved medicine for multiple myeloma and mantle cell lymphoma. These data demonstrate that LRBA is regulated by Ubiquitin-dependent protein degradation system, seen in FIGS. 28(A) through (H).

Both absence of LRBA and defective cytokines can cause immunodeficiency. LRBA$^{-/-}$ inhibit the production and secretion of cytokines, resulting in defective cytokines, which cannot be recapitulated by transformed primary cell culture models. As such, the primary cultures appear to provide accurate results that are similar to the in vivo settings. The mouse BMM cell culture model is an excellent models to study the LPS pathway.

BMMs were obtained by the protocol described by Weischenfeldt, et al. (Weischenfeldt & Porse, Bone Marrow-Derived Macrophages (BMM): Isolation and Applications. 2008. *CSH Protoc* 2008, pdb prot5080). Bone marrow cells were obtained by flushing the femurs and tibias from 8-12-week-old C57BL/6 wild type mice and LRBA$^{-/-}$ mice, and the bone marrow cells plated in 10-cm bacteriological plastic plates at $2\times10^6$ cells/mL with 10% FCS in RPMI 1640 supplemented with 100 ng/ml of recombinant murine M-CSF. On day 7, BMMs were plated at $1\times10^5$ cells/ml in 24-well plates and cultured with or without 100 ng/ml of LPS for 7 h (Nagai, et al., Essential role of MD-2 in LPS responsiveness and TLR4 distribution. 2002. *Nat Immunol* 3, 667-72). Culture supernatants were collected for ELISA assay as disclosed in other Examples. While there is a concern BMMs from LRBA$^{-/-}$ mice may produce less cytokines compared to wild-type mice, data from transformed cell culture models was used to confirm results on cytokine levels.

It was first examined whether replenishing LRBA cured LRBA-deficient inflammatory diseases. LRBA's presence in plasma may provide a way to easily modulate LRBA to cure the incurable (Burns, et al., LRBA gene deletion in a patient presenting with autoimmunity without hypogammaglobulinemia. 2012. *J Allergy Clin Immunol* 130, 1428-32) LRBA-deficient patients are treated by replenishing LRBA, and to cure LRBA-overexpressing patients by using anti-LRBA reagents to block LRBA. LRBA can be secreted. This can explain why LRBA$^{-/-}$ ES cells can be obtained but failed to grow after being thawed from freezer storage.

As pure LRBA proteins are not available, LRBA protein must be expressed in insect cells or mammalian cells for testing. Mice and C57BL6 mononuclear leukocytes cell cultures in lymphocyte culture media (RPMI 1640, fetal bovine serum 10%, L-glutamine 2 mM, Na pyruvate 1 mM, 0.5 µM 2-mercaptoethanol) were stimulated by injection of LPS, resulting in high levels of LRBA in the plasma or the culture supernatants. Mouse plasma was collected 24 hour after LPS stimulation and 100 µl of the mouse plasma (~250 pg LRBA) applied into 10 ml culture media and observed growth stimulation.

LRBA$^{-/-}$ ES cells were selected from LRBA$^{+/-}$ ES cells by using a high concentration of G418. The LRBA$^{-/-}$ ES cells grow during the selection as the media containing LRBA proteins secreted by the parent cells, but cannot grow without these secreted proteins. Growth was rescued for several types of LRBA-deficient cells, data not shown, by adding conditioned media or plasma from LPS-stimulated mice, which contain high levels of LRBA, seen in FIG. 2(A). The growth defect is manifested by retarded growth (Lopez-Herrera, et al., Deleterious mutations in LRBA are associated with a syndrome of immune deficiency and autoimmunity. 2012. *Am J Hum Genet* 90, 986-1001; Burns, et al., LRBA gene deletion in a patient presenting with autoimmunity without hypogammaglobulinemia. 2012. *J Allergy Clin Immunol* 130, 1428-32; Alangari, et al., LPS-responsive beige-like anchor (LRBA) gene mutation in a family with inflammatory bowel disease and combined immunodeficiency. 2012. J Allergy Clin Immunol 130, 481-8 e2), and reduced T-cell proliferation in LRBA-deficient patients (Alangari, et al., LPS-responsive beige-like anchor (LRBA) gene mutation in a family with inflammatory bowel disease and combined immunodeficiency. 2012. *J Allergy Clin Immunol* 130, 481-8 e2).

It is possible that the enhancement of cytokine secretion are dose-dependent, or cell-type dependent. As such, H293 and Raji stable clones that over-express LRBA fused with EGFP were used. To confirm the attachment of EGFP to the LRBA C-Terminus does not affect its function, a sequence and ligation-independent cloning (SLIC) seamless cloning technology, which can insert DNA fragments anywhere in the vector without the limitation of restriction enzyme sites (Li, M. Z. & Elledge, S. J. Harnessing homologous recombination in vitro to generate recombinant DNA via SLIC. *Nat Methods* 4, 251-6 (2007)) was used to remove the EGFP tag and compare the two versions of LRBA on the cytokine secretion. The expression vector was transfected into RAW246.7 cells, and stable clones obtained by G418 selection, as seen in FIGS. 29(A) and (B). LRBA overexpression was judged by the GFP brightness and Western blots. The control clones that overexpress EGFP (RAW$^{GFP}$) were obtained by the same strategy. The proinflammatory cytokine (TNF, IL-6 and IFN) production induced by LPS stimulation was compared in the three cell lines: RAW246.7, RAW$^{LRBA\text{-}GFP}$ and RAW$^{GFP}$ seen in FIGS. 26(C) & (D). It is likely that higher levels of cytokines in the culture supernatants of the RAW$^{LRBA\text{-}GFP}$ than RAW$^{GFP}$ suggest that overexpression of LRBA enhances cytokine secretion and is associated with inflammatory diseases.

Example 8

As LRBA is involved in apoptosis (Wang, et al., Deregulated expression of LRBA facilitates cancer cell growth. 2004. *Oncogene* 23, 4089-97), and LRBA-deficient B cells have slower growth and are susceptible to apoptosis (Lopez-Herrera, et al. Deleterious mutations in LRBA are associated with a syndrome of immune deficiency and autoimmunity 2012. *Am J Hum Genet* 90, 986-1001), the amount of apoptotic cells induced by serum deprivation was used to judge the rescue effects by replenishing LRBA. Apoptosis assays were conducted (Lopez-Herrera, et al., Deleterious mutations in LRBA are associated with a syndrome of immune deficiency and autoimmunity 2012. *Am J Hum Genet* 90, 986-1001) using LRBA$^{-/-}$ and LRBA$^{+/+}$ B cells (1×10$^6$ cells/ml) cultured under serum deprivation for 6 h. Each 18 wells are treated with equal amount of protein, i.e. anti-LRBA antibody, anti-actin antibody (A2066, Sigma) or bovine serum albumin (BSA). After six days, the cell number is measured using the CellTiter-Glo® Luminescent Cell Viability Assay (Promega). After starvation, cells were harvested, and apoptosis measured by Annexin V and propidium iodide (PI) staining, with a threshold of 10,000 events as analyzed by flow cytometry, to determine the percentage of cells in early apoptosis (positive for Annexin V and negative for PI). Viability numbers are determined in triplicate using CellTiter-Glo® kit (Promega) seeded in serum deprivation conditions in 96-well plates for 6 hours. Cells were given LRBA protein and collected at 24, 48, 72, 96 and 120 h after.

LRBA$^{-/-}$ ES cells do not grow or grow slowly. The ES cells were cultured at 37° C., 5% CO$_2$, using mouse ES culture media under the conditions recommended by the company (Emdmillipore). Treatment of the cultures with LRBA plasma or conditioned media resulted in detected LRBA levels in the culture supernatants at up to 2.4 ng/ml, which can rescue LRBA$^{-/-}$ ES cells, data not shown. Increased apoptosis and retarded growth of LRBA$^{-/-}$ were rescued by adding LRBA to the media, suggesting that LRBA$^{-/-}$ patients may be cured by replenishing LRBA. This suggests that LRBA functions as an autocrine growth factor.

Anti-LRBA antibodies were tested as a therapeutic strategy to treat inflammatory diseases. Data show that LRBA levels are significantly increased in plasma from mice stimulated with LPS or OVA, seen in FIGS. 32(A) & (B), from asthma patients with an exacerbation, seen in FIGS. 32(C) & (D), and in the culture supernatants of human mononuclear leukocytes stimulated with LPS, indicating that LRBA is involved in LPS-induced inflammation, and suggesting that overexpression of LRBA may be associated with inflammatory diseases. The presence of LRBA in plasma is also confirmed by Western blots, seen in FIG. 32(D) (inset).

Blocking LRBA in plasma is therefore proposed to inhibit inflammation, and thus be useful to treat inflammatory diseases. TNF is highly expressed in RA patients and anti-TNF is an effective therapeutic. The same strategy used for anti-TNF may apply to anti-LRBA: a monoclonal antibody against LRBA targets LRBA in the plasma to treat inflammatory disease and cancers having overexpression of LRBA (Wang, et al., Deregulated expression of LRBA facilitates cancer cell growth. 2004. *Oncogene* 23, 4089-97).

LRBA antibody was used at 400 ng/ml, about four hundred times the molar ratio of antibody to protein, to bind LRBA protein in the supernatant. LRBA antibody eliminated the effects seen by exogenous LRBA, indicating the antibody inhibits LRBA-stimulated cell growth, and that blocking LRBA in the culture supernatant inhibits cell growth. The highest concentration of LRBA detected in the culture supernatants was 2.4 ng/ml. LRBA antibody, was used at 400 ng/ml, about four hundred times the molar ratio of antibody to protein, to bind LRBA protein in the supernatant, to ensure adequate LRBA neutralization.

Anti-LRBA antibody, anti-actin antibody and BSA have no effect on the growth of EBV LRBA$^{-/-}$ B cells, as these cells lack LRBA, and actually serve as a control. However, anti-LRBA antibody inhibits the growth of EBV LRBA$^{+/+}$ B cells, confirming that extracellular LRBA is required for the growth of the cells and possibly confirming that anti-LRBA antibody can be used as a therapeutic to inflammatory diseases and cancers with overexpression of LRBA.

Testing also showed LRBA is regulated by microRNAs. MicroRNAs (miRs) are ~22 nucleotides long non-coding RNAs that are believed to inhibit most human genes and the spectrum of biological pathways through inhibition of mRNA translation by the base pairing rule at the accuracy of one base. Deregulation of miRs may contribute to various diseases. Overexpression of the miRNAs miR-150 and miR-181 show LRBA is downregulated by overexpression of the miRNA, as seen in FIGS. 30(A) through (D).

Example 9

About two-third of CVID patients have autoimmune problems (Cunningham-Rundles & Bodian, Common variable immunodeficiency: clinical and immunological features of 248 patients. 1999. *Clinical immunology* 92: 34-48; Podjasek & Abraham, Autoimmune cytopenias in common variable immunodeficiency. 2012. *Frontiers in immunology* 3: 189). As opposed to other CVID genes, the immunodeficiency caused by LRBA deficiency is highly associated with autoimmunity. To date, the 11 identified LRBA-deficient CVID patients had autoimmunity (Lopez-Herrera, et al., Deleterious Mutations in LRBA Are Associated with a Syndrome of Immune Deficiency and Autoimmunity. 2012. *American journal of human genetics* 90: 986-1001; Shamloula, et al., rugose (rg), a *Drosophila* A kinase anchor protein, is required for retinal pattern formation and interacts genetically with multiple signaling pathways. 2002. *Genetics* 161: 693-710; Parvaneh, et al., Primary immunodeficiencies: a rapidly evolving story. 2013. *The Journal of allergy and clinical immunology* 131: 314-323.). TACI mutations also are associated with autoimmunity but to a lesser degree (36% vs. 23% of patients with wild-type TACI) (Salzer, et al., Relevance of biallelic versus monoallelic TNFRSF13B mutations in distinguishing disease-causing from risk-increasing TNFRSF13B variants in antibody deficiency syndromes. 2009. *Blood* 113: 1967-1976).

LRBA deficient patients have low switched memory B cells, low or absent immunoglobulins including IgG, IgA and IgM (Lopez-Herrera, et al., Deleterious Mutations in LRBA Are Associated with a Syndrome of Immune Deficiency and Autoimmunity. 2012. *American journal of human genetics* 90: 986-1001; Shamloula, et al., rugose (rg), a *Drosophila* A kinase anchor protein, is required for retinal pattern formation and interacts genetically with multiple signaling pathways. 2002. *Genetics* 161: 693-710; Parvaneh, et al., Primary immunodeficiencies: a rapidly evolving story. 2013. *The Journal of allergy and clinical immunology* 131: 314-323). These patients have markedly reduced T-cell proliferation in response to phytohaemagglutinin (PHA) and anti-CD3 mAb, and reduced B cell survival. These cellular defects may account for immunodeficiency. However, LRBA deficient patients also have more peripheral T cells, more CD20 positive B cells, lymphocyte infiltration and respond to anti-CD20 therapy (Lopez-Herrera, et al., Deleterious Mutations in LRBA Are Associated with a Syndrome of Immune Deficiency and Autoimmunity 2012. *American journal of human genetics* 90: 986-1001; Shamloula, et al., rugose (rg), a *Drosophila* A kinase anchor protein, is required for retinal pattern formation and interacts genetically with multiple signaling pathways. 2002. *Genetics* 161: 693-710; Alangari, et al., LPS-responsive beige-like anchor (LRBA) gene mutation in a family with inflammatory bowel disease and combined immunodeficiency. 2012. *The Journal of allergy and clinical immunology* 130: 481-488 e482). These cellular defects may contribute to variable autoimmune disorders, such as thrombocytopenic purpura, autoimmune hemolytic anemia, inflammatory bowel disease (IBD).

Mutations in TACI impair the development of IgA- and IgG-secreting plasma cells and promote lymphoproliferation, and are associated with IgA deficiency and autoimmunity (Salzer, U., H. M. Chapel, A. D. Webster, Q. Pan-Hammarstrom, A. Schmitt-Graeff, et al., Mutations in TNFRSF13B encoding TACI are associated with common variable immunodeficiency in humans. 2005. *Nat Genet* 37: 820-828; Castigli, et al., TACI is mutant in common variable immunodeficiency and IgA deficiency. 2005. *Nat Genet* 37: 829-834). TACI is required for antibody class switching and is a negative regulator of B-cells (Seshasayee, et al., Loss of TACI causes fatal lymphoproliferation and autoimmunity, establishing TACI as an inhibitory BLyS receptor. 2003. *Immunity* 18: 279-288; Yan, et al., Activation and accumulation of B cells in TACI-deficient mice. 2001. Nat Immunol 2: 638-643).

BAFF-R deficiency blocks B-cell development at the stage of transitional B cells (Barkett & Gilmore, Control of apoptosis by Rel/NF-kappaB transcription factors. 1999. *Oncogene* 18: 6910-6924). High levels of BAFF in mice lead to an autoimmune disease similar to systemic lupus erythematosus (SLE) (Gross, et al., TACI and BCMA are receptors for a TNF homologue implicated in B-cell autoimmune disease. 2000. *Nature* 404: 995-999).

CVID receptors were examined in the cell culture and mouse LPS/sepsis models. LRBA was repressed in Raji B cells by the short hairpin RNA (shRNA) knocked down (KD) technique or LRBA dominant negative mutants (DNMs). A mouse model that has LRBA overexpression was also used. The results demonstrate that LRBA repression deregulates the three parameters (protein levels, response speed and phase) of CVID receptors, while overexpression of LRBA in a mouse model has opposite effects on these receptors, which are responsive to LPS stimulation, as seen in FIGS. 31(A) and (B), and NFκB inhibitors, and have NFκB binding sites. LRBA deficiency may exert its effects on immunodeficiency and autoimmunity by deregulating these receptors through NFκB.

HEK293 cell line were purchased from the American Type Culture Collection (Manassas, Va., USA) and maintained according to the company's instructions. Raji B cell line (Burkitt's lymphoma) was kindly provided by Dr. George Blanck (University of South Florida Morsani College of Medicine). These cells were cultured in RPMI1640 supplemented with 10% FBS and penicillin-streptomycin (5,000 IU/ml penicillin and 5,000 µg/ml streptomycin). The mouse studies have been reviewed and approved by the Institutional Animal Care and Use Committee (IACUC) at the University of South Florida.

Cloning of LRBA Dominant Negative Mutants:

The LRBA dominant negative mutants were amplified using the following primers and cloned into the pEGFP-C3 vector using the Gibson cloning method: (Seq ID No. 9) GFPLRBAF, TGTACAAGTACTCAGATCGGCTCATGCTTCAGACAAATTTAATC; (Seq ID No. 16) GFPLRBAR, AGTTATCTAGATCCGGTGGAACTCAGGAATACGAAACACAG; (Se ID No. 10) GFPVHSR, AGTTATCTAGATCCGGTGGTAAAGCAGGATTCTGAATATG; (Seq ID No. 17) GFPLIRF, TGTACAAGTACTCAGATCGTGGCTGGCGTGTATGGGTAG; (Seq ID No. 18) GFPLIRR, AGTTATCTAGATCCGGTGTAGATTAGCTTCCTCAGTAG. The GFP gene was fused at the C-terminal of every one of these LRBA fragments and expressed as LRBA GFP fusion proteins.

Immunofluorescent Confocal Microscopy:

HEK293 cells at concentration of 5×10$^6$/ml were plated on glass coverslips in Dulbecco's modified minimum essential medium (D-MEM) supplemented with 10% fetal calf serum (Gemini Bio-Products, West Sacramento, Calif.), penicillin and streptomycin. After 24 h, cells were fixed, permeabilized, and stained following the immuno-fluorescence staining protocol from the Human Protein Atlas Project (Sigma). Briefly, growth medium was removed and the cells were washed in 1×PBS, the cells were fixed for 15 minutes in ice cold 4% paraformaldehyde pH 7.2-7.3 in growth medium supplemented with 10% fetal bovine serum (FBS). The cells were permeabilized 3 times for 5 minutes each with 0.1% TRITON® X-100 in PBS. The cells were washed with 1×PBS and incubated overnight at 4° C. with the primary antibodies in 1×PBS supplemented with 4% FBS. The following day the cells were washed 4 times for 10 minutes each with 1×PBS and incubated for 1.5 hours at room temperature with the secondary antibodies in 1×PBS supplemented with 4% FBS. The cells were counterstained for 4 minutes with the nuclear stain DAPI (0.6 µM in 1×PBS). The cells were washed 4 times for 10 minutes with 1×PBS and then mounted in glycerol+10% 10×PBS. The LRBA antibodies and three Golgi protein primary antibodies were used at 1:500 (volume to volume dilution). The anti-mouse IgG-Alexa Fluor® 555 and anti-rabbit IgG-Alexa Fluor® 488 secondary antibodies were used at 1:400. The confocal imaging was acquired with an Olympus FV1000 MPE multiphoton laser scanning microscope using 60× objective (U Plan APO 1.42 N.A. oil) and sequential scanning with 0.5 µm per slice. Colocalization analysis for dual stained samples was carried out using JACop and FV10-ASW software.

Electroporation:

Three million Raji B cells in the exponential phase were mixed with 20 µg of plasmid DNA expressing a specific LRBA dominant negative (LRBA-BEACH, LRBA-VHS-LIR, LRBA-VHS and LRBA-LIR) in 800 µl of culture media and electroporated by a Bio-Rad Gene Pulser at 400

V, 400 Ohms and 500 μF. After 24 hours, cells were stained with specific antibodies conjugated with different fluorophores against CVID cell surface proteins and 7AAD for dead/live discrimination. About half a million cells were acquired and analyzed with GFP positive and negative populations. The percentage and intensity of these markers were analyzed in the two populations.

Cell Survival Assay and LRBA Antibody Blockage.

Raji B cells and Rajisi9 B cells (Raji B cells stably transfected with shRNA plasmid against LRBA) were cultured in a 96 well plate with 10 cells per well for 9 days. Blockage of LRBA promotes THP1 cell proliferation. THP1 cells (human acute monocytic leukemia cell line) were cultured in 100 μl of RPMI1640 media with or without human LRBA polyclonal IgG antibody at 0.67 μg/ml or the same amount of human actin polyclonal IgG antibody on a 96 well plate with 10 cells per well for 9 days. Viable cells were counted by the trypan blue live/dead discrimination method with a hemocytometer.

Mouse Model and LRBA Antibodies Treatment:

A) Mice stimulated with LPS (5 μg/g body weight) for 6 hours. (B) OVA induced asthma mouse model; (C) Asthma patients with an exacerbation or controlled symptoms; (D) Human mononuclear leukocytes stimulated with LPS (1 μg/ml). LRBA levels were determined by LRBA ELISA Kit using 100 μl of plasma or conditioned media in each well. C57BL/6J mice were injected intraperitoneally with 500 μl of 12 mg/kg (body weight) of LRBA antibody or control normal rabbit 1 gG suspended in saline three times. LPS at 7.5 mg/kg in 0.2 ml PBS i.p was followed. About 100 μl of blood was collected by submandibular venipuncture after 2 hours of LPS injection. Plasma samples were obtained by centrifugation at 3000 rpm for 15 min and used for cytokine assay. The TNFα and IL-6 concentrations were detected using the mouse CBA Th1/Th2/Th17 cytokine kit. The Phosflow Starter Kit contains Cytofix Fixation Buffer, Phosflow Perm Buffer III and Stain Buffer BSA.

Polynomial Fitting and Slope Calculation:

Polynomial fitting was used to represent nonlinear dataset in this study. High $R^2$ values ($R^2>=0.9$) were used to describe the fitting accuracy and a polynomial trend line equation were used to represent the dataset. The slopes at each time point were calculated by $n \cdot k \cdot x^{(n-1)}$ calculus method.

Statistics Analysis:

Comparisons of sample means was done using two-sample t test, assuming equal variance, and p value was calculated based on two-tailed test. Significance was taken as $p<0.05$. Data are expressed as mean±standard deviation (SD) and are representative of two to three independent experiments. P value indications: <0.001 Extremely significant *, 0.001 to 0.01 Very significant  0.01 to 0.05 Significant * >0.05 Not significant ns #>≈0.05.

LRBA is Involved in the LPS/TLR4 Pathway:

The Toll-like receptor 4 (TLR4) pathway is one of the most important immune pathways to eliminate bacteria, fungi and viral infections. TLR4-mutated mice respond less to Gram-negative bacteria and are highly susceptible to infection (Cook, et al., Toll-like receptors in the pathogenesis of human disease. 2004. *Nature immunology* 5: 975-979). LRBA is upregulated in vitro by LPS (Wang, et al., Identification of a novel lipopolysaccharide-inducible gene with key features of both A kinase anchor proteins and chs1/beige proteins. 2001. *J Immunol* 166: 4586-4595; Kerr, et al., Analysis of lipopolysaccharide-response genes in B-lineage cells demonstrates that they can have differentiation stage-restricted expression and contain SH2 domains. 1996. *Proceedings of the National Academy of Sciences of the United States of America* 93: 3947-3952), which activates NF-κB. Agreeably LRBA gene has multiple NF-κB binding sites in or around the promoter range (Supplemental Table 1). Its paralogue (Lyst) deficient cells exhibit defective TLR signaling, specifically in TLR4 pathways (Cheng, et al., 2012. Novel functions of a regulator of lysosomal trafficking, LYST in TLR4 signal transduction. 2012. *Immunology* 137: 299-300). Vesicle-mediated localization and trafficking of TLR4 are required for its activation (Cheng, et al., 2012. Novel functions of a regulator of lysosomal trafficking, LYST in TLR4 signal transduction. 2012. *Immunology* 137: 299-300; Latz, et al., Lipopolysaccharide rapidly traffics to and from the Golgi apparatus with the toll-like receptor 4-MD-2-CD14 complex in a process that is distinct from the initiation of signal transduction. 2002. *The Journal of biological chemistry* 277: 47834-47843; Thieblemont & Wright, Transport of bacterial lipopolysaccharide to the golgi apparatus. 1999. *The Journal of experimental medicine* 190: 523-534). Recurrent bacterial infections in LRBA-deficient patients indicate an impaired TLR4/LPS pathway. These data suggest that LRBA is involved in the TLR4/LPS pathway.

Supplemental table 1
Mouse CVID genes have multiple NFkB sites*

| Gene | NFκB site (GGGRNWYYCC, N: any base, R: purine, W: A or T, Y: T or C) and the surrounding sequences | | | |
|------|------|------|------|------|
| TACI | CTTCCTGG<br>GTTTTCCC<br>CTTCG<br>(-, promoter) | CAGTAGGGCA<br>TCCCCATCTT<br>(+, exon) | TAGTTGGGAC<br>GTCCCTTTG<br>(+, exon) | |
| BAFFR | CCCTCTGG<br>CATTTCCC<br>AGGC<br>(+, promoter) | GGGACAGGG<br>AGGTCCCTTG<br>C<br>(+, promoter) | CCTGTGGGCA<br>TTCCCATGGG<br>(+, promoter) | |
| ICOS | GTGGTGGG<br>AAATGCCT<br>TTAA<br>(+, 1st intron) | TGTTAGGGCA<br>TTCCCCAAGT<br>(+, exon) | CTGCTGGGGA<br>TGTCCCTTTG<br>(+, exon) | GCTGCTGGGATTT<br>CCATGCT<br>(+, exon) |

Supplemental table 1
Mouse CVID genes have multiple NFkB sites*

| Gene | NFκB site (GGGRNWYYCC, N: any base, R: purine, W: A or T, Y: T or C) and the surrounding sequences | | | |
|---|---|---|---|---|
| CD19 | GGGCTGGGGCTCCCCTTTTC (1st intron) | CCACTGGGACTATCCATCCA (-, exon) | AATGCGTGGATTTCCATAGG (-, exon) | AGAATGGGGACTCACCCTGGGA (-, exon) |
| CD20 | ACAGAGAGACTTTCCCTGTT (+, 1st intron) | TGTGTTGGGAATATCCATCC (-, 1st intron) | | |
| CD21 | TGGTTTGGAGATTCCTCAAC (-, promoter) | | | |
| CD81 | CCTCCGGGAAAGTCCAAGGC (+, promoter) | CCTTTGGGGAGCCCCACCCC (+, 1st intron) | | |
| LRBA | GCGCGGGACTACCCCTATGC (-, promoter) | GACCAAGGACTTTCCTGCTT (+, exon) | AAGCCGGGGCTCCCCATCAG (+, exon) | |

☐☐B sites are in bold and underlined in the promoter, intron or exon on the positive/negative (+/-) DNA strand.

To explore whether this gene is involved in inflammation induced by LPS and other stimuli in vivo, LRBA levels were examined in inflammatory mouse models and human asthmatic subjects. LRBA levels are significantly increased in plasma from mice stimulated with LPS, as seen in FIG. 32(A) or ovalbumin (OVA), seen in FIG. 32(B), in the culture supernatants of human mononuclear leukocytes stimulated with LPS, as seen in FIG. 32(C), and in plasma from asthmatic subjects undergoing an exacerbation of the disease, seen in seen in FIG. 32(D) and FIGS. 33(A)-(C). The presence of LRBA in human plasma also was confirmed by Western blots. 1 ml of human plasma was ultracentrifugated at 1200000 g then 20 µl of supernatant and all precipitation were used to load the PAGE gel. Cell extracts were prepared using radioimmunoprecipitation assay buffer (RIPA) buffer supplemented with protease and phosphatase inhibitors and Western blot detection/densitometry used to quantitate protein levels of specific gene products using a ChemiDoc XRS (Bio-Rad, Richmond, Calif.) imager and Quantity One software (Bio-Rad, Richmond, Calif.). Testing indicated that LRBA was indeed in the plasma, seen in FIG. 32(D, inset) and is supported by the fact that LRBA is detected in the plasma from trauma patients or subjects stimulated with LPS (Qian, et al., Inflammation, and P. the Host Response to Injury Large Scale Collaborative Research. Quantitative proteome analysis of human plasma following in vivo lipopolysaccharide administration using 16O/18O labeling and the accurate mass and time tag approach. 2005. *Molecular & cellular proteomics: MCP* 4: 700-709; Liu, et al., Inflammation, and P. the Host Response to Injury Large Scale Collaborative Research. High dynamic range characterization of the trauma patient plasma proteome. 2006. *Molecular & cellular proteomics: MCP* 5: 1899-1913).

CVID Receptor Genes are Involved in the LPS/TLR4 Pathway:

Similar to LRBA, deficiency of any CVID gene is associated with immunodeficiency, e.g. recurrent bacterial infections. Moreover, CVID genes have multiple NF-κB binding sites in or around the promoter range (Supplemental Table 1). These data suggest that these CVID genes may be involved in the TLR4/LPS pathway.

To investigate whether CVID genes also respond to LPS, mice were injected intraperitoneally with LPS. Twenty-four hours later the spleen and bone marrow cells were harvested and subjected to cytometry assay. The levels of B220, CD19 and TACI are significantly upregulated in both tissues while the levels of BAFFR, CD21 and TLR4 are significantly downregulated, as seen in Table 6 and FIGS. 34 and 35 and 37. The splenocytes and bone marrow cells were also subjected to ex vivo cell culture study with 24 h LPS stimulation, as seen in FIGS. 34 and 35. TACI is significantly upregulated by LPS on splenocytes and bone marrow cells. Interestingly, with LPS stimulation, the percentage of BAFFR is significantly decreased in the spleen and increased in the bone marrow in vivo, but is slightly increased in the splenocytes and decreased in the bone marrow cells, while the intensity of BAFFR is increased in cells from both tissues in ex vivo.

TABLE 6

LPS regulates CVID receptors, B220 and TLR4 in vivo.

|  |  | Percentage (%) | | | | Median Intensity (arbitrary fluorescence intensity units) | | | |
| --- | --- | --- | --- | --- | --- | --- | --- | --- | --- |
|  |  | PBS | LPS | fold | P value | PBS | LPS | fold | P value |
| Bone Marrow | B220 | 15.8 ± 1.2 | 15.5 ± 5.1 | 1.02 | 0.443 | 1672.3 ± 124.1 | 2423 ± 396.6 | 0.69↑ | 0.09 |
|  | CD19 | 14.9 ± 0.9 | 17.9 ± 5.5 | 0.83 | 0.88 | 1829.646.5 | 1951105 | 0.94 | 0.32 |
|  | CD21 | 26.9 ± 0.49 | 24.5 ± 1.23 | 1.1 | 0.07↓ | 764.7 ± 35.0 | 378 ± 53.8 | 2.02↓ | 0.0006 |
|  | BAFFR | 35.2 ± 2.3 | 43.7 ± 4.9 | 0.81 | 0.14 | 1094.3 ± 55.4 | 693.3 ± 84.1 | 1.58↓ | 0.012 |
|  | TACI | 3.1 ± 1.3 | 1.4 ± 0.35 | 2.16 | 0.22 | 637.730.7 | 617.719.7 | 1.03 | 0.39 |
|  | TLR4 | 57.4 ± 2.0 | 50.9 ± 3.3 | 1.13↓ | 0.08 | 576.3 ± 12.6 | 592 ± 28.8 | 0.97 | 0.85 |
| Spleen | B220 | 47.0 ± 3.2 | 58.7 ± 4.5 | 0.8↑ | 0.021 | 4015.3 ± 89.3 | 4031.3 ± 153.2 | 1 | 0.88 |
|  | CD19 | 49.3 ± 3.8 | 59 ± 4.1 | 0.8↑ | 0.04 | 1928.362.4 | 1792237 | 1.07 | 0.39 |
|  | CD21 | 88.8 ± 1.8 | 80.9 ± 9.7 | 1.1 | 0.24 | 846 ± 29.5 | 580.71 ± 56.5 | 1.45↓ | 0.04 |
|  | BAFFR | 93.1 ± 2.6 | 94.7 ± 0.92 | 0.98 | 0.36 | 1002 ± 19.5 | 842.7 ± 73.1 | 1.19↓ | 0.022 |
|  | TACI | 2.7 ± 0.40 | 7.9 ± 2.70 | 0.35↑ | 0.03 | 479.3 ± 30.0 | 560.7 ± 60.1 | 1.1 | 0.85 |
|  | TLR4 | 64.6 ± 2.3 | 55.7 ± 4.0 | 1.16↓ | 0.03 | 511.3 ± 17.0 | 502.7 ± 3.1 | 1.02 | 0.43 |

Numbers in bold indicate significant change, numbers underlined indicate near significant change.

The regulation of NFκB on the BAFFR, CD19 and TACI was further investigated in LRBA WT and LRBA KD Raji cells using two proteasome inhibitors, MG132 and PS341, with three different doses for 4 and 14 hours to inhibit NFκB by blocking proteasome-mediated IκB degradation. As expected, the levels of BAFFR and CD19 are decreased by NFκB inhibitors in a dose-dependent manner, but the levels of TACI are increased in Raji cells. The levels of the receptor change significantly from 4 to 24 h but less significantly among different doses. However, there are significant changes among the different doses in the levels of for CD19 and TACI at 24 h in the LRBA WT cells. Interestingly, TACI in LRBA KD cells is not affected by either of the two inhibitors, as seen in FIGS. 36(A)-(C) and 37(A)-(C), indicating that LRBA may regulate TACI by proteasome degradation.

LRBA Regulates CVID Receptors In Vitro:

LRBA is an important vesicle trafficking regulator (Wang, et al., Identification of a novel lipopolysaccharide-inducible gene with key features of both A kinase anchor proteins and chs1/beige proteins. 2001. *J Immunol* 166: 4586-4595; Cullinane, et al., The BEACH Is Hot: A LYST of Emerging Roles for BEACH-Domain Containing Proteins in Human Disease. 2013. *Traffic*) and may function as a master regulator of multiple CVID receptors. To test this, LRBA WT and LRBA KD Raji cells were stimulated with LPS, and the cell surface levels of CVID receptors and TLR4 were analyzed by flow cytometry. BD FACSelect Multicolor Panel Designer was used to search antibodies and build up the panel for multiple color cytometry for LSRII FACS machine. Fluorophores directly conjugated antibodies against cell surface CVID proteins were used: CD19-PerCP-Cy5.5, CD20-PE-Cy7, CD21-V450, BAFFR-PE, TACI-APC, and CD81-APC-H7. Two panels were used when use live/dead discrimination with DAPI (overlap with PerCP-Cy5.5) or 7AAD (overlap with V450). The standard staining procedures were followed and 20,000 to half million cells were acquired. Data acquisition was performed using FACS LSRII flow cytometers and analyzed using FACSDiva version 6.1.2.

The results demonstrate that the knockdown of LRBA significantly decreases the cell surface levels of TACI, CD19 and CD20 but increases the cell surface levels of CD21 and BAFFR. The LRBA knockdown also significantly decreases TACI and TLR4 positive cell numbers by four fold and two fold, respectively, but increases CD21 positive cell numbers by two fold, seen in FIGS. 38 and 39 and Table 7.

TABLE 7

Influence of LRBA knockdown on the cell surface levels of CVID and TLR4 receptors.

|  | Wild type | Knockdown | fold | p value |
| --- | --- | --- | --- | --- |
|  | Percentage (%) | | | |
| CD19 | 98.93 ± 0.50 | 98.57 ± 0.28 | 1.00 | 0.15 |
| CD20 | 99.32 ± 0.95 | 99.18 ± 0.04 | 1.00 | 0.74 |
| CD21 | 27.25 ± 3.54 | 55.08 ± 5.00 | 0.49↑ | 6E-07 |
| BAFFR | 87.30 ± 1.24 | 90.83 ± 0.93 | 0.96↑ | 0.0002 |
| TACI | 30.06 ± 3.41 | 7.38 ± 1.49 | 4.07↓ | 8E-07 |
| TLR4 | 56.88 ± 6.21 | 31.27 ± 11.42 | 1.82↓ | 0.0007 |
|  | Median Intensity (arbitrary fluorescence intensity units) | | | |
| CD19 | 7167.33 ± 215.86 | 5830.17 ± 159.95 | 1.23↓ | 3E-07 |
| CD20 | 35802.00 ± 4300.52 | 29541.25 ± 332.06 | 1.21↓ | 0.03 |
| CD21 | 1591.00 ± 41.19 | 1659.50 ± 72.48 | 0.96↑ | 0.002 |
| BAFFR | 3391.50 ± 312.08 | 4198.00 ± 496.75 | 0.81↑ | 0.007 |
| TACI | 2411.83 ± 114.57 | 1813.50 ± 412.89 | 1.33↓ | 0.01 |
| TLR4 | 11664.40 ± 3828.47 | 11204.60 ± 2171.10 | 1.04 | 0.81 |

Numbers in bold indicate significant change.

As seen in FIGS. 38 and 39, each experimental data was represented by a marker on the figure, while each set of the experimental data obtained from LRBA WT or LRBA KD Raji cells stimulated with LPS over a series of time points was fitted to a polynomial trend line. High $R^2$ values ($R^2=1$) were obtained, demonstrating that each set of data can be represented by a polynomial trend line equation. Then, the slope at each time point can be used to measure the rate of CVID receptor level change in response to LPS. The results, seen in Table 8, demonstrate that the slopes of the response curves at most points from LRBA KD cells are less than the curves from LRBA WT cells. This indicates that CVID receptors in the LRBA WT cells are more responsive to stimulators, as seen in FIG. 36(A)-(C) and 37(A)-(C). In addition to response speed change, the response phase of the CVID receptor response curves from WT and KD also are different with most are opposite or out of phase, seen in Table 8.

TABLE 8

Comparison of the change rate of the gene expression levels in response to stimulators in cells with LRBA knock down or overexpression (Fold change ratio)*.

| Fold | Gene | Time point | | | | | | | | Fluctuation phase | FIG. # |
|---|---|---|---|---|---|---|---|---|---|---|---|
| | | 1 | 2 | 3 | 4 | 5 | 6 | 7 | 8 | | |
| LRBA KD LPS or EGF (WT/KD) | CD19 | 0.91 | 2.08 | 1.00 | 0.50 | 7.06 | 5.99 | | | Opposite phase | 40, 41 |
| | CD20 | 7.63 | 8.84 | 85.84 | 4.73 | 42.97 | 3.24 | | | Out of phase | 40, 41 |
| | BAFFR | 1.16 | 2.01 | 1.56 | 2.18 | 1.26 | 0.52 | | | Opposite phase | 40, 41 |
| | TACI | 0.01 | 1.39 | 5.75 | 3.69 | 2.76 | 2.50 | | | Opposite phase | 40, 41 |
| KD protease inhibitor (WT/KD) | CD19 | 0.91 | 1.80 | 0.10 | 9.81 | 1.18 | 0.86 | 0.60 | 1.09 | Opposite phase | 38, 39 |
| | BAFFR | 145.3 | 3.33 | 1.15 | 2.08 | 1.51 | 6.26 | 5.01 | 3.68 | In phase | 38, 39 |
| | TACI | 1.41 | 0.84 | 5.94 | 0.53 | 4.39 | 5.79 | 5.14 | 2.04 | Opposite phase | 38, 39 |
| LRBA$^{+++}$ LPS LRBA$^{+++}$/WT | B220 | 0.90 | 1.18 | 0.06 | 0.20 | 1.37 | 1.31 | 1.07 | 0.29 | Opposite phase | 7 |
| | CD69 | 1.36 | 0.88 | 1.97 | 1.12 | 0.90 | 0.83 | 0.81 | 0.77 | In phase | 7 |
| | BAFFR | 1.30 | 5.19 | 4.95 | 1.43 | 0.60 | 17.88 | 4.50 | 20.40 | Opposite phase | 7 |
| | TACI | 1.52 | 1.99 | 0.14 | 2.35 | 0.52 | 1.26 | 0.32 | 1.13 | In phase | 7 |

KD/WT.
KD = knockdown,
WT = wild-type,
LRBA$^{+++}$ = LRBA Overexpression.
CD19 is based on percentage others are Median Intensity (arbitrary fluorescence intensity units).

Figure 44B:
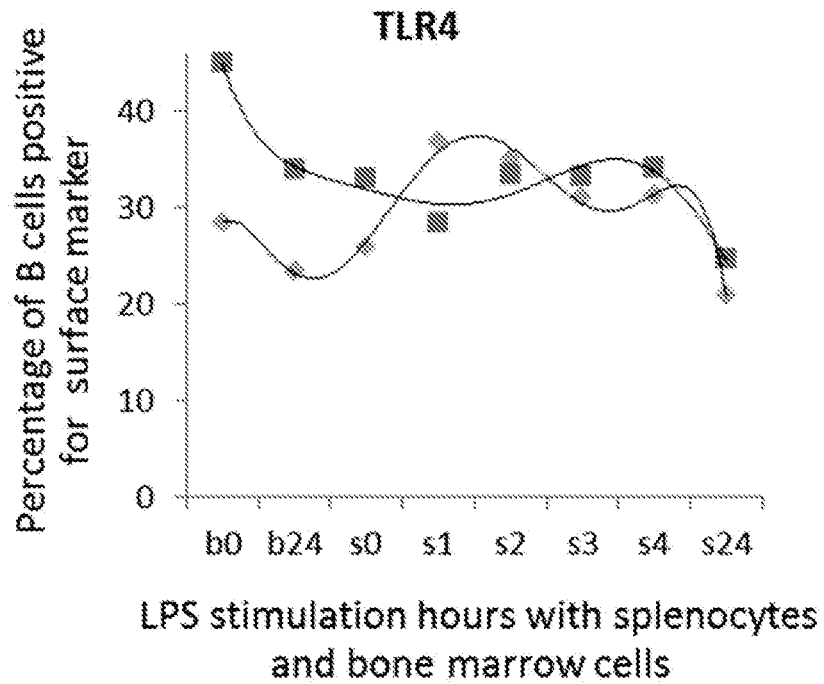

To confirm these results, four LRBA potential dominant negative mutants (DNM) fused with green fluorescent protein (GFP) were constructed from BEACH (Beige and Chediak-Higashi), VHS-LIR [VPS (vacuolar protein sorting), Hrs (hepatocyte growth factor-regulated tyrosine kinase substrate) and STAM (signal transducing adaptor molecule), LC3 (light chain 3) Interacting Region], VHS and LIR domains and transfected into Raji cells. CVID and TLR4 receptors were analyzed in the GFP positive and negative populations. All LRBA DNMs significantly decrease cell surface CVID receptor positive cell numbers and cell surface intensity, as seen in FIGS. 40 and 41. VHS-LIR DNM decreases CD21, BAFFR and TACI by 2 to 3 times. The MFI downregulation of CD19 and CD20 by the LIR was further confirmed in several clones stably transfected with the GFP-LIR DNM constructs, as seen in FIGS. 42-44. The percentage of these receptors in wild type cells remains consistent indicating that the changes of these receptors in GFP positive cells (transfected) were induced specifically by LRBA DNMs.

LRBA Regulates CVID Receptors In Vivo:

The knockdown of LRBA downregulates CVID receptors, while the overexpression of LRBA may upregulate CVID receptors. The miR-150 knockout (KO) mice were used to test this possibility. There is one miR-150 potential site conserved in the LRBA coding region of the human and mouse LRBA genes, as seen in FIG. 42. Overexpression of miR-150 down-regulates LRBA, while in the miR-150 ko mice, LRBA is overexpressed, as seen in FIGS. 43 and 44. The B cell surface levels of BAFFR, TACI, CD69 (B cell activation marker), B220 and LRBA are increased in the splenocytes and bone marrow cells from the wild type C57BL/6J and the miR-150 KO mice after LPS stimulation, and are higher in the miR-150 KO mice in most cases. B220 and CD69 were increased over the entire stimulation time in both splenocytes and bone marrow cells. TACI increased dramatically after 24 h LPS stimulation. In the KO spleen, CD69, BAFFR and LRBA are higher, while TACI is lower at the beginning of the stimulation (0 to 2 h), and higher later (3 to 24 h). BAFFR, TLR4 and TACI are lower on bone marrow cells in KO mice, as seen in FIGS. 43 and 44. The results from these different methods confirm each other and demonstrate that LRBA regulates multiple cell membrane receptors, including CVID and TLR4.

To understand the underlying molecular mechanism by which LRBA deficiency causes CVID and autoimmunity, first we examined the involvement of CVID receptors and LRBA in the LPS/TLR4/NFκB pathway, which is one of most important signal pathways in immune response, and is closely related to immunodeficiency and autoimmunity. Toll is an essential receptor for host defense against fungal and Gram-positive bacterial infections in Drosophila (Lemaitre, et al., The dorsoventral regulatory gene cassette spatzle/Toll/cactus controls the potent antifungal response in Drosophila adults. 1996. Cell 86: 973-983). The mammal TLR4 recognizes LPS from Gram-negative bacteria, fibrinogen cleaved by proteases from fungi and Gram-positive bacteria, and viral proteins (F protein from respiratory syncytial virus, vesicular stomatis virus glycoprotein G, poxviral protein A46) (Stack & Bowie, Poxviral protein A46 antagonizes Toll-like receptor 4 signaling by targeting BB loop motifs in Toll-IL-1 receptor adaptor proteins to disrupt receptor:adaptor interactions. 2012. *The Journal of biological chemistry* 287: 22672-22682; Bezemer, et al., Dual role of Toll-like receptors in asthma and chronic obstructive pulmonary disease. 2012. *Pharmacological reviews* 64: 337-358). LPS is a crucial structural component of Gram-negative bacteria and a potent immunostimulators. Excessive LPS stimulation can result in systemic inflammation and death (Beutler & Rietschel, Innate immune sensing and its roots: the story of endotoxin. 2003. *Nature reviews. Immunology* 3: 169-176). It interacts with TLR4, activating the downstream transcription factors of the nuclear factor κB (NF-κB) family to produce several hundred inflammatory genes (Beutler & Rietschel, Innate immune sensing and its roots: the story of endotoxin. 2003. *Nature reviews. Immunology* 3: 169-176;

Poltorak, et al., Defective LPS signaling in C3H/HeJ and C57BL/10ScCr mice: mutations in Tlr4 gene. 1998. *Science* 282: 2085-2088; Akira, et al., Pathogen recognition and innate immunity. 2006. *Cell* 124: 783-801). NF-κB plays a pivotal role in inflammation and immune responses including inflammatory and immune responses (Baltimore, NF-kappaB is 25. 2011. Nat Immunol 12: 683-685; Hayden & Ghosh, NF-kappaB, the first quarter-century: remarkable progress and outstanding questions. 2012. *Genes & development* 26: 203-234), and is a hub transcription factor downstream of many proteins, defects of which cause immunodeficiency (Cunningham-Rundles, Human B cell defects in perspective. 2012. *Immunologic research* 54: 227-232). Therefore, LPS/TLR4 is one of most important signal pathways in immune response. It is important to defend against Gram-negative and some Gram-positive bacteria (Koppe, et al., Recognition of *Streptococcus pneumoniae* by the innate immune system. 2012. *Cellular microbiology* 14: 460-466), fungi (Millien, et al., Cleavage of fibrinogen by proteinases elicits allergic responses through Toll-like receptor 4. 2013. Science 341: 792-796) and viruses (Shinya, et al., The TLR4-TRIF pathway protects against H5N1 influenza virus infection. 2012. *Journal of virology* 86: 19-24). LRBA is involved in the signal transduction pathway initiated by LPS (Wang, et al., Identification of a novel lipopolysaccharide-inducible gene with key features of both A kinase anchor proteins and chs1/beige proteins. 2001. *J Immunol* 166: 4586-4595). Its deficiency is hypothesized to impair the TLR4 pathway. Other CVID genes are critical immune regulators, involved in the stimulation, survival and development of B cells. However, their involvements in LPS/TLR4 pathway have not been explored yet. Levels of LRBA and the CVID receptors are shown responsive to LPS stimulation, suggesting that they are involved in LPS/TLR4 signal pathways, agreeing with their critical roles in the immune system.

The data from proteasome inhibitors, which inhibit NFκB by blocking proteasome-mediated IκB degradation, suggests that LPS may regulate CVID receptors through NFκB. Intriguingly, TACI levels cannot be increased in Raji9 cells treated with proteasome inhibitors: 250 nM of MG-132 or 50 nM of PS-341 for 24 hr as in Raji cells, as seen in FIG. 42, suggesting that the deactivation of NFκB may be blocked by LRBA knockdown and thus the expression of TACI may be continually inhibited. In contrast, BAFFR and CD19 are decreased by the two NF-κB inhibitors in a dose-dependent manner, suggesting that the two genes are positively regulated by NF-κB.

LRBA was tested to determine if it is a master regulator for CVID receptors. LRBA is a unique CVID gene extraordinarily different from other CVID genes. First, it is a large gene encoding a 319 kD protein composed of multiple domains (Wang, et al., Identification of a novel lipopolysaccharide-inducible gene with key features of both A kinase anchor proteins and chs1/beige proteins. 2001. J Immunol 166: 4586-4595; Kerr, et al., Analysis of lipopolysaccharide-response genes in B-lineage cells demonstrates that they can have differentiation stage-restricted expression and contain SH2 domains. 1996. *Proceedings of the National Academy of Sciences of the United States of America* 93: 3947-3952), and could serve as a scaffold to interact with multiple proteins. Other CVID proteins are relative small: ICOS is 27 kD; TACI, 32 kD; BAFFR, 19 kD; CD81, 26 kD; CD21, 145 kD; CD20, 35 kD; and CD19, 61 kD. Second, CVID proteins are plasma membrane receptors on B cells except for ICOS which is on T cells. LRBA is expressed in every kind of cells and locates to almost everywhere in the cell and is a regulator for vesicle trafficking. Vesicle trafficking is required for homeostasis and activation of plasma membrane receptors (Wang, et al., Identification of a novel lipopolysaccharide-inducible gene with key features of both A kinase anchor proteins and chs1/beige proteins. 2001. *J Immunol* 166: 4586-4595; Cullinane, et al., The BEACH Is Hot: A LYST of Emerging Roles for BEACH-Domain Containing Proteins in Human Disease. 2013. *Traffic*). Third, LRBA deficiency causes both immunodeficiency and autoimmunity in LRBA deficient patient, a phenomenon not seen with other CVID genes. TACI mutations also are associated with autoimmunity but to a much lesser extent (Salzer, et al., Relevance of biallelic versus monoallelic TNFRSF13B mutations in distinguishing disease-causing from risk-increasing TNFRSF13B variants in antibody deficiency syndromes. 2009. *Blood* 113: 1967-1976). Fourth, LRBA is the only CVID protein that is a protein kinase A anchor and can regulate protein activity by phosphorylation. Agreeably, LRBA deficiency causes more severe diseases, and in addition to immunodeficiency and autoimmunity, other medical conditions such as severe retarded growth and failure to thrive, growth hormone deficiency, asthma, monoarthritis, seizures, granulomatous infiltration, finger clubbing, hepatosplenomegaly, allergic dermatitis, and nephrotic syndrome are also observed in LRBA deficient patients. LRBA was shown to extensively associated with the endomembrane system including the Golgi complex, endosomes, lysosomes, plasma membrane, nucleus, pseudopodia and microtubules, and vesicle trafficking, which is responsive to LPS stimulation, suggesting that LRBA plays a regulatory but not a structural role in vesicle trafficking, which is essential for signal transduction of immune effectors. These results suggest that LRBA plays a role in vesicle trafficking and signal transduction essential for the immune system, deficiency of which caused by LRBA deficiency may cause the aforementioned diseases. Our previous study shows that LRBA regulate EGFR activation. Neurobeachin (Nbea) is required for the disposition of surface levels of glutamate and GABA, γ-aminobutyric acid (GABA) receptors at synapses (Nair, et al., Neurobeachin regulates neurotransmitter receptor trafficking to synapses. 2013. *The Journal of cell biology* 200: 61-80). Thus, LRBA may regulate other CVID genes, for example, CD19, CD20 and BAFFR, because their levels are low when LRBA is absent.

Therefore, the cell surface receptors (CVID receptors and TLR4) were examined for LRBA regulation. LRBA repression by multiple methods downregulates the levels of CD19, CD20, TACI and TLR4, seen in Table 6. In contrast, overexpression of LRBA in a mouse model has opposite effects, i.e., upregulation of these B cell markers, seen in FIGS. 36 and 37. The response speed for all genes, except for BAFFR, is decreased in the LRBA repressed cells but increased in LRBA overexpressed cells. The response phase for most genes in LRBA deregulated cells is out of phase or opposite to that of wild type (WT) cells, seen in Table 6 and FIGS. 36 and 37. The results demonstrate that the deregulated LRBA deregulates the four parameters (protein levels/activity, response speed and response phase) of these critical effectors, and subsequently may result in deregulated immune response, which requires high coordination among genes involved.

Interestingly, survival genes, BAFFR is increased, while anti-survival genes, e.g. TACI(18, 19),TLR4(54), and other CVID receptors (CD19, CD20 and CD21) are decreased with LRBA repression, seen in Table 6, which appears to result in enhanced survival signaling and more cells. This is supported by the findings that LRBA deficient patients have more peripheral T cells, more CD20 positive B cells, lymphocyte infiltration and respond to anti-CD20 therapy. The effects of miR-150 on CVID receptors are mediated by LRBA. In another word, miR-150 K/O mice represent LRBA overexpression model in terms of CVID receptor regulation.

LRBA's presence in plasma and cell membranes may provide an easy way to modulate LRBA levels. Antibodies to LRBA also decrease the proinflammatory cytokines, IL-6 and TNFα in vivo, as seen in FIG. 41. Thus, LRBA, a critical regulator for multiple inflammatory diseases, may be an ideal therapeutic target to treat chronic inflammatory diseases.

The mammal Toll-like receptor 4 (TLR4) recognizes LPS from Gram-negative bacteria, fibrinogen cleaved by proteases from fungi and Gram-positive bacteria, and viral proteins (F protein from respiratory syncytial virus, vesicular stomatis virus glycoprotein G, poxviral protein A46) (38, 39). Therefore, this receptor is important to defend against Gram-negative and some Gram-positive bacteria(46), fungi (47) and viruses(48). LRBA is involved in the signal transduction pathway initiated by LPS(5), which is a crucial structural component of Gram-negative bacteria and a potent immunostimulator. Excessive LPS stimulation can result in systemic inflammation and death(40). It interacts with TLR4, activating the downstream transcription factors of the nuclear factor κB (NF-κB) family, to produce proinflammatory cytokines, IL-6 and TNFα. NF-κB plays a pivotal role in inflammation and immune responses. In signal transduction, it is downstream of many proteins, defects of which cause immunodeficiency and autoimmunity. LRBA deficiency impairs the TLR4 pathway by deregulating hub proteins such as NF-κB and mitogen-activated protein kinases (MAPKs), which, in turn, deregulate multiple critical immune genes such as CVID receptors, resulting in immunodeficiency and autoimmunity.

Example 10

Lipopolysaccharide (LPS)-responsive beige-like anchor (LRBA) deficiency causes both immunodeficiency (CVID) and autoimmunity with manifestations of antibody deficiency (1-3), indicating that it plays a fundamental role in the immune system. CVID is the most common late-onset primary immunodeficiency disease (PID). Transmembrane activator and calcium modulator and cyclophilin ligand interactor (TACI)(4) and B cell-activating factor receptor (BAFFR)(5), CD20(6), inducible costimulator (ICOS)(7) and members of the B cell coreceptor complex (CD19(8), CD21(9) and CD81(10)), also are associated with or cause CVID(11). About two-third of CVID patients have autoimmune problems (12, 13). As opposed to other CVID genes, the immunodeficiency caused by LRBA deficiency is highly associated with autoimmunity. To date, the 11 identified LRBA-deficient CVID patients had autoimmunity(1, 2, 14). TACI mutations also are associated with autoimmunity but to a lesser degree (36% vs. 23% of patients with wild-type TACI) (15). The association of immunodeficiency with autoimmunity is paradoxical, since immunodeficiency is lacking immunity, while autoimmunity is overactivation of the immunity to the body. LRBA deficient patients have markedly reduced T-cell proliferation in response to phytohaemagglutinin (PHA) and anti-CD3 mAb stimulations(3), and reduced B cell survival(1). On another hand, LRBA deficient patients have more CD20 positive B cells, lymphocyte infiltration and respond to anti-CD20 therapy(1-3), suggesting that overactivation of B cells may contribute to the autoimmunity.

LRBA was initially identified as an LPS-upregulated gene in B cells (16, 17). It belongs to the WDL-BEACH-WD40 (WBW) gene family containing the WBW super domain. LRBA and other WBW proteins appear to function as scaffolding proteins in vesicle trafficking(1, 16, 18, 19) and are important for human disease(18). Vesicle trafficking is required for homeostasis of inflammatory receptors and cytokines through cell membrane deposition, oligomerization, phosphorylation, internalization, recycling and degradation(20). To explain the paradoxical association of immunodeficiency and autoimmunity, it is hypothesized that LRBA deficient patients have defective vesicle trafficking, resulting in attenuation of both activation and deactivation of immune mediators. The attenuation of activation of immune mediators may lead to immunodeficiency, while the attenuation of deactivation of immune mediators may result in prolonged activation of the immunity and then autoimmunity. To test this hypothesis, LRBA was stably knocked down in Raji cells by the short hairpin (sh) RNA technique to study the effects of LRBA repression on NF-κB activity. The results demonstrate that repression of LRBA attenuates both NF-κB activation and deactivation, which may result in insufficient NF-κB activity and prolonged NF-κB activation, leading to immunodeficiency and autoimmunity.

LRBA Regulates NF-κB in a Dual Mode:

NF-κB is the central regulator of the immune system and plays a pivotal role in inflammation and immune responses. Disturbed NF-κB signaling is implicated in the pathogenesis of human immunodeficiency and chronic autoimmune inflammatory diseases(21). Defects of several genes upstream of NF-κB cause immunodeficiency(22). Therefore, deregulation of NF-κB signaling may be involved in LRBA deficiency associated immunodeficiency and autoimmunity. In another word, LRBA may be a regulator of NF-κB. To test this hypothesis, LRBA was knocked down in Raji cells by the short hairpin (sh) RNA technique as previously described(23). Several stable clones were obtained and named Raji9 cells. Raji cells were stimulated with LPS for different times from zero to several hours, and the NF-κB activity was measured by NF-κB luciferase reporter. The average levels of the NF-κB activity are higher in Raji cells with LRBA knockdown, as seen in FIG. 45(A). This is also confirmed by the flow cytometry measurements of the phospho-NFκB (pS529) levels, as seen in FIG. 45(B). The phosphorylation of 5529 in the activation domain stimulates NF-κB transcriptional activity, and thus may be used to reflect NF-κB activation(24). The results also show that the NF-κB activity is not stable but fluctuates over the time period of the stimulation. Without stimulation, the NF-κB activity is higher in Raji9 cells (LRBA KD) but declines and is lower with stimulation at 15 min and 30 min, then goes up and is higher. On the other hand, the NF-κB activity in Raji cells is the opposite of its activity in Raji9 cells, as seen in FIG. 46(B). The observed fluctuation of the NF-κB activity agrees with the finding that NF-κB activity oscillates during stimulation. Therefore, the levels of the NF-κB activity can be both lower and higher in Raji or Raji9 cells depending on the time when the activity is observed.

These results demonstrate that NF-κB activity is regulated by LRBA. To test if the regulation is dose-dependent, A549 cells were transfected with the LRBA shRNA plasmid DNA to knockdown LRBA. Three stable clones that have different levels of GFP expression were obtained, as seen in FIG. 45(D). The GFP expression levels may be used to indicate LRBA shRNA levels, which should be inversely related to the levels of LRBA. The results show that the luciferase activity corresponds to the GFP levels and is inversely related to the levels of LRBA, as seen in FIG. 45(C), suggesting that knockdown of LRBA increases NF☐B activity in a dose-dependent manner in A549 cells.

As the NF-κB activity oscillates during stimulation, to measure the speed of the NF-κB activity change in response to stimulation, a trend line for each dataset was obtained by polynomial fitting, as seen in FIG. 46(B). The $R^2$ value is 1, suggesting a perfect fitting, and the trend line can be used to represent the corresponding dataset. In another word, the dataset can be described by the trend line equation. Then the slope of the curve at each time point can be calculated and used for the speed of the NF-κB activity change at that time point. The results show that the speed of the NF-κB activity change in the wild type cells at most time point is higher than LRBA knockdown cells in Raji cells, as seen in Table 9, suggesting that LRBA knockdown attenuates both activation and deactivation of NF-κB activity. It also shows that the oscillation curve for Raji control cells is more regular than Raji9 cells, suggesting that NF-κB activity is deregulated by LRBA knockdown. These data also show that the NF-κB activity is lower at the beginning of the stimulation but is higher after prolonged stimulation.

LRBA Regulates MAPKs:

Like NF-κB, the mitogen-activated protein kinases (MAPKs) act as funnels to collect many stress-activated signals but function as bottle necks to filter and process these signals, and then have many diverse targets(26). Specifically, MAPKs are critical downstream hubs of the TLR4/LPS signal transduction(27) and may be affected by LRBA deficiency. The expression and activation of the three major MAPKs [p42/44, p38 and Jun N-terminal kinase (JNK)] were examined in Raji cells. The results suggest that the p42/44 kinase activity is reduced, while the JNK and p38 kinase activities are increased, as seen in FIG. 47, in LRBA KD cells. The phospho-p42/44 measured by flow cytometry intracellular staining also is decreased (data not shown). Similar results were observed in *Drosophila* where MAPK (p42/44 orthologue) is downregulated but JNK is increased when rugose (rg, LRBA orthologue) is mutated(28). The *Drosophila* MAPK and JNK have 82% and 78% identities with their human orthologues, respectively.

LRBA Regulates Cytokines:

The results show that LRBA regulates NF-κB and signal transduction kinase hubs, which suggests that cytokines regulated by these proteins also may be regulated by LRBA. To this end, we measured cytokines. The secreted levels of TNFα and IL-10 measured by the cytometric bead array (CBA) are significantly increased by knocking down LRBA, as seen in FIG. 48. The levels of TNFα are the highest at 1 hr stimulation, IL-10 is the highest at 4 hr stimulation. Interestingly, the speed of the TNFα or IL-10 levels change in the wild type cells at all-time points is lower than LRBA knockdown cells in Raji cells, seen in Table 9, suggesting that LRBA knockdown speed up level change of TNFα or IL-10. The level of IFNγ is the highest at 30 min stimulation, IL-4 is the highest at 2 hr. IL-2 is lower in LRBA KD cells at 15 and 30 min. At other time point the difference is not obvious. The ELISA assays of intracellular and extracellular TNFa also confirm the CBA TNFα are higher when LRBA is knocked down. Similar to the above data, increased secretion of carboxypeptidase Y were observed in *Saccharomyces cerevisiae* with the deletion of LRBA orthologue, BPH1(29). Agreeably, the LRBA isoform, neurobeachin (NBEA) is a negative regulator of vesicle secretion(30).

TABLE 9

Comparison of the change rate of the gene expression levels or activity in response to stimulators in cells with LRBA knock down or overexpression (Fold change ratio)*

| Fold | Gene | Time point | | | | | | | | Fluctuation phase | FIG. |
|---|---|---|---|---|---|---|---|---|---|---|---|
| | | 1 | 2 | 3 | 4 | 5 | 6 | 7 | 8 | | |
| LRBA KD LPS or EGF (WT/KD) | NF-κB | 1.24 | 0.82 | 0.85 | 0.13 | 3.08 | 1.17 | 0.93 | | Opposite and out of phase | 1A |
| | TNFα | *2.33* | *4.04* | *3.03* | *3.31* | *2.23* | | | | In phase | 2D |
| | IL-10 | *19.28* | *1.73* | *4.17* | *5.75* | *1.68* | | | | Opposite phase | 2D |

*Numbers in bold and italic are reversed ratios, i.e. KD/WT.
KD = knockdown,
WT = wild-type.

LRBA Immunodeficiency In Vitro Model.

In order for pathogens to efficiently spread to neighboring cells and evade the immune cells, and/or gain nutrients, one prominent strategy of many bacterial pathogens is to cause host cell death (31). On another hand, the host cell, first will try to kill the evaded pathogens. As such, cell death may be used as a hallmark of immunodeficiency. This study demonstrates that repression of LRBA deregulates multiple critical immune genes and can explain why LRBA deficiency causes immunodeficiency. It is hypothesized that Raji cells with LRBA knockdown can serve as an immunodeficiency in vitro model, i.e. they cannot fight pathogens efficiently when compared to wild type cells, manifested as more cell death. To test this assumption, Raji and Raji9 cells were infected separately with adenoviruses and Gram-negative bacteria and the annexin V apoptosis assay was conducted after 24 hrs, as seen in FIGS. 49(A) and (B). The results show that there are more dead cells or apoptotic cells when LRBA is knocked down, as seen in FIGS. 49(C) and (D).

Despite the tremendous progress in understanding the regulation of NF-κB, there is much that remains to be understood(32). Therapeutic strategies based on specifically targeting the NF-κB pathway have failed to show efficacy in human disease, although NF-κB is implicated to be critical in a host of human diseases(33). This study identified a new category of NF-κB regulator, LRBA, a vesicle trafficking regulator. LRBA is the first vesicle trafficking regulator that regulates NF☐B. Vesicle trafficking is required for both activation and deactivation of many immune effectors. Agreeably, LRBA regulates both NF-κB activation and deactivation.

Based on these results, a dual regulation model of immune mediators is proposed for LRBA's regulating NF-κB and other genes, and in turn, regulating the immune system, as seen in FIG. 50. According to this model, at first, the activation of NF-κB is attenuated with LRBA repression, resulting in low transcription activity due to attenuated nuclear translocation of NF-κB, as seen in FIGS. 45(E) & (F) (First phase, before 30 min). The deactivation of NF-κB, however, also is attenuated with LRBA repression, resulting in higher transcription activity, due to the attenuated cytoplasmic translocation of NF-κB, as seen in FIGS. 45(A)-(D) and 46(A) & (B) (Second phase, after 30 min). The insufficient NF-κB activity at beginning may result in immunodeficiency, while prolonged NF-κB activity at a later phase, may result in autoimmunity due to increased production of proinflammatory cytokines, especially TNFα, as seen in FIG. 48. The fact that the response speed and levels of proinflammatory cytokines (TNFα and IL-10) are increased, seen in Table 9, may partially explain how LRBA deficiency causes autoimmunity. TNFα and IL-10 are implicated in the pathogenesis of Crohn's disease. TNFα levels are high in the gastrointestinal (GI) tract of IBD and may play a role in the inflammatory pathology of the disease(26). IL-10 has both immunoregulatory and immunostimulatory properties. It can facilitate B-cell proliferation, differentiation, and antibody production and CD8$^+$ T cell activation. TNFα is overexpressed in rheumatoid arthritis (RA) and other inflammatory diseases (27). IBD and RA are associated with LRBA deficiency (1-3), which suggest overexpression of these cytokines caused by LRBA deficiency may be responsible for the autoimmunity. Thus, LRBA may regulate both NF-κB activation and deactivation through regulating the levels, response speed and response phase of activity. Repression of LRBA may attenuate both the activation and deactivation of NF-κB and other genes.

Several fundamental implications can be obtained from this model: First, the immune system requires a rapid response, and the insufficient activation of immune effectors may cause immunodeficiency (phase 1); Second, the delayed and prolonged activation of immune effectors may cause autoimmunity (phase 2); Third, although autoimmunity and normal immunity may involve the same genes, they may be different, as autoimmunity results from the four deregulated parameters (protein levels, activation levels, response speed and response phase) of the immune effectors; Fourth, autoimmunity (phase 2) occurs following immunodeficiency (phase 1) and may be as a result of the immunodeficiency.

The members of NF-κB and MAPK protein families act as funnels to collect a great number of stress-activated signals but function as bottle necks to filter and process these signals, and then to participate in the regulation of hundreds of genes (26). They were examined in this study for LRBA regulation to investigate the molecular mechanism by which LRBA deficiency causes immunodeficiency and autoimmunity. LRBA knockdown upregulates NF-κB activity, TNFα and IL-10 levels. It also increases the phosphorylation levels (activity) of p38 and JNK but decreases that of p42/44, as seen in FIG. 45. The response speed for NF-κB and proinflammatory cytokines (TNFα and IL-10) is increased in the LRBA repressed cells but decreased in LRBA overexpressed cells. The response phase for most genes in LRBA deregulated cells is out of phase or opposite to that of wild type (WT) cells (Table 9 and FIG. 48. The results demonstrate that the deregulated LRBA deregulates the four parameters (protein levels/activity, response speed and response phase) of these critical effectors, and subsequently may result in deregulated immune response, which requires high coordination among genes involved.

NF-KB is the master gene regulator in the immune response and plays a pivotal role in the immune system, including inflammatory and immune responses, and is a hub transcription factor downstream of many proteins, defects of which cause immunodeficiency(22). Other genes in this study also encode critical immune effectors closely associated with PIDs and autoimmunity, and may be controlled by NF-κB directly such as those genes that are known or potential NF-κB target genes (TNFα), or indirectly, e.g. NF-κB activates TNFα which can activate JNK and p38(34, 35). Thus, LRBA may exert its effects on immunodeficiency and autoimmunity via its regulation of these genes through NF-κB.

Survival genes, i.e. NF-κB, AKT, TNFα and IL-10, or stress genes, i.e. p38 and JNK, are increased, while anti-survival genes, e.g. proliferation gene (p42/44)(36, 37) are decreased with LRBA repression (Table 9). This may result in enhanced survival signaling and more cells, which is supported by the findings that LRBA knockdown significantly increases cell survival, and that LRBA deficient patients have more peripheral T cells, more CD20 positive B cells, lymphocyte infiltration and respond to anti-CD20 therapy(1-3). These data suggest that the autoimmunity caused by LRBA deficiency may be associated with deregulated cell survival. Self-reactive T and B cells are deleted by apoptosis during the development of T and B cells in the thymus and bone marrow, respectively. The increased survival may enable self-reactive B or T cells to escape from destined apoptosis and to enter the blood stream and cause autoimmunity. However, when these cells are infected with Gram-negative bacteria or adenoviruses, more Raji9 cells die and become apoptotic. This suggests that Raji9 cells cannot efficiently fight infection and could be used as an in vitro immunodeficiency model.

Finally, current therapeutic strategies to treat inflammatory diseases are based on single cytokines. The cytokine cascade is highly redundant, and chronic inflammatory diseases, more often than not, are complex involving multiple cytokines(38). Therefore, inhibition of a single cytokine may not be sufficient to treat the disease and blocking a variety of different cytokines with multiple agents is theoretically impractical. Targeting a gene such as LRBA, that regulates multiple cytokines and other immune effectors, may be desirable. This gene is crucial in the regulation of multiple immune effectors, including various cytokines. LRBA's presence in plasma and cell membranes may provide an easy way to modulate LRBA levels. Antibodies to LRBA also decrease the proinflammatory cytokines, IL-6 and TNFα in vivo, as seen in FIG. 50. Thus, LRBA, a critical regulator for multiple inflammatory diseases, may be an ideal therapeutic target to treat chronic inflammatory diseases.

Although in contrast with most other cell types, NF-κB is constitutively activated in primary B cells and B cell lines, much of the NF-κB is still sequestered in the cytoplasm hence can be activated upon stimulation as shown in this study. In non immune cells, such as HeLa and NIH3T3 cells, the NF-κB nuclear translocation oscillates upon stimulation as a results of negative feedback loop of the NF-κB sequester I-κB, which is produced by NF-κB activation. In this study, it seems that NF-κB activity also oscillate in Raji B cells in response to stimulation, as seen in FIG. 45(E).

NFκB is constitutively active in Raji cells due to the EBV onco-protein, the latent membrane protein 1 (LMP1), which functions as a constitutively activated member of the tumor necrosis factor receptor (TNFR) superfamily activating a number of signaling pathways in a ligand-independent manner(39, 40). As the NFκB activity oscillates, i.e. the activation and deactivation of NFκB activity, in cells that NFκB is constitutively activated, it is able to study LRBA knockdown effects on attenuation for both activation and deactivation of NFκB activity in such cells as in this study.

To prove that these in vitro studies are clinically relevant. We explored if Raji cells can be used as a in vitro model of immunodeficiency. The results demonstrate that Raji LRBA KD cells can be used as a novel LRBA immunodeficiency in vitro model, which can be used to study at least apoptosis caused by pathogens. Due to the convenience of in vitro study, it will greatly facilitate studies on immunodeficiency.

Chronic inflammation leads to many chronic diseases, affecting almost half of American population. Overactivation of inflammatory mediators, e.g. NF-κB, TNFα and IL-6 plays a critical role in chronic inflammation. However, the regulation of CI is largely unknown. NFκB overactivation is central to the pathogenesis of atherosclerosis, its blockage even interferes with resolution of inflammation. (41)

In summary, LRBA regulates the bottleneck immune genes, NF-κB and MAPKs (p42/44, p38 and JNK), and critical immune effectors, IL-10 and TNFα at protein levels/activity, response speed and response phase. The proposed dual model of LRBA's regulating immune mediators, for the first time, provides a united way to explain the paradoxical association of immunodeficiency with autoimmunity at molecular levels. In LRBA deficient patients, in response to pathogens, the attenuated activation of immune effectors at phase 1 may result in insufficient immunity and thus immunodeficiency, while attenuated deactivation of immune effectors at phase 2 may lead to overactivated immunity and thus autoimmunity.

Reagents:

Monoclonal antibodies against the following proteins were purchased from BD Biosciences (San Jose, Calif., USA): Phosflow Starter Kit, Erk1/2 (pT202/pY204) PE-CF594, JNK (PT183/PY185) Alexa 647, NF-KpaB p65 (pS529) PE-Cy7 and p38 MAPK (pT180/pY182) PerCP-Cy5.5. The LRBA Prestige antibodies (NBP1-90764 and NBP1-90765) were purchased from Novus Biologicals (Littleton, Colo., USA). The Alexa Fluor Conjugated secondary antibodies: Anti-mouse IgG-Alexa Fluor® 555 and anti-rabbit IgG-Alexa Fluor® 488 were purchased from Life Technologies (Grand Island, N.Y., USA). Phospho-MAPK Family Antibody Sampler Kit (9910S), MAPK Family Antibody Sampler (9926S), NF-κB Family Member Antibody Sampler Kit (#4766) were from Cell Signaling Technology (Danvers, Mass., USA).

Cell Culture and Stimulation:

HEK293 cell line were purchased from the American Type Culture Collection (Manassas, Va., USA) and maintained according to the company's instructions. Raji B cell line (Burkitt's lymphoma) was kindly provided by Dr. George Blanck (University of South Florida Morsani College of Medicine). These cells were cultured in RPMI1640 supplemented with 10% FBS and penicillin-streptomycin (5,000 IU/ml penicillin and 5,000 µg/ml streptomycin). Raji cells were stimulated with LPS (1 µg/ml).

Multiparametric Flow Cytometry:

BD FACSelect Multicolor Panel Designer was used to search antibodies and build up the panel for multiple color cytometry for LSRII FACS machine. Two panels were used when use live/dead discrimination with DAPI (overlap with PerCP-Cy5.5) or 7AAD (overlap with V450). The standard staining procedures were followed and 20,000 to half million cells were acquired. Data acquisition was performed using FACS LSRII flow cytometers and analyzed using FACSDiva version 6.1.2.

Cytometric Bead Array (CBA) and ELISA Cytokine Assay:

Cell culture supernatants were directly used to detect human Th1 and Th2 cytokines (IL-2, IL-4, IL-5, IL-6, IL-10, TNFα and IFN-γ) using the human Th1/Th2 cytokine bead-array kit (BD Biosciences, San Jose, Calif.) according to the manufacturer's instructions. The TNFα concentrations were also measured by Human TNFα DuoSet ELISA kit (R&D, Catalog #DY210).

Western Blots:

Cell extracts were prepared using radioimmunoprecipitation assay buffer (RIPA) buffer supplemented with protease inhibitor cocktail set III, EDTA-free (Millipore, Cat. No. 539134) and phosphatase inhibitor cocktail set II (Millipore, Cat. No. 524625). PVDF transfer membranes (Thermo, Rockford, Ill.) were used for Western blotting. Blots were imaged and protein levels of specific gene products quantitated by a ChemiDoc XRS (Bio-Rad, Richmond, Calif.) imager and Quantity One software (Bio-Rad, Richmond, Calif.).

Luciferase Assay:

Ready-To-Glow™ NF-κB Secreted Luciferase Reporter System (Clontech) and Firefly Luciferase Assay Kit (Biotium, Calif., USA) were used following the manufacture's instruction.

Polynomial Fitting and Slope Calculation:

Polynomial fitting in Microsoft Excel was used to represent nonlinear dataset in this study. High $R^2$ values ($R^2 \geq 0.9$) were used to describe the fitting accuracy and a polynomial trend line equation were used to represent the dataset. The slopes at each time point were calculated by $n \cdot k \cdot x^{(n-1)}$ calculus method.

Statistics Analysis:

Comparisons of sample means was done using two-sample t test, assuming equal variance, and p value was calculated based on two-tailed test. Significance was taken as $p<0.05$. Data are expressed as mean±standard deviation (SD) and are representative of two to three independent experiments. P value indications: <0.001 Extremely significant *, 0.001 to 0.01 Very significant  0.01 to 0.05 Significant * >0.05 Not significant ns #>≈0.05.

REFERENCES

1. Lopez-Herrera, G., G. Tampella, Q. Pan-Hammarstrom, P. Herholz, C. M. Trujillo-Vargas, K. Phadwal, A. K. Simon, M. Moutschen, A. Etzioni, A. Mory, I. Srugo, D. Melamed, K. Hultenby, C. Liu, M. Baronio, M. Vitali, P. Philippet, V. Dideberg, A. Aghamohammadi, N. Rezaei, V. Enright, L. Du, U. Salzer, H. Eibel, D. Pfeifer, H. Veelken, H. Stauss, V. Lougaris, A. Plebani, E. M. Gertz, A. A. Schaffer, L. Hammarstrom, and B. Grimbacher. 2012. Deleterious Mutations in LRBA Are Associated with a Syndrome of Immune Deficiency and Autoimmunity. *American journal of human genetics* 90: 986-1001.
2. Burns, S. O., H. L. Zenner, V. Plagnol, J. Curtis, K. Mok, M. Eisenhut, D. Kumararatne, R. Doffinger, A. J. Thrasher, and S. Nejentsev. 2012. LRBA gene deletion in a patient presenting with autoimmunity without hypogammaglobulinemia. *The Journal of allergy and clinical immunology* 130: 1428-1432.

3. Alangari, A., A. Alsultan, N. Adly, M. J. Massaad, I. S. Kiani, A. Aljebreen, E. Raddaoui, A. K. Almomen, S. Al-Muhsen, R. S. Geha, and F. S. Alkuraya. 2012. LPS-responsive beige-like anchor (LRBA) gene mutation in a family with inflammatory bowel disease and combined immunodeficiency. *The Journal of allergy and clinical immunology* 130: 481-488 e482.
4. Salzer, U., H. M. Chapel, A. D. Webster, Q. Pan-Hammarstrom, A. Schmitt-Graeff, M. Schlesier, H. H. Peter, J. K. Rockstroh, P. Schneider, A. A. Schaffer, L. Hammarstrom, and B. Grimbacher. 2005. Mutations in TNFRSF13B encoding TACI are associated with common variable immunodeficiency in humans. *Nat Genet* 37: 820-828.
5. Warnatz, K., U. Salzer, M. Rizzi, B. Fischer, S. Gutenberger, J. Bohm, A. K. Kienzler, Q. Pan-Hammarstrom, L. Hammarstrom, M. Rakhmanov, M. Schlesier, B. Grimbacher, H. H. Peter, and H. Eibel. 2009. B-cell activating factor receptor deficiency is associated with an adult-onset antibody deficiency syndrome in humans. *Proceedings of the National Academy of Sciences of the United States of America* 106: 13945-13950.
6. Kuijpers, T. W., R. J. Bende, P. A. Baars, A. Grummels, I. A. M. Derks, K. M. Dolman, T. Beaumont, T. F. Tedder, C. J. M. van Noesel, E. Eldering, and R. A. W. van Lier. 2010. CD20 deficiency in humans results in impaired T cell-independent antibody responses. *Journal of Clinical Investigation* 120: 214-222.
7. Grimbacher, B., A. Hutloff, M. Schlesier, E. Glocker, K. Warnatz, R. Drager, H. Eibel, B. Fischer, A. A. Schaffer, H. W. Mages, R. A. Kroczek, and H. H. Peter. 2003. Homozygous loss of ICOS is associated with adult-onset common variable immunodeficiency. *Nat Immunol* 4: 261-268.
8. van Zelm, M. C., I. Reisli, M. van der Burg, D. Castano, C. J. M. van Noesel, M. J. D. van Tol, C. Woellner, B. Grimbacher, P. J. Patino, J. J. M. van Dongen, and J. L. Franco. 2006. An antibody-deficiency syndrome due to mutations in the CD19 gene. *New England Journal of Medicine* 354: 1901-1912.
9. Thiel, J., L. Kimmig, U. Salzer, M. Grudzien, D. Lebrecht, T. Hagena, R. Draeger, N. Volxen, A. Bergbreiter, S. Jennings, S. Gutenberger, A. Aichem, H. Illges, J. P. Hannan, A. K. Kienzler, M. Rizzi, H. Eibel, H. H. Peter, K. Warnatz, B. Grimbacher, J. A. Rump, and M. Schlesier. 2012. Genetic CD21 deficiency is associated with hypogammaglobulinemia. *The Journal of allergy and clinical immunology* 129: 801-810 e806.
10. van Zelm, M. C., J. Smet, B. Adams, F. Mascart, L. Schandene, F. Janssen, A. Ferster, C.-C. Kuo, S. Levy, J. J. M. van Dongen, and M. van der Burg. 2010. CD81 gene defect in humans disrupts CD19 complex formation and leads to antibody deficiency. *Journal of Clinical Investigation* 120: 1265-1274.
11. Eibel, H., U. Salzer, and K. Warnatz. 2010. Common variable immunodeficiency at the end of a prospering decade: towards novel gene defects and beyond. *Current opinion in allergy and clinical immunology* 10: 526-533.
12. Podjasek, J. C., and R. S. Abraham. 2012. Autoimmune cytopenias in common variable immunodeficiency. *Frontiers in immunology* 3: 189.
13. Cunningham-Rundles, C., and C. Bodian. 1999. Common variable immunodeficiency: clinical and immunological features of 248 patients. *Clinical immunology* 92: 34-48.
14. Parvaneh, N., J. L. Casanova, L. D. Notarangelo, and M. E. Conley. 2013. Primary immunodeficiencies: a rapidly evolving story. *The Journal of allergy and clinical immunology* 131: 314-323.
15. Salzer, U., C. Bacchelli, S. Buckridge, Q. Pan-Hammarstrom, S. Jennings, V. Lougaris, A. Bergbreiter, T. Hagena, J. Birmelin, A. Plebani, A. D. Webster, H. H. Peter, D. Suez, H. Chapel, A. McLean-Tooke, G. P. Spickett, S. Anover-Sombke, H. D. Ochs, S. Urschel, B. H. Belohradsky, S. Ugrinovic, D. S. Kumararatne, T. C. Lawrence, A. M. Holm, J. L. Franco, I. Schulze, P. Schneider, E. M. Gertz, A. A. Schaffer, L. Hammarstrom, A. J. Thrasher, H. B. Gaspar, and B. Grimbacher. 2009. Relevance of biallelic versus monoallelic TNFRSF13B mutations in distinguishing disease-causing from risk-increasing TNFRSF13B variants in antibody deficiency syndromes. *Blood* 113: 1967-1976.
16. Wang, J. W., J. Howson, E. Haller, and W. G. Kerr. 2001. Identification of a novel lipopolysaccharide-inducible gene with key features of both A kinase anchor proteins and chs1/beige proteins. *J Immunol* 166: 4586-4595.
17. Kerr, W. G., M. Heller, and L. A. Herzenberg. 1996. Analysis of lipopolysaccharide-response genes in B-lineage cells demonstrates that they can have differentiation stage-restricted expression and contain SH2 domains. *Proceedings of the National Academy of Sciences of the United States of America* 93: 3947-3952.
18. Cullinane, A. R., A. A. Schaffer, and M. Huizing. 2013. The BEACH Is Hot: A LYST of Emerging Roles for BEACH-Domain Containing Proteins in Human Disease. *Traffic*.
19. Wang, J. W., J. J. Gamsby, S. L. Highfill, L. B. Mora, G. C. Bloom, T. J. Yeatman, T. C. Pan, A. L. Ramne, L. A. Chodosh, W. D. Cress, J. Chen, and W. G. Kerr. 2004. Deregulated expression of LRBA facilitates cancer cell growth. *Oncogene* 23: 4089-4097.
20. Wiley, H. S. 2003. Trafficking of the ErbB receptors and its influence on signaling. *Experimental cell research* 284: 78-88.
21. Kurylowicz, A., and J. Nauman. 2008. The role of nuclear factor-kappaB in the development of autoimmune diseases: a link between genes and environment. *Acta biochimica Polonica* 55: 629-647.
22. Cunningham-Rundles, C. 2012. Human B cell defects in perspective. *Immunologic research* 54: 227-232.
23. Wang, J. W., J. J. Gamsby, S. L. Highfill, L. B. Mora, G. C. Bloom, T. J. Yeatman, T. C. Pan, A. L. Ramne, L. A. Chodosh, W. D. Cress, J. D. Chen, and W. G. Kerr. 2004. Deregulated expression of LRBA facilitates cancer cell growth. *Oncogene* 23: 4089-4097.
24. Hoesel, B., and J. A. Schmid. 2013. The complexity of NF-kappaB signaling in inflammation and cancer. *Mol Cancer* 12: 86.
25. Nelson, D. E., A. E. Ihekwaba, M. Elliott, J. R. Johnson, C. A. Gibney, B. E. Foreman, G. Nelson, V. See, C. A. Horton, D. G. Spiller, S. W. Edwards, H. P. McDowell, J. F. Unitt, E. Sullivan, R. Grimley, N. Benson, D. Broomhead, D. B. Kell, and M. R. White. 2004. Oscillations in NF-kappaB signaling control the dynamics of gene expression. *Science* 306: 704-708.
26. Boring, L., J. Gosling, M. Cleary, and I. F. Charo. 1998. Decreased lesion formation in CCR2−/− mice reveals a role for chemokines in the initiation of atherosclerosis. *Nature* 394: 894-897.
27. Oeckinghaus, A., M. S. Hayden, and S. Ghosh. 2011. Crosstalk in NF-kappaB signaling pathways. *Nature immunology* 12: 695-708.

28. Wech, I., and A. C. Nagel. 2005. Mutations in rugose promote cell type-specific apoptosis in the *Drosophila* eye. *Cell death and differentiation* 12: 145-152.
29. Shiflett, S. L., M. B. Vaughn, D. Huynh, J. Kaplan, and D. M. Ward. 2004. Bph1p, the *Saccharomyces cerevisiae* homologue of CHS1/Beige, functions in cell wall formation and protein sorting. *Traffic* 5: 700-710.
30. Volders, K., K. Nuytens, and J. W. M. Creemers. 2011. The Autism Candidate Gene Neurobeachin Encodes a Scaffolding Protein Implicated in Membrane Trafficking and Signaling. *Current Molecular Medicine* 11: 204-217.
31. Ashida, H., H. Mimuro, M. Ogawa, T. Kobayashi, T. Sanada, M. Kim, and C. Sasakawa. 2011. Cell death and infection: a double-edged sword for host and pathogen survival. *The Journal of cell biology* 195: 931-942.
32. Baltimore, D. 2011. NF-kappaB is 25. *Nat Immunol* 12: 683-685.
33. Hayden, M. S., and S. Ghosh. 2012. NF-kappaB, the first quarter-century: remarkable progress and outstanding questions. Genes & development 26: 203-234.
34. Han, J., J. D. Lee, L. Bibbs, and R. J. Ulevitch. 1994. A MAP kinase targeted by endotoxin and hyperosmolarity in mammalian cells. *Science* 265: 808-811.
35. Huang, G., L. Z. Shi, and H. Chi. 2009. Regulation of JNK and p38 MAPK in the immune system: signal integration, propagation and termination. *Cytokine* 48: 161-169.
36. Schrofelbauer, B., and A. Hoffmann. 2011. How do pleiotropic kinase hubs mediate specific signaling by TNFR superfamily members? *Immunological reviews* 244: 29-43.
37. DeSilva, D. R., E. A. Jones, M. F. Favata, B. D. Jaffee, R. L. Magolda, J. M. Trzaskos, and P. A. Scherle. 1998. Inhibition of mitogen-activated protein kinase kinase blocks T cell proliferation but does not induce or prevent anergy. *Journal of immunology* (Baltimore, Md.: 1950) 160: 4175-4181.
38. Holgate, S. T. 2009. Novel targets of therapy in asthma. *Curr Opin Pulm Med* 15: 63-71.
39. Gires, O., U Zimber-Strobl, R. Gonnella, M. Ueffing, G. Marschall, R. Zeidler, D. Pich, and W. Hammerschmidt. 1997. Latent membrane protein 1 of Epstein-Barr virus mimics a constitutively active receptor molecule. *The EMBO journal* 16: 6131-6140.
40. Kilger, E., A. Kieser, M. Baumann, and W. Hammerschmidt. 1998. Epstein-Barr virus-mediated B-cell proliferation is dependent upon latent membrane protein 1, which simulates an activated CD40 receptor. *The EMBO journal* 17: 1700-1709.
41. Monaco, C., and E. Paleolog. 2004. Nuclear factor kappaB: a potential therapeutic target in atherosclerosis and thrombosis. *Cardiovasc Res* 61: 671-682.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method of treating a disease based on lipopolysaccharide-responsive beige-like anchor (LRBA) up-regulation, comprising:
   determining the cause of the disease based on LRBA up-regulation, wherein the cause is up-regulation of LRBA;
   treating the disease based on LRBA up-regulation, wherein the treatment is:
      down-regulating LRBA in the immune-based disease having LRBA up-regulation, further comprising:
         administering a composition further comprising a dominant-negative LRBA composition, an anti-LRBA siRNA, an anti-LRBA shRNA, miRNA miR-150, miRNA miR-181, or a combination thereof;
   wherein the dominant-negative LRBA composition is an LRBA-VHSLIR1 peptide of SEQ ID NO: 14 or an LRBA-VHS peptide of SEQ ID NO: 12;
   wherein the disease based on LRBA up-regulation is asthma.

2. The method of claim 1, wherein the anti-LRBA shRNA targets an amino acid sequence shown in SEQ ID NO: 15.

3. The method of claim 2, wherein the anti-LRBA shRNA is shown in SEQ ID NO: 43, 44, or a combination thereof.

4. The method of claim 2, wherein the anti-LRBA shRNA is inserted into a plasmid construct.

5. The method of claim 4, wherein a vector for the plasmid construct is pLAsiGFP or PhmsiGFP.

6. A method of treating a disease based on lipopolysaccharide-responsive beige-like anchor (LRBA) up-regulation, comprising:
   determining the cause of the disease based on LRBA up-regulation, wherein the cause is up-regulation of LRBA;
   treating the disease based on LRBA up-regulation, wherein the treatment is:
      administering a composition further comprising a dominant-negative LRBA composition, an anti-LRBA siRNA, an anti-LRBA shRNA, miRNA miR-150, miRNA miR-181, or a combination thereof;
      wherein the dominant-negative LRBA composition targets an amino acid sequence shown in SEQ ID NO: 2, 3, 4, 5, 6, 7, or 11;
      wherein the anti-LRBA shRNA targets an amino acid sequence shown in SEQ ID NO: 15; and
   wherein the dominant-negative LRBA composition is an LRBA-VHSLIR1 peptide having the sequence of SEQ ID NO: 14 or an LRBA-VHS peptide having the sequence of SEQ ID NO: 12;
   wherein the disease based on LRBA up-regulation is asthma.

7. The method of claim 6, wherein the anti-LRBA siRNA is shown in SEQ ID NO: 43, 44, or a combination thereof.

* * * * *